US010852220B2

(12) United States Patent
D'Silva et al.

(10) Patent No.: US 10,852,220 B2
(45) Date of Patent: *Dec. 1, 2020

(54) METHODS AND DEVICES FOR HIGH THROUGHPUT PURIFICATION

(71) Applicants: UNIVERSITY OF MARYLAND, BALTIMORE, Baltimore, MD (US); THE TRUSTEES OF PRINCETON UNIVERSITY, Princeton, NJ (US)

(72) Inventors: Joseph D'Silva, Hillsboro, OR (US); Robert H. Austin, Princeton, NJ (US); Curt Civin, Baltimore, MD (US); James C. Sturm, Princeton, NJ (US)

(73) Assignees: The Trustees of Princeton University, Princeton, NJ (US); University of Maryland, Baltimore, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/588,137

(22) Filed: Sep. 30, 2019

(65) Prior Publication Data

US 2020/0025657 A1 Jan. 23, 2020

Related U.S. Application Data

(63) Continuation of application No. 16/123,056, filed on Sep. 6, 2018, which is a continuation of application No. 14/774,260, filed as application No. PCT/US2014/029736 on Mar. 14, 2014, now Pat. No. 10,324,011.

(60) Provisional application No. 61/799,835, filed on Mar. 15, 2013, provisional application No. 61/939,044, filed on Feb. 12, 2014.

(51) Int. Cl.
| | |
|---|---|
| *G01N 1/34* | (2006.01) |
| *G01N 33/50* | (2006.01) |
| *G01N 15/14* | (2006.01) |
| *B01L 3/00* | (2006.01) |
| *A61K 35/14* | (2015.01) |
| *A61K 35/28* | (2015.01) |
| *G01N 15/00* | (2006.01) |
| *G01N 15/10* | (2006.01) |

(52) U.S. Cl.
CPC .............. *G01N 1/34* (2013.01); *A61K 35/14* (2013.01); *A61K 35/28* (2013.01); *B01L 3/502753* (2013.01); *B01L 3/502761* (2013.01); *G01N 15/1404* (2013.01); *G01N 33/5094* (2013.01); *B01L 2200/0652* (2013.01); *B01L 2300/0816* (2013.01); *B01L 2300/0864* (2013.01); *B01L 2300/0867* (2013.01); *B01L 2300/1894* (2013.01); *B01L 2400/086* (2013.01); *G01N 2015/008* (2013.01); *G01N 2015/1006* (2013.01); *G01N 2015/1493* (2013.01); *G01N 2333/70596* (2013.01)

(58) Field of Classification Search
None
See application file for complete search history.

(56) References Cited

U.S. PATENT DOCUMENTS

| | | |
|---|---|---|
| 4,675,286 A | 6/1987 | Calenoff |
| 4,756,427 A | 7/1988 | Gohde et al. |
| 5,030,002 A | 7/1991 | North |
| 5,240,856 A | 8/1993 | Goffe et al. |
| 5,427,663 A | 6/1995 | Austin et al. |
| 5,541,164 A | 7/1996 | Carson et al. |
| 5,676,849 A | 10/1997 | Sammons et al. |
| 5,707,799 A | 1/1998 | Hansmann et al. |
| 5,837,115 A | 11/1998 | Austin et al. |
| 5,872,128 A | 2/1999 | Patel et al. |
| 5,948,278 A | 9/1999 | Sammons et al. |
| 5,968,820 A | 10/1999 | Zborowski et al. |
| 5,981,180 A | 11/1999 | Chandler et al. |
| 6,241,894 B1 | 6/2001 | Briggs et al. |
| 6,268,222 B1 | 7/2001 | Chandler et al. |
| 6,514,295 B1 | 2/2003 | Chandler et al. |
| 6,524,793 B1 | 2/2003 | Chandler et al. |
| 6,528,165 B2 | 3/2003 | Chandler et al. |
| 6,632,652 B1 | 10/2003 | Austin et al. |
| 6,685,841 B2 | 2/2004 | Lopez et al. |
| 6,692,952 B1 | 2/2004 | Braff et al. |
| 6,881,315 B2 | 4/2005 | Iida et al. |
| 6,881,317 B2 | 4/2005 | Huang et al. |
| 6,913,697 B2 | 7/2005 | Lopez et al. |
| 6,949,355 B2 | 9/2005 | Yamanishi et al. |
| 6,960,449 B2 | 11/2005 | Wang et al. |
| 7,150,812 B2 | 12/2006 | Huang et al. |

(Continued)

FOREIGN PATENT DOCUMENTS

| | | |
|---|---|---|
| CA | 1 248 873 | 1/1989 |
| EP | 1462800 A1 | 9/2004 |

(Continued)

OTHER PUBLICATIONS

U.S. Appl. No. 60/414,258, filed Apr. 8, 2004 (posted by WIPO), Toner et al.

(Continued)

*Primary Examiner* — Robert J Yamasaki
(74) *Attorney, Agent, or Firm* — Law Office of: Michael A. Sanzo, LLC

(57) ABSTRACT

Described herein are devices and methods for high throughput purification of particles. In some cases, methods and devices described herein can be used to remove erythrocytes and purify leukocytes and raise the quality of umbilical cord blood and other transplant grafts, thereby significantly improving patient outcomes.

14 Claims, 43 Drawing Sheets

(56) References Cited

U.S. PATENT DOCUMENTS

| | | |
|---|---|---|
| 7,276,170 B2 | 10/2007 | Oakey et al. |
| 7,318,902 B2 | 1/2008 | Oakey et al. |
| 7,472,794 B2 | 1/2009 | Oakey et al. |
| 7,682,838 B2 | 3/2010 | Wang et al. |
| 7,735,652 B2 | 6/2010 | Inglis et al. |
| 7,837,944 B2 | 11/2010 | Auner et al. |
| 7,846,393 B2 | 12/2010 | Tai et al. |
| 7,863,012 B2 | 1/2011 | Rao et al. |
| 7,977,095 B2 | 7/2011 | Bonyhadi et al. |
| 7,988,840 B2 | 8/2011 | Huang et al. |
| 7,993,821 B2 | 8/2011 | Chiu et al. |
| 8,008,032 B2 | 8/2011 | Forsyth et al. |
| 8,021,614 B2 | 9/2011 | Huang et al. |
| 8,088,715 B2 | 1/2012 | Bodmer et al. |
| 8,137,912 B2 | 3/2012 | Kapur et al. |
| 8,168,389 B2 | 5/2012 | Shoemaker et al. |
| 8,186,913 B2 | 5/2012 | Toner et al. |
| 8,263,023 B2 | 9/2012 | Le Vot et al. |
| 8,263,404 B2 | 9/2012 | Olken et al. |
| 8,282,799 B2 | 10/2012 | Huang et al. |
| 8,304,230 B2 | 11/2012 | Toner et al. |
| 8,329,422 B2 | 12/2012 | Rao et al. |
| 8,354,075 B1 | 1/2013 | Tai et al. |
| 8,372,579 B2 | 2/2013 | Toner et al. |
| 8,372,584 B2 | 2/2013 | Shoemaker et al. |
| 8,579,117 B2 | 11/2013 | Loutherback et al. |
| 8,585,971 B2 | 11/2013 | Huang et al. |
| 8,783,467 B2 | 7/2014 | Loutherback et al. |
| 8,895,298 B2 | 11/2014 | Toner et al. |
| 8,906,682 B2 | 12/2014 | June et al. |
| 8,921,102 B2 | 12/2014 | Fuchs et al. |
| 8,951,484 B2 | 2/2015 | Bersano-Begey et al. |
| 8,986,966 B2 | 3/2015 | Toner et al. |
| 9,017,942 B2 | 4/2015 | Shoemaker et al. |
| 9,034,658 B2 | 5/2015 | Barber et al. |
| 9,273,355 B2 | 3/2016 | Shoemaker et al. |
| 9,328,156 B2 | 5/2016 | June et al. |
| 9,347,100 B2 | 5/2016 | Shoemaker et al. |
| 9,427,688 B2 | 8/2016 | Reichenbach |
| 9,610,582 B2 | 4/2017 | Kapur et al. |
| 9,629,877 B2 | 4/2017 | Cooper et al. |
| 9,878,327 B2 | 1/2018 | Smith et al. |
| 9,895,694 B2 | 2/2018 | Kapur et al. |
| 9,956,562 B2 | 5/2018 | Huang et al. |
| 10,324,011 B2 | 6/2019 | D'Silva |
| 10,359,429 B2 | 7/2019 | Forsyth |
| 2001/0036624 A1 | 11/2001 | Sumita et al. |
| 2002/0005354 A1 | 1/2002 | Spence et al. |
| 2002/0090741 A1 | 7/2002 | Jurgensen et al. |
| 2002/0110835 A1 | 8/2002 | Kumar et al. |
| 2002/0115163 A1 | 8/2002 | Wang et al. |
| 2002/0119482 A1 | 8/2002 | Nelson et al. |
| 2002/0123078 A1 | 9/2002 | Seul et al. |
| 2002/0164825 A1 | 11/2002 | Chen |
| 2003/0049563 A1 | 3/2003 | Iida et al. |
| 2003/0096405 A1 | 5/2003 | Takayama et al. |
| 2003/0113528 A1 | 6/2003 | Moya |
| 2003/0119077 A1 | 6/2003 | Tso et al. |
| 2003/0159999 A1 | 8/2003 | Oakey et al. |
| 2003/0180762 A1 | 9/2003 | Tuma et al. |
| 2004/0018116 A1 | 1/2004 | Desmond et al. |
| 2004/0018611 A1 | 1/2004 | Ward et al. |
| 2004/0019300 A1 | 1/2004 | Leonard |
| 2004/0033515 A1 | 2/2004 | Cao |
| 2004/0043506 A1 | 3/2004 | Haussecker et al. |
| 2004/0144651 A1 | 7/2004 | Huang et al. |
| 2004/0166555 A1 | 8/2004 | Braff et al. |
| 2004/0224402 A1 | 11/2004 | Bonyhadi et al. |
| 2004/0229349 A1 | 11/2004 | Daridon |
| 2004/0232074 A1 | 11/2004 | Peters et al. |
| 2005/0061962 A1 | 3/2005 | Mueth et al. |
| 2005/0164158 A1 | 7/2005 | Wang et al. |
| 2005/0207940 A1 | 9/2005 | Butler et al. |
| 2005/0266433 A1 | 12/2005 | Kapur et al. |
| 2005/0272103 A1 | 12/2005 | Chen |
| 2005/0282293 A1 | 12/2005 | Cosman et al. |
| 2006/0035386 A1 | 2/2006 | Hattori et al. |
| 2006/0121624 A1 | 6/2006 | Huang et al. |
| 2006/0128006 A1 | 6/2006 | Gerhardt et al. |
| 2006/0134599 A1 | 6/2006 | Toner et al. |
| 2006/0160243 A1 | 7/2006 | Tang et al. |
| 2006/0223178 A1 | 10/2006 | Barber et al. |
| 2006/0252087 A1 | 11/2006 | Tang et al. |
| 2007/0026381 A1 | 2/2007 | Huang et al. |
| 2007/0026413 A1 | 2/2007 | Toner et al. |
| 2007/0026414 A1 | 2/2007 | Fuchs et al. |
| 2007/0026415 A1 | 2/2007 | Fuchs et al. |
| 2007/0026416 A1 | 2/2007 | Fuchs et al. |
| 2007/0026417 A1 | 2/2007 | Fuchs et al. |
| 2007/0026418 A1 | 2/2007 | Fuchs et al. |
| 2007/0026419 A1 | 2/2007 | Fuchs et al. |
| 2007/0026469 A1 | 2/2007 | Fuchs et al. |
| 2007/0042339 A1 | 2/2007 | Toner et al. |
| 2007/0059680 A1 | 3/2007 | Kapur et al. |
| 2007/0059716 A1 | 3/2007 | Balis et al. |
| 2007/0059718 A1 | 3/2007 | Kapur et al. |
| 2007/0059719 A1 | 3/2007 | Kapur et al. |
| 2007/0059774 A1 | 3/2007 | Kapur et al. |
| 2007/0059781 A1 | 3/2007 | Kapur et al. |
| 2007/0072290 A1 | 3/2007 | Hvichia et al. |
| 2007/0099207 A1 | 5/2007 | Fuchs et al. |
| 2007/0160503 A1 | 7/2007 | Sethu et al. |
| 2007/0172903 A1 | 7/2007 | Toner et al. |
| 2007/0187250 A1 | 8/2007 | Huang et al. |
| 2007/0196820 A1 | 8/2007 | Kapur et al. |
| 2007/0231851 A1 | 10/2007 | Toner et al. |
| 2007/0259424 A1 | 11/2007 | Toner et al. |
| 2007/0264675 A1 | 11/2007 | Toner et al. |
| 2007/0292401 A1 | 12/2007 | Harmon et al. |
| 2008/0070792 A1 | 3/2008 | Stoughton et al. |
| 2008/0090239 A1 | 4/2008 | Shoemaker et al. |
| 2008/0113358 A1 | 5/2008 | Kapur et al. |
| 2008/0124721 A1 | 5/2008 | Fuchs et al. |
| 2008/0248499 A1 | 10/2008 | Chiu et al. |
| 2008/0314161 A1 | 12/2008 | Sparks et al. |
| 2009/0136982 A1 | 5/2009 | Tang et al. |
| 2009/0291443 A1 | 11/2009 | Stoughton et al. |
| 2010/0006479 A1 | 1/2010 | Reichenbach |
| 2010/0055758 A1 | 3/2010 | Kapur et al. |
| 2010/0059414 A1 | 3/2010 | Sturm et al. |
| 2010/0066880 A1 | 3/2010 | Sato et al. |
| 2010/0167337 A1 | 7/2010 | Tsinberg et al. |
| 2010/0233694 A1 | 9/2010 | Kopf-Sill et al. |
| 2010/0234674 A1 | 9/2010 | Wheeler et al. |
| 2010/0291572 A1 | 11/2010 | Stoughton et al. |
| 2010/0297733 A1 | 11/2010 | Lin et al. |
| 2010/0301171 A1 | 12/2010 | Wood |
| 2010/0326916 A1 | 12/2010 | Wrazel et al. |
| 2011/0003293 A1 | 1/2011 | Stoughton et al. |
| 2011/0070642 A1 | 3/2011 | Cayre |
| 2011/0189650 A1 | 8/2011 | Ayliffe et al. |
| 2011/0212440 A1 | 9/2011 | Viovy et al. |
| 2011/0213288 A1 | 9/2011 | Choi et al. |
| 2011/0294186 A1 | 12/2011 | Fuchs et al. |
| 2011/0306043 A1 | 12/2011 | Fuchs et al. |
| 2012/0006728 A1 | 1/2012 | Huang et al. |
| 2012/0006760 A1 | 1/2012 | Toner et al. |
| 2012/0015835 A1 | 1/2012 | Fuchs et al. |
| 2012/0037544 A1 | 2/2012 | Lane et al. |
| 2012/0063971 A1 | 3/2012 | Carlo et al. |
| 2012/0078531 A1 | 3/2012 | Lo et al. |
| 2012/0100521 A1 | 4/2012 | Soper et al. |
| 2012/0100560 A1 | 4/2012 | Searson et al. |
| 2012/0115755 A1 | 5/2012 | Oh et al. |
| 2012/0171667 A1 | 7/2012 | Shoemaker et al. |
| 2012/0178097 A1 | 7/2012 | Tai et al. |
| 2012/0196273 A1 | 8/2012 | Huang et al. |
| 2012/0258459 A1 | 10/2012 | Huang |
| 2012/0258475 A1 | 10/2012 | Tang et al. |
| 2012/0270209 A1 | 10/2012 | Shah et al. |
| 2012/0295246 A1 | 11/2012 | Faustman et al. |
| 2013/0079251 A1 | 3/2013 | Boles |
| 2013/0083315 A1 | 4/2013 | Lo et al. |
| 2013/0143197 A1 | 6/2013 | Heyneker |

(56) References Cited

U.S. PATENT DOCUMENTS

| | | |
|---|---|---|
| 2013/0189689 A1 | 7/2013 | Shoemaker et al. |
| 2013/0209988 A1 | 8/2013 | Barber |
| 2013/0210644 A1 | 8/2013 | Stoughton et al. |
| 2013/0260392 A1 | 10/2013 | Forsyth et al. |
| 2013/0288903 A1 | 10/2013 | Kapur et al. |
| 2013/0302796 A1 | 11/2013 | Fuchs et al. |
| 2013/0302797 A1 | 11/2013 | Kopf-Sill et al. |
| 2013/0324418 A1 | 12/2013 | Fuchs et al. |
| 2014/0017776 A1 | 1/2014 | Koph-Sill |
| 2014/0030788 A1 | 1/2014 | Chen et al. |
| 2014/0051064 A1 | 2/2014 | van den Engh |
| 2014/0093867 A1 | 4/2014 | Burke et al. |
| 2014/0106975 A1 | 4/2014 | Stoughton et al. |
| 2014/0154703 A1 | 6/2014 | Skelley et al. |
| 2014/0227777 A1 | 8/2014 | Choi et al. |
| 2014/0234986 A1 | 8/2014 | Forsyth et al. |
| 2014/0342375 A1 | 11/2014 | Grisham et al. |
| 2015/0024482 A1 | 1/2015 | Frigault et al. |
| 2015/0025243 A1 | 1/2015 | Mosher et al. |
| 2015/0064153 A1 | 3/2015 | Civin et al. |
| 2015/0232936 A1 | 8/2015 | Shoemaker et al. |
| 2015/0233931 A1 | 8/2015 | Koph-Sill et al. |
| 2015/0260711 A1 | 9/2015 | Toner et al. |
| 2015/0268244 A1 | 9/2015 | Cho |
| 2015/0299317 A1 | 10/2015 | Orentas et al. |
| 2015/0316555 A1 | 11/2015 | Fuchs et al. |
| 2015/0344956 A1 | 12/2015 | Kapur et al. |
| 2016/0002737 A1 | 1/2016 | Fuchs et al. |
| 2016/0047735 A1 | 2/2016 | Grisham et al. |
| 2016/0081314 A1 | 3/2016 | Thurston et al. |
| 2016/0103044 A1 | 4/2016 | Kopf-Sill et al. |
| 2016/0139012 A1 | 5/2016 | D'Silva et al. |
| 2016/0168539 A1 | 6/2016 | Civin et al. |
| 2016/0244714 A1 | 8/2016 | Spuhler et al. |
| 2016/0339434 A1 | 11/2016 | Toner et al. |
| 2016/0361360 A1 | 12/2016 | Chang et al. |
| 2017/0023578 A1 | 1/2017 | Forsyth et al. |
| 2017/0101680 A1 | 4/2017 | Kopf-Sill et al. |
| 2017/0137515 A1 | 5/2017 | Chang et al. |
| 2017/0166866 A1 | 6/2017 | Lliang et al. |
| 2017/0209864 A1 | 7/2017 | Grisham et al. |
| 2017/0224789 A1 | 8/2017 | Sonavaria et al. |
| 2017/0248508 A1 | 8/2017 | Ward et al. |
| 2017/0333900 A1 | 11/2017 | Grisham et al. |
| 2018/0038876 A1 | 2/2018 | Arai |
| 2018/0282811 A1 | 10/2018 | Kopf-Sill et al. |
| 2019/0071639 A1 | 3/2019 | Ward et al. |
| 2019/0137369 A1 | 5/2019 | D'Silva et al. |
| 2019/0366342 A1 | 12/2019 | Ward et al. |
| 2020/0025656 A1 | 1/2020 | D'Silva et al. |
| 2020/0025669 A1 | 1/2020 | Ward et al. |
| 2020/0056153 A1 | 2/2020 | Ward et al. |

FOREIGN PATENT DOCUMENTS

| | | |
|---|---|---|
| EP | 1425294 B1 | 7/2008 |
| EP | 1585583 B1 | 4/2010 |
| EP | 1597353 B1 | 11/2010 |
| EP | 2201361 B1 | 5/2011 |
| EP | 1984030 B1 | 5/2013 |
| WO | WO 91/16452 A1 | 10/1991 |
| WO | WO 94/29707 A1 | 12/1994 |
| WO | WO 01/35071 A2 | 5/2001 |
| WO | WO 2004/029221 A2 | 4/2004 |
| WO | WO 2004/029221 A3 | 5/2004 |
| WO | WO 2004/037374 A2 | 5/2004 |
| WO | WO 2004/037374 A3 | 10/2004 |
| WO | WO 2004/113877 A1 | 12/2004 |
| WO | WO 2005/047529 A1 | 5/2005 |
| WO | WO 2005/049168 A2 | 6/2005 |
| WO | WO 2005/061075 A1 | 7/2005 |
| WO | WO 2005/049168 A3 | 9/2005 |
| WO | WO 2006/037561 A1 | 4/2006 |
| WO | WO 2006/078470 A2 | 7/2006 |
| WO | WO 2006/078470 A3 | 7/2006 |
| WO | WO 2006/108087 A2 | 10/2006 |
| WO | WO 2006/108101 A2 | 10/2006 |
| WO | WO 2006/133208 A2 | 12/2006 |
| WO | WO 2007/035498 A2 | 3/2007 |
| WO | WO 2007/035585 A2 | 3/2007 |
| WO | WO 2007/035586 A2 | 3/2007 |
| WO | WO 2007/079229 A2 | 7/2007 |
| WO | WO 2007/079250 A2 | 7/2007 |
| WO | WO 2007/147018 A1 | 12/2007 |
| WO | WO 2007/147074 A2 | 12/2007 |
| WO | WO 2007/147076 A2 | 12/2007 |
| WO | WO 2007/147079 A2 | 12/2007 |
| WO | WO 2008/008515 A2 | 1/2008 |
| WO | WO 2008/017871 A1 | 2/2008 |
| WO | WO 2008/111990 A1 | 9/2008 |
| WO | WO 2007/079229 A3 | 1/2009 |
| WO | WO 2007/079250 A3 | 3/2009 |
| WO | WO 2006/108101 A3 | 4/2009 |
| WO | WO 2006/108087 A3 | 6/2009 |
| WO | WO 2009/076560 A2 | 6/2009 |
| WO | WO 2010/011934 | 1/2010 |
| WO | WO 2010/124155 A1 | 10/2010 |
| WO | WO 2010/129441 | 11/2010 |
| WO | WO 2010/129441 A2 | 11/2010 |
| WO | WO 2010/144745 A2 | 12/2010 |
| WO | WO 2011/119962 | 9/2011 |
| WO | WO 2011/119962 A2 | 9/2011 |
| WO | WO 2012/016136 | 2/2012 |
| WO | WO 2012/024194 A2 | 2/2012 |
| WO | WO 2012/094642 A2 | 7/2012 |
| WO | WO 2014/004577 A1 | 1/2014 |
| WO | WO 2014/046621 A1 | 3/2014 |
| WO | WO 2014/116183 A1 | 7/2014 |
| WO | WO 2014/145075 A2 | 9/2014 |
| WO | WO 2014/145152 A2 | 9/2014 |
| WO | WO 2015/084257 | 6/2015 |
| WO | WO 2015/162211 | 10/2015 |
| WO | WO 2015/164745 | 10/2015 |
| WO | WO 2016/019393 A1 | 2/2016 |
| WO | WO 2016/073481 | 5/2016 |
| WO | WO 2017/035262 A1 | 3/2017 |
| WO | WO 2017/176764 | 10/2017 |
| WO | WO 2018/080997 | 5/2018 |
| WO | PCT/US2018/047426 | 8/2018 |
| WO | WO 2019/046052 | 3/2019 |
| WO | WO 2019/222049 | 11/2019 |
| WO | WO 2020/014538 | 1/2020 |

OTHER PUBLICATIONS

Office Action for co-pending U.S. Appl. No. 14/941,957, dated Jan. 12, 2017.

Response to Office Action dated Jan. 12, 2017 for co-pending U.S. Appl. No. 14/941,957, filed Jul. 1, 2017.

Notice of Non-Compliant Amendment for co-pending U.S. Appl. No. 14/941,957, dated Oct. 31, 2017.

Response to Notice of Non-Compliant Amendment for co-pending U.S. Appl. No. 14/941,957, filed Dec. 9, 2017.

International Preliminary Examination Report for counterpart international application PCT/US2014/029736, dated Sep. 15, 2015.

Amended claims filed for European counterpart application EP 2014763363.0, filed Apr. 28, 2016.

Supplementary European Search Report for EP 2014763363.0, dated Jul. 1, 2016.

European Search Opinion for EP 2014763363.0, dated Jul. 1, 2016.

Amended claims and Response to European Search Opinion for EP 2014763363.0, filed May 4, 2017.

Examination Report for EP 2014763363.0, dated Sep. 13, 2017.

Translation of amended claims filed in China for counterpart Chinese application 2014800285714.

Office Action for 2014800285714 with English language summary attached to its front, dated May 5, 2017.

Translation of amended claims filed in response to Office Action, filed Oct. 9, 2017.

International Search Report for PCT/US2016/048455, completed Oct. 17, 2016; which is related to copending U.S. Appl. No. 15/595,548.

(56) References Cited

OTHER PUBLICATIONS

Written Opinion for PCT/US2016/048455, completed Oct. 17, 2016; which is related to copending U.S. Appl. No. 15/595,548.
International Preliminary Report on Patentability for PCT/US2016/048455, completed Oct. 17, 2016; which is related to copending U.S. Appl. No. 15/595,548.
International Preliminary Report on Patentability for PCT/US2014/029866; completed Sep. 15, 2015; which is related to copending U.S. Appl. No. 14/774,268.
International Preliminary Report on Patentability for PCT/US2015/043500; completed Feb. 17, 2017; which is related to copending U.S. Appl. No. 15/329,753.
Amended Claims and Response to Examination Report for European counterpart application EP 2014763363.0, filed Mar. 20, 2018.
English translation of Office Action with Response for counterpart Chinese application CN 2014800285714 dated May 17, 2018.
Supplementary Examination Report for EP 14764615, which is the European counterpart of copending U.S. Appl. No. 14/774,268, dated Jul. 1, 2016.
European Search Opinion for EP 14764615, dated Jul. 1, 2016.
Response to European Search Opinion for EP 14764615, filed May 10, 2017.
Amended Claims with Annotations in response to European Search Opinion for EP 14764615, filed May 10, 2017.
Examination Report for EP 14764615, dated Sep. 13, 2017.
Amended Claims and Response to Examination Report for EP 14764615, filed Sep. 23, 2018.
English language translation of First Office Action for CN 201480028570X, which is the Chinese counterpart of copending U.S. Appl. No. 14/774,268, dated Feb. 21, 2017.
Claims in response to First Office Action for CN 201480028570X, filed Jul. 5, 2017.
Second Office Action for Chinese application 201480028570X, with English language summary attached to the front of the document, dated Nov. 15, 2017.
Amended claims in response to Second Office Action for CN 201480028570X, filed Jan. 30, 2018.
Amended claims filed in Response to Office Action, filed May 16, 2015; (CN 20140028714; Chinese counterpart of U.S. Appl. No. 14/774,260).
Partial English translation summarizing 3rd Office Action, dated Nov. 5, 2018; (CN 20140028714; Chinese counterpart of U.S. Appl. No. 14/774,260).
European Search Opinion and Search Report for EP 15827324.3, EP counterpart of copending U.S. Appl. No. 15/329,753, dated Dec. 12, 2017.
Response to European Search Opinion and Search Report for EP 15827324.3, EP counterpart of copending U.S. Appl. No. 15/329,753, filed Jul. 12, 2018.
Amended Claims with Response to Search Opinion and Search Report for EP 15827324.3, EP counterpart of copending U.S. Appl. No. 15/329,753, filed Jul. 12, 2018.
English language summary of Office Action for CN 201480028570X, which is the Chinese counterpart for copending U.S. Appl. No. 14/774,268, dated May 28, 2018.
English translation of amended claims filed in response to 3rd Office Action for CN 201480028570X, which is the Chinese counterpart of copending U.S. Appl. No. 14/774,268, filed Aug. 13, 2018.
Communication from EPO regarding intention to grant and grant text for EP 2014764615 dated Sep. 25, 2018. EP counterpart of copending U.S. Appl. No. 14/774,268.
Restriction Requirement for copending U.S. Appl. No. 14/774,268, dated May 21, 2018.
Response to Restriction Requirement for copending U.S. Appl. No. 14/774,268, filed Aug. 21, 2018.
Office Action for copending U.S. Appl. No. 14/774,268, dated Nov. 13, 2018.
Office Action for copending U.S. Appl. No. 14/941,957, dated May 14, 2018.
Response to Office Action and RCE for copending U.S. Appl. No. 14/941,957, filed Sep. 12, 2018.
Restriction Requirement for copending U.S. Appl. No. 15/478,405, dated Jun. 12, 2018.
Response to Restriction Requirement with accompanying amendment attached for copending U.S. Appl. No. 15/478,405, filed Sep. 12, 2018.
Office Action for copending U.S. Appl. No. 15/478,405, dated Nov. 16, 2018.
Restriction Requirement for copending U.S. Appl. No. 15/329,753, dated Jul. 24, 2018.
Response to Restriction Requirement with accompanying amendment attached for copending U.S. Appl. No. 15/329,753, filed Sep. 24, 2018.
Office Action for copending U.S. Appl. No. 15/329,753, dated Oct. 15, 2018.
International Search Report and Written Opinion dated Dec. 29, 2015 for PCT Application No. PCT/US2015/43500.
Alessandrino, et al., "Adverse events occurring during bone marrow or peripheral blood progenitor cell infusion: analysis of 126 cases," *Bone Marrow Transplant* 23(6):533-537 (Mar. 1999).
Agrawal, et al., "PDGF upregulates CLEC-2 to induce T regulatory cells," *Oncotarget* 6(30):28621-28632 (Sep. 2015).
Al-Fundi, et al., "New design for the separation of microorganisms using microfluidic deterministic lateral displacement," *Robotics and Computer Integrated Manufacturing* 27(2):237-244 (2011).
Alix-Panabieres, et al., "Challenges in circulating tumor cell research," *Nature Reviews/Cancer* 14(9):623-631 ((Sep. 2014).
Apocell, ApoStream Technology; available at http://www.apocell.com/ete-technology-2/apostreamtm-technology; accessed Nov. 20, 2015.
Barker, et al., "Umbilical cord blood transplantation: current state of art," *Curr. Opin. Oncol.* 14(2):160-164 (Mar. 2002).
Basford, et al., "Umbilical cord blood processing using Prepacyte-CB increases haematopoietic progenitor cell availability over conventional Hetastarch separation," *Cell Prolif.* 42(6):751-761 (Dec. 2009).
Bauer, "Advances in cell separation: recent developments in counterflow centrifugal elutriation and continuous flow cell separation," *Journal of Chromatography* 722:55-69 (1999).
Beech, et al., "Sorting cells by size, shape and deformability," *Lab Chip* 12(6):1048-1051 (Mar. 2012).
Beech, et al., "Tipping the balance of deterministic lateral displacement devices using dielectrophoresis," *Lab Chip* 9(18)2698-2706 (Sep. 2009).
Bendall, et al., "A deep profiler's guide to cytometry," *Trends Immunol.* 33(7):323-332 (Jul. 2012).
Bendall, et al., "Single-cell mass cytometry of differential immune and drug responses across a human hemaotpoietic continuum," *Science* 332(6030):687-696 (May 2011).
Best, et al., "RNA-Seq of Tumor-Educated Platelets Enables Blood-Based Pan-Cancer, Multiclass, and Molecular Pathway Cancer Diagnostics," *Cancer Cell* 28:666-676 (Nov. 2015).
Bowman, et al., "Inertia and scaling in deterministic lateral displacement," *Biomicrofluidics* 7(6) 64111:1-9 (Dec. 2013).
Böyum, "Isolation of mononuclear cells and granulocytes from human blood,", *Scand. J. Clin. Lab. Invest. Suppl.* 97:77-89 (1968).
Böyum, "Separation of White Blood Cells," *Nature* 204:793-794 (Nov. 1964).
Campos-Gonzalez, et al., "Deterministic Lateral Displacement: The Next Generation Car T-Cell Processing?" *SLAS* 23(4):338-351 (Jan. 2018).
CDC. Advanced Abstracting: Breast Cancer Stage of Disease (Part 3); available at http://www.cdc.gov/cancer/nper/training/nets/module9/nets9_3pdf. Accessed Apr. 13, 2015.
Chang, et al., "A continuous multi-size particle separator using negative dielectrophoretic virtual pillars induced by a planar spot electrode array," Proceedings of the IEEE International Conference on Micro Electro Mechanical Systems (MEMS), (Feb. 2007).
Chen, et al., "Microfluidic chemical processing with on-chip washing by deterministic lateral displacement arrays with separator walls," *Biomicrofluidics* 9(5):054105 (Sep. 2015).

(56) References Cited

OTHER PUBLICATIONS

Chen, et al., "Rare cell isolation and analysis in microfluidics," *Lab Chip* 14(4):626-645 (Feb. 2014).
Chen, et al., "Reduction of Output Contamination in On-chip Chemical Treatment and Washing using Separator Walls in Deterministic Lateral Displacement Arrays," Spring Symp Mat Res Soc; San Francisco, CA (Apr. 21-25, 2014).
Chiche-Lapierre, et al., "Comparative analysis of Sepax S-100, COBE 2991, and Manual DMSO Removal Techniques From Cryopreserved Hematopoietic Stem Cell Apheresis Product," *Cytotherapy* 18(6):S47 (2016).
Chou, et al., "Sorting by diffusion: An asymmetric obstacle course for continuous molecular separation," *PNAS* 96(24):13762-13765 (Nov. 1999).
Chow, et al., "Whole blood fixation and permeabilization protocol with red blood cell lysis for flow cytometry of intracellular phosphorylated epitopes in leukocyte subpopulations," *Cytometry A* 67(1):4-17 (Sep. 2005).
Civin, et al., "Automated Leukocyte Processing by Microfluidic Deterministic Lateral Displacement," *Cytometry A* 89:1073-1083 (2016).
Colase, et al., "Microfluidics and coagulation biology," *Annu. Rev. Biomed. Eng.* 15:283-303 (May 2013).
Collins, et al., "Particle separation using virtual deterministic lateral displacement (vDLD)," *Lab Chip* 14(9):1595-1603 (May 2014).
Copelan, et al., "Hematopoietic stem-cell transplantation," *N Engl J Med* 354(17):1813-1826 (Apr. 2006).
Coulter® Ac T diff2™, Safety and Performance at a Remarkable Value, Product information; BeckmanCoulter; accessed Mar. 13, 2014.
Couzin-Frankel, et al., "Supply of Promising T-Cell Therapy is Strained," *Science* 356:1112 (Jun. 2017).
Cynvenio Technology. LiquidBiopsy Rare Cell Isolation Platform. Available at http://www.cynvenio.com/technology. Accessed on Nov. 20, 2015.
Davis, et al., "Deterministic hydrodynamics: Taking blood apart," *PNAS* 103(40):14779-14784 (Oct. 2006).
Davis, "Microfluidic Separation of Blood Components through Deterministic Lateral Displacement," Ph.D. Thesis, Princeton University, (Sep. 2008).
Deng, et al., "Manipulation of magnetic microbeads in suspension using micromagnetic systems fabricated with soft lithography," *Applied Physics Letters* 78:1775 (Mar. 2001).
Department of Transport Merchant Shipping Notice No. 1214. Recommendations to Prevent Contamination of Ships Freshwater Storage and Distribution Systems. Available at: http://www.octomarine.net/mca_flag_regulations/mca_reg_m-1214_contamination_prevention.php. Accessed on Aug. 3, 2015.
Devendra, et al., "Deterministic fractionation of binary suspensions moving past a line of microposts," *Microfluidics Nanofluidics* 17(3):519-526 (Apr. 2014).
D'Silva, et al., "Inhibition of Clot Formation in Deterministic Lateral Displacement Arrays for Processing Large Volumes of Blood for Rare Cell Capture," *Lab Chip* 15(10):2240-2247 (May 2015).
D'Silva, "Post Geometry Design for High-Throughput Harvesting of Nucleated Cells from Blood with Minimal Eryhtrocyte Contaimination Using DLD Arrays," Chapter 4: 53-113, Ph.D. Dissertation, Princeton University (May 2016).
Disilva, J., "Throughput Microfluidic Capture of Rare Cells from Large Volumes of Blood," A Dissertation Presented to the Faculty of Princeton University in Candidacy for the Degree of Doctor of Philosophy, (May 2016).
Ernst, et al., "Efficacy of High-Dose Bolus Tirofiban Compared to Regular-Dose Glycoprotein IIb/IIIa Inhibitors on Platelet Aggregation Inhibition in Myocardial Infarction Patients Treated with Primary Angioplasty," European Society of Cardiology. Abstract 239. (Aug. 2003).
Feng, et al., "Maximizing particle concentration in deterministic lateral displacement arrays," *Biomicrofluidics* 11:024121 (published online Apr. 2017).
Fiorini, et al., "Disposable microfluidic devices: fabrication, function and application," *Biotechniques* 38(3):429-446 (Mar. 2005).
Flow Cytometry and Sorting Core Facility. One-step fix/perm Protocol St. Michael's Hospital, Toronto, Ontario, Canada. Accessed Aug. 26, 2014. http://www.stmichaelshospital.com/research/facilities/docs/Protocol1-Onestep-Fix-perm.doc.
Foundation Medicine. Foundation Medicine Initiates Multi-Center Clinical Study Evaluating Its Circulating Tumor DNA (ctDNA) Assay in Multiple Tumor Types. Accessed Jul. 28, 2015. Available at: http://investors.foundationmedicine.com/releasedetail.cfm?releaseid=924086.
Fousek, et al., "The Evolution of T-cell Therapies for Solid Malignancies," *Clinical Cancer Research* 21(5):3384-3392 (Aug. 2015).
Gajkowska, et al., "Flow cytometric enumeration of CD34+ hematopoietic stem and progenitor cells in leukapheresis product and bone marrow for clinical transplantation: a comparison of three methods," *Folia Histochem Cytobiol* 44(1):53-60 (2006).
Geffken, et al., "The measurement of fibrinogen in population-based research. Studies on instrumentation and methodology," *Arch Pathol Lab Med* 118(11):1106-1109 (Nov. 1994).
Gervais, Capillary Microfluidic Chips for Point-of-Care Testing: from Research Tools to Decentralized Medical Diagnostics. Lausanne: EPFL, 2011.
Gluckman, et al., "Outcome of cord-blood transplantation from related and unrelated donors," *N Engl J Med* 337(6):373-381 (Aug. 1997).
Gluckman, et al., "Current status of umbilical cord blood hematopoietic stem cell transplantation," *Exp. Hematol.* 28:1197-1205 (2000).
Gutensohn, et al., "Semi-automated flow cytometric analysis of CD34-expressing hematopoietic cells in peripheral blood progenitor cell apheresis products," *Transfusion* 39(11-12):1220-1226 (Nov.-Dec. 1999).
Han, et al., "Separation of long DNA molecules in a microfabricated entropic trap array," *Science* 288(5468):1026-1029 (May 2000).
Harris, et al., "Single-Molecule DNA Sequencing of a Viral Genome," *Science* 320:106 (Apr. 2008).
Hematopoietic Stem Cells. In Stem Cell Information. Bethesda, MD: National Institutes of Health, US Department of Health and Human Services, 2011. Available at: <http://stemcells.nih.gov/info/scireport/pages/chapter5.aspx>.
Herault, et al., "A rapid single-laser flow cytometric method for discrimination of early apoptotic cells in a heterogenous cell population," *Br J Haematol* 104(3):530-537 (Mar. 1999).
Herold, et al., Lab on a Chip Technology: Biomolecular separation and analysis. (edited) vol. 2. Horizon Scientific Press, 2009.
Hodgkinson, et al., "Tumorigenicity and genetic profiling of circulating tumor cells in small-cell lung cancer," *Nat. Med.* 20(8):897-903 (Aug. 2014).
Hokland, et al., "The Isopaque-Ficoll Method Re-evaluated: Selective Loss of Autologous Rosette-forming Lymphocytes During Isolation of Mononuclear Cells from Human Peripheral Blood," *Scand. J.Immunol.* 11(3):353-356 (Mar. 1980).
Holm, et al., "Separation of parasites from human blood using deterministic lateral displacement," *Lab Chip* 11(7):1326-1332 (Apr. 2011). Epub Feb. 18, 2011, Supplemental Information.
Holmes, et al., "Separation of blood cells with differing deformability using deterministic lateral displacement," *Interface Focus* 4(6):20140011 (Dec. 2014).
Huang, et al., "A Microfluidics approach for the isolation of nucleated red blood cells (NRBCs) from the peripheral blood of a pregnant women," *Prenat. Diagn.* 28(10):892-899 (Oct. 2008).
Huang, et al., "Continuous Particle Separation Through Deterministic Lateral Displacement," *Science* 304(5673):987-990 (May 2004).
Huang, et al., "Role of Molecular Size in Ratcher Fractionation," *Physical Review Letters* 89(17):178301 (Oct. 2002).
Huang, et al., "A DNA prism for high-speed continuous fractionation of large DNA molecules," *Nat. Biotechnol.* 20(10):1048-1051 (Oct. 2002).

(56) References Cited

OTHER PUBLICATIONS

Huh, et al., "Gravity-driven microhydrodynamics-based cell sorter (microHYCS) for rapid, inexpensive and efficient cell separation and size profiling," 2nd Annual International IEEE-EMBS Special Topic Conference on Microtechnology in Medicine and Biology. Madison, Wisconsin USA; May 204, 2002:466-469.
ICellate cancer cell detection, "Cancer cell detection system for individualized cancer research and detection," available at: http://www.icellate.se (accessed Oct. 27, 2015).
Igout, et al., "Evaluation of the coulter LH 750 haematology analyzer compared with flow cytometry as the reference method for WBC, platelet and nucleated RBC count," *Clin Lab Haematol* 26(1):1-7 (Feb. 2004).
Inglis, et al., "Critical particle size for fractionation by deterministic lateral displacement," *Lab Chip* 6(5):655-658 (May 2006).
Inglis, et al., "Determining blood cell size using microfluidic hydrodynamics," *J. Immunol. Methods* 329(1-2):151-156 ((Jan. 2008).
Inglis, et al., "Scaling deterministic lateral displacement arrays for high throughput and dilution-free enrichment of leukocytes," *J. Micromech. Microeng.* 21:054024 (2011).
International search report and written opinion dated Jan. 9, 2015 for PCT application PCT/US/2014/029866.
International search report and written opinion dated Aug. 27, 2014 for PCT application PCT/US2014/029736.
Jiang, et al., "Fractionation by shape in deterministic lateral displacement microfluidic devices," *Microfluidics and Nanofluidics* 19(2):427-434 (Aug. 2015).
Johnson, et al., "Driving Gene-engineered T-cell Immunotherapy of Cancer," *Cell Res.* 27:38-58 (2017).
Kanwar, et al., "Microfluidic device (ExoChip) for On-Chip isolation, quantification and characterization of circulating exosomes," *Lab Chip* 14(11):1891-1900 (Jun. 2014).
Karabacak, et al., "Microfluidic, marker-free isolation of circulating tumor cells from blood samples," *Nature Protocols* 9(3):694-710 (Mar. 2014).
Kenis, et al., "Microfabrication Inside Capillaries Using Multiphase Laminar Flow Patterning," *Science* 285:83-85 (1999).
Keung, et al., "Cardiac arrhythmia after infusion of cryopreserved stem cells," *Bone Marrow Transplant* 14(3):363-367 (Sep. 1994).
Khodaee, et al., "Numerical Simulation of Separation of Circulating Tumor Cells from blood Stream in Deterministic Lateral Displacement (DLD) Microfluidic Channel," *Journal of Mechanics* 32(4):463-471 (Aug. 2016).
Koesdjojo, et al., "DLD Microfluidic Purification and Characterization of Intact and Viable Circulating Tumor Cells in Peripheral Blood," *AACR Annual Meeting* Abstract #3956 (2016).
Krüger, et al., "Deformability-based red blood cell separation in deterministic lateral displacement devices—A simulation study," *Biomicrofluidics* 8(5):054114 (Oct. 2014).
Kurihara, et al., "Imaging Brain Tumors by Targeting Peptide Radiopharmaceuticals through the Blood-Brain Barrier," *Cancer Research* 59(24):6159-6163 (Dec. 1999).
Kurtzberg, et al., "Results of the cord blood transplantation (COBLT) study unrelated donor banking program," *Transfusion* 45(6):842-855 (Jun. 2005).
Kwon, et al., "Endothelium." Human Adult Stem Cells. Springer, Dordrecht, 2009. 73-89 (2009).
Lasky, et al., "In utero or ex utero cord blood collection: which is better," *Transfusion* 42(10):1261-1267 (Oct. 2002).
Lee, et al., "Exosomes and microvesicles: extracellular vesicles for genetic information transfer and gene therapy," *Human Molecular Genetics* 21(rev. issue 1):R125-R134 (Aug. 2012).
Levine, et al., "Global Manufacturing of CAR T-cell Therapy," *Mol. Therapy: Meth. Clin. Dev.* 4:92-101 (2017).
Li, et al., "Knock-in internal tandem duplication mutation into murine FLT3 confers myeloproliferative disease in a mouse model," *Blood* 111(7):3849-3858 (Apr. 2008).
Li, et al., "Comparison of anti-CD3 and anti-CD28-coated beads with soluble anti-CD3 for expanding Human T-Cells: Differing impact on CD8 T-cell phenotype and responsiveness to restimulation," *J. Transl. Med.* 8:104-118 (2010).
Liu, et al., "Rapid isolation of cancer cells using microfluidic deterministic lateral displacement structure," *Biomicrofluidics* 7(1):11801 (Jan. 2013).
Liu, et al., "High throughput capture of circulating tumor cells using an integrated microfluidic system," *Biosensors and Bioelectronics* 47:113-119 (2013).
Long, et al., "Multi-directional sorting modes in deterministic lateral displacement devices," *Physical Review* E 78:046304 (2008).
Loutherback, et al., "Deterministic Microfluidic Ratchet," *Physical Review Letters* 102(4):045301 (Jan. 2009).
Loutherback, et al., "Deterministic separation of cancer cells from blood at 10mL/min," *AIP Advances* 2(4):42107 (Dec. 2012).
Loutherback, et al., "Improved performance of deterministic lateral displacement arrays with triangular posts," *Microfluidics Nanofluidics* 9:1143-1149 (2010).
Loutherback, "Microfluidic Devices for High Throughput Cell Sorting and Chemical Treatment," Dissertation, Princeton University, (Nov. 2011).
Loutherback, "Parallelized Microfluidic Separations for Large-scale Dewatering of biofuel Algae," *Symp Mat Res Soc*, Boston, MA Abstract #S4.18 (Nov. 2010).
Loutherback, et al., "Critical size, dynamic range and throughput improvements in sorting by deterministic lateral displacement enabled by triangular posts," Presented at the Symposium of the Materials Research Society, San Francisco, CA (Apr. 2009).
Lubbersen, et al., "Particle suspension concentration with sparse obstacle arrays in a flow channel," *Chemical Engineering and Processing: Process Intensification*, 95:90-97 (2015).
Mahnke, et al., "The who's who of T-cell differentiation: Huamn memory T-cell subsets," *Eur. J. Immunol.* 43:2797-2809 (2013).
Maheswaran, et al., "Detection of mutations in EGFR in circulating lung-cancer cells," *N Engl J Med* 359(4):366-377 (Jul. 2008).
Mandy, et al., "Flow Cytometry Principles," Chapter 25 In: Vo-Dinh T, editor. Biomedical Photonics Handbook: CRC Press; pp. 1-20 (2003).
Marktkamcham, et al., "The Effects of Anti-CD3/CD28 Coated Beads and IL-2 on Expanded T Cell for Immunotherapy," *Adv. Clin. Exp. Med.* 25:821-828 (2016).
Margulies, et al., "Genome sequencing in microfabricated high-density picolitre reactors," *Nature* 437:376-380 (Sep. 2005).
Martinez-Lopez, et al., "Prognostic value of deep sequencing method for minimal residual disease detection in multiple myeloma," *Blood* 123(20)3073-3079 (May 2014).
Maus, et al., "Adoptive immunotherapy for cancer or viruses," *Annu Rev Immunol* 32:189-225 (2014).
McGrath, et al., "Deterministic lateral displacement for particle separation: a review," *Lab Chip* 14(21):4139-4158 (Sep. 2014).
MedGadget. Clearbridge Biomedics Launching ClearCell FX System for Capturing Circulating Tumor Cell. Available at: http://www.medgadget.com/2014/05/clearbridge-biomedics-launching-clearcell-fx-system-for-capturing-circulating-tumor-cell.html. Accessed on Nov. 20, 2015.
Mikolajczyk, et al., "Detection of EpCAM-Negative and Cytokeratin-Negative Circulating Tumor Cells in Peripheral Blood," *J Oncol* 2011:252361 (2011).
Milone, et al., "Adverse events after infusions of cryopreserved hematopoietic stem cells depend on non-mononuclear cells in the infused suspension and patient age," *Cytotherapy* 9(4):348-355 (2007).
Moore, et al., "High dimensional flow cytometry comes of age," *European Pharmaceutical Review* 17(4):20-24 (2012).
Morton, et al., "Crossing microfluidic streamlines to lyse, label and wash cells," *Lab Chip* 8(9):1448-1453 (Sep. 2008).
Nagrath, et al., "Isolation of rare circulating tumour cells in cancer patients by microchip technology," *Nature* 450(7173):1235-1239 (Dec. 2007).
National Cell Manufacturing Consortium. Achieving Large-Scale, Cost-Effective, Reproducible Manufacturing of High Quality Cells. A Technology Roadmap to 20205. (Feb. 2016).
Oakey, et al., "Laminar Flow-Based Separations at the Microscale," *Biotechnology Progress* 1439-1442 (2002).

(56) References Cited

OTHER PUBLICATIONS

Office Action dated May 18, 2015 for U.S. Appl. No. 14/212,885.
Office Action dated Sep. 2, 2014 for U.S. Appl. No. 13/803,741.
Ozkumur, et al., "Inertial focusing for tumor antigen-dependent and-independent sorting of rare circulating tumor cells," *Sci Transl Med* 5 (179):179ra47 (Apr. 2013).
Powell, et al., "Efficient clinical-scale enrichment of lymphocytes for use in adoptive immunotherapy using a modified counterflow centrifugal elutriation program," *Cytotherapy* 11(7):923-935 (2009).
Quek, et al., "Separation of deformable particles in deterministic lateral displacement devices," *Phys Rev E Stat Nonlin Soft Matter Phys* 83(5 Pt 2):056301 (May 2011).Quirk, et al.,.
Quirk, W.R., The 2015 Liquid Biopsy Report. Sep. 2015. Piper Jaffray Investment Research.
Radisic, et al., "Micro- and nanotechnology in cell separation," *International Journal of Nanomedicine* 1(1):3-14 (2006).
Ranjan, et al., "DLD pillar shape design for efficient separation of spherical and non-spherical bioparticles," *Lab Chip* 14(21):4250-4262 (Sep. 2014).
Reddy, et al., "Isolation of Stem Cells from Human Umbilical Cord Blood," in Vemuri (eds) Stem Cell Assays. Methods in Molecular Biology vol. 407, Human Press. pp. 149-163 (2007).
Rhee, M., "Advanced Components of Microfluidic Systems for Bioanalytical Applications," A dissertation submitted in partial fulfillment of the requirements for the degree of Doctor of Philosophy in The University of Michigan, 2009.
ReportLinker. Circulating Tumor Cell (CTC) Diagnostics: Technologies and Global Markets. Available at: http://www.reportlinker.com/p02009162-summary/Circulating-Tumor-Cell-CTC-Diagnostics-Technologies-and-Global-Markets.html. Accessed Oct. 2, 2015.
Rocha, et al., "Improving outcomes of cord blood transplantation: HLA matching, cell dose and other graft- and transplantation-related factors," *Br J Haematol* 147(2):1365-2141 (Oct. 2009).
Rocha, et al., "Umbilical cord blood transplantation," *Curr Opin Hematol* 11(6):375-385 (Nov. 2004).
Rubinstein, et al., "Outcomes among 562 recipients of placental-blood transplants from unrelated donors," *N Engl J Med* 339(22):1565-1577 (Nov. 1998).
Rubinstein, et al., "Processing and cryopreservation of placental/umbilical cord blood for unrelated bone marrow reconstitution," *Proc Natl Acad Sci USA* 92(22):10119-22 (Oct. 1995).
Sadelain, et al., "Therapeutic T cell engineering," *Nature* 545:423-431 (May 2017).
Savage, et al., "Functional self-association of von Willebrand factor during platelet adhesion under flow," *Proc Natl Acad Sci USA* 99(1):425-430 (Jan. 2002).
Sollier, et al., "Size-selective collection of circulating tumor cells using Vortex technology," *Lab Chip* 14(1):63-77 (2014).
Solves, et al., "A new automatic device for routine cord blood banking: critical analysis of different volume reduction methodologies," *Cytotherapy* 11(8):1101-1107 (2009).
Solves, et al., "Comparison between two strategies for umbilical cord blood collection," *Bone Marrow Transplant* 31(4):269-273 (Feb. 2003).
Sommanson, et al., "Deterministic lateral separation of cells," Lund University. Master's Thesis, (2006).
Soni, et al., "Progress toward Ultrafast DNA Sequencing Using Solid State Nanopores," *Clin. Chem.* 53:1996-2001 (2007).
Spectrolyse blood collection tubes. American Diagnostic Inc. (2010).
Stokstad, et al., "Tests used to ensure ships don't carry deadly cargo draw sharp criticism," Jan. 14, 2015. News.sciencemag.org/biology/2015/tests-used-ensure-ships-don't-carry-deadly cargo-draw-criticism. Accessed on Aug. 3, 2015.
Stroncek, et al., "Counter-flow elutriation of clinical peripheral blood mononuclear cell concentrates for the production of dendritic and T cell therapies," *J. Transl. Med*.12:241 (2014).
Strauss, et al., "Abstracts P5-10-07: The LiquidBiopsy in metastatic breast cancer (MBC): A novel diagnostic platform for next generation sequencing (NGS) of circulating tumor cells (CTCs)," *Cancer Research* 75(9):P5-10 (2015).
Stroncek, et al., "Adverse reactions in patients transfused with cryopreserved marrow," *Transfusion* 31(6):521-526 (Jul.-Aug. 1991).
Takayama, et al., "Patterning Cells and Their Environment Using Multiple Laminar Fluid Flows in Capillary Networks," *PNAS USA* 96(10): 5545-5548 (May 1999).
Toner, et al., "Blood-on-a-Chip," *Annu. Rev. Biomed. Eng.* 7:77-103, C1-C3 (2005).
Trickett, et al., "T-cell Stimulation and Expansion Using Anti-CD3/CD28 Beads," *J/Immunol. Meth.* 275:251-255 (Apr. 2003).
TriTest CD3 FITC/CD19 PE/CD45 PerCP Reagent. Informational package insert. BD Biosciences. (Aug. 2010).
Tsao, et al., "Bonding of thermoplastic polymer microfluidics," *Microfluidics and Nanofluidics* 6(1):1-16 (Jan. 2009).
Turner, et al., "Confinement-induced entropic recoil of single DNA molecules in a nanofluidic structure," *Phys Rev Lett* 88(12):128103 (Mar. 2002).
Van Lochem, et al., "Immunophenotypic differentiation patterns of normal hematopoiesis in bone marrow: reference patterns for age-related changes and disease-induced shifts," *Cytometry B Clin Cytom* 60(1):1-13 (Jul. 2004).
Vona, et al., "Isolation by size of epthelieal tumor cells," *Am J Pathol* 156:57-63 (2000).
Vonderheide, et al., "Engineering T cells for cancer: our synthetic future," *Immunol. Rev.* 257:7-13 (2014).
Vortex Biosciences. Overview: Cancer and CTCs. Available at: http://www.vortexbiosciences.com/overview. Accessed Oct. 27, 2015.
Wagner, et al., "Umbilical cord blood transplantation: the first 20 years," *Semin Hematol* 47(1):3-12 (Jan. 2010).
Wang, et al., "Clinical manufacturing of CAR T cells: a foundation of a promising therapy," *Mol. Ther. Oncolytics* 3:16015 (2016).
Wang, et al., "Single cell analysis: the new frontier in 'omics'," *Trends Biotechnol* 28(6):281-290 (Jun. 2010).
Wood, et al., "Ten-Color Immunophenotyping of Hematopoietic Cells," Current Protocols in Cytometry. John Wiley & Sons, Inc. (2001).
Yamada, et al., "Pinched flow fractionation: continuous size separation of particles utilizing a laminar flow profile in a pinched microchannel," *Anal. Chem.* 76(18):5465-5471 (Sep. 2004).
Yang, et al., "Microfluidic device fabrication by thermoplastic hot-embossing," *Methods Mol. Biol.* 949:115-123 (2013).
Ye, et al., "Effects of the particle deformability on the critical separation diameter in the deterministic lateral displacement device," *Journal of Fluid Mechanics* 743:60-74 (Mar. 2014).
Yi, et al., "Microfluidics technology for manipulation and analysis of biological cells," *Analytica Chimica Acta* 560:1-23 (2006).
Yu, et al., "A Microfluidic Approach for Whole Blood Leucocytes Isolation for Leucocytes Immunophenotyping by Flow Cytometry," Congress Center Leipzig, Lepzig, Germany, Poster B228, (Jun. 2012).
Zambelli, et al., "Clinical toxicity of cryopreserved circulating progenitor cells infusion," *Anticancer Res*. 18(6B):4705-4708 (Nov.-Dec. 1998).
Zeming, et al., "Asymmetrical Deterministic Lateral Displacement Gaps for dual Functions of Enhanced Separation and Throughput of Red Blood Cells," *Sci. Rep.* 6:22934 (Mar. 2016).
Zeming, et al., "Rotational separation of non-spherical bioparticles using l-shaped pillar arrays in a microfluidic device," *Nat. Commun.* 4:1625 (2013).
Zenhausern, et al., "Fatal cardiac arrhthmia after infusion of dimethyl sulfoxide-cryopreserved hematopoietic stem cells in a patient with severe primary cardiac amyloidosis and end-stage renal failure," *Ann Hematol* 79(9):523-526 (Sep. 2000).
Zhang, et al., "Electrospun TiO2 Nanofiber-Based Cell Capture Assay for Detecting Circulating Tumor Cells from Colorectal and Gastric Cancer Patients," *Adv. Mater*. 24(20):2756-2760 (May 2012).
Zhang, et al., "Label-free enrichment of functional cardiomyocytes using microfluidic deterministic lateral flow displacement," *PLoS One* 7(5):e37619 (2012).
Zhang, et al., "Optimized DNA electroporation for primary human T cell engineering," *BMC Biotechnology* 18:4 (2018).
Zhang, et al., "Applications of Microfluidics in Stem Cell Biology," *Bionanoscience* 2(4):277-286 (Dec. 2012).

(56) References Cited

OTHER PUBLICATIONS

Zhang, et al., "Behavior of rigid and deformable particles in deterministic lateral displacement devices with different post shapes," J. Chem. Phys. 143(24):243145 (Dec. 2015).
Zheng, et al., "Deterministic lateral displacement MEMS device for continuous blood cell separation," Micro Electro Mechanical Systems, 2005. 18th IEEE International Conference.
Zhu, et al., "Platelets Provoke Distinct Dynamics of Immune Response by Differentially Regulating CD4$^+$T-cell Proliferation," *J. Throm. Haem.* 12:1156-1165 (2014).
Zingsem, et al., "Cord blood processing with an automated and functionally closed system," *Transfusion* 43(6):806-813 (Jun. 2003).
Expired U.S. Appl. No. 62/032,520, filed Aug. 1, 2014.
Expired U.S. Appl. No. 60/414,065, filed Sep. 27, 2002.
Expired U.S. Appl. No. 60/414,102, filed Sep. 27, 2002.
Expired U.S. Appl. No. US 60/420,756, filed Oct. 23, 2002.
Expired U.S. Appl. No. 60/478,299, filed Jun. 13, 2003.
Expired U.S. Appl. No. 60/549,610, filed Mar. 3, 2004.
Expired U.S. Appl. No. 60/703,833, filed Jul. 29, 2005.
Expired U.S. Appl. No. 61/799,835, filed Mar. 15, 2013.
Expired U.S. Appl. No. 61/800,222, filed Mar. 15, 2013.
Response to Rule 71 Communication for EP 2014764615.2, filed by Applicant Jan. 28, 2019; European counterpart of U.S. Appl. No. 14/774,268.
Second Communication Under Rule 71(3) for EP20 14764615.2, sent by the EPO dated Mar. 7, 2019; European counterpart of U.S. Appl. No. 14/774,268.
Amended claims filed for CN 20140028714 in response to the 3rd Office Action filed Jan. 23, 2019; Chinese counterpart of copending U.S. Appl. No. 14/774,260.
Notice of Allowance for CN 201480028570X dated Mar. 2019 (in Chinese); Chinese counterpart of copending U.S. Appl. No. 14/774,268.
Office Action for copending U.S. Appl. No. 14/941,957, dated Jan. 7, 2019.
Response to Office Action for copending U.S. Appl. No. 15/329,753, filed Jan. 30, 2018.
Response to Office Action for copending U.S. Appl. No. 14/774,268, filed Apr. 5, 2019.
Response to Office Action for copending U.S. Appl. No. 15/478,405, filed Apr. 5, 2019.
Proposed Text for Grant for EP 14764615.2, dated Mar. 7, 2019; European counterpart of copending U.S. Appl. No. 14/774,268.
Request to file divisional of EP 14764615.2, filed Jun. 26, 2019; European counterpart of copending U.S. Appl. No. 14/774,268.
EPO form for filing of divisional of EP 14764615.2, filed Jun. 26, 2019; European counterpart of copending U.S. Appl. No. 14/774,268.
Specification and claims for divisional of EP 14764615.2, filed Jun. 26, 2019; European counterpart of copending U.S. Appl. No. 14/774,268.
Filing receipt for divisional assigning it EP 19182687.4, generated Jun. 26, 2019; European counterpart of copending U.S. Appl. No. 14/774,268.
Translation of Certificate of Invention Patent for Application CN 201480028570X, sent Apr. 9, 2019; Chinese counterpart of copending U.S. Appl. No. 14/774,268.
Claims for Patent for CN 201480028570X, of Apr. 9, 2019; Chinese counterpart of copending U.S. Appl. No. 14/774,268.
Translation of Filing Information for Divisional of CN 201480028570X, sent Apr. 26, 2019; Chinese counterpart of copending U.S. Appl. No. 14/774,268.
Communication Under Rule 71(3) for EP 14 763 363.0, dated May 24, 2019; European counterpart of U.S. Appl. No. 14/774,260.
Proposed text for grant for EP 14 763 363.0, dated May 24, 2019; European counterpart of U.S. Appl. No. 14/774,260.
First Examination Report for EP 15 827 324.3, dated May 24, 2019; European counterpart of copending U.S. Appl. No. 15/329,753.
Response to Examination Report for EP 15 827 324.3, filed Aug. 22, 2019; European counterpart of copending U.S. Appl. No. 15/329,753.
Amended claims submitted with Response to Examination Report for EP 15 827 324.3, filed Aug. 22, 2019; European counterpart of copending U.S. Appl. No. 15/329,753.
Amendment Under 37 CFR 1.312 filed Apr. 21, 2019, for parent U.S. Appl. No. 14/774,260.
Communication sent from the USPTO dated Apr. 25, 2019, for parent U.S. Appl. No. 14/774,260.
Issue Notification notifying applicant that patent will issue as U.S. Pat. No. 10,324,011 dated May 29, 2019, for parent U.S. Appl. No. 14/774,260.
Final Rejection dated May 31, 2019, for copending U.S. Appl. No. 14/774,268.
Final Rejection dated May 15, 2019, for copending U.S. Appl. No. 15/329,753.
Response and Amendment Under 37 CFR 1.312 sent to the USPTO dated Jul. 3, 2019, for copending U.S. Appl. No. 14/941,957.
Response to Restriction Requirement and Amendment Under 37 CFR 1.312 sent to the USPTO dated Aug. 30, 2019, for copending U.S. Appl. No. 14/478,405.
U.S. Appl. No. 14/774,268, filed Sep. 10, 2015, US 2016/0047735 A1, Feb. 18, 2016, Grisham, et al.
U.S. Appl. No. 14/941,957, filed Nov. 16, 2015, US 2016/0168539 A1, Jun. 16, 2016, Civin, et al.
U.S. Appl. No. 15/329,753, filed Jan. 27, 2017, US 2017/0209864 A1, Jul. 27, 2017, Grisham, et al.
U.S. Appl. No. 15/478,405, filed Apr. 4, 2017, US 2017/0333900 A1, Nov. 23, 2017 Grisham, et al.
U.S. Appl. No. 15/595,548, filed May 15, 2017, US 2017/0248508 A1, Aug. 31, 2017, Ward, et al.
U.S. Appl. No. 16/108,365, filed Aug. 22, 2018, US 2019/0071639 A1, Mar. 7, 2019, Ward, et al.
U.S. Appl. No. 16/123,056, filed Sep. 6, 2018, US 2019/0137369 A1, May 9, 2019, D'Silva, et al.
U.S. Appl. No. 16/343,754, filed Apr. 20, 2019, Ward et al.
Amendment and Reponse filed Apr. 21, 2020 for copending U.S. Appl. No. 14/774,268.
Amendment and Reponse filed Apr. 24, 2020 for copending U.S. Appl. No. 14/329,753.
International Search Report for PCT/US2014/029736, filed Mar. 14, 2014; which corresponds to grandparent U.S. Appl. No. 14/774,260.
Written Opinion of the International Searching Authority for PCT/US2014/029736, filed Mar. 14, 2014; which corresponds to grandparent U.S. Appl. No. 14/774,260.
International Preliminary Report on Patentability for PCT/US2014/029736, filed Mar. 14, 2014; which corresponds to grandparent U.S. Appl. No. 14/774,260.
Preliminary Amendment filed Jan. 4, 2016 for grandparent U.S. Appl. No. 14,774,260.
Restriction Requirement sent by the USPTO dated Oct. 4, 2017 for grandparent U.S. Appl. No. 14,774,260.
Response to Restriction Requirement filed Dec. 9, 2017 for grandparent U.S. Appl. No. 14,774,260.
Amendment to Accompany Response to Restriction Requirement filed Dec. 9, 2017 for grandparent U.S. Appl. No. 14,774,260.
Office Action dated Mar. 6, 2018 for grandparent U.S. Appl. No. 14,774,260.
Response to Office Action filed Jun. 6, 2018 for grandparent U.S. Appl. No. 14,774,260.
Notice of Allowance dated Sep. 19, 2018 for grandparent U.S. Appl. No. 14,774,260.
Request for Continued Examination filed Dec. 18, 2018 for grandparent U.S. Appl. No. 14,774,260.
Supplemental Amendment with replacement drawings filed Jan. 1, 2019 for grandparent U.S. Appl. No. 14,774,260.
Second Notice of Allowance dated Jun. 30, 2019 for grandparent U.S. Appl. No. 14,774,260.
Amendment Under 37 CFR Sec. 1.132 filed Apr. 9, 2019 for grandparent U.S. Appl. No. 14,774,260.
Response to Amendment Under 37 CFR Sec. 1.132 dated Apr. 15, 2019 for grandparent U.S. Appl. No. 14,774,260.
Second Amendment Under 37 CFR Sec. 1.312 filed Apr. 21, 2019 for grandparent U.S. Appl. No. 14,774,260.

(56) References Cited

OTHER PUBLICATIONS

Response to Second Amendment Under 37 CFR Sec. 1.312 dated Apr. 25, 2019 for grandparent U.S. Appl. No. 14/774,260.
Request to Correct Inventorship filed Apr. 25, 2019 for grandparent U.S. Appl. No. 14/774,260.
Acceptance of Request to Correct Inventorship dated Apr. 30, 2019 for grandparent U.S. Appl. No. 14/774,260.
Issue Notification dated May 29, 2019 for grandparent U.S. Appl. No. 14/774,260.
Amended claims filed before Examination for European application EP 14 76 3363; filed on Apr. 28, 2016.
Supplementary EP Search Report for European application EP 14 76 3363, posted on EP patent register dated Jul. 1, 2016.
EP Search Opinion for European application EP 14 76 3363, posted on EP patent register dated Jul. 1, 2016.
Amended claims filed after receipt of ESR including clean version of claims and claims with annotations, filed May 4, 2017.
Examination Report sent by EPO with Annex to the report attached, dated Sep. 13, 2017.
Reply to Examination Report filed Mar. 20, 2018.
Amended claims filed with Reply to Examination Report on Mar. 20, 2018.
Intention to Grant sent by the EPO dated May 24, 2019.
Text intended for grant with annotations sent May 24, 2018.
U.S. Appl. No. 16/123,056, filed Sep. 6, 2018, 2019-0137369 A1, May 9, 2019, D'Silva.
U.S. Appl. No. 16/587,022, filed Sep. 29, 2019, DiSilva.
Amended claims for CN 2019103452215 filed with Request for Substantive Examination dated Jun. 26, 2019; Chinese counterpart of U.S. Appl. No. 14/774,268.
Request to file divisional of EP 14764615.2, filed Jun. 26, 2019; European counterpart of U.S. Appl. No. 14/774,268.
EPO form for filing of divisional of EP 14764615.2, filed Jun. 26, 2019; European counterpart of U.S. Appl. No. 14/774,268.
Specification and claims for divisional of EP 14764615.2, filed Jun. 26, 2019; European counterpart of U.S. Appl. No. 14/774,268.
Filing receipt for divisional assigning it EP 19182687.4, generated Jun. 26, 2019; European counterpart of U.S. Appl. No. 14/774,268.
Extended European Search Report for EP 19182687.4 dated Oct. 7, 2019; European counterpart of U.S. Appl. No. 14/774,268.
Rule 69 Communication for EP 19182687.4 dated Nov. 25, 2019; European counterpart of U.S. Appl. No. 14/774,268.
Response to Examination Report for EP 15 827 324.3, filed on Aug. 22, 2019; European counterpart of copending U.S. Appl. No. 15/329,753.
Amended claims submitted with Response to Examination Report for EP 15 827 324.3, filed on Aug. 22, 2019; European counterpart of copending U.S. Appl. No. 15/329,753.
Canadian Search Report for CA 2942831 dated Feb. 5, 2019; Canadian counterpart of U.S. Appl. No. 14/774,260.
Amendment and Response to Accompany RCE filed Sep. 21, 2019 for copending U.S. Appl. No. 15/329,753.
Non Final Office Action dated Jan. 2, 2020 for copending U.S. Appl. No. 15/329,753.
Amendment and Response to Accompany RCE filed Sep. 21, 2019 for copending U.S. Appl. No. 14/774,268.
Non Final Office Action dated Jan. 2, 2020 for copending U.S. Appl. No. 14/774,268.
Amendment and Response to Restriction Requirement filed Aug. 30, 2019 for copending U.S. Appl. No. 15/478,405.
Final Office Action dated Dec. 4, 2019 for copending U.S. Appl. No. 15/478,405.
Final Office Action dated Oct. 22, 2019 for copending U.S. Appl. No. 14/941,957.
Amendment and Response to Accompany RCE filed Mar. 23, 2020 for copending U.S. Appl. No. 14/941,957.
Second Examnination Report for EP 15827324.3 dated Jan. 21, 2020; European counterpart of copending U.S. Appl. No. 15/329,753.
Response to Second Examnination Report for EP 15827324.3 filed Apr. 6, 2020; European counterpart of copending U.S. Appl. No. 15/329,753.
Amended Description filed with the Response to Second Examnination Report for EP 15827324.3 filed Apr. 6, 2020; European counterpart of copending U.S. Appl. No. 15/329,753.
Amended claims filed with the Response to Second Examnination Report for EP 15827324.3 filed Apr. 6, 2020; European counterpart of copending U.S. Appl. No. 15/329,753.
Lee, et al., "Continuous medium exchange and optically induced electroporation of cells in an integrated microfluidic system," *Microsystems and Nanoengineering* 1:1-9 (2015).
Song, et al.,"Automatic detecting and counting magnetic based-labeled target cells from a suspension in a microfluidic chip," *Electrophoresis* 40:897-905 (2019).
U.S. Appl. No. 16/587,057, filed Sep. 30, 2020, US-2020/0025669 A1, Jan. 23, 2020, Ward.
U.S. Appl. No. 16/662,033, filed Oct. 24, 2020, US-2020/0056153 A1, Feb. 20, 2020, Ward.
Communication Under Rule 71(3) for EP 15827324.3, sent May 14, 2020; European counterpart of copending U.S. Appl. No. 15/329,753.
Text proposed for Grant for Ep 15827324.3, sent May 14, 2020; European counterpart of copending US application 15/329,753.
Office Action in Canada for CA 2,942,831, sent Feb. 6, 2020; counterpart of copending U.S. Appl. No. 14/774,260.
Response to Office Action in Canada for CA 2,942,831, filed Jun. 5, 2020; Canadian counterpart of copending U.S. Appl. No. 14/774,260.
Claims filed with Response to Office Action in Canada for CA 2,942,831, filed Jun. 5, 2020; of copending U.S. Appl. No. 14/774,260.
Brief English language counterpart of copending Summary of Office Action in China for CN 2014800285714, sent Jun. 5, 2020; Chinese counterpart of copending U.S. Appl. No. 14/774,260.
Claims in CN 2014800285714 at time of Office Action, sent Jun. 5, 2020; Chinese counterpart of copending U.S. Appl. No. 14/774,260.
European Search Report for EP 19199294.0, dated Jan. 8, 2020, counterpart of copending U.S. Appl. No. 14/774,260.
Claims in EP 19199294.0, filed Jun. 8, 2020, European counterpart of copending U.S. Appl. No. 14/774,260.
Response to Rule 69 Communication for EP 19182687.4, filed May 18, 2020; European counterpart of copending U.S. Appl. No. 14/774,268.
Amended claims for EP 19182687.4, filed May 18, 2020; European counterpart of copending U.S. Appl. No. 14/774,268.
Supplemental Response to Office Action, filed Jul. 6, 2020 for copending U.S. Appl. No. 14/941,957.
Declaration Under 37 CFR 1.132 filed Jul. 6, 2020 for copending U.S. Appl. No. 14/941,957.
Inglis, Dav European Search Report for EP 19199294.0id, "Microfluidic Devices for Cell Separation," A Dissertation presented to the faculty of Princeton University, Sep. 2007.
Response to European Search Report for EP 19199294.0, filed Aug. 10, 2020, European counterpart of copending U.S. Appl. No. 14/774,260.
Office Action for copending U.S. Appl. No. 14/941,957, dated Sep. 17, 2020.

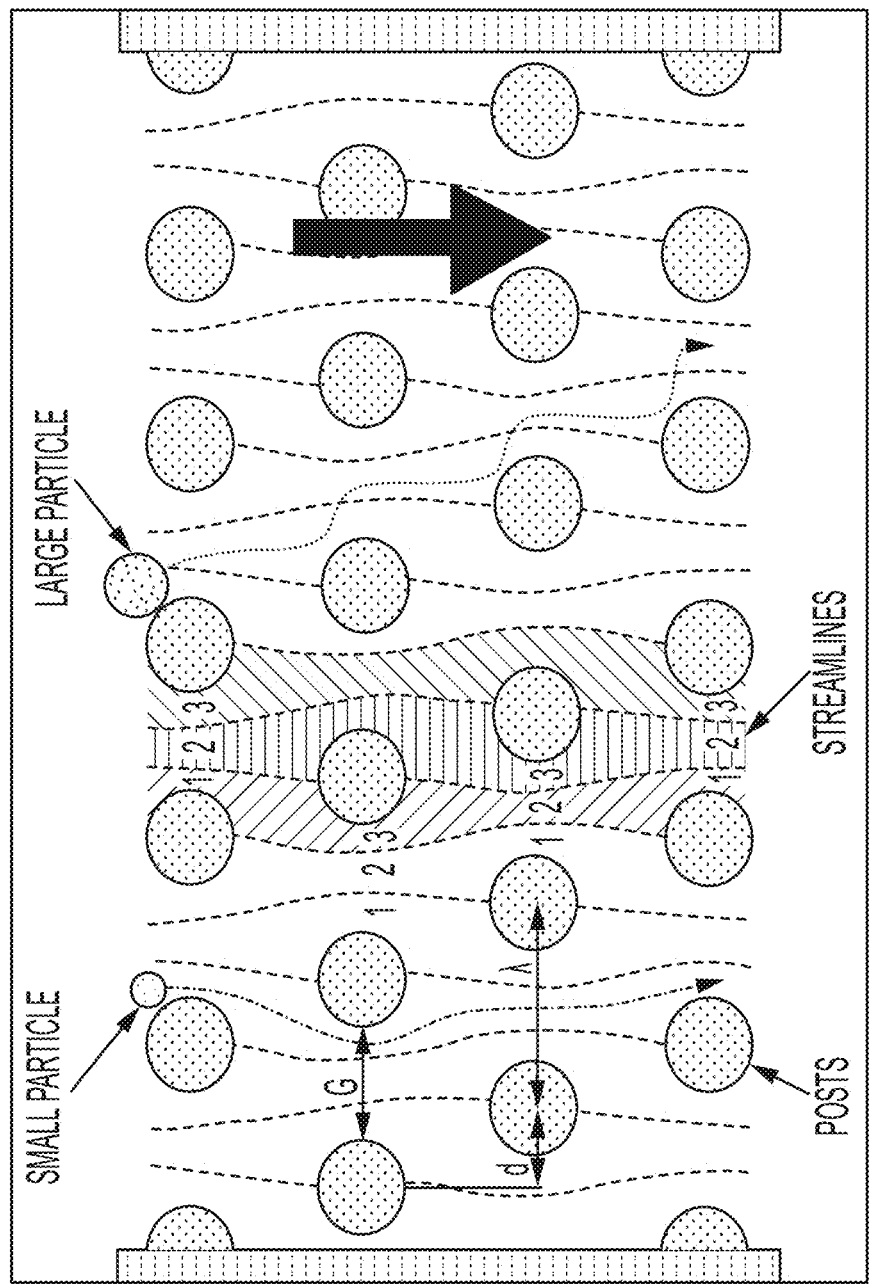

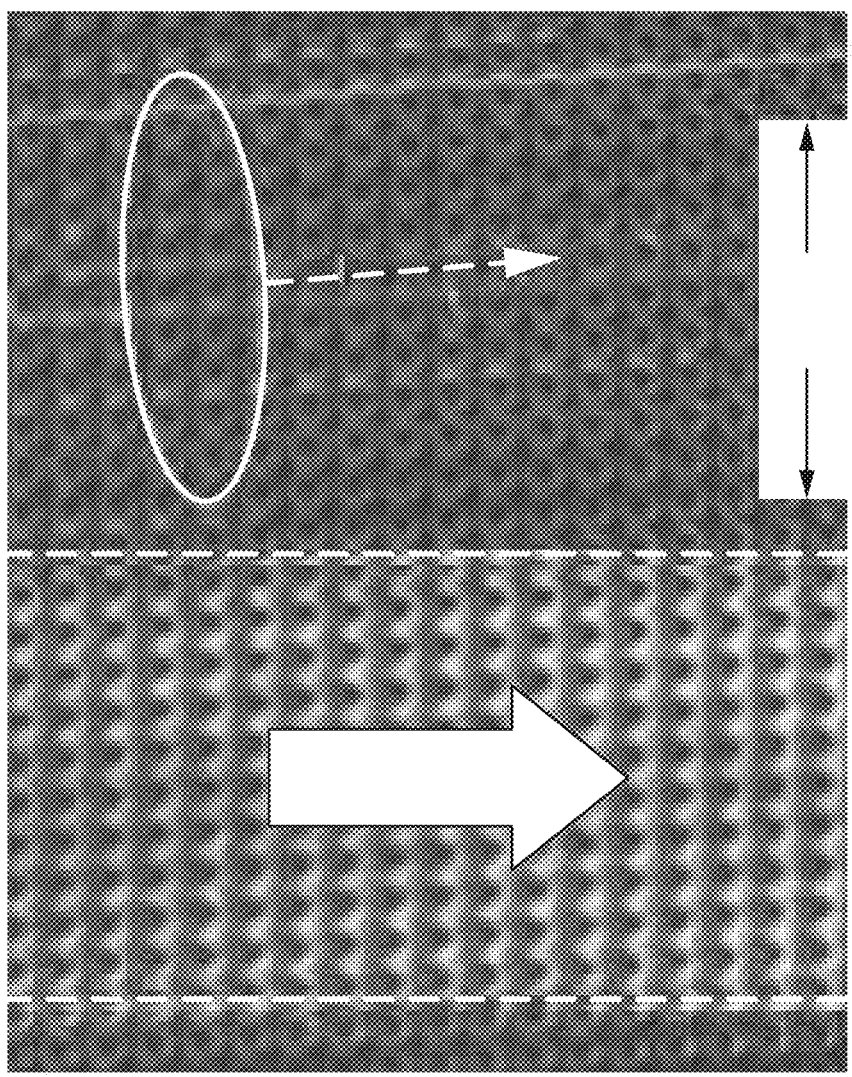

Si Chip

Plastic Chip

| Sample | Granulocyte / Monocyte | Lymphocytes / Monocytes | Granulocytes / Lymphocytes | CD3 / CD19 |
|---|---|---|---|---|
| #1: Starting blood | 7.38 (+/- 0.3) | 4.57 (+/- 0.68) | 1.63 (+/- 0.18) | 2.17 (+/- 0.02) |
| #1: WBC fraction | 7.6 (+/- 0.08) | 4.33 (+/- 0.02) | 1.76 (+/- 0.01) | 2.14 (+/- 0.04) |
| #2: Starting blood | 5.43 (+/- 0.12) | 6.21 (+/- 0.13) | 0.88 (+/- 0.04) | 5.65 (+/- 0.49) |
| #2: WBC fraction | 5.59 (+/- 0.01) | 6.36 (+/- 0.34) | 0.88 (+/- 0.05) | 6.17 (+/- 0.37) |
| #3: Starting blood | 4.19 (+/- 0.28) | 3.22 (+/- 0.24) | 1.3 (+/- 0.01) | 4.77 (+/- 0.49) |
| #3: WBC fraction (only one sample) | 4.36 | 2.82 | 1.55 | 5.04 |

FIG. 29

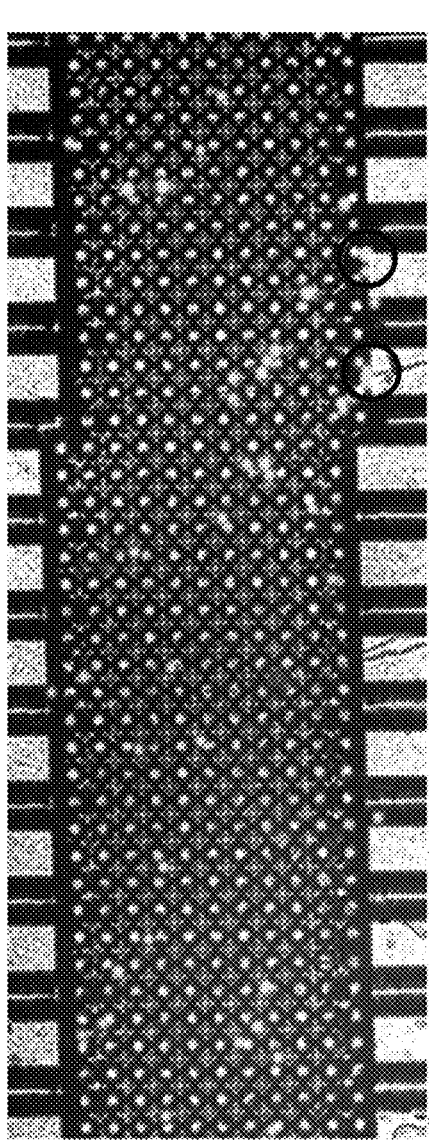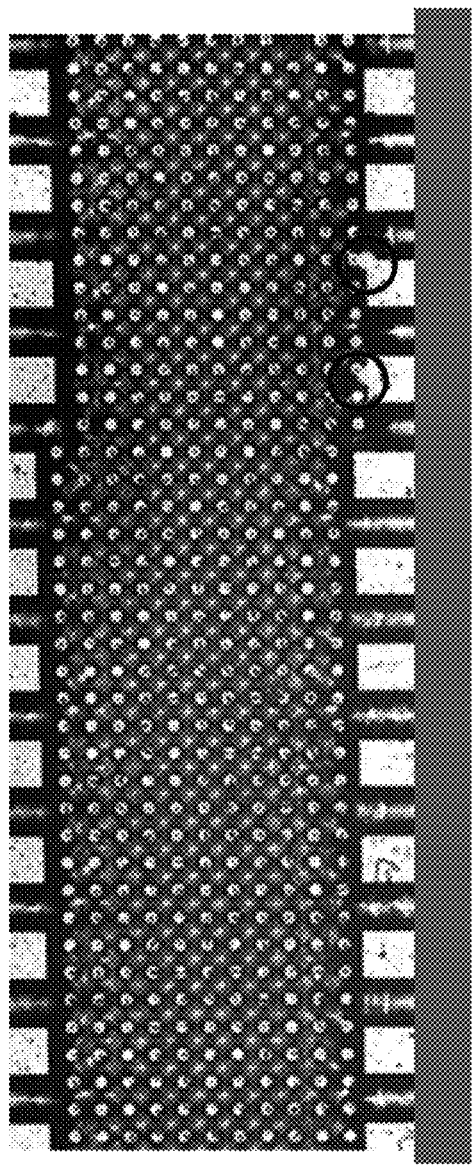
FIG. 35A
FIG. 35B

| Polymer | Acronym | $T_g$ (°C) | $T_m$ (°C) | CTE ($10^{-6}$ °C$^{-1}$) | Water absorption (%) | Solvent resistance | Acid/base resistance | Optical transmissivity | |
|---|---|---|---|---|---|---|---|---|---|
| | | | | | | | | Visible | UV[a] |
| Cyclic olefin (co)polymer | COC/COP | 70–155 | 190–320 | 60–80 | 0.01 | Excellent | Good | Excellent | Excellent |
| Polymethylmethacrylate | PMMA | 100–122 | 250–260 | 70–150 | 0.3–0.6 | Good | Good | Excellent | Good |
| Polycarbonate | PC | 145–148 | 260–270 | 60–70 | 0.12–0.34 | Good | Good | Excellent | Poor |
| Polystyrene | PS | 92–100 | 240–260 | 10–150 | 0.02–0.15 | Poor | Good | Excellent | Poor |
| Polypropylene | PP | −20 | 160 | 18–185 | 0.10 | Good | Good | Good | Fair |
| Polyetheretherketone | PEEK | 147–158 | 340–350 | 47–54 | 0.1–0.5 | Excellent | Good | Poor | Poor |
| Polyethylene terephthalate | PET | 69–78 | 248–260 | 48–78 | 0.1–0.3 | Excellent | Excellent | Good | Good |
| Polyethylene | PE | −30 | 120–130 | 180–230 | 0.01 | Excellent | Excellent | Fair | Fair |
| Polyvinylidene chloride | PVDC | 0 | 76 | 190 | 0.10 | Good | Good | Good | Poor |
| Polyvinyl chloride | PVC | 80 | 180–210 | 50 | 0.04–0.4 | Good | Excellent | Good | Poor |
| Polysulfone | PSU | 170–187 | 180–190 | 55–60 | 0.3–0.4 | Fair | Good | Fair | Poor |

$T_m$, melting temperature, CTE coefficient of thermal expansion
[a] high UV transmissivity often requires the selection of special polymer grades, e.g. without stabilizers or other additives

FIG. 36

Mirrored array, NO DOWNSHIFT

Mirrored array with downshift

METHODS AND DEVICES FOR HIGH THROUGHPUT PURIFICATION

CROSS-REFERENCE

This application is a continuation of U.S. Ser. No. 16/123,056, filed Sep. 6, 2018, which is a continuation of U.S. Ser. No. 14/774,260 (issued as U.S. Pat. No. 10,324,011 on Jun. 18, 2019), which was submitted to the USPTO on Sep. 10, 2015 as national stage of PCT/US2014/029736, filed Mar. 14, 2014, which claims the benefit of U.S. Provisional Patent Application No. 61/799,835, filed Mar. 15, 2013, and U.S. Provisional Patent Application No. 61/939,044, filed Feb. 12, 2014, all of which applications are herein incorporated by reference in their entireties.

STATEMENT AS TO FEDERALLY SPONSORED RESEARCH

This invention was made with government support under Grant No. CA174121, Grant No. HL110574, and Grant No. CA143803 awarded by the National Institutes of Health. The government has certain rights in the invention.

BACKGROUND

There is a need for improved methods for high throughput isolation of particles using devices such as microfluidic devices. Also, there is a critical unmet need for rapid, efficient methods to deplete erythrocytes and recover leukocytes from G-CSF mobilized peripheral blood (PBSC), bone marrow (BM), and especially umbilical cord blood (UCB), prior to cryopreservation. Incomplete erythrocyte removal from transplant grafts can increase the risk of harmful side effects in hematopoietic stem cell transplants, while poor recovery of viable leukocytes and CD34+ cells can reduce engraftment success and limits the treatable patient population.

SUMMARY

In one aspect, described herein is a highly efficient system to remove erythrocytes and purify leukocytes that can raise the quality of UCB and other transplant grafts, thereby significantly improving patient outcomes.

In one aspect, a method of purifying first particles of at least a predetermined size is provided, the method comprising: (a) applying at least 10 mL of a sample comprising the first particles of at least the predetermined size to a device, and (b) flowing the at least 10 mL of the sample through the device at a rate of at least 1 mL/min, wherein the device comprises an array of obstacles arranged in rows, wherein each subsequent row of obstacles is shifted laterally with respect to a previous row, wherein the obstacles differentially deflect the first particles of at least the first predetermined size to a first outlet and second particles in the sample of less than the predetermined size to a second outlet, thereby purifying the first particles of at least the predetermined size. The sample can be a blood sample. The blood sample can comprise an umbilical cord blood sample or placental cord blood sample. The sample can comprise peripheral blood. The peripheral blood can comprise G-CSF mobilized peripheral blood. The sample can comprise bone marrow. The first particles of at least the predetermined size can comprise cells. The first particles of at least the predetermined size can comprise leukocytes. The leukocytes can comprise CD34+ cells. The method can further comprise using the purified leukocytes to diagnose lymphoma or leukemia.

The first particles of at least the predetermined size can comprise stem cells. The stem cells can comprise peripheral blood stem cells (PBSCs). The stem cells can be hematopoietic stem cells (HSCs). The HSCs can comprise CD34+/CD45+ HSCs.

The method can further comprise transplanting the purified stem cells in a subject.

The second particles can comprise erythrocytes. The purified first particles of at least the predetermined size can be at least 90% pure. The purified first particles of at least the predetermined size can comprise at least 90% of the first particles in the sample. The purified cells can be at least 90% viable. The first particles can comprise cytotoxic T-cells, antigen-specific T-cells, regulatory T-cells, Natural Killer T-Cells, Natural Killer cells, dendritic cells, regulatory B cells, or regulatory macrophages. The first particles or second particles can comprise platelets, erythrocytes, granulocytes, or lymphocytes. The first particles can comprise algae, yeast, bacteria, or viruses. The first particles can comprise cancer cells.

In some cases, at least 100 mL of sample can be applied to the device. In some cases, at least 300 mL of sample can be applied to the device. The flowing can comprise flowing the sample at a rate of at least 1 mL/min through the device. The flowing can comprise flowing the sample at a rate of at least 5 mL/min through the device.

The method can further comprise analyzing the purified first particles of at least the predetermined first size. The analyzing can comprise use of a microscope. The analyzing can comprise flow cytometry.

The sample can be passed through a filter before the sample is applied to the device.

The first particles can comprise nucleic acid. The nucleic acid can comprise deoxyribonucleic acid. The method can comprise generating a sequencing library from the purified deoxyribonucleic acid. The sequencing library can be a next generation sequencing library.

The sample can be a cell-free nucleic acid sample. The sample can be a cell culture sample.

In some cases, the first particles are not labeled. The purified first particles can be cryopreserved. A cryopreservant can be added to the purified first particles, wherein the cryopreservant comprises dimethylsulfoxide (DMSO). In some cases, the method does not involve use of Ficoll-Paque or hydroxyethyl starch (HES).

In some cases, the method does not comprise use of a centrifuge. In some cases, the fluid velocity is at least 5 mm/sec. In some cases, the calculated shear rate is at least 500 $\sec^{-1}$.

The device can comprise at least three zones with progressively smaller obstacles and gaps. The obstacles can comprise a cylindrical cross-section. The obstacles can comprise a triangular cross-section.

The sample can be anticoagulated before being applied to the device. The sample can be diluted before being applied to the device. The sample can comprise an agent that reduces the activity of calcium-dependent integrins. The sample can comprise an agent that reduces calcium dependent thrombin formation. The sample can comprise EDTA. The concentration of EDTA in the sample can be at least 5 mM. The sample can comprise acid citrate dextrose. The sample can comprise a thrombin inhibitor. The thrombin inhibitor can be PPACK. The concentration of PPACK in the sample can be at least 40 μM. The sample can comprise an agent that reduces the activity of calcium-dependent integrins or an agent that reduces calcium dependent thrombin formation and a thrombin inhibitor.

In another aspect, a method of purifying cells of at least a predetermined size in a sample is provided, the method comprising (a) applying the sample comprising the cells of at least a predetermined size to a device, and (b) flowing the sample through the device at a flow rate of at least 1 mL/min, wherein the device comprises an array of obstacles, wherein each subsequent row of obstacles is shifted laterally with respect to a previous row, wherein the obstacles differentially deflect the cells of at least the predetermined size in the sample to a first outlet and particles of less than a predetermined size in the sample to a second outlet, thereby generating purified cells of at least the predetermined size, wherein the purified cells of at least the predetermined size are at least 90% pure, wherein the purified cells of at least the predetermined size comprise at least 90% of the cells of at least the predetermined size in the sample, and wherein at least 90% of the purified cells of at least the predetermined size are viable.

The sample can be a blood sample. The blood sample can comprise an umbilical cord blood sample or placental cord blood sample. The sample can comprise peripheral blood. The peripheral blood can comprise G-CSF mobilized peripheral blood. The sample can comprise bone marrow. The cells of at least the predetermined size can comprise leukocytes. The leukocytes can comprise CD34+ cells. The method can further comprise using the purified leukocytes to diagnose lymphoma or leukemia.

The first particles of at least the predetermined size can comprise stem cells. The stem cells can be peripheral blood stem cells (PBSCs). The stem cells can be hematopoietic stem cells (HSCs). The HSCs can comprise CD34+/CD45+ HSCs. The method can further comprise transplanting the purified stem cells in a subject. The particles of less than the determined size can comprise erythrocytes. The cells can comprise cytotoxic T-cells, antigen-specific T-cells, regulatory T-cells, Natural Killer T-Cells, Natural Killer cells, dendritic cells, regulatory B cells, or regulatory macrophages. The cells or particles can comprise platelets, erythrocytes, granulocytes, or lymphocytes. The cells can comprise algae, yeast, bacteria, or viruses. The cells can comprise cancer cells.

The method can comprise flowing at least 100 mL of sample to the device. The method can comprise flowing at least 300 mL of sample to the device. The flowing can comprise flowing the sample at a rate of at least 5 mL/min through the device.

The method can further comprise analyzing the purified first particles of at least the predetermined first size. The analyzing can comprise use of a microscope. The analyzing can comprise flow cytometry. The sample can be passed through a filter before the sample is applied to the device. In some cases, the cells of at least a predetermined size are not labeled. The purified cells can be cryopreserved. A cryopreservant can be added to the purified cells, wherein the cryopreservant comprises dimethylsulfoxide (DMSO). In some cases, the method does not involve use of Ficoll-Paque or hydroxyethyl starch (HES). In some cases, the method does not comprise use of a centrifuge. In some cases, the fluid velocity is at least 5 mm/sec. In some cases, calculated shear rate is at least 500 sec$^{-1}$. In some cases, the device comprises at least three zones with progressively smaller obstacles and gaps. In some cases, the obstacles comprise a cylindrical cross-section. The obstacles can comprise a triangular cross-section. The sample can be anticoagulated before being applied to the device. The sample can be diluted before being applied to the device. The sample can comprise an agent that reduces the activity of calcium-dependent integrins. The sample can comprise an agent that reduces calcium dependent thrombin formation.

The sample can comprise EDTA. The concentration of EDTA in the sample can be at least 5 mM. In some cases, the sample comprises acid citrate dextrose. In some case, the sample comprises a thrombin inhibitor. The thrombin inhibitor can be PPACK. The concentration of PPACK in the sample can be at least 40 µM. The sample can comprise an agent that reduces the activity of calcium-dependent integrins or an agent that reduces calcium dependent thrombin formation and a thrombin inhibitor.

In another aspect, a method for purifying stem cells is provided, the method comprising (a) applying a sample comprising stem cells to a device, and (b) flowing the sample through the device at a flow rate of at least 1 mL/min, wherein the device comprises an array of obstacles, wherein each subsequent row of obstacles is shifted laterally with respect to a previous row, wherein the obstacles differentially deflect the stem cells to a first outlet and particles in the sample of less than the predetermined size to a second outlet, thereby purifying the stem cells.

The sample can be a blood sample. The blood sample can comprise an umbilical cord blood sample or placental cord blood sample. The sample can comprise peripheral blood. The peripheral blood can comprise G-CSF mobilized peripheral blood. The sample can comprise bone marrow. The stem cells can be peripheral blood stem cells (PBSCs). The stem cells can be hematopoietic stem cells (HSCs). The HSCs can comprise CD34+/CD45+ HSCs.

The method can further comprise transplanting the purified stem cells in a subject. In some cases, particles of less than the predetermined size comprise erythrocytes.

The method can comprise flowing at least 100 mL of sample to the device. The method can comprise flowing at least 300 mL of sample to the device.

In some cases, the flowing comprises flowing the sample at a rate of at least 5 mL/min through the device. The sample can be passed through a filter before the sample is applied to the device. In some cases, the stem cells are not labeled. In some cases, the purified stem cells are cryopreserved. In some cases, a cryopreservant is added to the purified stem cells, wherein the cryopreservant comprises dimethylsulfoxide (DMSO).

In some cases, the method does not involve use of Ficoll-Paque or hydroxyethyl starch (HES). In some cases, the method does not comprise use of a centrifuge. In some cases, the fluid velocity is at least 5 mm/sec. A calculated shear rate can be at least 500 sec$^{-1}$.

The device can comprise at least three zones with progressively smaller obstacles and gaps. The obstacles can comprise a cylindrical cross-section. The obstacles can comprise a triangular cross-section.

The sample can be anticoagulated before being applied to the device. The sample can be diluted before being applied to the device. The sample can comprise an agent that reduces the activity of calcium-dependent integrins. The sample can comprise an agent that reduces calcium dependent thrombin formation. The sample can comprise EDTA. The concentration of EDTA in the sample can be at least 5 mM. The sample can comprise acid citrate dextrose. The sample can comprise a thrombin inhibitor. The thrombin inhibitor can be PPACK. The concentration of PPACK in the sample can be at least 40 µM.

The sample can comprise an agent that reduces the activity of calcium-dependent integrins or an agent that reduces calcium dependent thrombin formation and a thrombin inhibitor.

In another aspect, a method of removing a particle trapped in a channel comprising an ordered array of obstacles is provided, wherein the array of obstacles is bounded by a wall, the method comprising flowing a liquid from at least one flow path in a side of the wall, thereby releasing the particle. The wall can comprise a plurality of flow paths. The array of obstacles can be bounded by two walls, wherein both walls comprise a plurality of flow paths. Each of the flow paths can reversibly blockable. The channel can comprise at least one inlet and one outlet, wherein the at least one inlet and at least one oulet are at opposite ends of the channel.

The at least one inlet and at least one outlet can be reversible blockable.

In another aspect, a device comprising a channel comprising an ordered array of obstacles is provided, wherein the array of obstacles is bounded by a wall, wherein the wall comprises a flow path, wherein the flow path is configured to permit fluid flow to release a particle trapped in the array of obstacles. The wall can comprise a plurality of flow paths. The array of obstacles can be bounded by two walls, wherein both walls comprise a plurality of flow paths. Each of the flow paths can be configured to be reversibly blockable. The channel can comprise at least one inlet and one outlet, wherein the at least one inlet and at least one oulet are at opposite ends of the channel. The at least one inlet and at least one outlet can be reversible blockable.

In another aspect, a method for reducing trapped particles from a blood sample in a device comprising an array of obstacles is provided, the method comprising (a) obtaining a blood sample;
(b) adding a calcium chelating agent to the blood sample; (c) adding a direct thrombin inhibitor to the blood sample; and (d) passing the blood sample comprising the calcium chelating agent and the direct thrombin inhibitor through the device, wherein the device comprises an array of obstacles arranged in rows, wherein each subsequent row of obstacles is shifted laterally with respect to a previous row, wherein the obstacles are configured to differentially deflect a first particle of at least the first predetermined size to a first outlet a second particle in the sample of less than the predetermined size to a second outlet, wherein fewer particles from the blood sample comprising the calcium chelating agent and the direct thrombin inhibitor are trapped in the device relative to the number of particles trapped in the device from the blood sample lacking the calcium chelating agent and the direct thrombin inhibitor. The direct thrombin inhibitor can be PPACK. The concentration of PPACK in the blood sample can be about 40 μM. The calcium chelating agent can be EDTA. The concentration of EDTA in the blood sample can be about 5 mM. The calcium chelating agent can be acid citrate dextrose (ACD). Gaps between the obstacles can be about 27 μm.

In some cases, the method further comprises diluting the blood sample at least 3-fold. In some cases, the blood sample comprising the calcium chelating agent and the direct thrombin inhibitor is passed through the device at a rate of at least 4 cm/s. The device can comprise a channel, wherein the channel comprises at least two arrays of obstacles, wherein each array of obstacles deflects particles of at least a predetermined size to a central bypass channel. The bypass channel can comprise a wall. In some cases, the bypass channel does not comprise a wall.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3A shows simulated trajectories of 1.0-micrometer diameter particles moving through an array of right triangular posts disposed in a microfluidic flow channel in which fluid flow alternates between the right-to-left and left to-right directions. FIG. 3B shows simulated trajectories of 3.6-micrometer diameter particles moving through an array of right triangular posts disposed in a microfluidic flow channel in which fluid flow alternates between the right-to-left and left-to-right directions. FIG. 3C shows simulated trajectories of 3.2-micrometer diameter particles moving through an array of right triangular posts disposed in a microfluidic flow channel in which fluid flow alternates between the right-to-left and left to-right directions. In these diagrams, the 1.0-micrometer diameter particles are smaller than the critical size of the array in both fluid flow directions, the 3.6-micrometer diameter particles are larger than the critical size of the array in both fluid flow directions, and the 3.2-micrometer diameter particles are smaller than the critical size of the array in one (right-to-left) flow direction, but larger than the critical size of the array in the other (left-to-right) flow direction.

FIG. 16A shows a schematic top view drawing of a chip

FIG. 16B shows time lapse images of leukocytes being enriched.

FIG. 24A illustrates a microfluidic device made of silicon. FIG. 24B illustrates a chip made of silicon and a chip made of plastic. FIG. 24C illustrates an embossed plastic A-channel chip. FIG. 24D illustrates an embossed plastic A-channel chip.

FIG. 26A illustrates an SEM of a polymer device fabricated by soft embossing. FIG. 26A illustrates an SEM of PP (polypropylene) chip, zone 3. In some cases, a device can have high aspect ratios, precise control over pillar (post, obstacle)

diameters and gaps. FIG. 26B illustrates an SEM of a polymer device fabricated by soft embossing.

FIG. 29 illustrates cell ratio data, N of 3 runs.

FIGS. 35A and 35B illustrate a DLD array before and after running an on-chip cleaning system. FIG. 35A illustrates a DLD array before running an on-chip cleaning system. Clogged beads are shown. FIG. 35B illustrates the DLD array after running on-chip clean system (most clogged beads are cleaned away).

FIG. 36 summarizes physical properties for common microfluidic thermoplastics.

DETAILED DESCRIPTION

I. Overview

Figure 1:
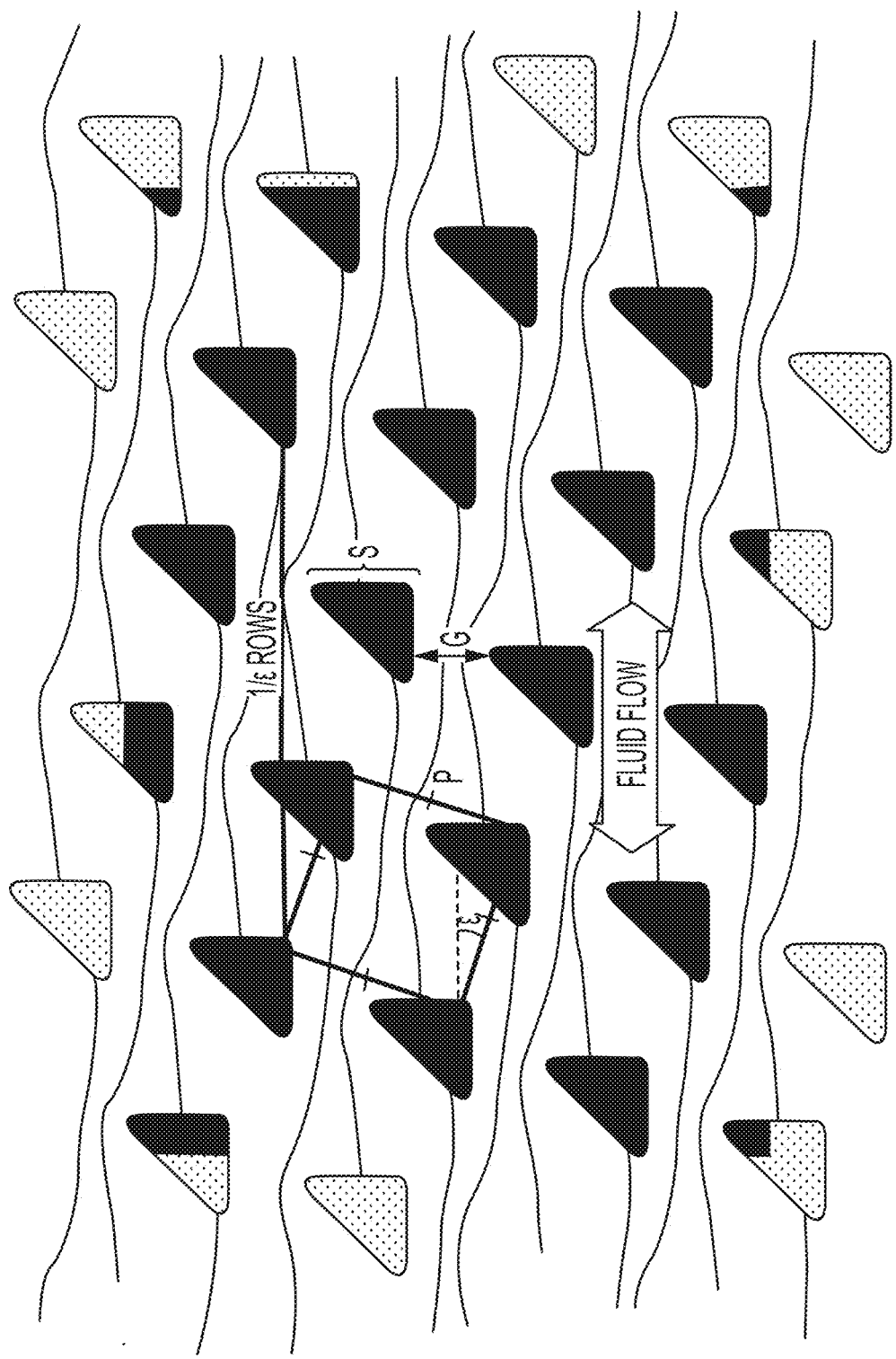
FIG. 1 is a schematic diagram of cross-section of a "bump array" device having right triangularly-shaped obstacles disposed in a microfluidic channel. In the figure, fluid flow alternates between the right-to-left and left-to-right directions, as indicated by the double-headed arrow marked, "Fluid Flow." In this array, right triangular posts are disposed in a square lattice arrangement that is tilted with respect directions of fluid flow. The tilt angle ϵ (epsilon) is chosen so the device is periodic. In this embodiment, a tilt angle of 18.4 degrees (⅓ radian) makes the device periodic after three rows. The gap between posts is denoted G with triangle side length S and array pitch P. Streamlines are shown extending between the posts, dividing the fluid flow between the posts into three regions ("stream tubes") of equal volumetric flow.

Provided herein are methods, compositions, devices, systems, and kits for high-throughput purification, isolation, and/or concentration of particles. The high-throughput purification, isolation, and/or concentration of particles can involve separating particles based on size, e.g., flowing a sample through an array of obstacles, e.g., deterministic lateral displacement. Devices for separating particles based on size and/or using deterministic lateral displacement are described, e.g., in U.S. Pat. Nos. 7,150,812, 7,318,902, 7,472,794, 7,735,652, 7,988,840, 8,021,614, 8,282,799, 8,304,230, 8,579,117, PCT Publication No. WO2012094642, and Huang et al. *Science* 304:987-990 (2004), which are herein incorporated by reference in their entireties. In some cases, the high-throughput methods comprise flow rates of at least 1 mL/min, at least 5 mL/min, at least 10 mL/min or at least 20 mL/min. In some cases, devices described herein can process at least 10 mL, at least 100 mL, or at least 300 mL of sample.

In one aspect, a method of purifying first particles of at least a predetermined size is provided, the method comprising applying at least 10 mL of a sample comprising the first particles of at least the predetermined size to a device, and flowing the at least 10 mL of the sample through the device at a rate of at least 1 mL/min, wherein the device comprises an array of obstacles wherein each subsequent row of obstacles is shifted laterally with respect to a previous row, wherein the obstacles differentially deflect the first particles of at least the first predetermined size to a first outlet and second particles in the sample of less than the predetermined size to a second outlet, thereby purifying the first particles of at least the predetermined size.

In another aspect, a method of purifying first particles of at least a predetermined size in a sample is provided, the method comprising applying the sample comprising the first particles of at least the predetermined size to a device, and flowing the sample through the device at a flow rate of at least 20 mL/min, wherein the device comprises an array of obstacles, wherein each subsequent row of obstacles is shifted laterally with respect to a previous row wherein the obstacles differentially deflect first particles of at least the predetermined size to a first outlet and second particles in the sample of less than a predetermined size to a second outlet, thereby purifying the first particles of at least the predetermined size.

In another aspect, a method for purifying stem cells is provided, the method comprising applying a sample comprising stem cells to a device, and flowing the sample through the device at a flow rate of at least 1 mL/min, wherein the device comprises an array of obstacles, wherein each subsequent row of obstacles is shifted laterally with respect to a previous row, wherein the obstacles differentially deflect the stem cells to a first outlet and particles in the sample of less than the predetermined size to a second outlet, thereby purifying the stem cells.

In another aspect, a method of purifying leukocytes is provided, the method comprising applying a sample comprising leukocytes to a device, and flowing the sample through the device at a flow rate of at least 10 mL/min, wherein the device comprises an array of obstacles, wherein each subsequent row of obstacles is shifted laterally with respect to a previous row, wherein the obstacles differentially deflect the leukocytes to a first outlet and particles in the sample of less than the predetermined size to a second outlet, thereby purifying the leukocytes.

In another aspect, a method for purifying first particles of at least a predetermined size in a sample is provided, wherein the first particles do not comprise circulating tumor cells, white blood cells, or algae, the method comprising applying the sample comprising the first particles to a device, and flowing the sample through the device at a flow rate of at least 1 mL/min, wherein the device comprises an array of obstacles, wherein each subsequent row of obstacles is shifted laterally with respect to a previous row, wherein the obstacles differentially deflect the first particles to a first outlet and second particles of less than the predetermined size in the sample to a second outlet, thereby isolating the first particles of at least the predetermined size.

In another aspect, a method of purifying cells of at least a predetermined size in a sample is provided, the method comprising applying the sample comprising the cells of at least a predetermined size to a device, and flowing the sample through the device at a flow rate of at least 1 mL/min, wherein the device comprises an array of obstacles, wherein each subsequent row of obstacles is shifted laterally with respect to a previous row wherein the obstacles differentially deflect the cells of at least the predetermined size in the sample to a first outlet and particles of less than a predetermined size in the sample to a second outlet, thereby generating purified cells of at least the predetermined size, wherein the purified cells of at least the predetermined size are at least 90% pure, wherein the purified cells of at least the predetermined size comprise at least 90% of the cells of at least the predetermined size in the sample, and wherein at least 90% of the purified cells of at least the predetermined size are viable.

In some cases, a method of removing a particle trapped in a channel comprising an ordered array of obstacles is provided, wherein the array obstacles is bounded by a wall, the method comprising flowing a liquid from at least one flow path in a side of the wall, thereby releasing the particle.

In some cases, a device comprising a channel comprising an ordered array of obstacles is provided, wherein the array of obstacles is bounded by a wall, wherein the wall comprises a flow path, wherein the flow path is configured to permit fluid flow to release a particle trapped in the array of obstacles.

A method for reducing trapped particles from a blood sample in a device comprising an array of obstacles, the method comprising a) obtaining a blood sample; b) adding a calcium chelating agent to the blood sample; c) adding a direct thrombin inhibitor to the blood sample; and passing the blood sample comprising the calcium chelating agent and the direct thrombin inhibitor through the device, wherein the device comprises an array of obstacles arranged in rows, wherein each subsequent row of obstacles is shifted laterally with respect to a previous row, wherein the obstacles are configured to differentially deflect a first particle of at least the first predetermined size to a first outlet a second particle in the sample of less than the predetermined size to a second outlet, wherein fewer particles from the blood sample comprising the calcium chelating agent and the direct thrombin inhibitor are trapped in the device relative to the number of particles trapped in the device from the blood sample lacking the calcium chelating agent and the direct thrombin inhibitor.

In some cases, sample processing is automated. In some cases, multiple steps in processing a sample are automated, e.g., for cytometry, microscopy, and cell therapy applications such as leukocyte isolation, cell washing, and cell staining, and unbound label removal in small volumes (cytometry, bead assays) to very large volumes (cell therapy). In some cases, sample processing is automated for next generation DNA sequencing. In some cases, devices and methods are described herein to separate cells from soluble material in a sample.

In some cases, devices and/or methods described herein can be used to remove unbound label (e.g., antibody) from cells.

II. Particles

In some cases, a particle that can be purified, isolated, and/or concentrated using methods, compositions, devices, systems, and/or kits described herein can be a cell, cellular fragment, or nucleic acid. In some cases, a particle is not a cell, cellular fragment, or nucleic acid, e.g., a particle is a bead.

A. Blood Components

In some cases, a particle is a blood component. In some cases, methods, compositions, devices, systems, and/or kits described herein can be used to purify or separate blood components, e.g., for blood banking. In some cases, a blood component comprises a platelet, red blood cell (erythrocyte), white blood cell (e.g., granulocytes, e.g., neutrophil, basophil, or eosinophil, or agranulocyte, e.g., lymphocyte, monocyte, or macrophage).

In some cases, devices and/or methods described herein can be used for leukocyte depletion from erythrocytes or platelets (e.g., to replace leukocyte filters in processing of blood products for transfusion of patients). In some cases, leukocytes in transfused blood can cause fever and/or chills. In some cases, at least 60, 70, 80, 90, 95, 99 or 100% of leukocytes are depleted from a sample comprising erythrocytes or platelets. In some cases, at least 60, 70, 80, 90, 95, 99 or 100% of erythrocytes are recovered from a sample. In some cases, at least 60, 70, 80, 90, 95, 99 or 100% of platelets are recovered from sample. In some cases, the frequency of febrile transfusion reactions in subjects transfused with erythrocytes or platelets purified using devices and/or methods described herein is about 0.01% to about 0.5%, or less than 0.5%, 0.4%, 0.3%, 0.2%, 0.1%, 0.09%, 0.08%, 0.07%, 0.06%, 0.05%, 0.04%, 0.03%, 0.02%, or 0.01%.

In some cases, leukocytes in a sample used for transfusion can result in refractoriness or alloimmunization. In some cases, transfusion of erythrocytes or platelets purified using devices and/or methods described herein can result in a frequency of refractoriness or alloimmunization of less than 50, 40, 30, 20, 10, 5, 1, or 0.5%, or about 40 to about 50%, about 30 to about 40%, about 20 to about 30%, about 10 to about 20%, about 5 to about 10%, or about 1 to about 5%.

In some cases, methods described herein can be used for in-line leukocyte or platelet isolation (e.g., to replace centrifugal apheresis). In some cases, methods, compositions, devices, systems, and/or kits described herein can be used to deplete erythrocytes from a blood sample, e.g., a umbilical cord blood sample. In some cases, a cell is a dendritic cell. In some cases, a cell is any cell or subset of cells of the innate or adaptive immune system. In some cases, particles comprise CD34+/CD45+ HSPCs.

B. Leukocytes (White Blood Cells)

In some cases, a cell purified, isolated, and/or concentrated using methods, compositions, devices, systems, and/or kits described herein is a leukocyte (white blood cell). A leukocyte can be, e.g, a neutrophil, eosinophil, basophil, lymphocyte, or monocyte. A leukocyte can be, e.g, a granulocyte or agranulocyte. In some cases, a granulocyte is a neutrophil, basophil, or eosinophil. In some cases, an agranulocyte is a lymphocyte, monocyte, or macrophage. A lymphocyte can be, e.g., a B-cell or a T-cell. A T-cell can be, e.g., a CD4+ T helper cell (e.g, $T_H1$, $T_H2$, $T_H3$, $T_H17$, $T_H9$, or $T_{FH}$), a cytotoxic T-cell (e.g., CD8+ cytotoxic T-cell), a γδ T cell, a regulatory (suppressor) T-cell, a Natural Killer T (NKT) cell, an or antigen-specific T-cell, e.g., memory T cell, e.g., central memory T-cells, $T_{EM}$ cells, or $T_{EMRA}$ cell. In some cases, a lymphocyte is a Natural Killer (NK) cell. A B-cell can be a plasma B-cell, a memory B-cell, a B-1 cell, a B-2 cell, a marginal-zone B-cell, a follicular B-cell, or a regulatory B-cell. In some cases, a cell is a regulatory macrophage.

C. Stem Cells

In some cases, a cell purified, isolated, and/or concentrated using methods, compositions, devices, systems, and/or kits described herein is a stem cell. In some cases, the stem cell is an adult stem cell (somatic stem cell). In some cases, an adult stem cell is a hematopoietic stem cell (HSC) or hematopoietic progenitor cell (HPC). In some cases, a HSC is from bone marrow (e.g., bone marrow of pelvis, femur, or sternum). In some cases, an HSC is in a cord blood sample, e.g., umbilical cord blood. In some cases, an HSC is from placenta. In some cases, granulocyte-colony stimulating factor (G-CSF) is administered to a subject; G-CSF can induce HSCs to leave bone marrow and circulate in blood vessels. In some cases, an HSC is in peripheral blood (e.g., G-CSF mobilized adult peripheral blood). In some cases, a stem cell is a long-term stem cell or a short-term progenitor cell. In some cases, stem cells are used for ex vivo expansion, and the products of ex vivo expansion are purified using methods and devices described herein. In some cases, a stem cell is derived from adipose tissue (adipose-derived stem cells (ASCs)). In some cases, stem cells are derived from a collengase digest of adipose tissue.

In some cases, a HSC (e.g., undifferentiated HSC) comprises one or more cell surface markers. In some cases, a HSC (e.g., undifferentiated HSC) can be identified by one or more cell surface markers. A human HSC cell surface marker can be, e.g., CD34+, CD59+, Thy1$^+$, CD38$^{low/-}$, C-kit$^{-/low}$, or lin$^-$. A mouse HSC cell surface marker can be, e.g., CD34low/-, SCA-1+, Thy1$^{+/low}$, CD38+, C-kit+, or lin-.

An HSC can give rise to blood cells, e.g., red blood cells, B lymphocytes, T lymphocytes, natural killer cells, neutrophils, basophils, eosinophils, monocytes, and macrophages.

An adult stem cell (somatic stem cell) can be an HSC, a mesenchymal stem cell, a neural stem cell, an epithelial stem cell, or a skin stem cell. In some cases, a stem cell is a mesenchymal stem cell. A mesenchymal stem cell can give rise to, e.g., bone cells (osteocytes), cartilage cells (chondrocytes), fat cells (adipocytes), and other kinds of connective tissue cells such as those in tendons. In some cases, a stem cell is neural stem cell. A neural stem cell can be found in a brain. A neural stem cell can give rise to, e.g., nerve cells (neurons) and two categories of non-neuronal cells, e.g., astrocytes and oligodendrocytes. In some cases, a stem cell is an epithelial stem cell. An intestinal epithelial stem cell can line the digestive tract and can occur in deep crypts. An intestinal epithelial stem cell can give rise to absorptive cells, goblet cells, paneth cells, and/or enteroendocrine cells. In some cases, a stem cell is skin stem cell. A skin stem cell can occur in the basal layer of epidermis and at the base of hair follicles. An epidermal stem cell can give rise to keratinocytes, which can migrate to the surface of the skin and form a protective layer. Follicular stem cells can give rise to both the hair follicle and to the epidermis. In some cases, a stem cell is an embryonic stem (ES) cell. An embryonic stem cell can be derived from embryos that develop from an egg that has been fertilized in vitro. In some cases, an embryonic stem is a human embryonic stem cell. In some cases, a stem cell is an induced pluripotent stem cell (iPSC). An iPSC can be a somatic cell that is genetically reprogrammed to an embryonic stem cell-like state. In some cases, a stem cell is an undifferentiated stem cell. In some cases, a stem cell is cancer stem cell.

Isolation of stem cells using microfluidics is described, e.g., in Zhang and Austin, (2012) Applications of Microfluidics in Stem Cell Biology, BioNanoSci, 2:277-826, which is herein incorporated by reference in its entirety.

D. Other Particles

In some cases, a particle that can be purified, isolated, and/or concentrated using methods, compositions, devices, systems, and/or kits described herein can be a cancer cell, a circulating tumor cell (CTC), an epithelial cell, a circulating endothelial cell (CEC), a circulating stem cell (CSC), or cancer stem cells. In some cases, a particle is a bone marrow cell, progenitor cell foam cell, fetal cell, mesenchymal cell, circulating epithelial cell, circulating endometrial cell, trophoblast, immune system cell (host or graft), connective tissue cell, bacterium, fungus, virus, protozoan, algae, or plant cell. In some cases, a particle is a microparticle.

In some cases, a virus is a human immunodeficiency virus, herpes simplex virus, or influenza virus, avian influenza virus, or SARS virus. In some cases, a virus is a dsDNA virus, ssDNA virus, dsRNA virus, (+)ssRNA virus, (-)ssRNA-RT virus, or dsDNA-RT virus.

In some cases, a particle is a cellular fragment. In some cases, a cellular fragment is a protein. In some cases, a protein is an antibody, or antibody fragment. In some cases, a cellular fragment is a T-cell receptor. In some cases, a protein is an immunoglobulin. In some cases, a particle is a polypeptide.

In some cases, a particle is a rare cell, e.g., a cell type with an abundance of less than 1000 in a one mL sample, e.g., circulating tumor cells (CTCs), circulating fetal cells, stem cells, or cells infected by a virus or parasite. If sample is a water sample, a rare cell can be a pathogenic bacterium or cell infected with a virus.

In some cases, a cellular fragment is a nucleic acid. A nucleic acid can be, e.g., DNA or RNA. DNA can be genomic DNA, mitochondrial DNA, and/or cell-free DNA. RNA can be, e.g., messenger RNA (mRNA), ribosomal RNA (rRNA), transfer RNA (tRNA), signal recognition particle RNA, small nuclear RNA, small nucleoar RNA, SmY RNA, small Cajal body-specific RNA, telomerase RNA, spliced leader RNA, antisense RNA, CRISPR RNA, long noncoding RNA (long ncRNA), microRNA (miRNA), short interfering RNA (siRNA), short hairpin RNA (shRNA), trans-acting siRNA, repeat associated siRNA, and/or cell-free RNA. In some cases, a nucleic acid is double stranded. In some cases, a nucleic acid is single stranded. In some cases, a nucleic acid comprises one or two overhangs. In some cases, a nucleic acid comprises a 5' overhang. In some cases, a nucleic acid comprises a 3' overhang. In some cases, the nucleic acid comprises "high molecular weight" nucleic acid. In some cases, a nucleic acid is a low molecular weight nucleic acid. In some cases, the nucleic acid is intranuclear, intracellular, or extracellular.

The term "polynucleotide", "nucleic acid", or grammatical equivalents, can refer to two or more nucleotides covalently linked together. A nucleic acid described herein can contain phosphodiester bonds, although in some cases, as outlined below (for example in the construction of primers and probes such as label probes), nucleic acid analogs are included that can have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid (also referred to herein as "PNA") backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with bicyclic structures including locked nucleic acids (also referred to herein as "LNA"), Koshkin et al., J. Am. Chem. Soc. 120.13252 3 (1998); positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469, 863; Kiedrowski et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743

(1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169 176). Several nucleic acid analogs are described in Rawls, C & E News Jun. 2, 1997 page 35. "Locked nucleic acids" are also included within the definition of nucleic acid analogs. LNAs can be a class of nucleic acid analogues in which the ribose ring is "locked" by a methylene bridge connecting the 2'-O atom with the 4'-C atom. All of these references are hereby expressly incorporated by reference. These modifications of the ribose-phosphate backbone can be done to increase the stability and half-life of such molecules in physiological environments. For example, PNA:DNA and LNA-DNA hybrids can exhibit higher stability and thus can be used in some embodiments. Nucleic acids can be single stranded or double stranded, as specified, or contain portions of both double stranded or single stranded sequence. Depending on the application, the nucleic acids can be DNA (including, e.g., genomic DNA, mitochondrial DNA, and cDNA), RNA (including, e.g., mRNA and rRNA) or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

A nucleic acid can be derived from any sample described herein, e.g., mammal, virus, plant, bacterium, fungi, cell, e.g., a leukocyte. In some cases, a nucleic acid has been treated with an enzyme, e.g., a restriction enzyme, phosphatase, ligase, topoisomerase, terminal deoxynucleotidyl transferase (TDT), telomerase, or transposase. In some cases, a nucleic acid is a nucleic acid fragment generated by, e.g., sonication, restriction digest, or mechanical shearing.

In some cases, methods and devices described in U.S. Patent Application Publication No. 20130079251 are used to purify a particle. U.S. Patent Application Publication No. 20130079251 is hereby incorporated by reference in its entirety for all purposes.

In some cases, a cellular fragment is a membrane, cellular organelle, nucleosome, exosome, or nucleus. In some cases, a cellular fragment is a mitochondria, rough endoplasmic reticulum, ribosome, smooth endoplasmic reticulum, chloroplast, golgi apparatus, golgi body, glycoprotein, glycolipid, cisternae, liposome, peroxisome, glyoxysome, centriole, cytoskeleton, lysosome, cilia, flagellum, contractile vacuole, vesicle, nuclear envelope, vacuole, cell membrane, microtubule, nucleolus, plasma membrane, or chromatin.

One or more particles described herein can be in a sample. In some cases, one or more different types of particles described herein can be in a sample.

E. Particle Sizes

In some cases, a particle purified, isolated, and/or concentrated using methods, compositions, devices, systems, and/or kits described herein has a predetermined particle size (or critical particle size). In some cases, particles with a size at least that of a predetermined particle size are directed to a first outlet in a device, whereas particles less than a predetermined size are directed to a second outlet in a device. In some cases, particle size is a diameter of a particle. In some cases, a particle size is at least 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1000 µm. In some cases, a particle size is about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1000 µm. In some cases, a particle size is less than 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 µm, 200, 300, 400, 500, 600, 700, 800, 900, or 1000 µm. In some cases, a particle size is about 0.1 to about 1 µm, about 1 to about 5 µm, about 5 to about 10 µm, about 10 to about 15 µm, about 10 to about 20 µm, about 10 to about 25 µm, about 15 to about 25 µm, about 20 to about 30 µm, about 30 to about 40 µm, about 40 to about 50 µm, about 50 to about 60 µm, about 60 to about 70 µm, about 70 to about 80 µm, about 80 to about 90 µm, about 90 to about 100 µm, about 100 to about 200 µm, about 200 to about 300 µm, about 300 to about 400 µm, about 400 to about 500 µm, about 500 to about 600 µm, or about 500 to about 1000 µm.

In some cases, where a particle is polynucleotide, the polynucleotide comprises at least 2, 5, 10, 20, 30, 40, 50, 60, 70, 80, 90, 100, 150, 200, 250, 300, 350, 400, 450, 500, 600, 700, 800, 900, 1000, 1500, 2000, 3000, 4000, 5000, 6000, 7000, 8000, 9000, 10,000, 20,000, 30,000, 40,000, 50,000, 60,000, 70,000, 80,000, 90,000, 100,000, 500,000, 1,000,000, 5,000,000, or 10,000,000 bases. In some cases, a polynucleotide is a whole chromosome. In some cases, a polynucleotide is a human chromosome 1, 2, 3, 4, 5, 6, 7, 8, 9, 10, 11, 12, 13, 14, 15, 16, 17, 18, 19, 20, 21, 22, X or Y. In some cases, where a particle is a polynucleotide, the polynucleotide comprises about 2, 5, 10, 20, 30, 40, 50, 60, 70, 80, 90, 100, 150, 200, 250, 300, 350, 400, 450, 500, 600, 700, 800, 900, 1000, 1500, 2000, 3000, 4000, 5000, 6000, 7000, 8000, 9000, 10,000, 20,000, 30,000, 40,000, 50,000, 60,000, 70,000, 80,000, 90,000, 100,000, 500,000, 1,000,000, 5,000,000, or 10,000,000 bases. In some cases, where a particle is a polynucleotide, the polynucleotide comprises less than 2, 5, 10, 20, 30, 40, 50, 60, 70, 80, 90, 100, 150, 200, 250, 300, 350, 400, 450, 500, 600, 700, 800, 900, 1000, 1500, 2000, 3000, 4000, 5000, 6000, 7000, 8000, 9000, 10,000, 20,000, 30,000, 40,000, 50,000, 60,000, 70,000, 80,000, 90,000, 100,000, 500,000, 1,000,000, 5,000,000, or 10,000,000 bases. In some cases, a polynucleotide comprises about 10 to about 100 bases, about 50 to about 100 bases, about 100 to about 200 bases, about 500 to about 1000 bases, about 1000 to about 2000 bases, about 2000 to about 5000 bases, about 5000 to about 10,000 bases, about 10,000 to about 50,000 bases, or about 50,000 to about 100,000 bases.

In some cases, particles that are isolated, purified, and/or concentrated are not labeled. In some cases, cells are not labeled. In some cases, nucleic acids (e.g., DNA) are not labeled.

III. Samples

Particles from samples can be purified, isolated, and/or concentrated using the methods, compositions, devices, systems, and/or kits described herein.

A. Types of Samples

In some cases, a sample is a biological sample. In some case, the biological sample is blood. The blood sample can be, e.g., peripheral blood, maternal blood, G-CSF mobilized adult peripheral blood, or cord blood. Cord blood can be, e.g., umbilical cord blood, or placental cord blood. In some cases, a biological sample is serum, plasma, sweat, tears, ear flow, sputum, synovial fluid, lymph, bone marrow suspension, urine, saliva, semen, vaginal flow or secretion, cerebrospinal fluid, feces, cervical lavage, sebum, semen, prostatic fluid, Cowper's fluid, pre-ejaculatory fluid, female ejaculate, brain fluid (e.g., cerebrospinal fluid), ascites, milk (e.g., breast milk), cerumen, secretions of the respiratory, intestinal or genitourinary tract, broncheoalveolar lavage fluid, amniotic fluid, aqueous humor, and water samples. A sample can be a fluid into which cells have been introduced (for example, culture media and liquefied tissue samples). A sample can be a lysate. A biological sample can be hair, cyst fluid, pleural fluid, peritoneal fluid, pericardial fluid, lymph, chyme, chyle, bile, interstitial fluid, menses, pus, sebum, mucosal secretion, stool water, pancreatic juice, lavage fluid from sinus cavities, bronchopulmonary aspirate, or blastocyl cavity fluid. A biological sample can be a tissue sample or biopsy. A fluid sample from an organism or one that has been solubilized can be at least 0.1, 0.5, 1, 2, 3, 4, 5, 6, 7, 7.5, 8, 9, 10, 20, 50, 75, 100, 200, 500, 1000 or 1500 mL.

In some cases, a biological sample is from an animal, e.g., human, mouse, rat, cat, dog, cow, chicken, donkey, rabbit, chimpanzee, gorilla, orangutan, horse, guinea pig, pig, or rhesus monkey. In some cases, a biological sample is from a plant. In some cases, a biological sample comprises a plant. In some cases, a biological sample is from a fugus. In some cases, a biological sample comprises a fungus. In some cases, a sample comprises leukocytes and erythrocytes.

In some cases, a sample comprises cells. In some cases, a sample comprises dead cells, and/or debris. The methods, compositions, devices, systems, and/or kits described herein can be used for size-based removal of debris and/or dead cells from a sample comprising cells.

The methods, compositions, devices, systems, and/or kits described herein can be used for cell wash procedures. In some cases, the sample is a cell culture sample. In some cases, the methods, compositions, devices, systems, and/or kits described herein can be used to isolate, purify, and/or concentrate cells from other components in a cell culture sample, e.g, medium, growth factors, etc. In some cases, devices are used to exchange a cell culture media.

In some cases, a sample comprises a buffer. In some cases, the methods, compositions, devices, systems, and/or kits described herein can be used for buffer/medium exchange.

In some cases, a sample comprises enzyme digested adipose tissue. In some cases, the enzyme digested adipose tissue is a source for autologous progenitor cells. In some cases, the methods, compositions, devices, systems, and/or kits described herein can be used to clean-up enzyme (e.g., collagenase) digested adipose tissue as a source for autologous progenitor cells, e.g., purify stem cells from the enzyme digested adipose tissue.

In some cases, a sample comprises cancer cells from tumors. In some cases, the methods, compositions, devices, systems, and/or kits described herein can be used to isolate, purify, and/or concentrate cancer cells from tumors.

In some cases, a sample comprises infiltrating cells or stromal host cells from a tumor. In some cases, the methods, compositions, devices, systems, and/or kits described herein can be used to isolate, purify, and/or concentrate infiltrating cells or stromal host cells from a tumor. For example, tumor-infiltrating lymphocytes can be white blood cells that have left the bloodstream and migrated to a tumor. Stromal cells can be connective tissue. Stromal cells can provide an extracellular matrix on which tumors can grow.

In some cases, a sample is an industrial sample. In some cases, the methods, compositions, devices, systems, and/or kits described herein can be used to isolate, purify, and/or concentrate particles in an industrial sample.

In some cases, a sample comprises algae, yeast, bacteria, or a virus. In some cases, methods, compositions, devices, systems, and/or kits described herein can be used to isolate, purify, and/or concentrate algae, yeast, bacteria, and/or a virus. For example, a sample with yeast can be a beer production sample. Methods, compositions, devices, systems, and/or kits described herein can be used to isolate, purify, and/or concentrate yeast from the sample from a beer production sample.

In some cases, a sample comprises an antibody. In some cases, methods, compositions, devices, systems, and/or kits described herein can be used to isolate, purify, and/or concentrate and antibody from a sample comprising an antibody.

In some cases, a sample comprises plants, mitochondria, lentivirus, exosomes, or dividing cells. Methods, compositions, devices, systems, and/or kits described herein can be used to isolate, purify, and/or concentrate plants, mitochondria, lentivirus, exosomes, or dividing cells from the sample.

In some cases, a sample comprises cells at different stages in the cell cycle, G0 (Gap 0/Resting), G1 (Gap 1), S (Synthesis), M (Mitosis), or G2 (Gap 2). Cells can have different sizes at different stages of the cell cycle. In some cases, the methods and devices described herein are used to separate cells at different stages of the cell cycle.

In some cases, a sample is from a body of water. A body of water can be, e.g., from a creek, pond, river, ocean, lake, sea, puddle, stream canal, wetland, marsh, reservoir, harbor, bay, artificial lake, barachois, basin, bayou, beck, bight, billabong, boil, brook, burn, channel, cove, draw, estuary, firth, fjord, glacier, gulf, inlet, kettle, kill, lagoon, loch, mangrove swamp, Mediterranean sea, mere, mill pond, moat, oxbow lake, phytotelma, pool (swimming pool, reflecting pool), pothole, rapid, roadstead, run, salt marsh, sea loch, sea lough, source, spring, strait, stream, subglacial lake, swamp, tarn, tide pool, vernal pool, wash, or wetland.

In some cases, a sample is from a bioterror attack. In some cases, a sample from a bioterror attack comprises a virus, e.g., smallpox virus or influenza virus. In some cases, a sample from a bioterror attack comprises anthrax. In some cases, a sample from a bioterror attack comprises more than one type of infective agent.

In some cases, the methods described herein are used purify viruses from cells, e.g., a lentivirus. Examples of lentivirus include human immunodeficiency virus (HIV), simian immunodeficiency virus, feline immunodeficiency virus, puma lentivirus, equine infectious anemia virus, bovine immunodeficiency virus, caprine arthritis encephalitis virus, or Visna virus. In some cases, a virus can be purified away from cells and/or cellular debris.

In some cases, a sample is from a hospital or other medical health care facility. In some cases, a sample is from a wastewater treatment facility. In some cases, a sample is from an algal biofuel production facility. In some cases, devices and/or methods described herein can be used to separate algae from a fluid, e.g., a pond comprising algae and biofuel produced by the algae. In some cases, a sample is from a brewery. In some cases, devices and/or methods described herein can be used to separate yeast from a fluid. In some cases, a sample is from a public water system. In some cases, a sample is from a sewage system.

In some cases, a sample is from a chemical spill. In some cases, a sample is from a mine, e.g., coal mine. In some cases, a sample is an archeological sample. In some cases, a sample is a forensic sample.

In some cases, the erythrocytes in samples are not lysed. In some cases, erythrocytes in samples are lysed.

In some cases, a sample comprises one or more labels. In some cases, a sample comprises at least 2, 3, 4, 5, 6, 7, 8, 9, 10, 11, 12, 13, 14, 15, 16, 17, 18, 19, or 20 different labels. In some cases, a label is a antibody, antibody fragment, dye, stain (e.g., ethidium bromide), nucleic acid adapter, radioactive particle, fluorescent particle, oligonucleotide, probe, or fluorescently-labeled probe.

In some cases, a sample comprises an enzyme, e.g., a restriction enzyme, kinase (e.g., DNA kinase (e.g., T4 polynucleotide kinase), protein kinase, e.g., serine kinase, threonine kinase, tyrosine kinase), DNase, RNase, phosphatase, ligase (e.g., RNA ligase, DNA ligase), horseradish peroxidase (HRP), alkaline phosphatase (AP), glucose oxidase, polymerase (e.g., DNA polymerase (e.g., thermostable DNA polymerase, Taq polymerase) RNA polymerase), terminal deoxynucleotidyl transferase, reverse transcriptase (e.g., viral reverse-transcriptase, non-viral reverse transcriptase), telomerase, methylase, or topoisomerase. In some cases, methods and/or device used herein can be used to separate a label or enzyme from another component of a sample, e.g., a polynucleotide or cell.

B. Number of Particles/Numbers of Different Types of Particles in a Sample

A sample can comprise one or more first particles. In some cases, a sample can comprise at least 1, 2, 3, 4, 5, 6, 7, 8, 9, 10, 50, 100, 500, 1000, 10,000, 100,000, 1,000,000, 10,000,000, 100,000,000, 1,000,000,000, 10,000,000,000, 100,000,000,000, or 1,000,000,000,000 first particles. A sample can comprise about 1, 2, 3, 4, 5, 6, 7, 8, 9, 10, 50, 100, 500, 1000, 10,000, 100,000, 1,000,000, 10,000,000, 100,000,000, 1,000,000,000, 10,000,000,000, 100,000,000,000, 000, or 1,000,000,000,000 first particles. In some cases, a sample comprises about 10 to about 100 first particles, about 5 to about 10 first particles, about 10 to about 50 first particles, about 50 to about 100 first particles, about 100 to about 1000 first particles, about 1000 to about 10,000 first particles, about 10,000 to about 100,000 first particles, about 100,000 to about 1,000,000 first particles, about 1,000,000 to about 10,000,000 first particles, about 10,000,000 to about 100,000,000 first particles, about 100,000,000 to about 1,000,000,000 first particles, about 1,000,000,000 to about 10,000,000,000 first particles, about 10,000,000,000 to about 100,000,000,000 first particles, or about 100,000,000,000 to about 1,000,000,000,000 first particles.

In some cases, a sample comprises at least 1, 2, 3, 4, 5, 6, 7, 8, 9, 10, 50, 100, 500, 1000, 10,000, 100,000, 1,000,000, 10,000,000, 100,000,000, 1,000,000,000, 10,000,000,000, 100,000,000,000, or 1,000,000,000,000 total particles. A sample can comprise about 1, 2, 3, 4, 5, 6, 7, 8, 9, 10, 50, 100, 500, 1000, 10,000, 100,000, 1,000,000, 10,000,000, 100,000,000, 1,000,000,000, 10,000,000,000, 100,000,000,000, or 1,000,000,000,000 first particles, In some cases, a sample comprises about 10 to about 100 total particles, about 5 to about 10 total particles, about 10 to about 50 total particles, about 50 to about 100 total particles, or about 100 to about 1000 total particles, about 1000 to about 10,000 total particles, about 10,000 to about 100,000 total particles, about 100,000 to about 1,000,000 total particles, about 1,000,000 to about 10,000,000 total particles, about 10,000,000 to about 100,000,000 total particles, about 100,000,000 to about 1,000,000,000 total particles, about 1,000,000,000 to about 10,000,000,000 total particles, about 10,000,000,000 to about 100,000,000,000 total particles, or about 100,000,000,000 to about 1,000,000,000,000 total particles.

A sample can comprise one or more different types of particles. A sample can comprise at least 1, 2, 3, 4, 5, 6, 7, 8, 9, 10, 50, 100, 500, 1000, 10,000, 100,000, 1,000,000, 10,000,000, 100,000,000, 1,000,000,000, 10,000,000,000, 100,000,000,000, or 1,000,000,000,000 different types of particles. A sample can comprise about 1, 2, 3, 4, 5, 6, 7, 8, 9, 10, 50, 100, 500, 1000, 10,000, 100,000, 1,000,000, 10,000,000, 100,000,000, 1,000,000,000, 10,000,000,000, 100,000,000,000, or 1,000,000,000,000 different types of particles. In some cases, a sample comprises about 10 to about 100 different types of particles, about 5 to about 10 different types of particles, about 10 to about 50 different types of particles, about 50 to about 100 different types of particles, or about 100 to about 1000 different types of particles, about 1000 to about 10,000 different types of particles, about 10,000 to about 100,000 different types of particles, about 100,000 to about 1,000,000 different types of particles, about 1,000,000 to about 10,000,000 different types of particles, about 10,000,000 to about 100,000,000 different types of particles, about 100,000,000 to about 1,000,000,000 different types of particles, about 1,000,000,000 to about 10,000,000,000 different types of particles, about 10,000,000,000 to about 100,000,000,000 different types of particles, or about 100,000,000,000 to about 1,000,000,000,000 different types of particles.

C. Ratio of First and Second Particles in a Sample

In some cases, a sample comprises a first particle and a second particle. In some cases, the ratio of the abundance of the first particle to the second particle in the sample is less than 1:1, 1:10, 1:100, 1:1000, 1:10,000, 1:100,000, 1:1,000,000, 1:10,000,000, 1:100,000,000, or 1:1,000,000,000. In some cases, the ratio of the abundance of the first particle to the second particle in the sample is greater than 1:1, 1:10, 1:100, 1:1000, 1:10,000, 1:100,000, 1:1,000,000, 1:10,000,000, 1:100,000,000, or 1:1,000,000,000. In some cases, the ratio of the abundance of the first particle to the second particle in the sample is about 1:1, 1:10, 1:100, 1:1000, 1:10,000, 1:100,000, or 1:1,000,000, 1:10,000,000, 1:100,000,000, or 1:1,000,000,000. In some cases, a sample comprises a rare cell type. In some cases, the ratio of the abundance of the rare cell type to the abundance of cells of one or more other cell types in a sample is about 1:100, 1:1000, 1:10,000, 1:100,000, 1:1,000,000, 1:10,000,000, 1:100,000,000, or 1:1,000,000,000. In some cases the ratio of abundance of cells of the rare cell type to the abundance of cells of one or more other cell types is less than 1:100, 1:1000, 1:10,000, 1:100,000, 1:1,000,000, 1:10,000,000, 1:100,000,000, or 1:1,000,000,000.

D. Sample Dilution

In some cases, a sample is diluted. In some cases, a sample, e.g., a blood sample, is diluted before it is applied to a device described herein. A sample can be diluted, e.g., in order to prevent clogging of a device described herein. In some cases, a sample is diluted after being passed through a device described herein. A sample can be diluted at least 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or 3000, 4000, 5000, 6000, 7000, 8000, 9000, or 10,000-fold. In some cases, a sample is diluted about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or 3000, 4000, 5000, 6000, 7000, 8000, 9000, or 10,000-fold. A sample can be diluted, e.g., by adding water, buffer, and/or other fluid to the sample. In some cases, a sample is diluted by adding an additive.

E. Clogging and Sample Additives

Disclosed herein are methods for processing large volumes of blood with deterministic lateral displacement arrays, e.g., for isolation of rare cells. In some cases, the disclosed methods can be used to extract circulating tumor cells from large volumes (~100 mL) of whole blood of cancer patients, or, e.g, to extract stem cells from large volumes of umbilical cord blood. The disclosed methods are also useful for general processing of blood using DLD arrays.

In some cases, deterministic lateral displacement (DLD) arrays are used to extract rare cells from hundreds of microliters of blood. Using the disclosed methods, DLD arrays can be used to extract rare cells from hundreds of milliliters of blood. The "robustness" of the technique against clogging and fouling for lower throughputs for other blood applications is also improved.

In some cases, a process for reducing clogging comprises a combination of four techniques: 1) increase in the concentration of the calcium-chelating anti-coagulant EDTA from, e.g., 1 mM to, e.g, 5 mM; 2) add a direct thrombin inhibitor, e.g., PPACK at a concentration of, e.g., 40 µM; 3) increase in the flow velocity 10×; and a 3× increase in the dilution of blood. In some cases, only one technique is performed. In some cases, two or more of the techniques are performed.

In some cases, a kit is provided comprising a calcium-chelating agent and a thrombin inhibitor. In some cases, the kit comprises EDTA and PPACK.

Using blood, e.g., whole blood with fluorescently stained leukocytes, the level of clogging can be measured as a function of the volume of blood that had passed through the DLD array. Employing the disclosed approach, ~100 mL of blood can pass through the DLD array before clogging using a combination of the four methods above, compared to a few hundred microliters previously.

The combination of EDTA and PPACK can be used as a running buffer for dilution of the blood in preparation for processing of the blood with DLD arrays.

The references listed herein are also part of the application and are incorporated by reference in their entirety as if fully set forth herein.

Deterministic lateral displacement arrays can be used to capture leukocytes and circulating tumor cells from blood with high enrichment and at high flow rates.

In some cases, the volume of blood that can be processed with these devices is limited due to clogging of the micro-post (obstacle) array. In some cases, by removing platelets from blood before putting the blood in the arrays, platelets can be identified as a dominant contributor to clogging. For example, running leukocytes alone can leads to far less clogging than running blood. In some cases, a biological mechanism causing clogging can be disabled, which can yield at least a 40-fold reduction in clogging. In some cases, higher flow rates and greater dilution of blood can be used to achieve a further reduction in clogging of a micro-post array.

The physiological conditions in devices comprising an array of obstacles (high shear, rapid repeated acceleration and deceleration) can be different from those found in typical situations involving blood clotting studies. Clogging of a micro-post (obstacle) array can be caused by one or both of two complementary, mutually dependent processes involved in hemostasis: coagulation and platelet activation, which lead to a clot. In some cases, clots (which then can trap leukocytes) can cause the clogging.

Figure 20:
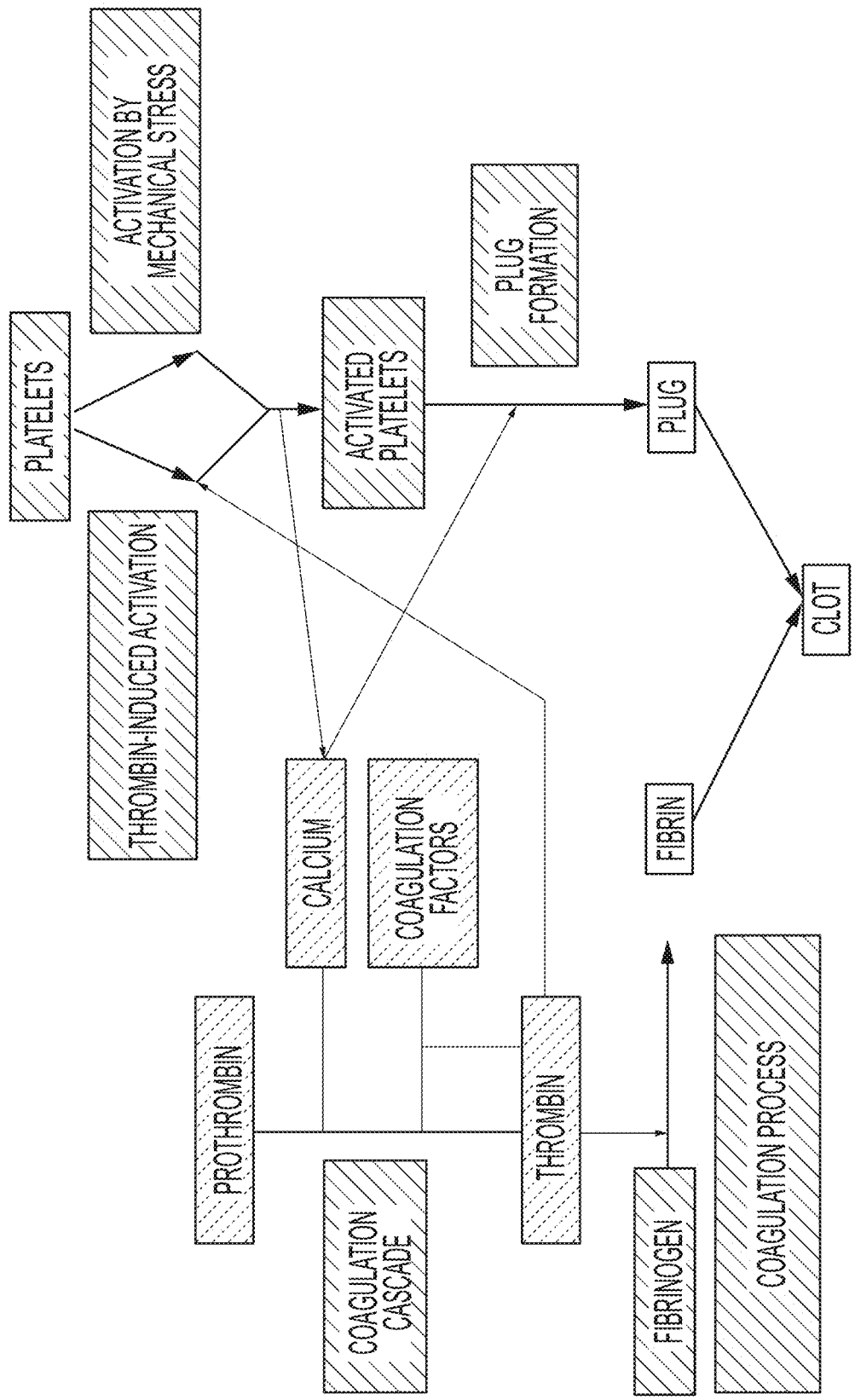
FIG. 20 illustrates a simplified diagram of a process by which platelet-induced clogging of the micro-post array can occur.

FIG. 20 illustrates a simplified view of possible ways in which these two processes can interact to cause clogging as well as underlying mechanisms which can be attacked to disable these mechanisms. The cycle may be initiated by mechanical stress on the platelets from shear forces as the platelets pass between the posts in a micro-post array, or their rapid acceleration and deceleration caused by a micro-array structure.

Coagulation-related processes are on the left side of the diagram, and the platelet processes are on the right side of the diagram. They can inter-relate through thrombin and calcium pathways and dependencies. In some cases, both the thrombin and the calcium pathways/dependencies can be addressed for maximum effectiveness.

In some cases, high flow rate and dilution both lead to an increase in the maximum throughput of whole blood before significant clogging can occur.

In some cases, a dominant clogging mechanism is the activity of calcium-dependent integrins on platelet surfaces, the interaction of which can lead to aggregation of platelets. In some cases, calcium-dependent integrins are one of the dominant contributors to platelet-induced clogging. In some cases, increasing the concentration of EDTA from 1 mM to 5 mM can result in an 8-fold reduction in clogging. In some cases, acid citrate dextrose (ACD), like EDTA, chelates calcium in blood plasma, has a similar effect. The chelation of calcium can also reduce the coagulation pathways (on the left of the diagram).

In some cases, a dominant clogging mechanism is due to thrombin effects, e.g., thrombin-induced platelet activation. Thrombin can catalyze the conversion of fibrinogen into fibrin as a part of a coagulation cascade. In some cases, thrombin is a potent platelet-activating agonist. Heparin can be effective in reducing clogging—it can reduce the formation of thrombin.

In some cases, a calcium chelator can be combined with a thrombin inhibitor. In some cases, inhibiting thrombin with the direct thrombin inhibitor PPACK can achieve a further 5-fold reduction in clogging on top of that achieved with a 5 mM concentration of EDTA.

Figure 21:
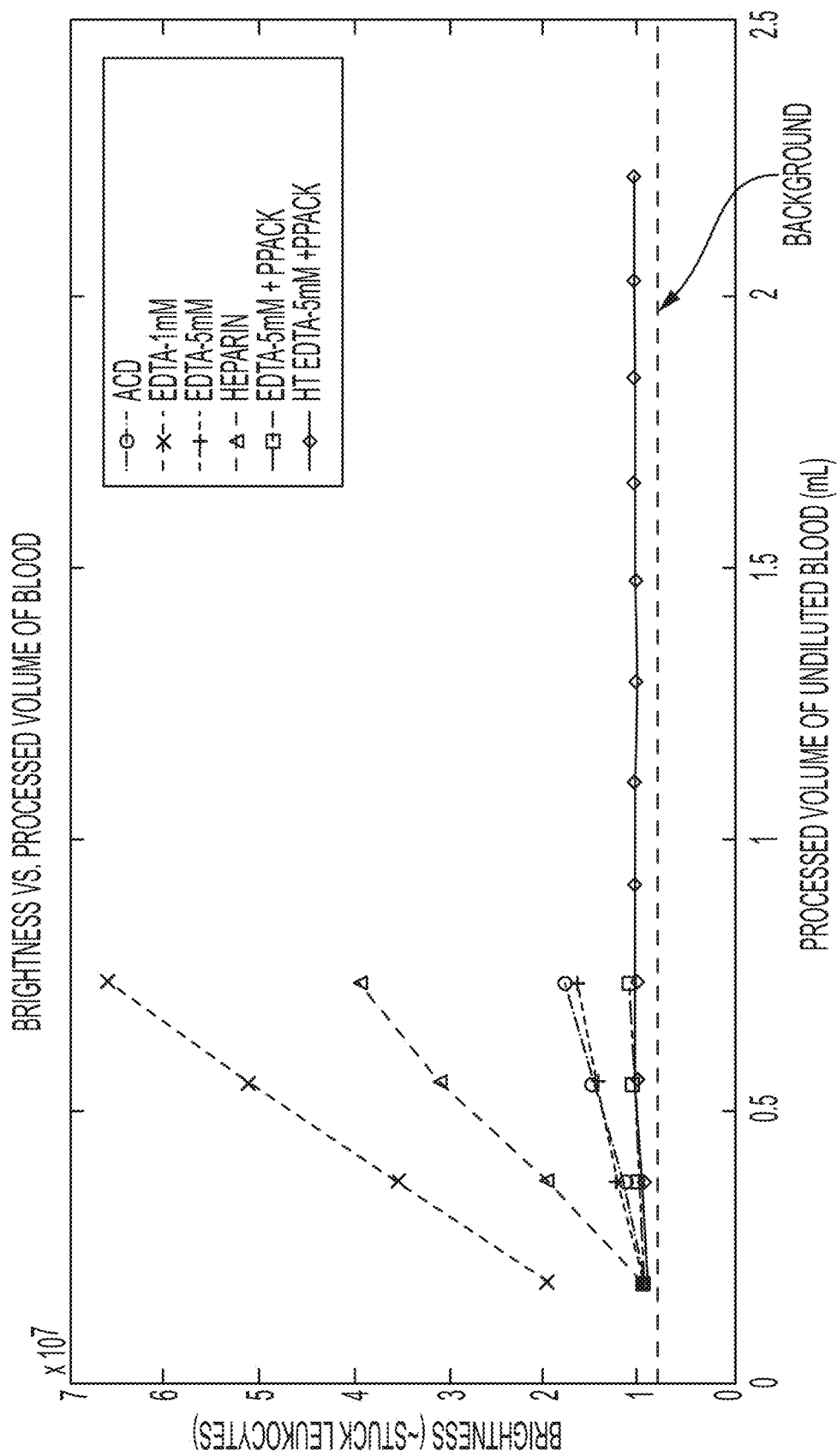
FIG. 21 shows these results for a case of an array with 40 um triangular posts with 27 um gaps for leukocyte separation from blood.

FIG. 21 shows these results for the case of an array with 40 um triangular posts with 27 um gaps for leukocyte separation from blood.

Deterministic lateral displacement (DLD) arrays have been used to concentrate circulating tumor cells (CTCs) in diluted whole blood at flow rates as high as 10 mL/min with capture efficiencies exceeding 85% (K. Loutherback et al., AIP Advances, 2012). In some cases, the equivalent volume of undiluted whole blood that can be processed is limited to 0.3 mL per DLD array due to clogging of the array. Since the concentration of CTCs can be as low as 1-10 cells/mL in clinical samples, increasing the volume of blood that can be processed with DLD arrays can allow for collection of sufficient numbers of CTCs for biological experiments or clinical diagnostic studies. Furthermore, by bumping large cells, such as typical CTCs, into a buffer stream, DLD arrays can be used to harvest CTCs free of the background of smaller particles, such as leukocytes, erythrocytes, and platelets, present in blood, or free of plasma, resulting in a highly enriched or concentrated product (see e.g., J. A. Davis, et al., PNAS, 2006).

In some cases, two biological mechanisms can cause clogging of the array, and these two mechanisms can be inhibited. In some cases, shear-induced platelet aggregation is only a minor contributor to clogging of the array. In some cases, by comparing the reduction in clogging achieved by the calcium-chelating anticoagulants EDTA and ACD to that achieved by the indirect thrombin inhibitor heparin as well as by measuring the EDTA concentration-dependent reduction in clogging, activity of calcium-dependent integrins as a dominant contributor to clogging can be identified. In some cases, combining EDTA with the direct thrombin inhibitor PPACK can be used to identify thrombin-induced platelet activation as the second dominant mechanism contributing to clogging. Using a combination of EDTA and PPACK, a 40-fold decrease in clogging of the array can be demonstrated, which can allow a commensurate increase in the volume of blood processed. Based on data in a single-channel device (2 mm wide), we can expect a complete chip to be able to process >100 mL quantities of whole blood in 30 minutes without significant clogging. Finally, in some cases, the glycoprotein 11b/IIIa integrin complex, which is activated by shear forces, can be inhibited using the glycoprotein 11b/IIIa inhibitor tirofiban to show that shear-induced platelet aggregation plays only a minor role in clogging of the array.

In some cases, a sample can comprise one or more additives. In some cases, a chelating agent is added to a sample. In some cases, the chelating agent comprises a calcium-chelating agent. In some cases, the chelating agent comprises acetylacetone, aerobactin, aminoethylethanolamine, aminopolycarboxylic acid, ATMP, BAPTA, BDTH2, benzotriazole, Bipyridine, 2,2'-Bipyridine, 4,4'-Bipyridine, 1,2-Bis(dimethylarsino)benzene, 1,2-Bis(dimethylphosphino)ethane, 1,2-Bis(diphenylphosphino)ethane, Catechol, Chelex 100, Citric acid, Corrole, Crown ether, 18-Crown-6, Cryptand, 2.2.2-Cryptand, Cyclen, Deferasirox, Deferiprone, Deferoxamine, Dexrazoxane, Trans-1,2-Diaminocyclohexane, 1,2-Diaminopropane, Dibenzoylmethane, Diethylenetriamine, Diglyme, 2,3-Dihydroxybenzoic acid, Dimercaprol, 2,3-Dimercapto-1-propanesulfonic acid, Dimercaptosuccinic acid, Dimethylglyoxime, DIOP, Diphenylethylenediamine, DOTA, DOTA-TATE, DTPMP, EDDH, EDDS, EDTMP, EGTA, 1,2-Ethanedithiol, Ethylenediamine, Ethylenediaminetetraacetic acid (EDTA), Etidronic acid, Extended porphyrins, Ferrichrome, Fluo-4, Fura-2, Gluconic acid, Glyoxal-bis(mesitylimine), Hexafluoroacetylacetone, Homocitric acid, Iminodiacetic acid, Indo-1, Metal acetylacetonates, Metal dithiolene complex, Metallacrown, Nitrilotriacetic acid, Pendetide, Penicillamine, Pentetic acid, Phanephos, Phenanthroline, O-Phenylenediamine, Phosphonate, Phytochelatin, Polyaspartic acid, Porphin, Porphyrin, 3-Pyridylnicotinamide, 4-Pyridylnicotinamide, Sodium diethyldithiocarbamate, Sodium polyaspartate, Terpyridine, Tetramethylethylenediamine, Tetraphenylporphyrin, 1,4,7-Triazacyclononane, Triethylenetetramine, Triphos, Trisodium citrate, or 1,4,7-Trithiacyclononane.

In some cases, a sample, e.g., a blood sample, is collected in a tube comprising $K_2$EDTA or $K_3$EDTA.

In some cases, the sample comprises an agent that reduces the activity of calcium-dependent integrins. In some cases, the sample comprises an agent that reduces calcium dependent thrombin formation. In some cases, an agent that chelates calcium comprises acid citrate dextrose (ACD). The final concentration of ACD in a sample, e.g., a blood sample, can be 10%.

In some cases, the chelating agent is EDTA. In some cases, the calcium chelating agent is EDTA. In some cases, the final concentration of the chelating agent in the sample is at least 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or 20 mM. In some cases, the final concentration of EDTA in the sample is at least 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, or 25 mM. In some cases, the concentration of EDTA is about 2 mM to about 7 mM, or about 3 mM to about 6 mM.

In some cases, one or more thrombin inhibitors are added to a sample, e.g., a blood sample. In some cases, a thrombin inhibitor is a direct thrombin inhibitor. In some cases, a direct thrombin inhibitor is a bivalent thrombin inhibitor. In some cases, a direct thrombin inhibitor is a univalent thrombin inhibitor. In some cases, a direct thrombin inhibitor is an allosteric inhibitor. A bivalent direct thrombin inhibitor can be hirudin, bivalirudin, lepirudin, or desirudin. A univalent direct thrombin inhibitor can be argatroban, melagatran, ximelagatran, or dabigatran. An allosteric direct thrombin inhibitor can be a DNA aptamer, benzofuran dimer, benzofuran trimer, or polymeric lignin. In some cases, a direct thrombin inhibitor is PPACK (D-Phe-Pro-Arg-CMK).

In some cases, a thrombin inhibitor is PPACK (D-Phe-Pro-Arg-CMK), benzamidine hydrochloride, p-APMSF, p-APMSF hydrochloride, TLCK hydrochloride, uPA inhibitor, PPACK dihydrochloride, or PPACK dihydrochloride biotinylated. In some cases, Heparin is a thrombin inhibitor.

In some cases, the final concentration of the thrombin inhibitor, e.g., direct thrombin inhibitor in a sample is at least 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 250, 300, 350, or 400 μM. In some cases, a final concentration a thrombin inhibitor in a sample is about 30 to about 50 μM, or about 20 to about 60 μM. In some cases, the final concentration of PPACK in a sample is at least 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 250, 300, 350, or 400 μM. In some cases, a final concentration of PPACK in a sample is about 30 to about 50 μM, or about 20 to about 60 μM.

In some cases, a chelating agent and a thrombin inhibitor are added to a sample. In some cases, a calcium chelating agent and a thrombin inhibitor are added to a sample. In some cases, a chelating agent and a thrombin inhibitor are added to a sample, and the sample is diluted at least 3 fold.

In some cases, a sample comprises EDTA and PPACK. In some cases, a sample comprises EDTA at a concentration of about 5 mM and PPACK at a concentration of about 40 μM. In some cases, a blood sample comprises EDTA at a concentration of about 5 mM and PPACK at a concentration of about 40 μM. In some cases, a blood sample is diluted about 3 fold, and the diluted blood sample comprises EDTA and PPACK. In some cases, a blood sample is diluted about 3 fold, and the diluted blood sample comprises EDTA at a concentration of about 5 mM and PPACK at a concentration of about 40 μM. In some cases, a sample, e.g., a blood sample, comprises one or more additives, e.g., sodium fluoride (NaF), Heparin, EDTA, or sodium citrate. In some cases, an additive is an anticoagulant or antiplatelet agent, e.g., clopidogrel, prasugrel, ticagrelor, ticlopidine, argatroban, bivalirudin, dalteparin, enoxaparin, fondaparinux, heparin, heparin lock flush, lepirudin, anagrelide, apixaban, aspirin, aspirin/dipyridamole, cilostazol, dabigatran, dipyridamole, batroxobin, hementin, rivaroxaban, warfarin, or urokinase. In some cases, an anticoagulant is an antithrombic, fibrinolytic, or thrombolytic. In some cases, whole blood is diluted with 1×PBS with 2 mM EDTA and 0.5% BSA.

F. Sample Volumes

Samples can be applied to devices described herein, e.g., devices with ordered arrays of obstacles, e.g., deterministic lateral displacement devices. The volume of sample that can be applied to a device and/or processed by a device can be at least 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or 3000 mL. The volume of sample that can be applied to a device and/or processed by a device can be less than 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or 3000 mL. The volume of sample that can be applied to a device and/or processed by a device can be about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or 3000 mL. The volume of sample that can be applied to device and/or processed by a device can be about 1 to about 10 mL, about 10 mL to about 20 mL, about 10 mL to about 50 mL, about 10 mL to about 100 mL, about 20 mL to about 100 mL, about 100 mL to about 300 mL, about 100 mL to about 1000 mL, about 100 mL to about 500 mL, or about 100 mL to about 3000 mL.

G. Concentration of Particles in a Sample

In some cases, a concentration of particles in a sample is about 1, 5, 10, 50, 100, 500, 1000, $10^4$, $10^5$, $10^6$, $10^7$, $10^8$, $10^9$, $10^{10}$, or $10^{11}$ per mL of sample. In some cases, a concentration of particle in a sample is less than 1, 5, 10, 50, 100, 500, 1000, $10^4$, $10^5$, $10^6$, $10^7$, $10^8$, $10^9$, $10^{10}$, or $10^{11}$ per mL of sample. In some cases, a concentration of particles in a sample is at least 1, 5, 10, 50, 100, 500, 1000, $10^4$, $10^5$, $10^6$, $10^7$, $10^8$, $10^9$, $10^{10}$, or $10^{11}$ per mL of sample.

IV. Devices

Exemplary devices for separating particles based on size are described, e.g., in U.S. Pat. Nos. 7,150,812, 7,318,902, 7,472,794, 7,735,652, 7,988,840, 8,021,614, 8,282,799, 8,304,230, 8,579,117, and PCT Publication No. WO2012094642, which are herein incorporated by reference in their entireties. Particles and samples described herein can be applied to devices described herein for size-based separation, e.g., high throughput size based separation.

The disclosure relates generally to the field of separation of particles such as spheres, cells, viruses, and molecules. The disclosure relates to separation of particles based on their flow behavior in a fluid-filled field of obstacles in which advective transport of particles by a moving fluid overwhelms the effects of diffusive particle transport.

Separation of particles by size or mass can be a fundamental analytical and preparative technique in biology, medicine, chemistry, and industry. Conventional methods include gel electrophoresis, field-flow fractionation, sedimentation and size exclusion chromatography. More recently, separation of particles and charged biopolymers has been described using arrays of obstacles through particles pass under the influence of fluid flow or an applied electrical field. Separation of particles by these obstacle-array devices can be mediated by interactions among the biopolymers and the obstacles and by the flow behavior of fluid passing between the obstacles.

A variety of microfabricated sieving matrices have been disclosed for separating particles (Chou et. al., 1999, Proc.

Natl. Acad. Sci. 96:13762; Han, et al., 2000, Science 288: 1026; Huang et al., 2002, Nat. Biotechnol. 20:1048; Turner et al., 2002, Phys. Rev. Lett. 88(12):128103; Huang et al., 2002, Phys. Rev. Lett. 89:178301; U.S. Pat. Nos. 5,427,663; 7,150,812; 6,881,317). These matrices can depend on accurate fabrication of small features (e.g., posts, or obstacles, in a microfluidic channel). The accuracy with which small features can be fabricated can be limited in all microfabrication methods, especially as feature size decreases. The strength and rigidity of materials in which small features of fabricated can also limit the practical usefulness of the fabricated device. Furthermore, the small size of the gaps between obstacles in such matrices can render the matrices susceptible to clogging by particles too large to fit between the obstacles. Micrometer- and nanometer-scale manufacturing can also require state-of-the-art fabrication techniques, and devices fabricated using such methods can have high cost.

Bump array (also known as "obstacle array") devices have been described, and their basic operation is explained, for example in U.S. Pat. No. 7,150,812, which is incorporated herein by reference in its entirety. Referring to FIGS. 3 and 4 of U.S. Pat. No. 7,150,812, a bump array can operate essentially by segregating particles passing through an array (generally, a periodically-ordered array) of obstacles, with segregation occurring between particles that follow an "array direction" that is offset from the direction of bulk fluid flow or from the direction of an applied field.

Figure 8:
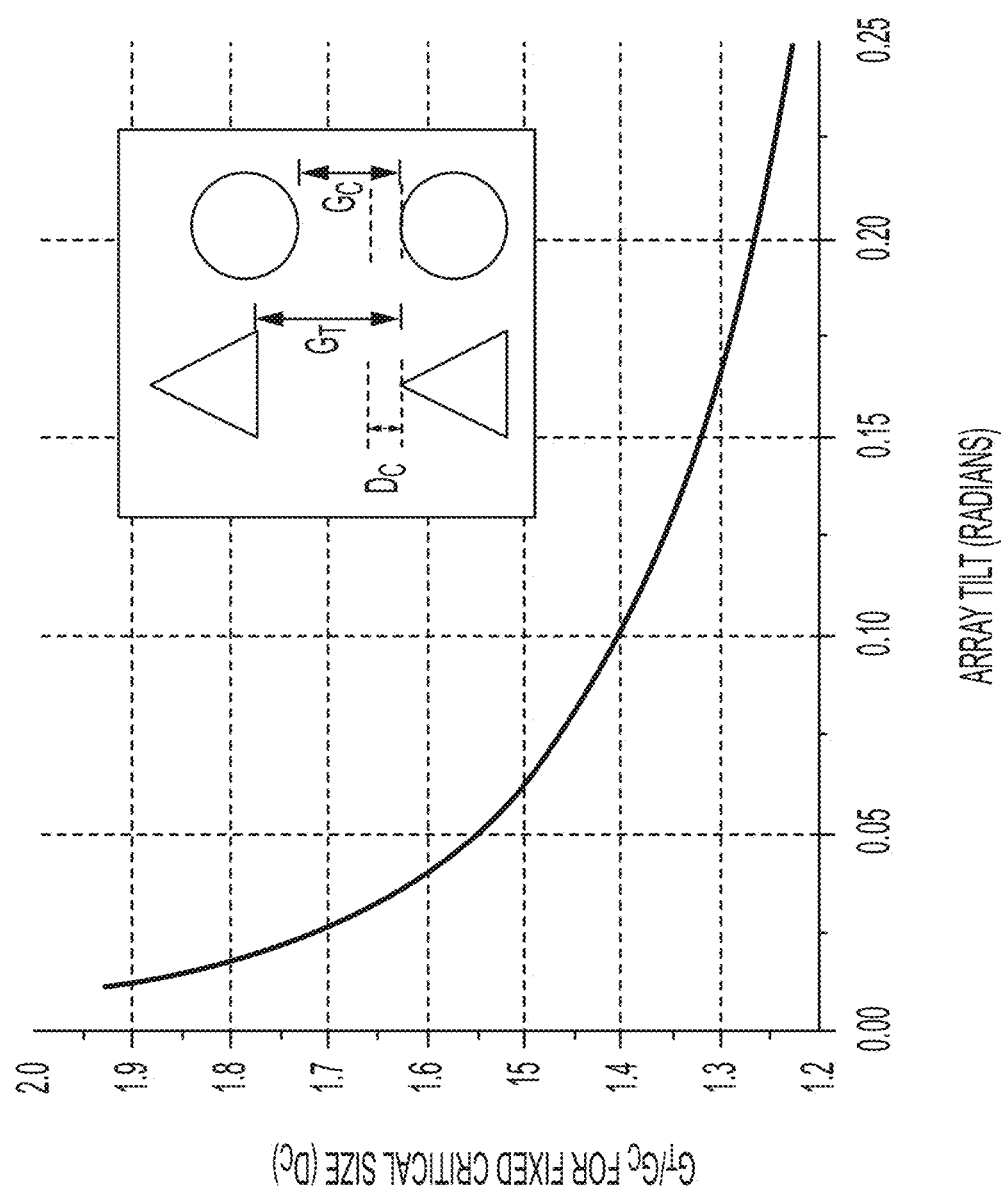
FIG. 8 is a graph illustrating the effect of the tilt angle ("Array Tilt" in FIG. 8) on gap length G. $G_T$ refers to the gap length between triangular posts, and $G_C$ refers to the gap length between round posts.

At the level of flow between two adjacent obstacles under conditions of relatively low Reynold's number, fluid flow can occurs in a laminar fashion. Considering the volumetric flow between two obstacles in hypothetical layers (e.g., modeling the flow by considering multiple adjacent stream tubes of equal volumetric flow between the obstacles, as shown in FIG. 8 of U.S. Pat. No. 7,150,812), the likelihood that fluid in a layer will pass on one side or the other of the next (i.e., downstream) obstacle can be calculable by standard methods (see, e.g., Inglis et al., 2006, Lab Chip 6:655-658). For an ordered array of obstacles offset from the direction of bulk fluid flow, the arrangement of the obstacles can define an array direction corresponding to the direction in which the majority of fluid layers between two obstacles travels. A minority of fluid layers will travel around the downstream obstacle in a direction other than the array direction.

The path that a particle passing between the two obstacles can take can depend on the flow of the fluid in the layers occupied by the particle. Conceptually, for a particle having a size equal to one of the hypothetical fluid layers described in the preceding paragraph, the particle can follow the path of the fluid layer in which it occurs, unless it diffuses to a different layer. For particles larger than a single fluid layer, the particle can take a path corresponding to the majority of the fluid layers acting upon it. Particles having a size greater than twice the sum of the thicknesses of the minority of layers that travel around a downstream obstacle in the direction other than the array direction can be acted upon by more fluid layers moving in the array direction, meaning that such particles will travel in the array direction. This concept is also illustrated in FIGS. 5-11 of U.S. Pat. No. 7,150,812. Thus, there can be a "critical size" for particles passing between two obstacles in such an array, such that particles having a size greater than that critical size can travel in the array direction, rather than in the direction of bulk fluid flow and particles having a size less than the critical size can travel in the direction of bulk fluid flow. Particles having a size precisely equal to the critical size can have an equal chance of flowing in either of the two directions. By operating such a device at a high Peclet number (i.e., such that advective particle transport by fluid layers greatly outweighs diffusive particle between layers), the effects of diffusion of particles between fluid layers can be ignored.

A. Bump Arrays

Described herein are ways of structuring and operating obstacle arrays for separating particles. In some obstacle arrays, obstacles have shapes and are arranged such that the profile of fluid flow through gaps between adjacent obstacles is symmetrical about the center line of the gap. The geometry of the adjacent obstacles can be such that the portions of the obstacles defining the gap are symmetrical about the axis of the gap that extends in the direction of bulk fluid flow. The velocity or volumetric profile of fluid flow through such gaps can be approximately parabolic across the gap, with fluid velocity and flux being zero at the surface of each obstacle defining the gap (assuming no-slip flow conditions) and reaches a maximum value at the center point of the gap. The profile being parabolic, a fluid layer of a given width adjacent to one of the obstacles defining the gap can contain an equal proportion of fluid flux as a fluid layer of the same width adjacent to the other obstacle that defines the gap meaning that the critical size of particles that are 'bumped' during passage through the gap is equal regardless of which obstacle the particle travels near.

In some cases, particle size-segregating performance of an obstacle array can be improved by shaping and disposing the obstacles such that the portions of adjacent obstacles that deflect fluid flow into a gap between obstacles are not symmetrical about the axis of the gap that extends in the direction of bulk fluid flow. Such lack of flow symmetry into the gap can lead to a non-symmetrical fluid flow profile within the gap. Concentration of fluid flow toward one side of a gap (i.e., a consequence of the non-symmetrical fluid flow profile through the gap) can reduce the critical size of particles that are induced to travel in the array direction, rather than in the direction of bulk fluid flow. This can be so because the non-symmetry of the flow profile can cause differences between the width of the flow layer adjacent to one obstacle that contains a selected proportion of fluid flux through the gap and the width of the flow layer that contains the same proportion of fluid flux and that is adjacent the other obstacle that defines the gap. The different widths of the fluid layers adjacent to obstacles define a gap that exhibits two different critical particle sizes. A particle traversing the gap can be bumped (i.e., travel in the array direction, rather than the bulk fluid flow direction) if it exceeds the critical size of the fluid layer in which it is carried. Thus, it is possible for a particle traversing a gap having a non-symmetrical flow profile to be bumped if the particle travels in the fluid layer adjacent to one obstacle, but to be not-bumped if it travels in the fluid layer adjacent to the other obstacle defining the gap.

Particles traversing an obstacle array pass through multiple gaps between obstacles, and have multiple opportunities to be bumped. When a particle traverses a gap having a non-symmetrical flow profile, the particle can be bumped if the size of the particle exceeds the (different) critical sizes defined by the flow layers adjacent to the two obstacles defining the gap. However, the particle can sometimes be bumped if the size of the particle exceeds the critical size defined by the flow layer adjacent to one of the two obstacles, but does not exceed the critical size defined by the flow layer adjacent to the other obstacle. In some cases, particles that do not exceed the critical size defined by the flow layer adjacent to either of the obstacles can not be bumped. There are at least two implications that follow from this observation.

First, in an obstacle array in which the obstacles define gaps having a non-symmetrical flow profile, particles having a size that exceeds the smaller of the two critical sizes defined by the flow layers adjacent to the obstacles can be separated from particles having a size smaller than that smaller critical size. The critical size defined by a gap can be decreased by altering the symmetry of flow through the gap without necessarily decreasing the size of the gap ("G" in FIG. 1). Decreasing gap size can increase the cost and difficulty of producing the array. Conversely, for a given critical size, the size of the gap defining that critical size can be increased by altering the symmetry of flow through the gap. Because smaller gaps are more likely to clog than larger ones, this arrangement can improve the operability of the arrays, allowing greater throughput and lower likelihood of clogging.

Second, in an obstacle array in which the obstacles define gaps having a non-symmetrical flow profile, particles can be separated into three populations: i) particles having a size smaller than either of the critical sizes defined by the flow layers adjacent the obstacles; ii) particles having a size intermediate between the two critical sizes defined by the flow layers adjacent the obstacles; and iii) particles having a size larger than either of the critical sizes defined by the flow layers adjacent the obstacles.

In another aspect, decreasing the roundness of edges of obstacles that define gaps can improve the particle size-segregating performance of an obstacle array. By way of example, arrays of obstacles having a triangular cross-section with sharp vertices can exhibit a lower critical particle size than do arrays of identically-sized and -spaced triangular obstacles having rounded vertices.

Thus, by sharpening the edges of obstacles defining gaps in an obstacle array, the critical size of particles deflected in the array direction under the influence of bulk fluid flow can be decreased without necessarily reducing the size of the obstacles. Conversely, obstacles having sharper edges can be spaced farther apart than, but still yield particle segregation properties equivalent to, identically-sized obstacles having less sharp edges.

In yet another aspect, shaping the obstacles in an obstacle array in such a way that the geometry of the obstacles encountered by fluid flowing through the array in one direction differs (and defines a different critical particle size) from the geometry of the obstacles encountered by fluid flowing through the array in a second direction. For example, fluid flowing through the array illustrated in FIG. 1 in a left-to-right direction encounters and flows around the rounded vertices of the right triangular posts of the array (in this flow direction, the profile of fluid flow through the gaps is asymmetric about the axis of the gaps). However, fluid flowing through the same array in a right-to-left direction encounters and flows around the flat edges of the right triangular posts of the array (in this flow direction, the profile of fluid flow through the gaps is symmetric about the axis of the gaps, being essentially parabolic).

B. Bump Arrays Having Gaps with Asymmetrical Flow Profiles

Described herein are bump array devices that are useful for segregating particles by size. In one embodiment, a device includes a body defining a microfluidic flow channel for containing fluid flow. An array of obstacles is disposed within the flow channel, such that fluid flowing through the channel flows around the obstacles. The obstacles extend across the flow channel, generally being either fixed to, integral with, or abutting the surface of the flow channel at each end of the obstacle.

The obstacles can be arranged in rows and columns, in such a configuration that the rows define an array direction that differs from the direction of fluid flow in the flow channel by a tilt angle ($\epsilon$) that has a magnitude greater than zero. The maximum operable value of $\epsilon$ can be ⅓ radian. The value of $\epsilon$ can be preferably ⅕ radian or less, and a value of 1/10 radian has been found to be suitable in various embodiments of the arrays described herein. The obstacles that are in columns define gaps between themselves, and fluid flowing through the flow channel is able to pass between these gaps, in a direction that is generally transverse with respect to the columns (i.e., generally perpendicular to the long axis of the obstacles in the column and generally perpendicular to a plane extending through the obstacles in the column).

The obstacles can have shapes so that the surfaces (upstream of, downstream of, or bridging the gap, relative to the direction of bulk fluid flow) of two obstacles defining a gap are asymmetrically oriented about the plane that extends through the center of the gap and that is parallel to the direction of bulk fluid flow through the channel. That is, the portions of the two obstacles can cause asymmetric fluid flow through the gap. The result can be that the velocity profile of fluid flow through the gap is asymmetrically oriented about the plane. As a result of this, the critical particle size for particles passing through the gap adjacent to one of the obstacles can be different from the critical particle size for particles passing through the gap adjacent to the other of the obstacles.

A device can be made from any of the materials from which micro- and nano-scale fluid handling devices are typically fabricated, including silicon, glasses, plastics, and hybrid materials. The flow channel can be constructed using two or more pieces which, when assembled, form a closed cavity (preferably one having orifices for adding or withdrawing fluids) having the obstacles disposed within it. The obstacles can be fabricated on one or more pieces that are assembled to form the flow channel, or they can be fabricated in the form of an insert that is sandwiched between two or more pieces that define the boundaries of the flow channel. Materials and methods for fabricating such devices are known in the art.

In some cases, the flow channel can be preferably formed between two parallel, substantially planar surfaces, with the obstacles formed in one of the two surfaces (e.g., by etching the surface to remove material that originally surrounded the non-etched portions that remain as obstacles). The obstacles can have a substantially constant cross-section along their length, it being recognized that techniques used to fabricate the obstacles can limit the uniformity of the cross section.

The obstacles can be solid bodies that extend across the flow channel, in some cases from one face of the flow channel to an opposite face of the flow channel. Where an obstacle is integral with (or an extension of) one of the faces of the flow channel at one end of the obstacle, the other end of the obstacle can be sealed to or pressed against the opposite face of the flow channel. A small space (preferably too small to accommodate any of particles of interest for an intended use) can be tolerable between one end of an obstacle and a face of the flow channel, provided the space does not adversely affect the structural stability of the obstacle or the relevant flow properties of the device.

In some embodiments described herein, obstacles are defined by a cross-sectional shape (e.g., round or triangular).

Methods of imparting a shape to an obstacle formed from a monolithic material are well known (e.g., photolithography and various micromachining techniques) and substantially any such techniques may be used to fabricate the obstacles described herein. The sizes of the gaps, obstacles, and other features of the arrays described herein depend on the identity and size of the particles to be handled and separated in the device, as described elsewhere herein. Typical dimensions are on the order of micrometers or hundreds of nanometers, but larger and smaller dimensions are possible, subject to the limitations of fabrication techniques.

As described herein, certain advantages can be realized by forming obstacles having sharp (i.e., non-rounded) edges, especially at the narrowest part of a gap between two obstacles. In order to take advantage of the benefits of sharp edges, a skilled artisan will recognize that certain microfabrication techniques can be preferable to others for forming such edges. Sharpness of edges can be described in any of a number of ways. By way of example, the radius of curvature of an edge (e.g., the vertex of a triangular post) can be measured or estimated and that radius can be compared with a characteristic dimension of the obstacle (e.g., the shorter side adjacent the vertex of a triangular, square, or rectangular post, or the radius of a round post having a pointed section). Sharpness can be described, for example, as a ratio of the radius of curvature to the characteristic dimension. Using equilateral triangular posts as an example, suitable ratios include those not greater than 0.25, and preferably not greater than 0.2.

In some cases, the number of obstacles that occur in an array is not critical, but the obstacles can be sufficiently numerous that the particle-separating properties of the arrays that are described herein can be realized. In some cases, the precise layout and shape of the array is not critical. In view of the disclosures described herein, a skilled artisan in this field is able to design the layout and number of obstacles necessary to make bump arrays capable of separating particles, taking into account the sizes and identities of particles to be separated, the volume of fluid in which the particles to be separated are contained, the strength and rigidity of the materials used to fabricate the array, the pressure capacity of fluid handling devices to be used with the array, and other ordinary design features.

The obstacles can generally be organized into rows and columns (use of the terms rows and columns does not mean or imply that the rows and columns are perpendicular to one another). Obstacles that are generally aligned in a direction transverse to fluid flow in the flow channel can be referred to as obstacles in a column. Obstacles adjacent to one another in a column can define a gap through which fluid flows. Obstacles in adjacent columns can be offset from one another by a degree characterized by a tilt angle, designated $\epsilon$ (epsilon). Thus, for several columns adjacent to one another (i.e., several columns of obstacles that are passed consecutively by fluid flow in a single direction generally transverse to the columns), corresponding obstacles in the columns can be offset from one another such that the corresponding obstacles form a row of obstacles that extends at the angle $\epsilon$ relative to the direction of fluid flow past the columns. The tilt angle can be selected and the columns can be spaced apart from each other such that $1/\epsilon$ (when $\epsilon$ is expressed in radians) is an integer, and the columns of obstacles repeat periodically. The obstacles in a single column can also be offset from one another by the same or a different tilt angle. By way of example, the rows and columns can be arranged at an angle of 90 degrees with respect to one another, with both the rows and the columns tilted, relative to the direction of bulk fluid flow through the flow channel, at the same angle of $\epsilon$.

One or more portions of two obstacles that define a gap can be shaped in such a way that the portions of the obstacles that are upstream from, downstream from, or bridging (or some combination of these, with reference to the direction of bulk fluid flow through the flow channel) the narrowest portion of the gap between the obstacles are asymmetrical about the plane that bisects the gap and is parallel to the direction of bulk fluid flow. Both for simplicity of fabrication and to aid modeling of array behavior, all obstacles in an array can be identical in size and shape, although this need not be the case. In some cases, all obstacles in an array are not identical in shape. Furthermore, arrays having portions in which obstacles are identical to one another within a single portion, but different from obstacles in other portions can be made.

Asymmetry in one or more portions of one or both of the obstacles defining a gap can lead to increased fluid flow on one side or the other of the gap. A particle can be bumped upon passage through a gap only if the particle exceeds the critical particle size corresponding to the gap. The critical particle size can be determined by the density of fluid flux near the boundaries of the gap (i.e., the edges of the obstacles that define the gap). Increased fluid flow on one side of a gap (i.e., against one of the two obstacles defining the narrowest portion of the gap) can intensify flux density near that side, reducing the size of the particle that will be bumped upon passage through that side of the gap.

In one embodiment of the device, the shape of each of multiple obstacles in a column can be substantially identical and symmetrical about the plane that bisects each of the multiple obstacles. That is, for any one column of obstacles, the geometry encountered by particles traveling in fluid flowing through the gaps between the obstacles in the column can be identical when the fluid is traveling in a first direction and when the fluid is travelling in a second direction that is separated from the first direction by 180 degrees (i.e., flow in the opposite direction).

The geometry encountered by particles traveling in fluid flowing through the gaps between the obstacles in the column can be different when the fluid is traveling in a first direction from the geometry encountered when the fluid is travelling in a second direction that is different from the first direction by 90-180 degrees. In this embodiment, fluid flow can, for example, be oscillated between the two flow directions, and the particles in the fluid can encounter the different obstacle geometry. If these geometrical differences can result in different fluid profiles through the gaps (compare the panels in FIG. 6B, for example), then the gap can exhibit different critical particle sizes in the two directions. If a gap exhibits different critical sizes for flow in the two directions, then the populations of particles that will be bumped upon passing through the gap can differ depending on the direction of flow. This difference in the populations bumped in the two directions can be used to effect segregation of the differently-acting particles.

For example, consider a gap that exhibits a first critical size for bulk fluid flow in one direction, but exhibits a different critical size for bulk fluid flow in a second direction. For fluid flow in the first direction, particles having a size greater than the first critical size can be bumped, and particles having a size less than the first critical size can not be bumped. Similarly, for fluid flow in the second direction, particles having a size greater than the second critical size can be bumped, and particles having a size less than the second critical size can not be bumped. If flow is oscillated between the first and second directions, then particles having a size larger than both the first and the second critical sizes can be bumped in both directions. Similarly, particles having a size smaller than both the first and the second critical sizes can not be bumped in either direction. For these two populations of particles, flow oscillations of approximately equal quantities in both directions can leave these particles substantially at their initial position. However, particles having a size intermediate between the two critical sizes can be bumped when bulk fluid flow is in one direction, but will not be bumped when bulk fluid flow is in the other direction. Thus, when flow oscillations of approximately equal quantities in both directions are performed, these particles can not be left in their initial position, but can instead have been displaced from that original position by an amount equal to (the size of an obstacle+ the gap distance G)×(the number of oscillations). In this way, these particles (the ones having a size intermediate between the two critical sizes) can be segregated from the other particles with which they were initially intermixed.

When the first and second directions differ by 180 degrees (i.e., the flows are in opposite directions), the particles having a size intermediate between the two critical sizes can be displaced at an angle of 90 degrees relative to the direction of oscillating flow.

The behavior of particles in a bump array is not a function of the absolute direction in which the particles (or the fluid in which they are suspended) move, but rather can be a function of the array geometry that the particles encounter. As an alternative to operating a bump array with alternating flow between first and second directions, the same particle-displacing effects can be obtained using flow only in the first direction by increasing the size of the array by two times the number of oscillations, maintaining one portion of the array in its original arrangement, but altering the second portion of the array such that the geometry of the array is identical to the geometry encountered by particles in fluid moving in the second direction in the original array (even though the fluid moves in the first direction only). Using the array illustrated in FIG. 1 by way of example, the same displacement effects on particles can be obtained by two oscillations of flow in this array (i.e., two units of flow left-to-right and two units of flow right-to-left) as can be obtained by four units of left-to-right flow through an array having four times the (left-to-right) length of the array in FIG. 1, so long as two lengths of the array are arranged as shown in FIG. 1 and two lengths of the array are arranged as the mirror image (left-to-right) of the array shown in FIG. 1.

Described herein is a microfluidic device designed to separate objects on the basis of physical size. The objects can be cells, biomolecules, inorganic beads, or other objects of round or other shape. Typical sizes fractionated can range from 100 nanometers to 50 micrometers; smaller or larger sizes can be fractionated. Use of these arrays can involve continuous flows in one direction, and particles can be separated from the flow direction by an angle which is a monotonic function of their size.

By changing the shape of the posts from circles to a shape that is asymmetric about an axis parallel to the fluid flow, functionalities may be added:

1. The critical particle size for bumping may be different depending on which direction a particle moves through the array. This has been experimentally verified with right triangular posts, and extends to arbitrary shapes that are asymmetric about the flow axis.

2. With such designs, the angle of displacement from the fluid flow of particles may be designed not to be monotonic—e.g. peaked at a certain particle size.

Such bump arrays have multiple uses, including all of the uses for which bump arrays were previously known.

The device can be used to separate particles in a selected size band out of a mixture by deterministic lateral displacement. The mechanism for separation can be the same as the bump array, but it can work under oscillatory flow (AC conditions; i.e., bulk fluid flow alternating between two directions) rather than continuous flow (DC conditions; i.e., bulk fluid flow in only a single direction). Under oscillatory flow, particles of a given size range can be separated perpendicularly from an input stream (perpendicular to the alternating flow axis when the alternating flows differ in direction by 180 degrees) without any net displacement of the bulk fluid or net displacement of particles outside the desired range. Thus, by injecting a sample including particles of the given range into an obstacle array and thereafter alternating fluid flow through the obstacle array in opposite directions (i.e., in directions separated from one another by 180 degrees), particles that exceed the critical size in one flow direction but do not exceed the critical size in the other flow direction can be separated from other particles in the sample by the bumping induced by the array. Such particles can be bumped (and follow the array direction) when fluid flows in one direction, but are not bumped (and follow the bulk fluid flow direction) when fluid flows in the opposite direction. Particles that do not exceed the critical size in either flow direction will not be bumped by the array (i.e., will follow the bulk fluid in both directions), and will remain with the sample bolus. Particles that exceed the critical size in both flow directions will be bumped by the array (i.e., will follow the array direction) when fluid flows in one direction, and are also bumped (i.e., will follow the array direction in the opposite direction) when fluid flows in the opposite direction, and will therefore remain with the sample bolus.

Critical particle size can depend on direction of fluid flow. Intermediate sized particles can be made to ratchet up a device under oscillatory flow.

Second, in a continuous flow mode, particles of a desired size can be induced to move to one side of a fluid stream, and particles above or below that size to the other side or not displaced at all. Thus collection of desired particles can be easier. In conventional devices, particles above a desired range are also displaced from the fluid flow to the same side of the flow, so separating the desired from undesired larger ones can be harder. In this embodiment, obstacles defining different critical sizes for fluid flow in opposite directions are employed in two configurations that are mirror images of one another. For example, with reference to FIG. 1, such an array would include right triangular posts arranged as shown in FIG. 1 (i.e., hypotenuse sloping from lower right to upper left and the tilt angle ε extending from the horizontal toward the bottom of the figure) and would also include right triangular posts arranged as they would appear in a mirror held perpendicularly at the right or left side of the array shown in FIG. 1 (i.e., right triangular posts having their hypotenuse sloping from upper right to lower left and the tilt angle ε extending from the horizontal toward the top of the figure). Particle separation achieved by bulk fluid flow in a single direction (i.e., either from left-to-right or right-to-left) through such an array would be equivalent to back-and-forth flow through the array illustrated in FIG. 1. Particles in the selected size range can be bumped toward the top of the array (as shown in FIG. 1), while particles having larger or smaller sizes can remain at the vertical level at which they enter the array (assuming approximately equal numbers of obstacles in each of the two configurations are encountered).

Reduction in critical particle size as a ratio of gap, compared to circular posts, can occur when particles bump off sharp edges. This can allow larger separation angle without fear of clogging the device faster separations.

These developments can reduce the necessary chip area compared to a continuous flow bump array.

A device described herein can be a microfabricated post array constructed using standard photolithography. A single mask layer can be etched into silicon or used to make a template for PDMS molding. Post arrays can be sealed with a PDMS coated cover slip to provide closed channels.

Oscillatory flow operation can require more complicated fluid control drivers and interfaces than continuous flow operation.

Figure 11:
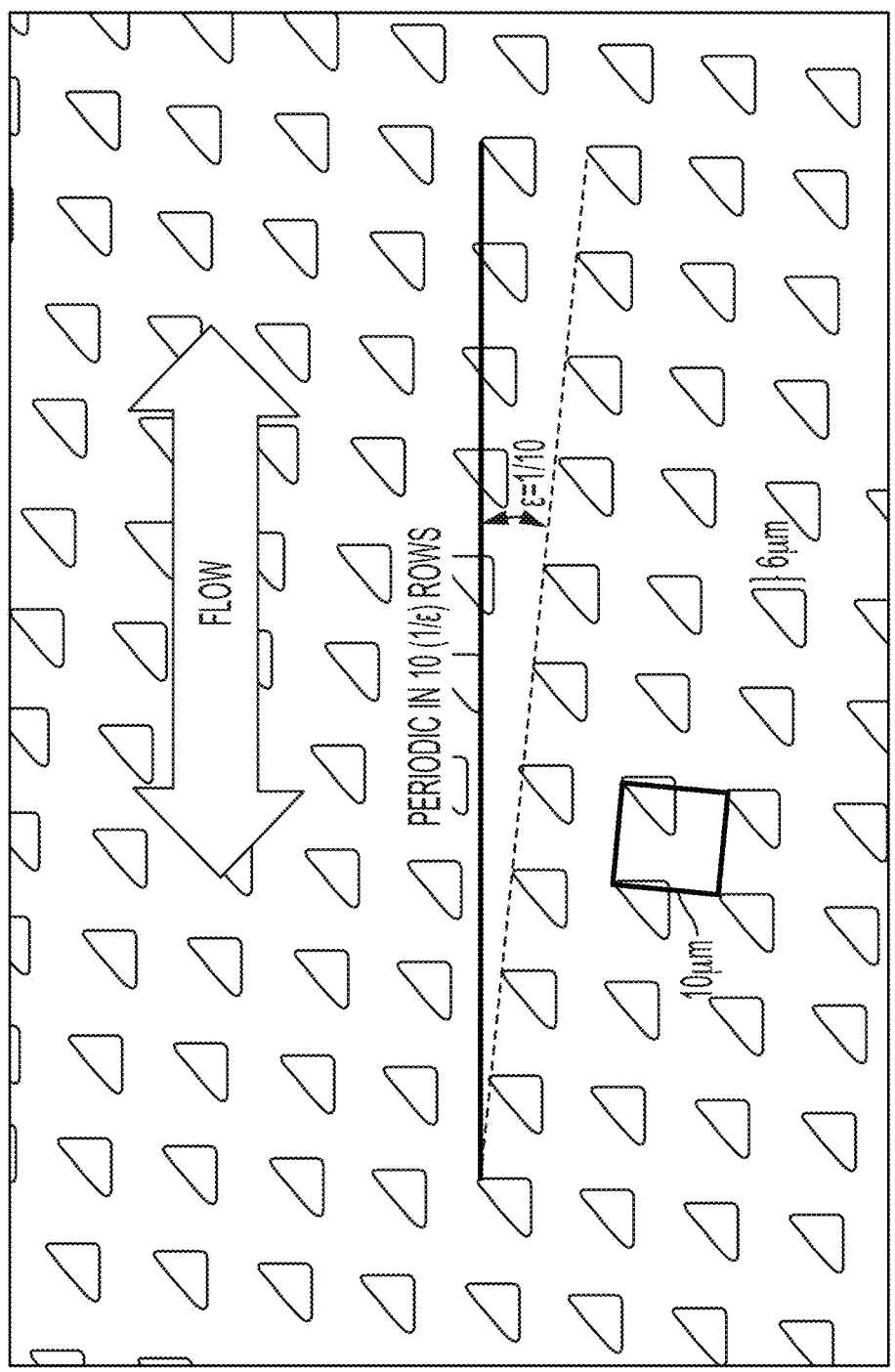
FIG. 11 is an image of an array constructed as described herein.

FIG. 11 is a scanning electron microscope image of posts in an obstacle array of a type described herein. Right isosceles triangular posts, 6 microns on a side, were placed on a square lattice with spacing of 10 microns, giving a gap of approximately 4 microns. The square lattice was tilted 5.71 degrees (0.1 radians) with respect to the device sidewalls to provide necessary asymmetry. Fluid flows along the horizontal axis.

In FIG. 1, the total fluid flux through each gap can be divided into $n=1/\epsilon'$ flow streams (stream tubes), where n is a whole number. Each flow stream can carries equal fluid flux, shown schematically in FIG. 1 for n=3. The stream tubes can be separated by stall lines, each stall line beginning and ending on a post. The stream tubes shift their positions cyclically so that after n rows each streamline returns to its initial position within the gap.

The width of the stream closest a post can determine the critical particle size. If the particle's radius is smaller than the width of the stream, then the particle's trajectory can be undisturbed by the posts and travel in the same direction of the flow. If the particle's radius is larger than the width of the closest stream, then it can be displaced across the stall line and it's trajectory can follow the tilted axis of the array (i.e., the array direction).

The width of the stream closest to the post can be determined by assuming that the velocity profile through a gap is parabolic—the case for fully-developed flow in a rectangular channel. Since each stream can carry equal flux and there are n streams, integrate can be done over the flow profile such that the flux through a stream of width Dc/2 (Dc is the critical diameter of a particle) closest to the post is equal to the total flux through the gap divided by n. That is, the integral from 0 to Dc/2 of u(x) dx (u being a function of flux at any position x within the gap) being equal to 1/n times the integral of u(x) dx over the entire gap.

Thus, the critical particle size can be determined from the flow profile. For the case of circular posts, a parabolic flow profile can closely approximate the flow profile through the gap and the critical particle size can be determined analytically.

Figure 4A:
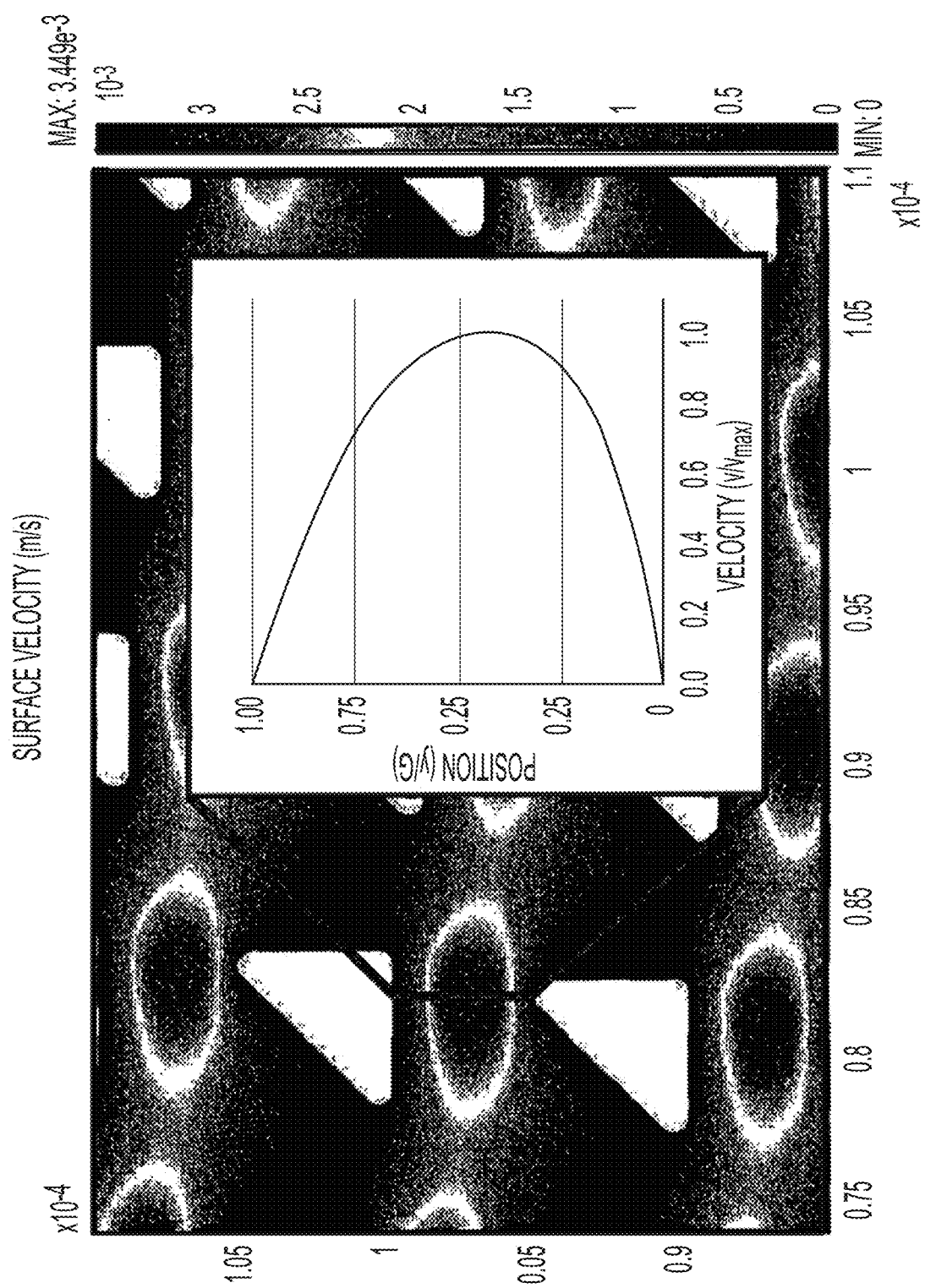
FIG. 4A is a graph showing simulated normalized velocity flow between two right triangular posts.

FIG. 4A shows a numerical simulation of flow profile for an array of triangular posts. In some cases, it cannot be assumed that flow profile through triangular posts is parabolic because of the broken symmetry. Therefore, flow profile through gaps of triangular posts was extracted from numerical simulation (program—COMSOL) of flow through an array with the same size and spacing as devices actually made.

Figure 4B:
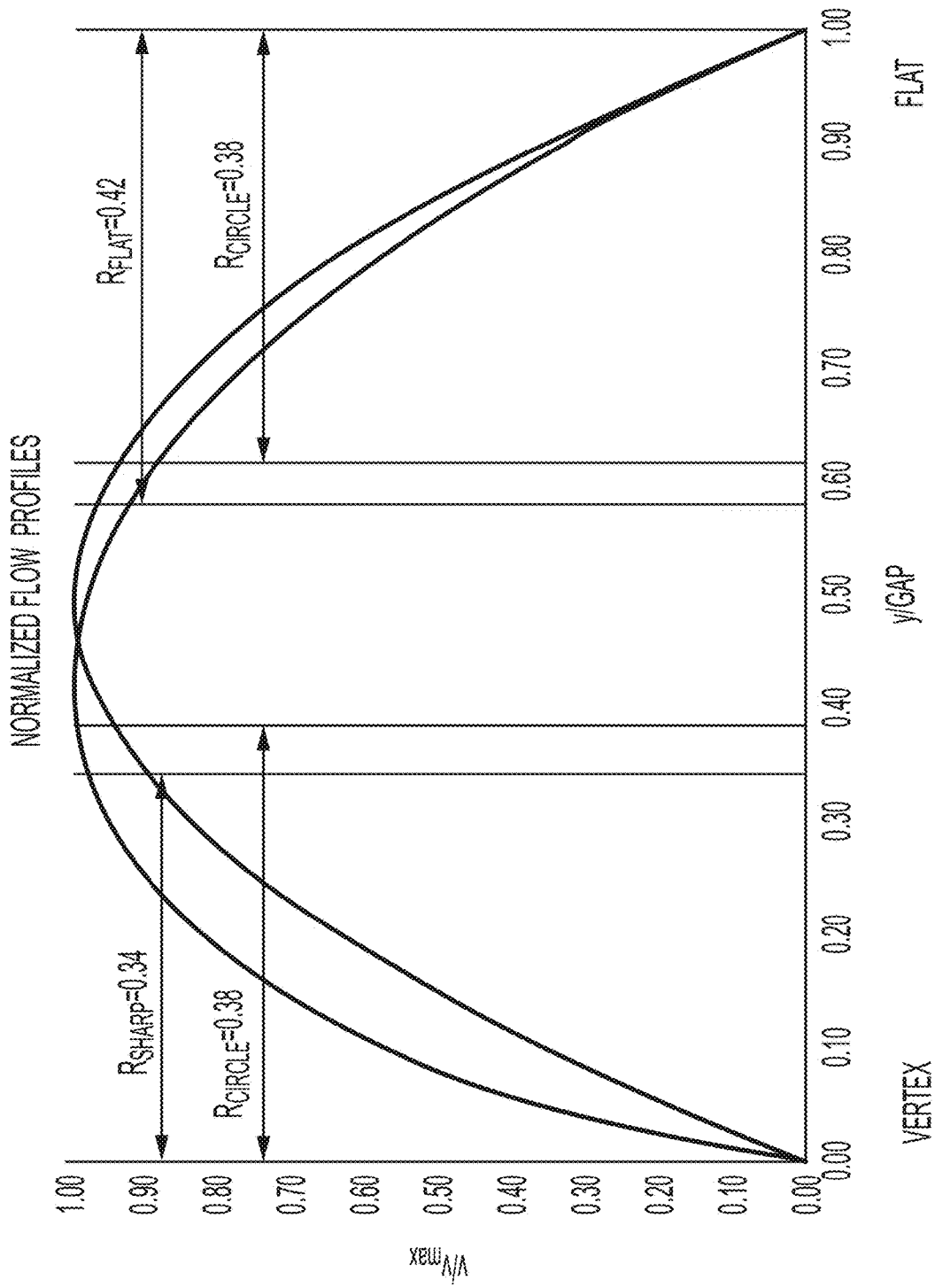
FIG. 4B is a graph showing normalized velocity profiles through gaps between round obstacles (curve that is symmetrical about Y/Gap=0.5) and right triangularly-shaped obstacles in an array of the type shown in FIG. 1 ($\epsilon$=⅓ radian). In these profiles, vertical lines delineate the areas under each curve into thirds, representing three stream tubes of equal volumetric flow. The curve for the round obstacles demonstrates that one third of the volumetric flow between round obstacles occurs in a stream tube that is adjacent to either obstacle and has a width that is 38% of the gap width. The curve for the triangular obstacles demonstrates that one third of the volumetric flow between triangular obstacles occurs in a stream tube that is adjacent to the flat side of one of the two triangular obstacles and has a width that is 42% of the gap width and that an additional one third occurs in a stream tube that is adjacent the sharp side of the pair of triangular obstacles and has a width that is 34% of the gap width.

FIG. 4B illustrates a comparison of velocity flow profiles between circular and triangular posts. Normalized velocity profiles through gaps between triangular and circular posts are shown. As shown, the flow profile for the triangle posts is asymmetric about the center of the gap; more fluid flows along the vertex of the triangle than along the flat edge.

Figure 12:
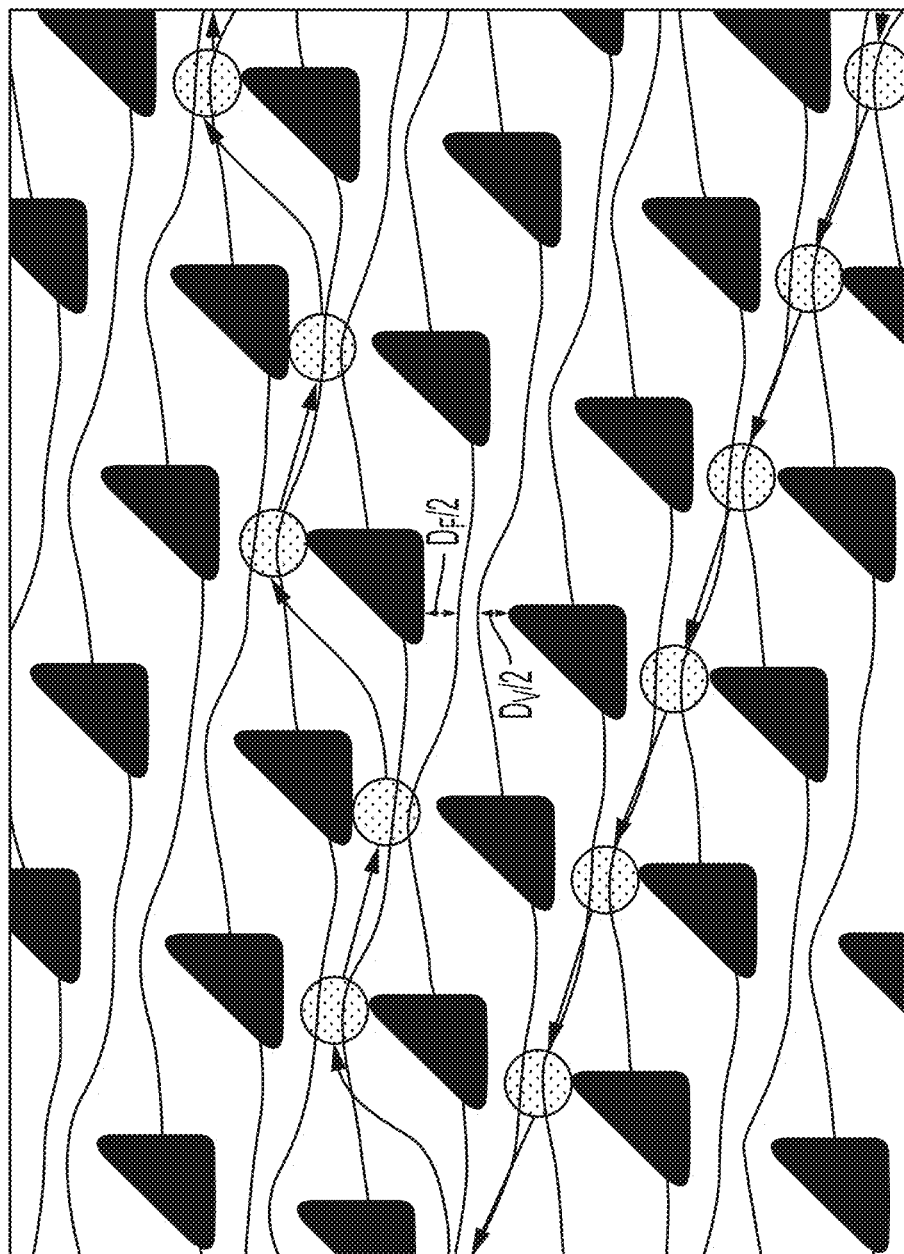
FIG. 12 illustrates particle motion in a ratchet bump array of the type described herein.
Figure 13:
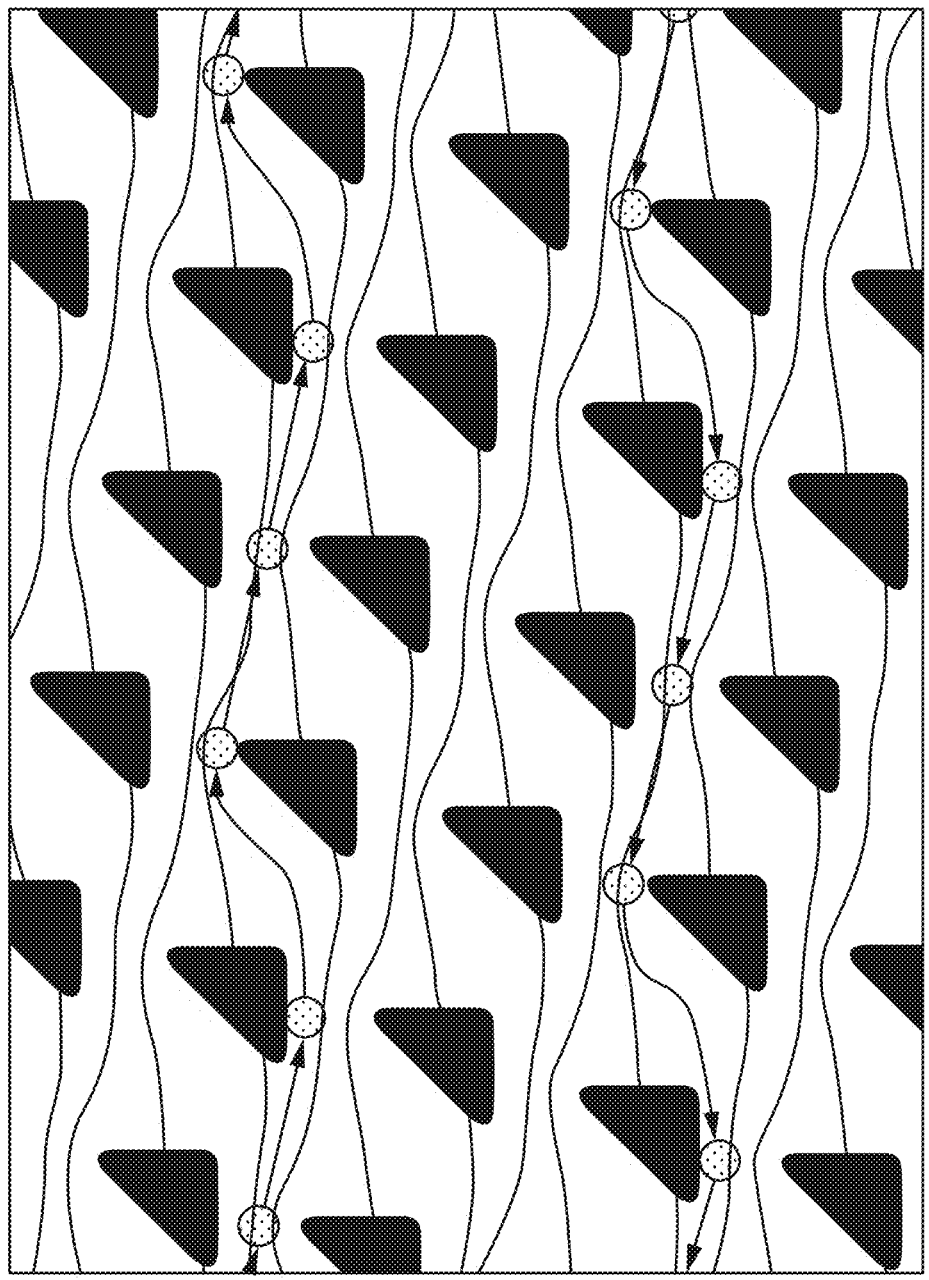
FIG. 13 illustrates particle motion in a ratchet bump array of the type described herein.
Figure 14:
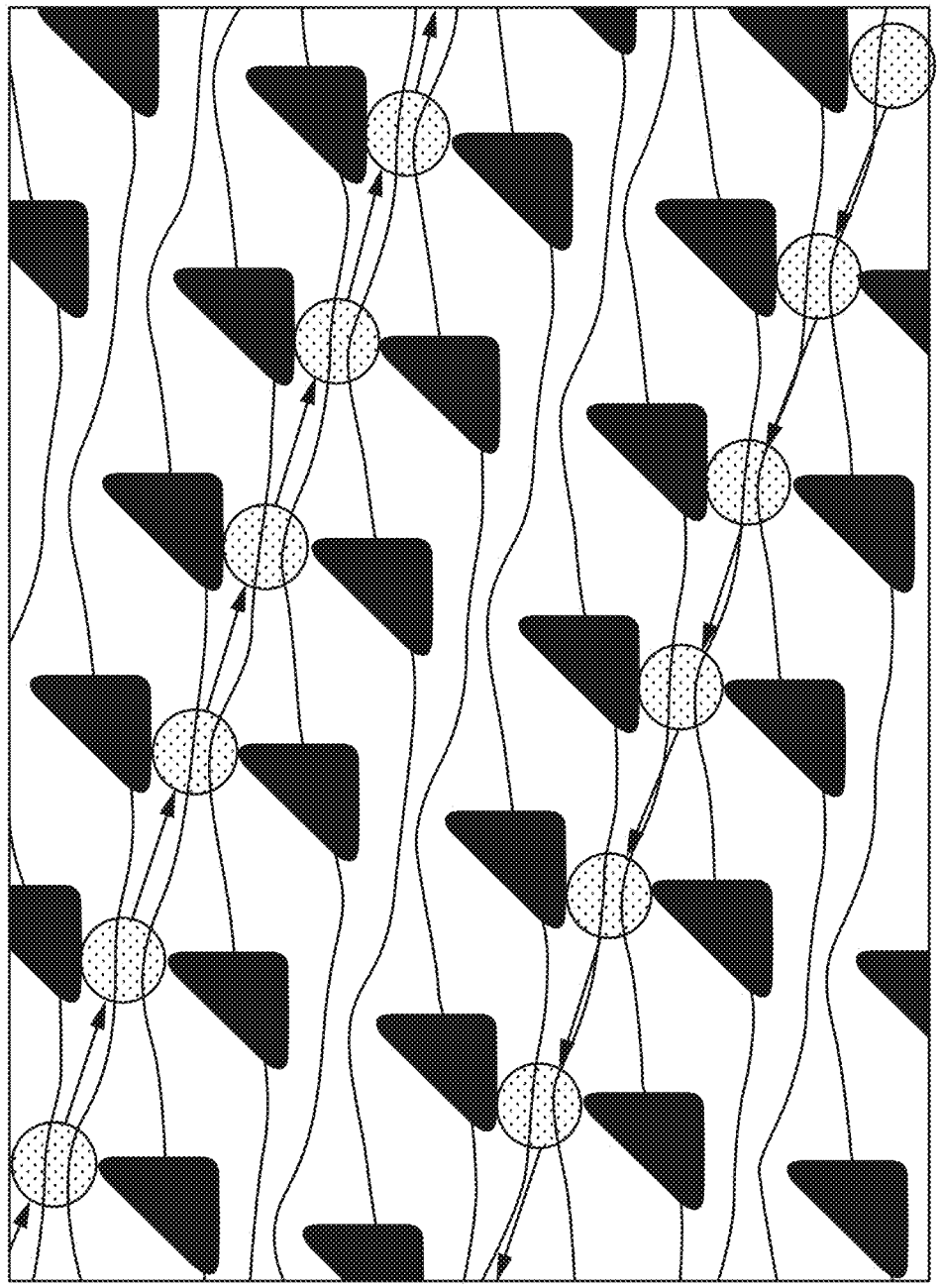
FIG. 14 illustrates particle motion in a ratchet bump array of the type described herein.

FIGS. 12-14 illustrate particle motion in a ratchet bump array of a type described herein. When particles move through the array, the side of the post they interact with depends on which direction they are moving in the array. In this case, when the particles are moving from right-to-left, they bump off the flat edge of the triangular posts. When the particles are moving from left-to-right, they bump off the sharp vertex of the triangular posts. Thus, since the flow profile is asymmetric, it cannot be expected that particles follow the same trajectory when travelling in both directions through the array.

Figure 15:
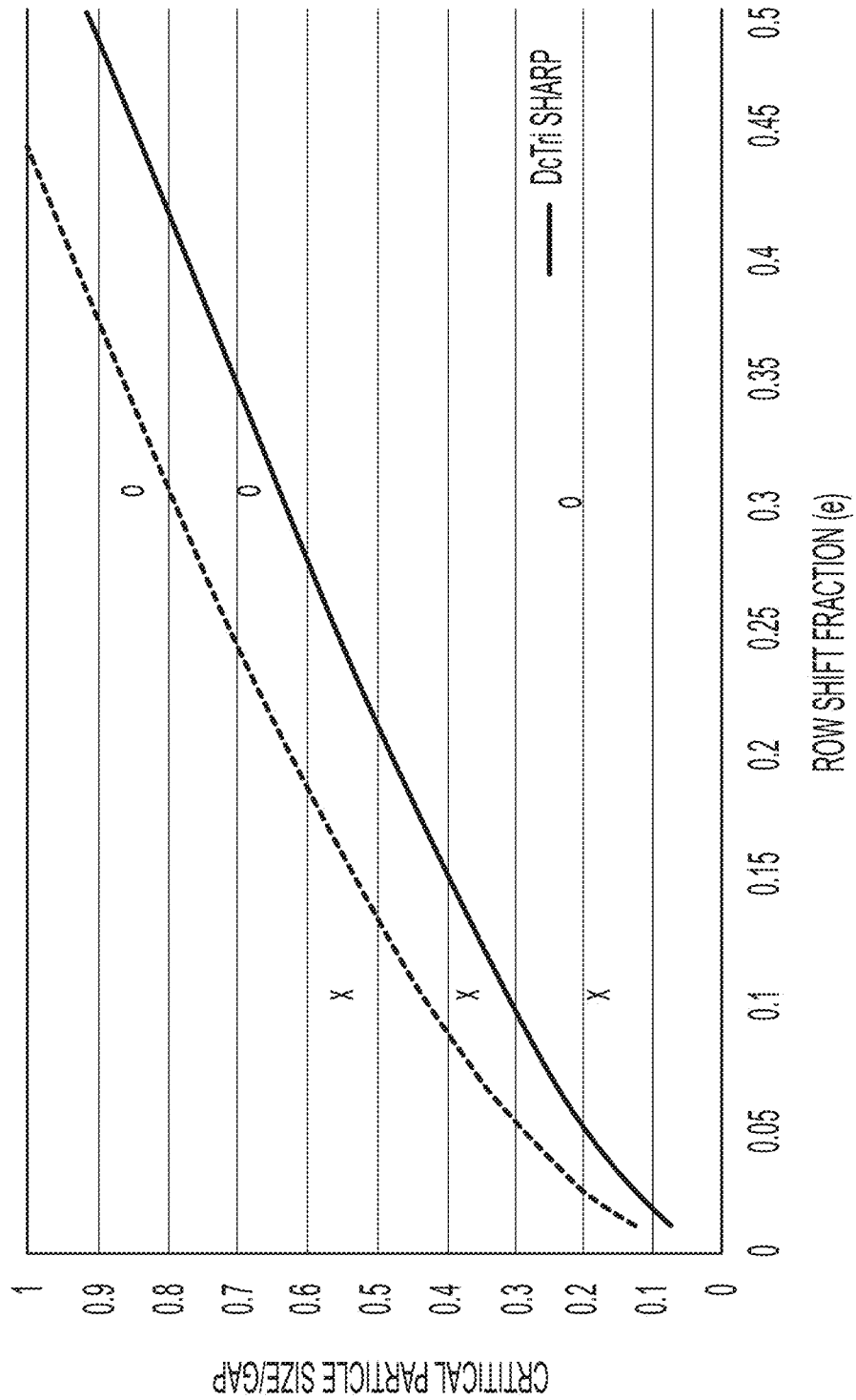
FIG. 15 is a graph comparing the critical size characteristics of round and triangular posts.

Critical Particle Size for Triangular Posts—Employing the same kind of analysis described in the Inglis et al., 2006, Lab Chip 6:655-658, integration can occur over the flow profile to find the width of characteristic streams. However, since the flow profile is asymmetric about the center of the gap, the stream width, and hence the critical particle size can be different depending on which side is examined. As shown in FIG. 4B, the result of the asymmetry introduced by the triangular posts is that the critical particle size can be different depending on which side of the triangular obstacle particles interact with. If they are moving along the sharp vertex, then the critical particle size can be smaller than if they are moving along the flat edge. Critical particle size verus array angle ($\epsilon$) are plotted in FIG. 15 compared to circular posts. The critical particle size for bumping along the sharp vertex of the triangle can be substantially smaller than for that of circular posts or the flat edge. This can allow higher angles of separation to be used without fear of clogging the devices. When the particle diameter is larger than the gap size (G in FIG. 1), there can be substantial risk that the array will become clogged if particle density is high.

Figure 3A:
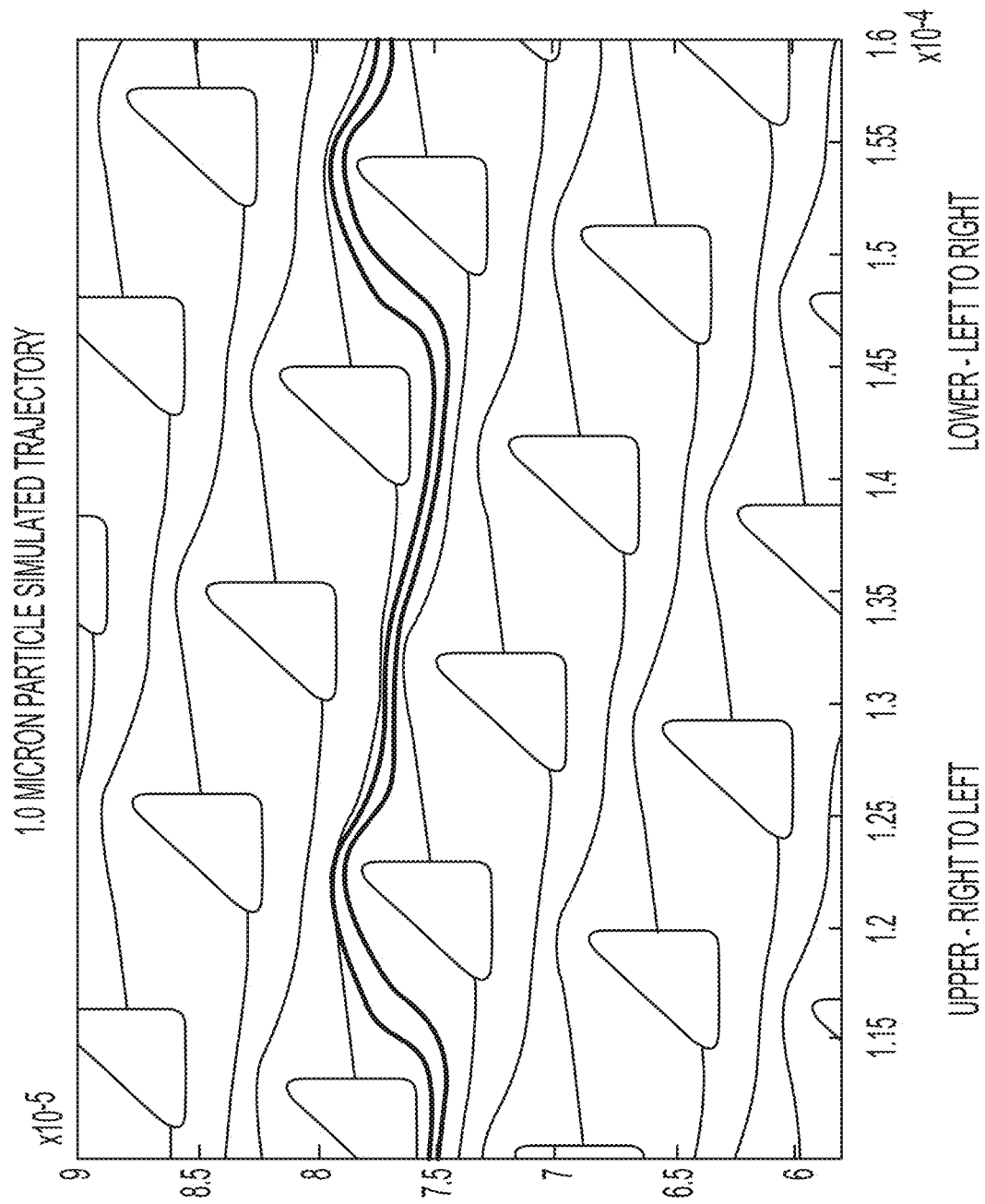
FIGS. 3A, 3B and 3C show simulated trajectories of particles of different sizes moving through an array of triangular posts.
Figure 3B:
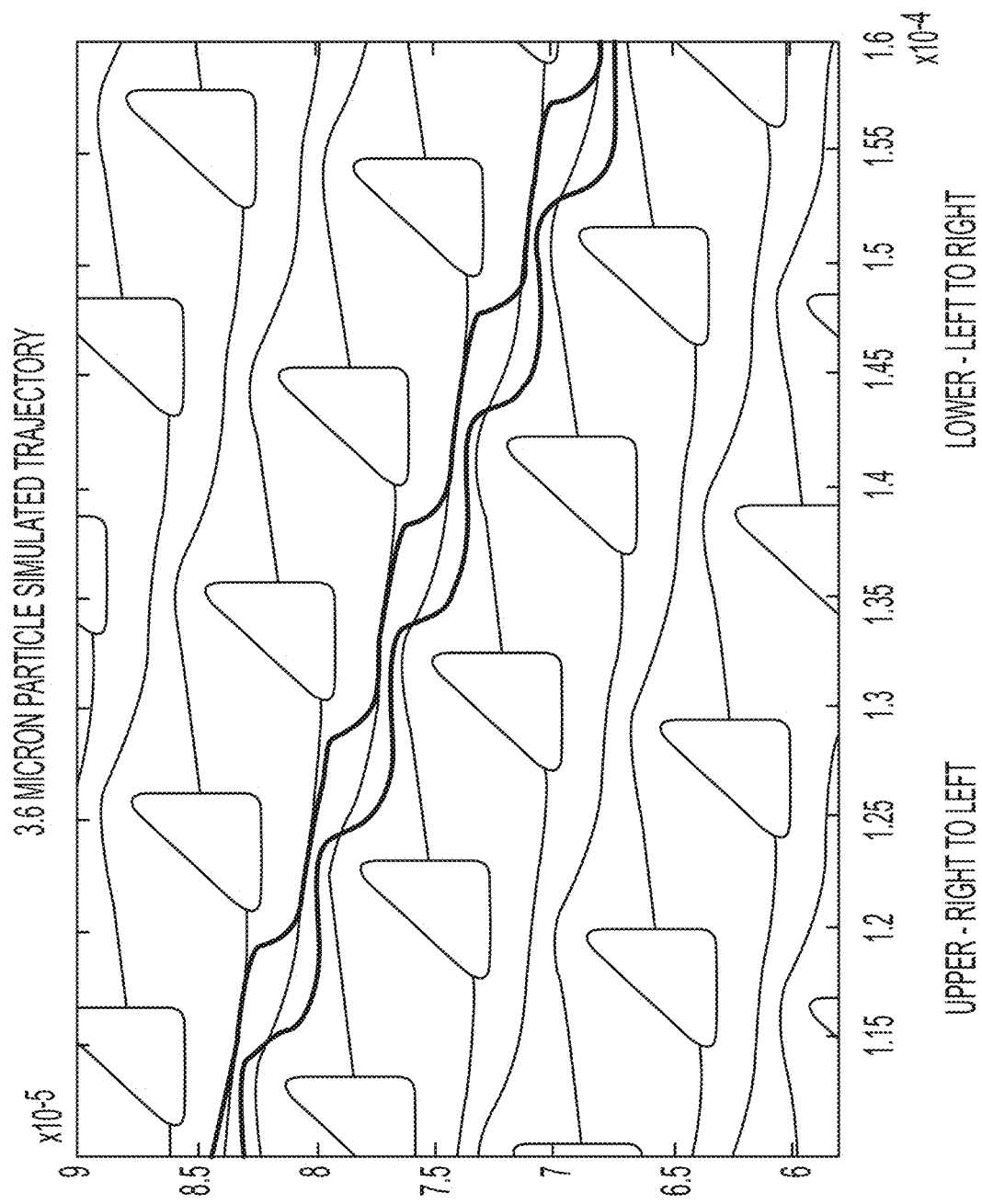
Figure 3C:
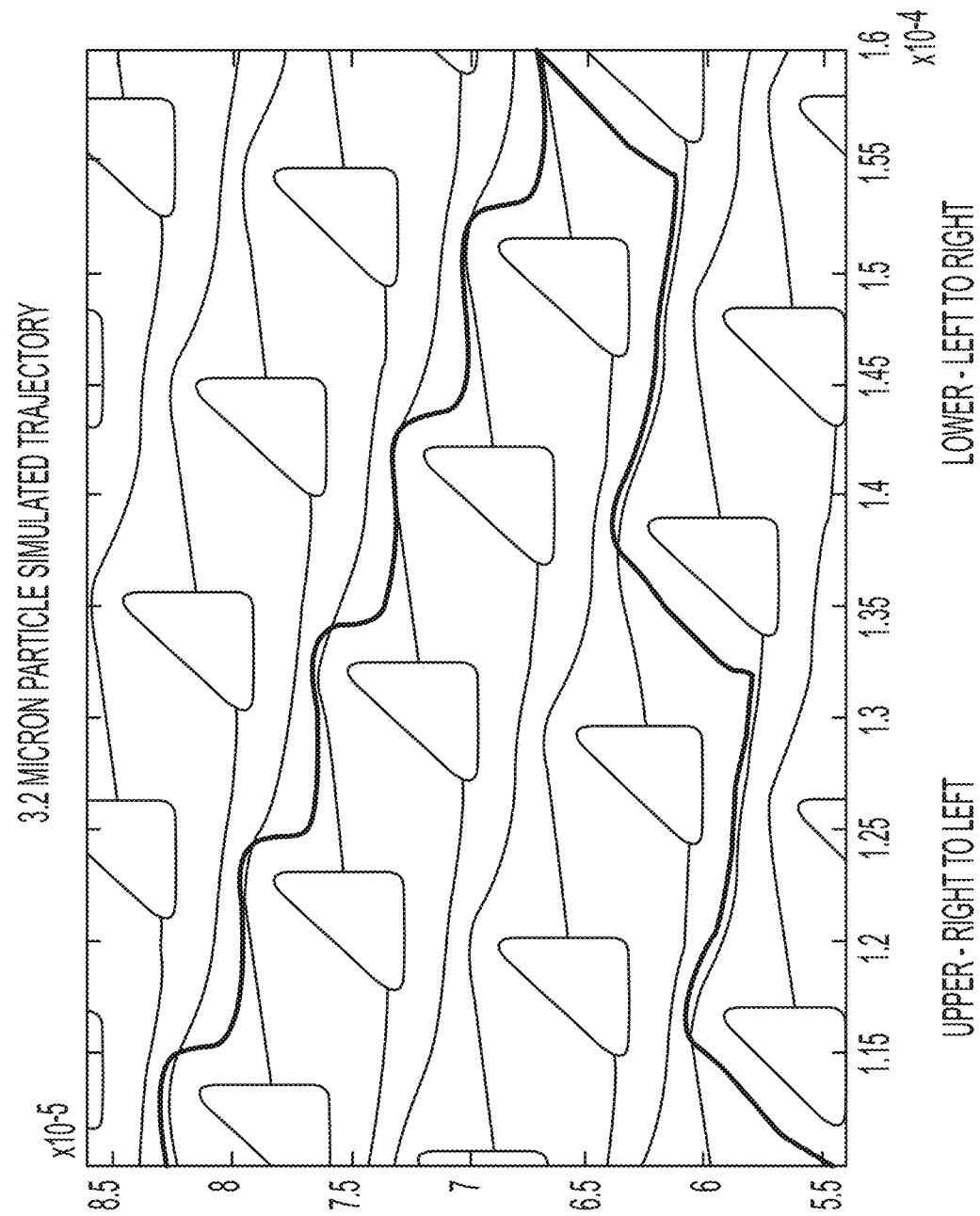

FIGS. 3A-3C illustrate representative particle behavior in a ratchet bump array. For a device constructed as shown in FIG. 11, three representative particles were chosen for this illustration. One particle (illustrated in FIG. 3B) was chosen larger than both critical particle sizes (i.e., larger than the critical particle sizes defined by right-to-left and left-to-right fluid flows). One particle (illustrated in FIG. 3A) was chosen that was smaller than both critical particle sizes. Finally, one particle (illustrated in FIG. 3C) was chosen in the intermediate range, i.e. smaller than the critical particle size ($D_F$ in FIG. 12) along the flat edge, but larger than the critical particle size ($D_V$ in FIG. 12) along the sharp edge. These figures illustrate the behavior of particles that were put into the device and their trajectory under oscillatory flow was observed.

Large Particle (FIG. 3B): Since the particle is larger than the critical particle size along both edges, it follows the array tilt axis (E) in both directions and shows no net displacement under oscillatory flow.

Small Particle (FIG. 3A): Since the particle is smaller than the critical particle size along both edges, it follows the fluid trajectory in both directions and shows no net displacement.

Intermediate Particle (FIG. 3C): When the particle moves to the right, it bumps off the flat edge of the triangular posts. Since it is smaller than the critical particle size ($D_F$), it follows the fluid trajectory. When the particle moves to the left, it bumps off the sharp vertex of the triangular posts. Since it is larger than the critical particle size on this side ($D_v$), it follows the array tilt axis and is displaced upward. As shown, under oscillatory flow, particles in the intermediate range are displaced perpendicular to the direction of the flow. After three cycles of moving back and forth, the bulk fluid has not been displaced, but the particle has moved over 200 microns.

If all three particle types were mixed and placed in a single array under oscillatory flow (i.e., fluid flow oscillating between the right-to-left and left-to-right directions), the intermediate particles would be displaced toward the top of these figures while the small and large particles would have no net motion.

In FIGS. 12-14, representations of intermediate, small, and large particles (respectively) were overlaid on top of numerical simulation of stream tubes to show motion of particles more clearly. $n=1/\epsilon$ was chosen to be 3 to allow periodicity to be seen more easily.

When intermediate particles (FIG. 12) travel along the sharp edge, they bump as expected. However, when the particles travel along the flat edge, their motion can be different from that of the small particles. When they perform their characteristic zig to continue in the same direction of the fluid, they are too large to stay in that stream that is close to the sharp vertex and they are displaced across the first stall line. The result is that their motion is periodic in two rows instead of three. With any other tilt angle, the motion can be similar and the periodicity is n−1. The result of this n−1 periodicity is that the intermediate sized particles are actually displaced against the axis tilt angle. Thus a mixture of large, small and intermediate particles will be separated into three streams. Small particles will go straight through (see FIG. 13). Large particles will follow the array tilt axis (see FIG. 14). Intermediate particles will follow a separate path that is dependent on the post geometry.

The applications for which devices described herein are useful include the same ones described in the Huang patent (U.S. Pat. No. 7,150,812): biotechnology and other microfluidic operations involving particle separation.

Continuous-flow fractionation of small particles in a liquid based on their size in a micropost "bump array" by deterministic lateral displacement was demonstrated previously (e.g., Huang et al., 2004, Science 304:987-990). A ratchet bump array described herein can possess all the same advantages of the previous work, but can add two new functionalities:

First, the devices can be used to separate particles in a selected size band out of a mixture by deterministic lateral displacement under oscillatory flow (AC conditions) rather than continuous flow (DC conditions). Under oscillatory flow, particles of a given size range can be separated perpendicularly from an input stream (perpendicular to the AC flow axis) without any net displacement of the bulk fluid or particles outside the desired range.

Second, in continuous flow mode, the device can exhibit trimodal behavior. Particles of a desired size range can be induced to move to one side of a fluid stream, and particles above or below that size to the other side or not displaced at all. Thus collection of these desired particles may be easier. In conventional devices, the devices were bimodal and all particles above a desired size range are displaced from the fluid flow to the same side of the flow, so separating the desired from undesired larger ones can require multiple stages, whereas the ratchet bump array can require only one.

As used herein, each of the following terms can have the meaning associated with it in this section.

The terms "bump array" and "obstacle array" are used synonymously herein and can describe an ordered array of obstacles that are disposed in a flow channel through which a particle-bearing fluid can be passed.

A "substantially planar" surface can be a surface that has been made about as flat as a surface can be made in view of the fabrication techniques used to obtain a flat surface. In some cases, no fabrication technique will yield a perfectly flat surface. So long as non-flat portions of a surface do not significantly alter the behavior of fluids and particles moving at or near the surface, the surface can be considered substantially planar.

In a bump array device, "fluid flow" and "bulk fluid flow" can be used synonymously to refer to the macroscopic movement of fluid in a general direction across an obstacle array. These terms do not take into account the temporary displacements of fluid streams for fluid to move around an obstacle in order for the fluid to continue to move in the general direction.

In a bump array device, the tilt angle $\epsilon$ can be the angle between the direction of bulk fluid flow and the direction defined by alignment of rows of sequential (in the direction of bulk fluid flow) obstacles in the array. This angle is illustrated in FIGS. 1, 6, and 11, for example.

In a bump array device, the "array direction" can be a direction defined by the alignment of rows of sequential (in the direction of bulk fluid flow) obstacles in the array.

A "critical size", or "predetermined size" of particles passing through an obstacle array can be a parameter that describes the size limit of particles that are able to follow the laminar flow of fluid nearest one side of a gap through which the particles are travelling when flow of that fluid diverges from the majority of fluid flow through the gap. Particles larger than the critical size can be 'bumped' from the flow path of the fluid nearest that side of the gap into the flow path of the majority of the fluid flowing through the gap. In a bump array device, such a particle can be displaced by the distance of (the size of one obstacle+ the size of the gap between obstacles) upon passing through the gap and encountering the downstream column of obstacles, while particles having sizes lower than the critical size (or predetermined size) will not necessarily be so displaced. When a profile of fluid flow through a gap is symmetrical about the plane that bisects the gap in the direction of bulk fluid flow, the critical size can be identical for both sides of the gap; however when the profile is asymmetrical, the critical sizes of the two sides of the gap can differ. When assessing a non-spherical particle, its size can be considered to be the spherical exclusion volume swept out by rotation of the particle about a center of gravity in a fluid, at least for particles moving rapidly in solution The size characteristics of non-spherical particles can be determined empirically using a variety of known methods, and such determinations can be used in selecting or designing appropriate obstacle arrays for use as described herein. Calculation, measurement, and estimation of exclusion volumes for particles of all sorts are well known.

A particle can be "bumped" in a bump array if, upon passing through a gap and encountering a downstream obstacle, the particle's overall trajectory follows the array direction of the bump array (i.e., travels at the tilt angle $\epsilon$ relative to bulk fluid flow). A particle is not bumped if its overall trajectory follows the direction of bulk fluid flow under those circumstances. Conceptually, if flow through a gap is visualized as being composed of multiple individual layers of fluid (i.e., stream tubes, if thought of in a cross-section of fluid flowing through the gap), a particle can be "bumped" if the particle is displaced by a post out of its incident flow tube into an adjacent flow tube as it traverses a gap bounded by the post.

"The direction of bulk fluid flow" in an obstacle array device can refer to the average (e.g., macroscopic) direction of fluid flow through the device (i.e., ignoring local flow deviations necessitated by flow around obstacles in the fluid channel).

C. A Deterministic Microfluidic Ratchet

This example describes a microfluidic device in which the trajectory of particles within a certain size range varies with the direction the particles move through the device. This ratcheting effect can be produced by employing triangular rather than the conventional circular posts in a deterministic lateral displacement device where an array of posts selectively displaces particles as they move through the array. This effect can then be used to demonstrate a fractionation technique where particles can be separated from a fluid plug without any net motion of the original fluid plug. The underlying mechanism of this method can be based on an asymmetric fluid velocity distribution through the gap between posts.

Microfluidic devices, such as those used in "lab on a chip" applications, can operate at low Reynolds number ("low" Reynolds number refers to Reynolds number not greater than 1, and preferably smaller, such as 0.1, $10^{-3}$, or smaller). In this regime, the fluid flow through an arbitrary geometry can be considered to be time-invariant; reversing the applied pressure gradient that drives the fluid will reverse the flow field because inertial effects are negligible. At high Peclet number ("high" Peclet number can refer to Peclet number greater than 1, and preferably much greater, such as 10, 100, or more), this can be extended to say that diffusive effects can be ignored and objects in the fluid will deterministically flow along a stream tube unless some other interaction, such as displacement by steric repulsion from a channel wall, disrupts their path and moves them to an adjacent stream tube. The degree to which the particle trajectory is shifted from its original path depends directly on its size; larger particles can be displaced farther than smaller particles and can consequently follow different stream tubes as they progress through the device. This phenomenon, which can be called deterministic lateral displacement, has been used in several schemes to perform microscale particle separations.

A "bump array" can be a microfluidic device that relies on deterministic lateral displacement to separate particles with high resolution. This device can rely on asymmetric bifurcation of fluid streams in a post array that is tilted at an angle ε (epsilon; typically on the order of 0.1 radians) with respect to the direction of the overall fluid flow. The fluid flowing through a gap splits around a post in the next row, with 1/ε of the fluid going through the gap on one side of the next post, while the other ε of fluid goes around the other side of the next post. As a result, the fluid motion can be characterized by 1/ε streams that cycle through positions in the gap, but travel straight on average. If a particle suspended in the fluid is small compared to the width of a stream in a gap, the posts will not affect it as it moves through the array and it will travel straight with the fluid flow. However, if the particle is large relative to the width of a stream, it can be displaced into an adjacent stream when the stream it occupies is nearest a post as it moves through a gap. Because of the cyclical way the streams move through gaps, this displacement or "bump" can occur at every row and the particle will travel at an angle with respect to the fluid and other small particles. With a sufficiently long device, significant separation can be obtained between large and small particles.

Figure 2:
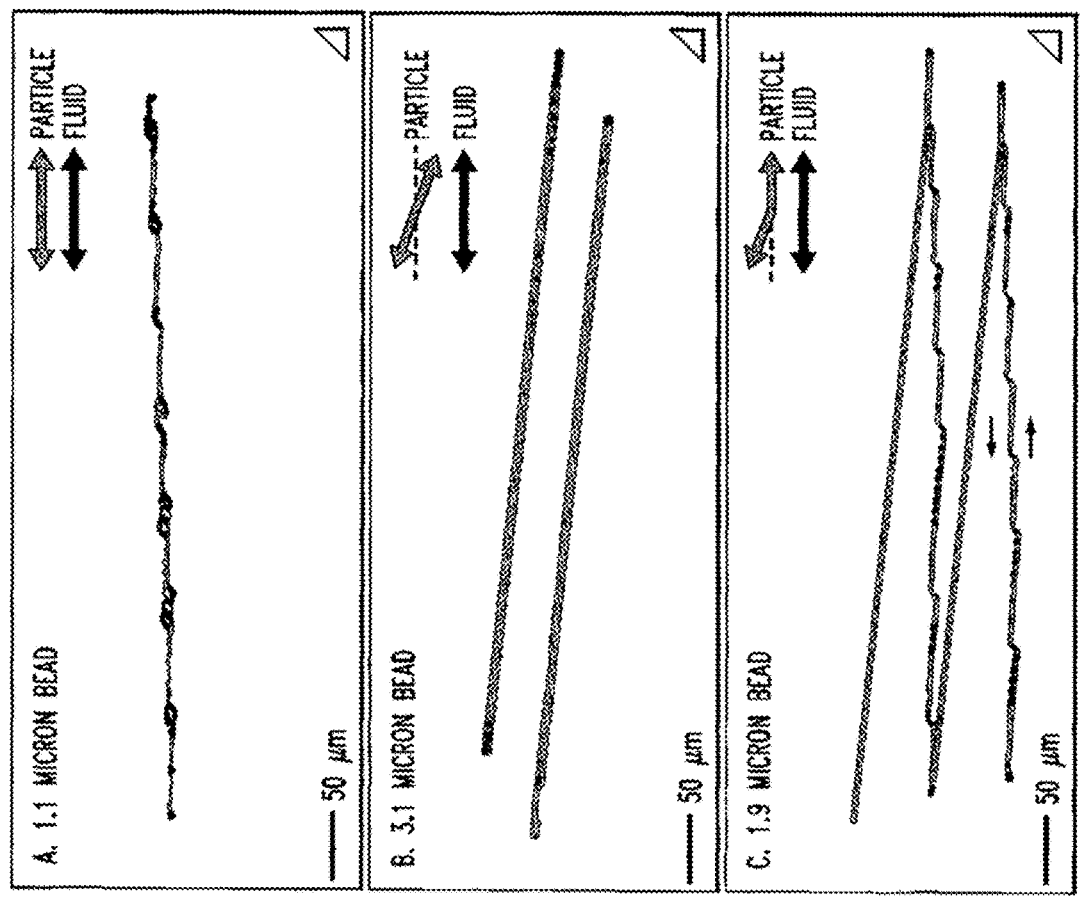
FIG. 2, in panels A, B, and C, shows trajectories of spherical polystyrene beads of three different sizes in an array of the type shown in FIG. 1 as the direction of fluid flow is cycled back and forth twice. The orientation of the right triangular posts is denoted in the lower right of each figure. Right isosceles triangles are 6 microns on a side with post to post separation of 10 microns and a tilt angle of 5.71 degrees (0.1 radian). Particle sizes are 1.1 microns in panel A, 3.1 microns in panel B, and 1.9 microns in panel C. Particles shown panels A and B retrace their paths when the direction of the fluid is switched, with the particles in panel A generally following the fluid direction in each fluid flow direction and the particles in panel B generally following the array direction in each fluid flow direction. By contrast, the trajectory of the particles shown in panel C varies with the direction of the fluid flow. In panel C, small arrows indicate the direction of the fluid along the particle path; the particles generally follow the fluid direction when the fluid flow direction is left-to-right and generally follow the array direction when the fluid flow direction is right-to-left.

FIG. 2A shows a fluorescent time-lapse image of a small particle (1.1 micron diameter polystyrene bead) flowing through such an array at a typical speed of 100 microns/sec. As the particle moves forward, it takes many small steps parallel to the array axis as it moves through, followed by one larger step perpendicular to the motion of the fluid (in what we refer to as "zig-zag mode"), so that the overall motion is to follow the plug of fluid which originally contained the particle. In taking the image of FIG. 2A, the fluid flow was cycled back and forth (by reversing the pressure) twice. The particle retraced its path, as expected from flows at low Reynolds and high Peclet number in a deterministic device not relying on diffusion.

FIG. 2B shows a similar image but for a larger particle (3.1 microns). In this case the particle clearly follows the array axis (i.e., travels in the array direction) and not the fluid flow. Because the particle is displaced from its flow path by the posts in each row, this can be referred to as "bumping mode." This difference in flow direction as a function particle size can be exploited to make fractionation devices for polystyrene beads as well as biological particles. As in FIG. 2A, the time lapse image shows the path of the particle over two cycles of flowing forward and back, and again the path of the particles is reversible (i.e., the particles end up where they began).

FIG. 2C shows the same experiment in the same array for a particle of intermediate size (1.9 microns). The results are very different from those shown if FIGS. 2A and 2B. This particle "zig-zags" when going to the right (i.e., moving from left-to-right) to follow the fluid flow but "bumps" when going to the left to follow the post array axis. Its path is not reversed when the fluid flow direction is reversed, with the net result that such particles are separated from a plug of fluid in a perpendicular direction when the fluid is subjected to an oscillatory flow.

The displacement of a particle off of a post can be an inherently irreversible interaction, but particle trajectories in a circular post bump array are ostensibly reversible because of symmetry. There is no controversy in this statement for small particles which follow the fluid because the fluid flow must be reversible in the low Reynolds number regime (typical Re 10e-3 for fluid velocity 100 microns/sec and length scale 10 microns). However, large particles do not follow the fluid; instead, they are displaced off posts by steric repulsion, so even though the fluid may reverse direction, the trajectory of particles which interact with the posts will not necessarily be reversible unless their interaction with the posts is symmetric with the direction of the fluid. In the schematic in FIG. 3A, particles moving to the left are displaced downward by the top row of posts while particles moving to the right are displaced the same amount by the bottom row of posts. However, if the image is rotated 180 degrees, which is analogous to switching the direction of the fluid, the situation is exactly switched, so the result must be the same in either direction. This rotation works because both the lattice points and post shape are invariant under 180 degree rotation. As a result, both large and small particles in bump array with a circular posts can retrace their steps if the flow is switched back and forth.

Numerical simulations showed that the velocity profile through a gap between triangular posts was shifted towards the side of the gap with the vertex. The fluid velocity profile through a gap between posts depends strongly on the local geometry at the gap. For the case of the triangular posts presented here, where there is a sharp vertex on the bottom and a flat edge on the top, a significant deviation from the parabolic flow profile used to describe pressure-driven flow through circular posts should be expected. FIG. 4A shows a numerical simulation of the fluid velocity in an array like that used to produce the particle trajectories in FIG. 2, along with a cross section of the velocity profile across the gap. The line was placed across the smallest spacing between posts corresponds with the narrowest stream widths where crossing stall lines is most likely to occur. The vertices of the triangle were rounded off with a curvature of 500 nm to approximate the rounding off of a sharp point that results from optical lithography. It was found that the flow profile was invariant under changes in the array tilt so this flow profile can be assumed to be the general flow profile for triangular posts arranged in this way.

FIG. 4B shows a comparison between the flow profiles of triangular and circular posts. For round posts, the profile is nearly parabolic as expected for Poiseuille flow through an infinitely long one-dimensional channel. For triangular posts, however, the flow profile is biased towards the sharp triangular corner pointing up into the flow stream. In other words, the streams bunch closer together near this vertex and the critical particle size for a particle to be bumped across a stall line is smaller than it would be for an array with the same gap size but with round obstacles. Along the flat edge, the opposite is true. Because the fluid travels preferentially along the vertex, the width of the stream along the flat edge is wider than for circular posts. The effect of the triangular posts is to create two separate critical particle sizes, one for moving along the vertex of the triangle and another for moving along the flat edge. Therefore, particles in between these two critical particle sizes can exhibit different behavior depending on which direction they are moving through the array. To show this, a technique used by Inglis et al., 2006, Lab Chip 6:655-658 was employed to estimate the critical particle size for circular posts by using the extracted velocity profile instead of the parabola assumed for circular posts.

Figure 5:
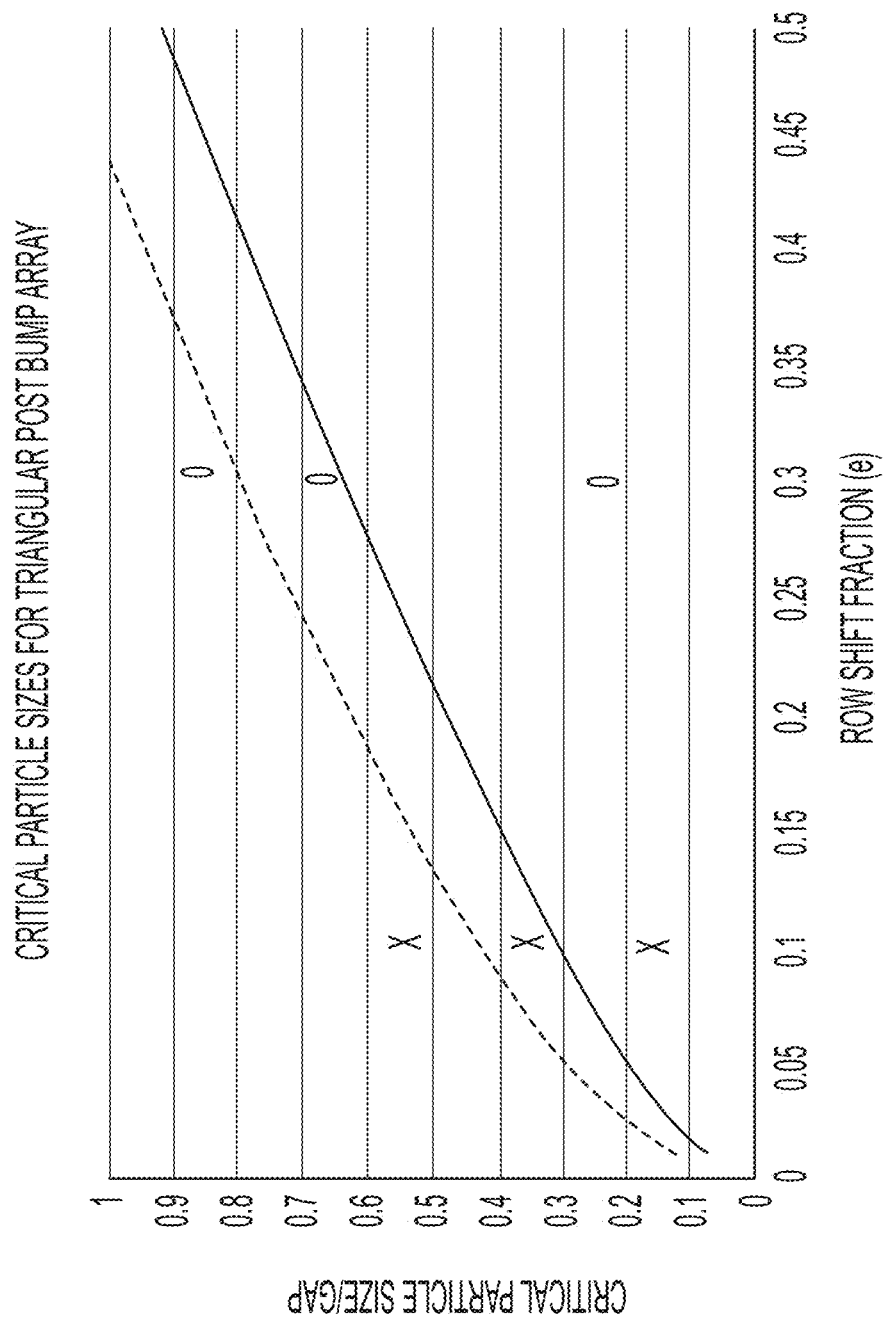
FIG. 5 is a graph of predicted critical diameter versus the array tilt angle ($\epsilon$) for arrays of triangular (lower line) and circular (upper line) obstacles.

FIG. 5 shows this calculation of the critical particle size as a ratio of the gap for the vertex and flat of the triangle as well as for circular posts versus array tilt angle. The particles shown in figure two are shown as circles on the plot. They show good agreement with the predicted behavior. The 1.1 micron bead is smaller than both critical particle sizes so it travels with the fluid in both directions and shows no net displacement when the fluid direction is cycled. The 3.1 micron particle is bigger than both critical particle sizes so it is displaced along the array axis in both directions and shows no net displacement when the fluid direction is cycled. The 1.9 micron particle is in between the two critical particle sizes so it travels with the fluid when it moves along the flat edge of the triangle and with the array axis when it moves along the vertex of the triangle. As a result, it shows a net displacement when the fluid flow is cycled. This is characteristic of a ratcheting behavior. With no net displacement of the fluid, particles in the intermediate range of an array show a net displacement after several fluid flow oscillations. This ratchet differs from other ratchets in that the ratcheting motion does not occur along the axis of the applied force corresponding to fluid flow in either direction. Rather, it is perpendicular to the motion of the fluid.

D. Bump Array Employing Triangular Posts

This example describes microfluidic arrays which sort particles based on size according to the deterministic lateral displacement method, by using triangular posts instead of round posts. When triangular posts are used rather than round posts, and the triangular posts are properly oriented (i.e., such that the surfaces defining the gap are asymmetric), the critical size is decreased for a given gap size between the posts. This is because the different post geometry on either side of the gap causes an asymmetric flow profile through the gap, with flux shifting towards the vertex of the triangle. This shift in fluid flux reduces the width of the stream that determines the critical particle size. In this example, both experiment and modeling are used to show that changing the post shape from circular to triangular results in several practical advantages over similar arrays with circular posts including increased dynamic range and throughput.

Figure 6A:
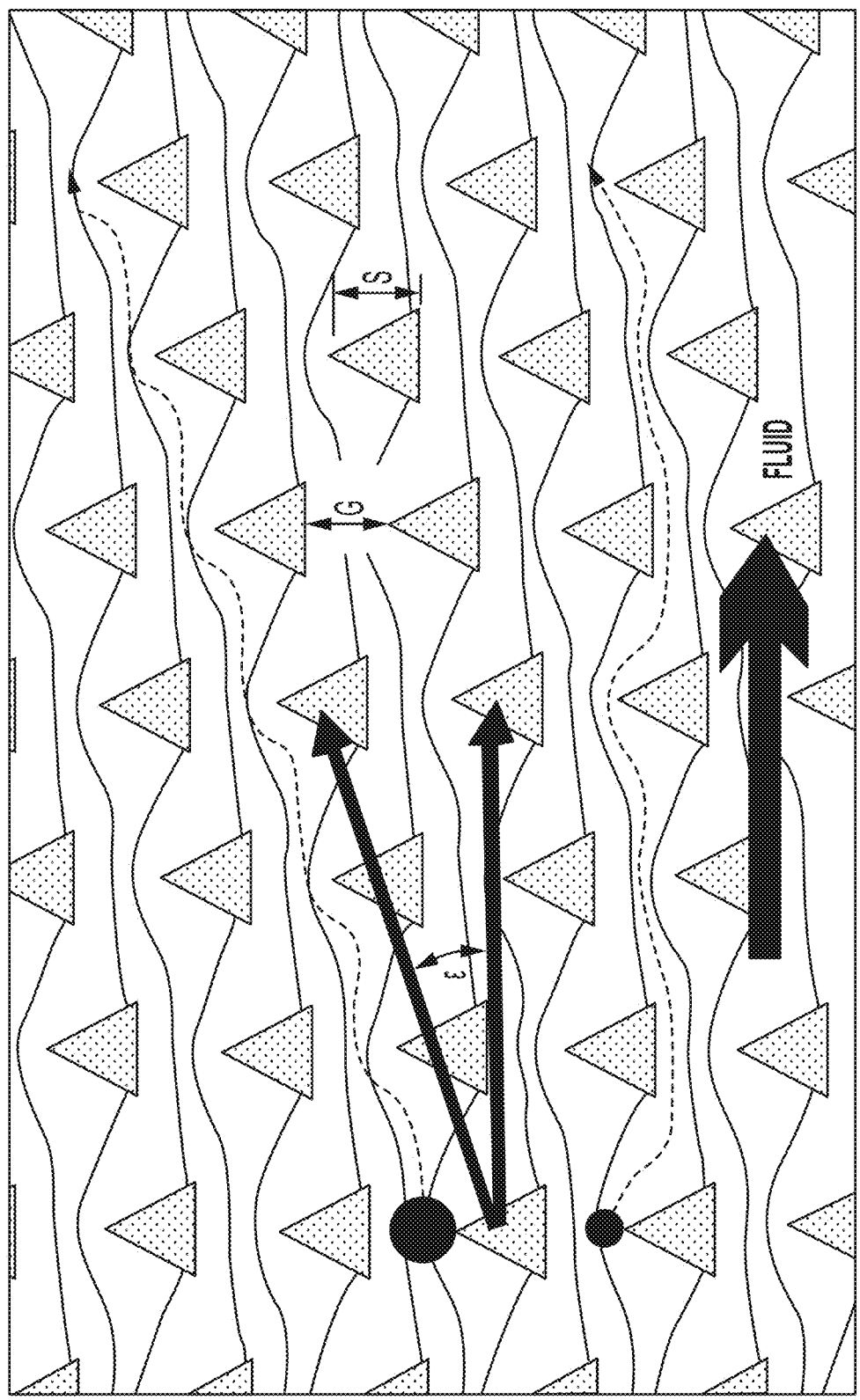
FIG. 6A is a schematic diagram of cross-section of a "bump array" device having equilateral triangularly-shaped obstacles disposed in a microfluidic channel. In the figure, fluid flows in the left-to-right direction, as indicated by the arrow marked, "Fluid." In this array, equilateral triangular posts are disposed in a parallelogram lattice arrangement that is tilted with respect to the directions of fluid flow. Other lattice arrangements (e.g., square, rectangular, trapezoidal, hexagonal, etc. lattices) can also be used. The tilt angle $\epsilon$ (epsilon) is chosen so the device is periodic. In this embodiment, a tilt angle of 18.4 degrees (⅓ radian) makes the device periodic after three rows. The tilt angle $\epsilon$ also represents the angle by which the array direction is offset from the fluid flow direction. The gap between posts is denoted G with equilateral triangle side length S. Streamlines are shown extending between the posts, dividing the fluid flow between the posts into three regions ("stream tubes") of equal volumetric flow. A relatively large particle (having a size greater than the critical size for the array) follows the array tilt angle when fluid flow is in the direction shown. A relatively small particle (having a size smaller than the critical size for the array) follows the direction of fluid flow.

Deterministic lateral displacement can be a size-based particle separation technique that relies on selective displacement of particles by an array of obstacles disposed in a flowing fluid. FIG. 6A illustrates a schematic of the relevant array parameters and important features of the devices described in this example. The obstacle array is composed of columns of posts in which each adjacent column is offset a small distance with respect to larger channel walls that dictate the direction of bulk fluid flow ("FLUID" in FIG. 6A). In this case, the posts are equilateral triangles with side length S (contrary to FIG. 6A, S is the side length, not the distance from a vertex of the triangle to the base opposite that vertex). This offset produces an array where an axis along which the obstacles are situated is situated at a tilt angle $\epsilon$ with respect to the direction of fluid flow. The tilt angle is selected such that the array is periodic after $1/\epsilon$ rows. In this case, the fluid flowing through gaps between posts (length of gap is designated in FIG. 6A) can be partitioned into an integer number of stream tubes delineated by stagnation streamlines. Constrained by the periodicity and the direction of average fluid flow, each of these stream tubes carries an equal volumetric flux.

Particles suspended in the fluid exhibit one of two behaviors depending on their size relative to the width of stream tube nearest to the post as they move through a gap. Unperturbed by other effects, particles can roughly follow the stream tubes in the fluid flow. This behavior can be observed for particles having radii narrower than the stream tube width. These particles, shown as the lower particle and dotted trajectory in FIG. 6A, are not affected by the posts and weave through the array while remain within the bounds of a single stream. As a result, they travel on average in the same direction as the bulk fluid flow. Particles having radii larger than the stream tube width, denoted as the upper particle and dotted trajectory in FIG. 6A, do not fit within a single stream tube as they travel through the gap. Those larger particles are deterministically displaced by the post across the stagnation streamline into the adjacent stream tube. Because of the way the stream tubes cycle through their position in the gap, this displacement will occur at every column of posts and the larger particle will travel along the array axis (i.e., in the array direction, which differs from the bulk fluid direction by the tilt angle E). This binary behavior leads us to describe a critical size which separates these two behaviors. As the particles to be separated are most frequently described by their diameter, we denote the critical size as twice the width of the stream tube nearest to the post in the gap between posts.

Figure 6B:
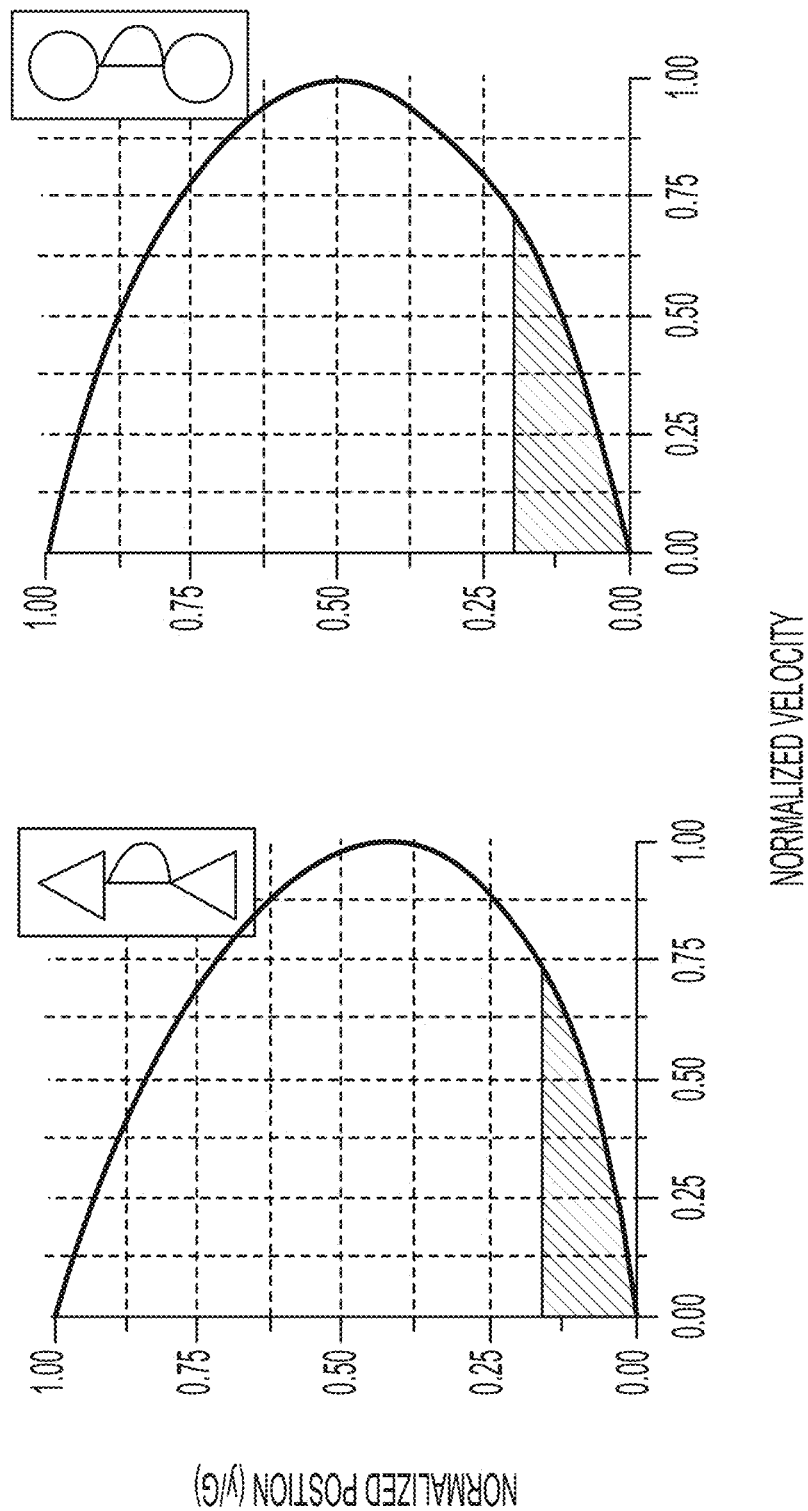
FIG. 6B is a comparison of normalized velocity flow between two equilateral triangular posts (left panel) and normalized velocity flow between two circular posts (right panel). The shaded portions represent an equal proportion of area-under-the-curve, demonstrating that the critical radius for particles flowing past the point of the triangle is significantly smaller (<15% gap width) than the critical radius for particles flowing past the round post (>20% gap width).

Changing the post shape can have a strong effect on the critical particle size by changing the shape of the flow profile through the gap. Alterations to the flow profile alter the width of the stream tubes nearest the posts that define a gap. Because critical particle size can be directly related to these widths, alteration to the flow profile within a gap also alters the critical size(s) defined by the gap. By changing the cross-sectional shape of the posts from circular shape to equilateral triangles, an asymmetry is created in the flow profile through the gap that shifts more fluid flux towards the triangle vertex, as shown in FIG. 6B. This results in different stream tube widths at the top (adjacent the flat edge of a triangular post) and bottom (adjacent the vertex of a triangular post) of the gap and gives the array two distinct critical particle sizes.

The shift in flux towards the vertex of the triangle can lead to a reduced stream tube width along this edge and hence can reduce the critical particle size corresponding to that stream tube and edge, relative to a similar array with circular posts. This is demonstrated in the two panels of FIG. 6B, which shows numerically simulated flow profiles across the gaps. The two flow profiles, normalized to the width of the gap between posts and the maximum velocity, are plotted side by side for comparison. The fluid constituting the first stream tube for tilt angle $\epsilon=1/10$ has been shaded to emphasize the difference in stream width, decreasing from about 20% of the gap bounded by circular posts to about 15% of the gap bounded by triangular posts. This shift is central to the reduction in critical particle size behavior exhibited by devices with triangular posts. The shifted flow profile created by triangular posts can be used to create a deterministic microfluidic ratchet 1. In the information discussed in this example, the focus is on improvement to continuous flow particle separation devices and the deterministic lateral displacement of particles within them that are enabled by changing the post shape.

Figure 7:
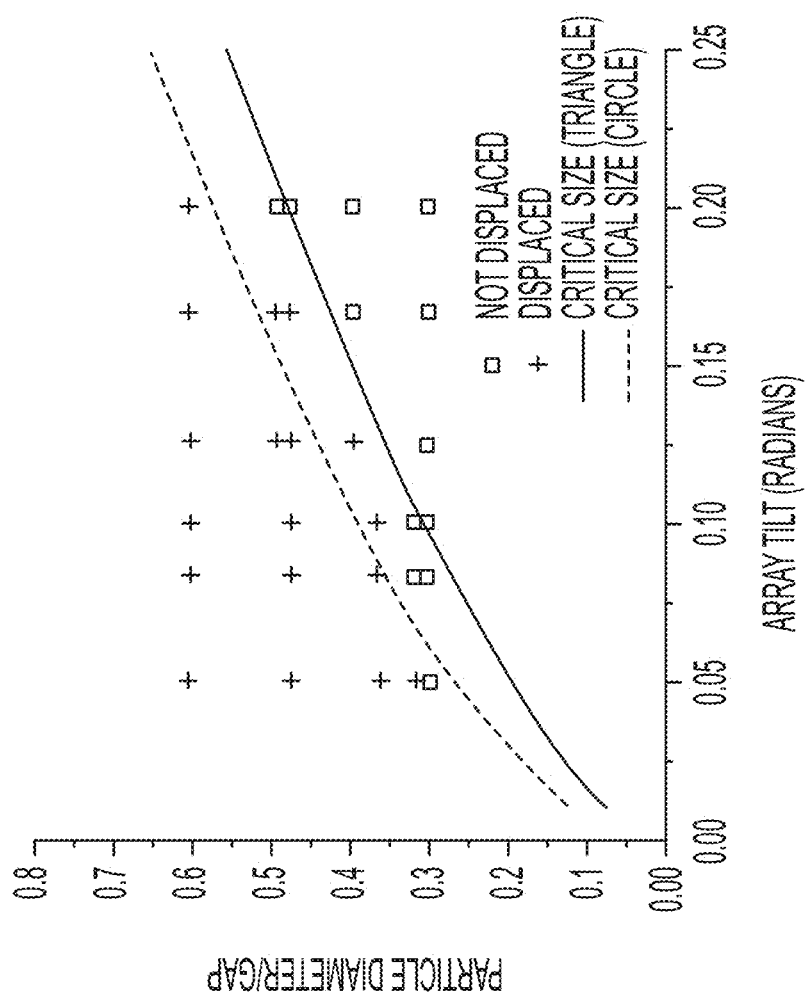
FIG. 7 is a graph illustrating hypothetical and experimental effects of the tilt angle ("Array Tilt" in FIG. 7) on particle displacement.

The reduction in critical particle size enabled by triangular posts was characterized by examining the behavior of fluorescent beads of in arrays with various amounts of array tilt and comparing the results to theoretically predictions. FIG. 7 shows observed particle behavior (displaced by the array or not displaced by the array) normalized to the gap size versus array tilt as well as predicted critical particle sizes using the method described by Inglis et al., 2006, Lab Chip 6:655-658. The lines in FIG. 7 represent the predicted critical particle size for a given tilt angle the solid line representing predictions for arrays with triangular posts and the dotted line representing predictions for arrays with round posts. Particles above the line are expected to be displaced by the array, particles below the line are not expected to be displaced. The data demonstrated that there is reasonable agreement with the predicted behavior for higher tilt angles while there is some deviation at the shallower tilt angles, especially at a tilt angle $\epsilon$ of $1/20$ radians. This deviation could be caused by the flow through the array not being completely horizontal, which will have a large affect at shallower array tilts, or because of rounding of the triangular post edges, which will be discussed later in this example.

The predicted particle behavior for circular posts, signified by the dotted line, has been added as a comparison. For any practical tilt angle (between $1/5$ and $1/100$), the critical size in an array with triangular posts can be substantially smaller than the critical size in a similar array with circular posts, the difference amounting to up to 10% of the gap for the steeper tilt angles. These properties allow smaller particles to be separated by an array of triangular posts than can be separated by an array of round posts having the same gap spacing. These properties also mean that the gap spacing for triangular posts that is necessary to separate particles of a selected size is larger than the corresponding gap spacing for round posts that would be necessary to separate the same particles.

In either case, a reduced critical particle size as a fraction of the gap can be useful in reducing clogging in the array. In some cases, biological samples contain species with a broad range of sizes. In some cases, filtering or multiple separation stages can be used to ensure that an array continues to function. Using triangular posts allows one to increase the size of the gap for a given critical particle size and reduce the chances that the array will clog. FIG. 8 illustrates how much larger the gap between posts can be made as a function of the array tilt. Plotted as a ratio of the two gaps for a fixed critical particle size, a minimum 20% improvement can be seen with increasing gap size as the tilt is reduced, with a ratio of 1.25 for a tilt angle of $1/4$ and a ratio of 1.94 for a tilt angle of $1/100$. Thus, shallower tilt angles can facilitate use of larger gaps at the cost of a smaller separation angle and increased array size. However, larger gaps can provide another benefit in terms of increased array throughput.

A throughput comparison between an array with triangular and circular posts showed a substantial increase in average velocity for a given pressure drop in the array with triangular posts. Arrays with triangular posts or with circular posts were constructed with nearly identical characteristics. They each had the same overall channel width and length, depth, tilt angle ($1/10$), and post size (the diameters of round posts were equal to the side lengths of the equilateral triangular posts). The single variation was the gap between posts, which was designed and verified with numerical simulation to give a critical particle diameter of approximately 3.2 microns for both arrays. Those numerical simulations indicated that the critical particle diameter was achieved using a gap of 10.5 microns in arrays with triangular posts and a gap of 8.3 microns in arrays with circular posts.

The trajectories of 500 nanometer fluorescent beads were recorded with an electron multiplying charged coupled device (EMCCD) camera capturing video at 10 frames per second and then analyzed using MATLAB™ software for a given pressure gradient across the array.

Small particles that would not be displaced (i.e., bumped) by the array were chosen so they would sample each of the flow streams evenly and provide an accurate representation of the overall average fluid velocity.

Figure 9:
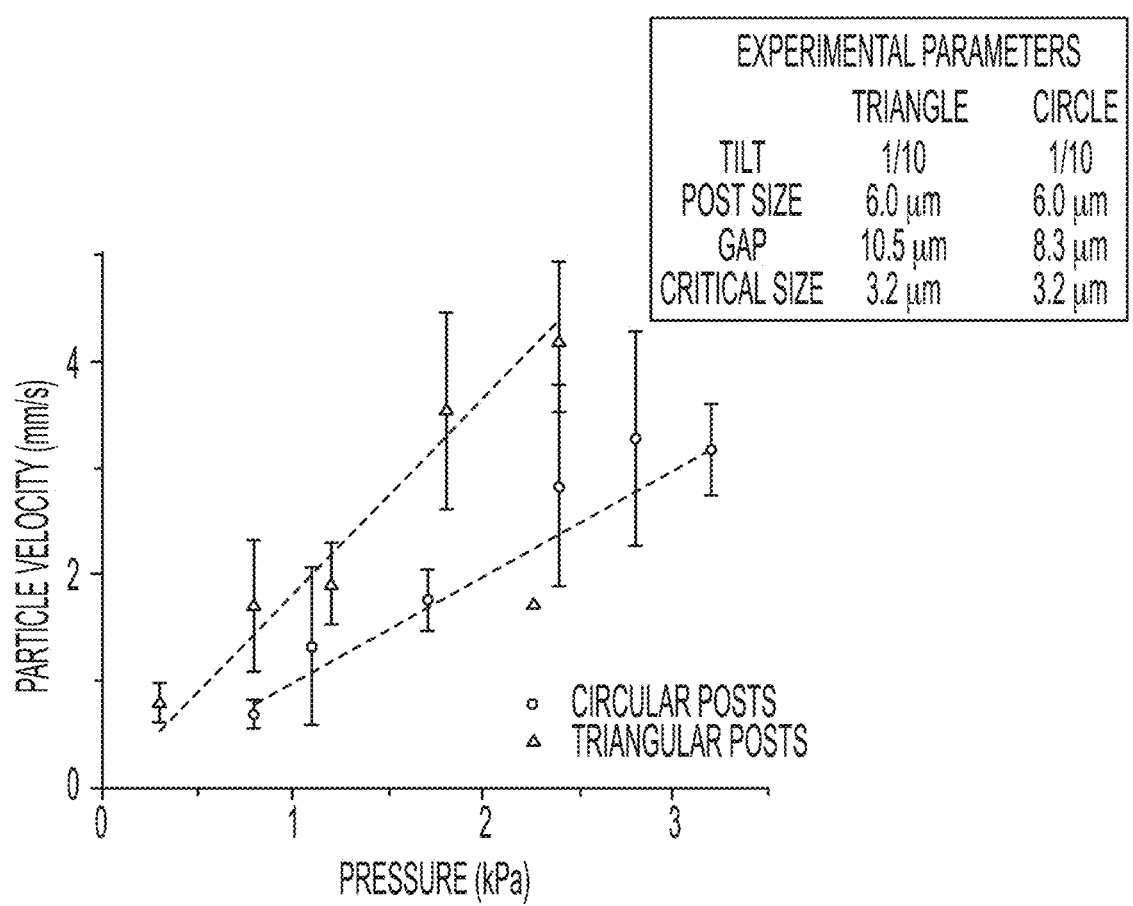
FIG. 9 is a graph illustrating the effect of applied pressure on particle velocity in bump arrays having triangular posts (data shown as triangles) and bump arrays having circular posts (data shown as circles).

The average particle velocities are plotted in FIG. 9 as a function of pressure gradient along with a weighted linear fit. The fitted lines demonstrate that particles in the triangular post array moved much faster. The upper range of pressures was limited by the field of view of the microscope and the capture speed of the camera. Beyond several kPa in pressure, the particles traversed the entire field of view within one or two frames of the video and no accurate estimate of velocity could be made. However, since the Reynolds number in these experiments is on the order of $10^{-2}$, the linear fit can safely be extended into the tens of kPa range to match the expected linear relationship between velocity and pressure that is seen for low Reynolds number flows. The posts need not be triangular in cross-section. Posts having other (square, oblong, or irregular) cross-sectional profiles can also be used, so long as the shape of the obstacles causes the gap to be asymmetric.

Comparing the slopes of the two linear fits in FIG. 9, it can be seen that particles in the array with triangular posts traveled 85% faster on average than those in an array with circular posts. This result agrees with numerical simulation performed with COMSOL™ software that showed that the average velocity for was 82% faster for triangular posts. The mechanism behind these findings can be understood by drawing an analogy to Poiseuille flow between two parallel plates, where the average velocity for a fixed pressure gradient is proportional to the smallest distance between the plates squared. The analogy is not exact because the confining structure is an array of posts instead of two parallel plates, but underscores the benefits of increasing the width of the gap, where just a few microns yields a substantial increase in throughput.

Figure 10:
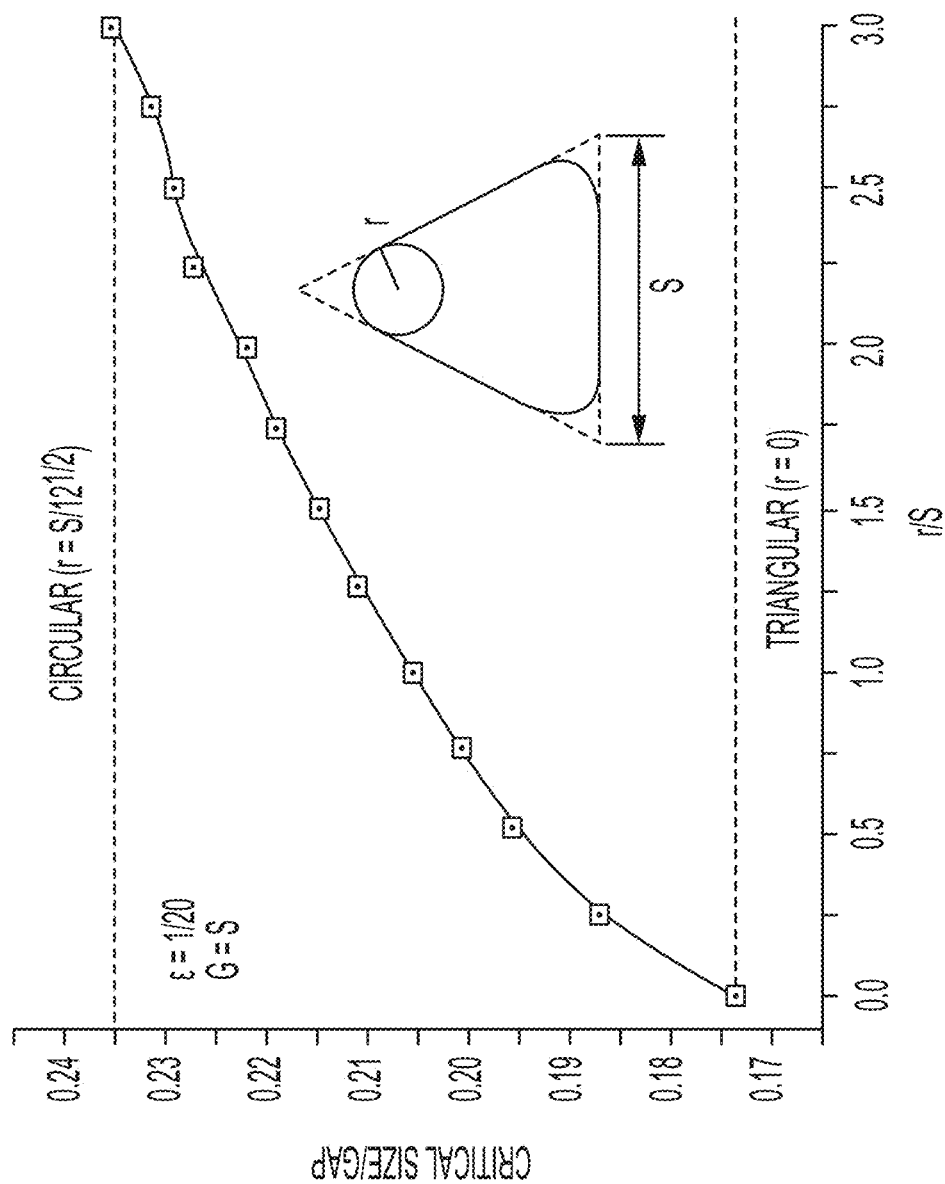
FIG. 10 is a graph illustrating the effect of obstacle edge roundness (expressed as r/S) on the critical size exhibited on the side of a gap bounded by the edge.

The gains achieved by changing the post shape are degraded if care is not taken to maintain sharp post vertices. FIG. 10 shows the effect of rounding triangular post edges on the critical particle size. An array with 10 micron posts, 10 micron gaps between posts, and tilt angle of 1/30 was simulated using COMSOL™ software, with the vertices rounded to various radii of curvature ranging from none (r=0) to complete rounding where the final shape is a circle (r=S/12$^{1/2}$). Flow profiles across the gaps were extracted for each rounding and the critical size for the given tilt was calculated using previously stated methods. As shown in FIG. 10, there is a dramatic increase in the critical particle size as the post shape transitions from triangular to circular. Starting at 0.174 G when the post is completely triangular (i.e., r=0), critical particle size increases 35% to 0.235 G when the post is completely circular (r=S/12$^{1/2}$). The transition suggests that if a fabrication process that produces an undesirable vertex rounding, using larger posts (increasing S) will help to maintain the decreased critical particle size that results from using triangular posts.

This observation also helps to explain the deviation from expected behavior observed for some of the fluorescent beads in FIG. 7. SEM images of the posts show vertex rounding (r/S) of 0.118±0.006, which corresponds to an increase in the critical particle size from 0.93 microns to 1.12 microns.

E. Device Features

Figure 18:
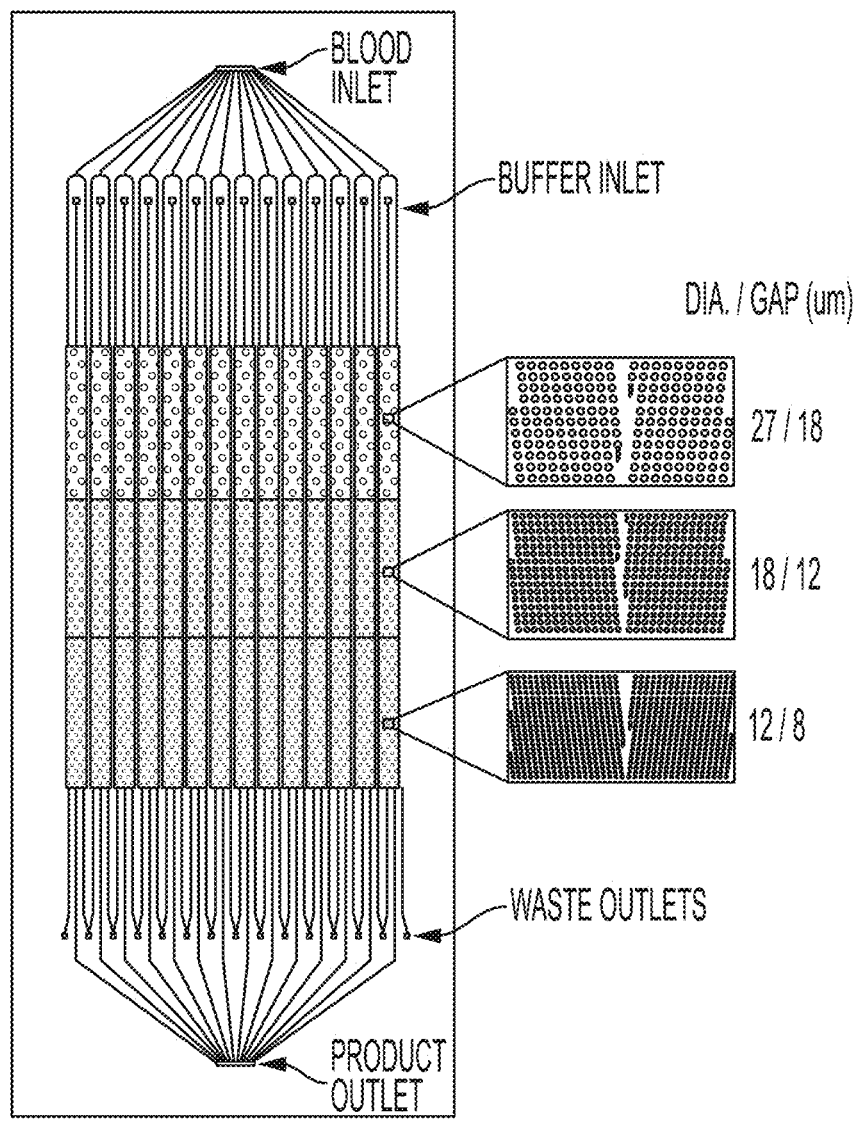
FIG. 18 illustrates an embodiment of a device comprising an array of obstacles comprising 14 channels.
Figure 19:
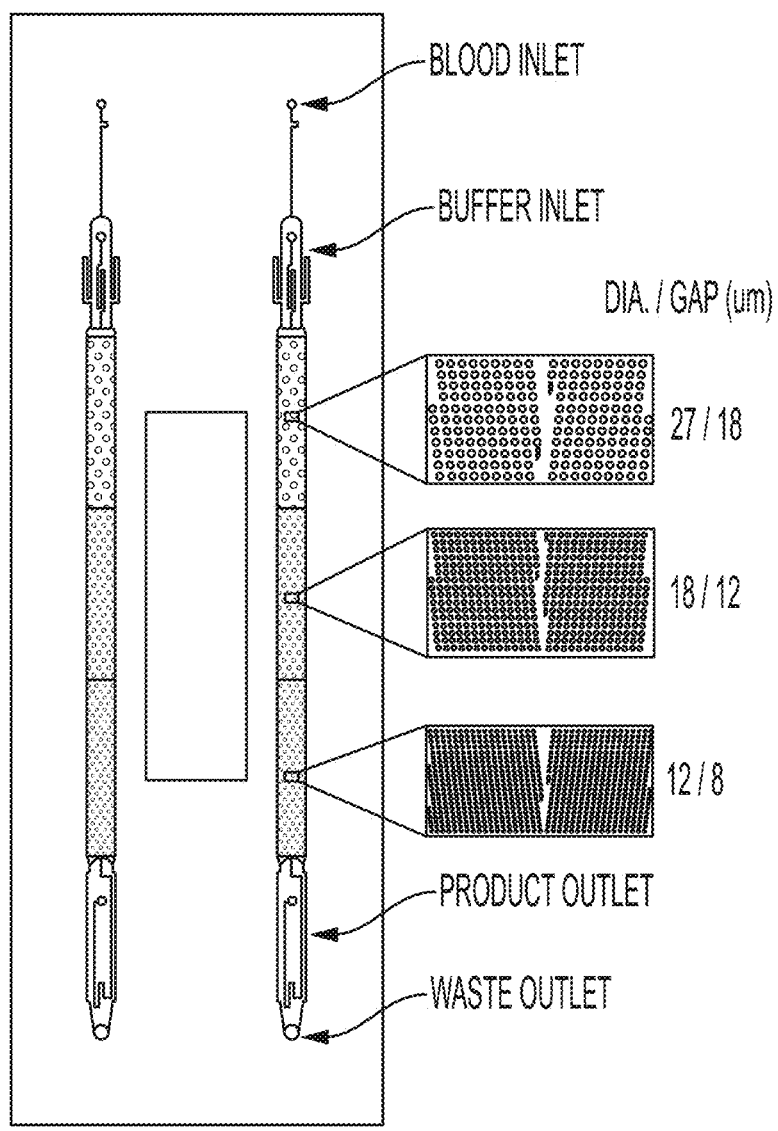
FIG. 19 illustrates an embodiment of a device comprising an array of obstacles comprising 2 channels.

Samples can be flowed through devices described herein, DLD devices, to isolate, purify, and/or concentrate particles in the samples. In some cases, a device can be used to process between about 10 μl to at least 500 μl of sample, between about 500 μl and about 40 mL of sample, between about 500 μl and about 20 mL of sample, between about 20 mL of sample and about 200 mL of sample, between about 40 mL of sample and about 200 mL of sample, or at least 200 mL of sample. A device can comprise a channel with at least one input, at least one output, and an array of obstacles disposed there-between. Examples of DLD devices are illustrated in FIG. 18 and FIG. 19. Examples of parameters of devices are illustrated in Table 1.

TABLE 1

Channel widths

|  | A/A2 | B | C |
| --- | --- | --- | --- |
| Blood inlet channel width (μm) | 50 | 100 | 150 |
| Buffer inlet channel width (μm) | 55 | 110 | 110 |
| Product outlet channel width (μm) | 49 | 98 | 98 |

TABLE 2

Gap size (edge-to-edge distance between posts)/post diameter (μm)

|  | A/A2 | B | C |
| --- | --- | --- | --- |
| Section 1 | 18/27 | 44/66 | 90/135 |
| Section 2 | 12/18 | 30/45 | 60/90 |
| Section 3 | 8/12 | 20/30 | 40/60 |

FIG. 18 shows a design of an A chip. The A chip comprises a three zone (section) design with progressively smaller pillars and gaps. Gap size and post diameter are described in Table 1. The device can comprise an inlet, e.g., for blood, an inlet for buffer, waste outlets, and a product outlet. The A chip can comprise 14 parallel channels. The total channel volume (including 0.5 mm vias) (a via can be a hole that can connect the backside of a chip (e.g., where the manifold connection can occur) to the top side of the chip (ie where the array is) can be about 118 μL. The throughput of the device can be about 4-8 mL/hr. The processing time for an 8 mL sample can be about 1 to about 2 hours. The A chip can be made with silicon. The A chip can be made with polypropylene, poly(methyl methacrylate) (PMMA), or cyclo-olefin polymer (COP). In some cases, between about 5 mL and about 20 mL of sample can be applied to the device.

FIG. 19 shows another example of a device (A2). The A2 chip comprises a three zone design with progressively smaller pillars and gaps. Gap sizes and post diameters are described in Table 2. The depth of the channel is 60 μm. Each A2 chip comprises 2 independent channels. The total channel volume (including 0.5 mm via) is about 3.85 μL. The throughput for the device can be about 0.12 to about 0.24 mL/hr, or about 0.4 to about 0.8 mL/hr. The processing time for a 100 μL sample can be about 25 to about 50 min. The A2 chip can be made with silicon. The A2 chip can be made with polypropylene, poly(methyl methacrylate) (PMMA), or cyclo-olefin polymer (COP). The device can be used to process about 50 to about 500 uL of sample.

Figure 37B:
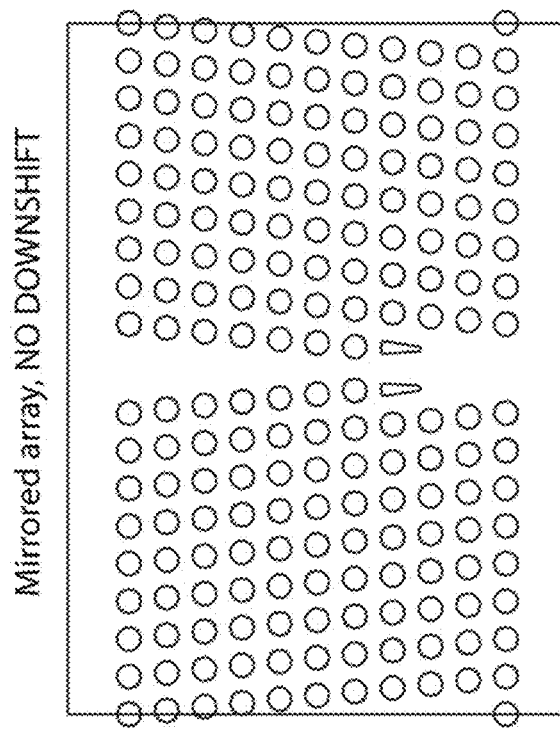
FIG. 37B illustrates a mirrored array of obstacles with no downshift.
Figure 37A:
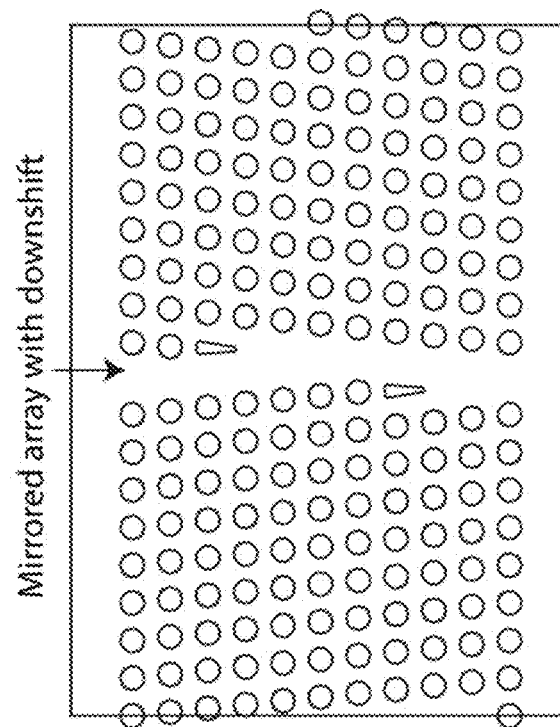
FIG. 37A shows an example of a mirrored array of obstacles with a downshift.

FIG. 37A shows an example of a mirrored array of obstacles with a downshift. A central channel exists between an array of obstacles on the left and on the right. The central channel can be a collection channel for particles of at least a critical size (i.e. particles of at least a critical size can be deflected by the arrays to the central channels, whereas particles of less than the critical size can pass through the channel with the bulk flow). An array can be shifted down towards the channel by, e.g., 1, 2, 3, 4, 5, 6, 7, 8, 9, 10, 11, 12, 13, 14, 15, 16, 17, 18, 19, or 20 rows. In some cases, each row in an array of obstacles has the same number of obstacles. In some cases, each row in an array of obstacles does not have the same number of obstacles. By downshifting rows, changes in the width of the channel relative to a mirrored array with a downshift can be achieved. The amount of downshift can vary based on the size and/or cross-sectional shape of the obstacles. FIG. 37B illustrates a mirrored array of obstacles with no downshift. An array on the left and an array on the right can deflect particles of at least a critical size to the central channel.

i. Channels

A device can comprise a channel with at least one inlet and at least one outlet. In some cases, a device comprises a channel with two inlets and two outlets. In some cases, a first inlet to a channel is a sample inlet and a second inlet to a channel is a buffer inlet. In some cases, a first outlet to a channel is a product outlet and a second outlet to a channel is a waste outlet. In some cases, a channel comprises an array of obstacles between an inlet and an outlet. In some cases, the array of obstacles comprises zones or sections of obstacles, wherein each section comprises obstacles of substantially the same diameter and size and gaps between obstacles of substantially the same size.

(a) Channel Width

A channel width can be about 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mm. A channel width can be at least 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mm. A channel width can be less than 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mm. A channel width can be about 1 to about 10 mm, about 2 to about 9 mm, about 3 to about 8 mm, about 10 to about 20 mm, about 20 to about 30 mm, about 30 to about 40 mm, about 40 to about 60 mm, about 60 to about 70 mm, or about 70 to about 100 mm.

(b) Channel Length

A channel length can be about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, or 200 mm. A channel length can be less than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, or 200 mm. A channel length can be at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, or 200 mm. A channel length can be about 1 to about 10 mm, about 2 to about 9 mm, about 3 to about 8 mm, about 10 to about 20 mm, about 20 to about 30 mm, about 30 to about 40 mm, about 40 to about 60 mm, about 60 to about 70 mm, about 70 to about 100 mm, or about 100 to about 200 mm.

(c) Channel Depth

A channel can have a depth of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 450, 500, 550, 600, 650, 700, 750, 800, 850, 900, 950 or 1000 µm. A channel can have a depth of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 450, 500, 550, 600, 650, 700, 750, 800, 850, 900, 950 or 1000 µm. A channel can have a depth less than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 450, 500, 550, 600, 650, 700, 750, 800, 850, 900, 950 or 1000 µm. A channel can have a depth of about 10 to about 30 µm, about 20 to about 40 µm, about 30 to about 50 µm, about 50 to about 100 µm, about 100 to about 200 µm, about 200 to about 400 µm, about 400 to about 600 µm, or about 600 to about 1000 µm.

(d) Number of Channels per Device (Chip)

A device can comprise about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 channels. A device can comprise at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 channels. A device can comprise about 2 to about 10 channels, about 10 to about 20 channels, about 20 to about 30 channels, about 30 to about 40 channels, about 40 to about 50 channels, about 50 to about 60 channels, about 60 to about 70 channels, or about 70 to about 100 channels.

(e) Channel Volume

A total volume of a channel can be about 0.001, 0.005, 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, or 200 mL. A total volume of a channel can be at least 0.001, 0.005, 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, or 200 mL. A total volume of a channel can be about 0.001 to about 0.01 mL, about 0.01 to about 0.1 mL, about 0.1 to about 0.5 mL, about 1 to about 2 mL, about 2 to about 3 mL, about 3 to about 5 mL, about 5 to about 10 mL, about 10 to about 20 mL, or about 20 to about 50 mL. A device can comprise multiple channels. In some cases, a total volume of the channels in a device is any of the volumes listed above multiplied by the number of channels in the device.

(f) Zones (Stages) within a Channel

A device described herein can have a plurality of zones (stages, sections). A zone can be an area on a device with the same or similar sized post (obstacles) and gaps. In some cases, a channel in a device comprises 1, 2, 3, 4, 5, 6, 7, 8, 9, or 10 zones. In some cases, a channel in a device comprises at least 1, 2, 3, 4, 5, 6, 7, 8, 9, or 10 zones. A sample can be, e.g., a biological sample, and can comprise particles with a broad range of sizes. If a particle in a sample is larger than a gap, the particle can clog the channel. In some cases, multiple separation stages with different gap and post sizes can be used. In some cases, post diameter and gap size is smaller in a second zone relative to a first zone. In some cases, a device comprises a plurality of zones, wherein when a fluid is applied to an inlet of the device, it flows through a plurality of zones in a channel, e.g., at least 1, 2, 3, 4, 5, 6, 7, 8, 9, or 10 zones. In some cases, post diameter and/or gap sizes get progressively smaller as a fluid flows from and inlet to an outlet across zones in a channel.

(g) Gap Size (Edge-to-Edge Distance Between Posts or Obstacles)

In some cases, gap size in an array of obstacles (edge-to-edge distance between posts or obstacles) is about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or 3000 μm. In some cases, gap size in an array of obstacles is at least 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or 3000 μm. In some cases, gap size in an array of obstacles is less than 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or 3000 μm. In some cases, gap size is about 1 μm to about 10 μm, about 10 μm to about 20 μm, about 20 μm to about 30 μm, about 30 μm to about 40 μm, about 40 μm to about 50 μm, about 50 μm to about 60 μm, about 60 μm to about 70 μm, about 70 μm to about 80 μm, about 80 μm to about 90 μm, about 90 μm to about 100 μm, about 100 μm to about 110 μm, about 110 μm to about 120 μm, about 120 μm to about 130 μm, about 130 μm to about 140 μm, about 140 μm to about 150 μm, about 150 μm to about 160 μm, about 160 μm to about 170 μm, about 170 μm to about 180 μm, about 180 μm to about 190 μm, about 190 μm to about 200 μm, about 200 μm to about 250 μm, about 250 μm to about 300 μm, about 300 μm to about 400 μm, about 400 μm to about 500 μm, about 500 μm to about 600 μm, about 600 μm to about 700 μm, about 700 μm to about 800 μm, about 800 μm to about 900 μm, about 900 μm to about 1000 μm, about 1000 μm to about 1500 μm, about 1500 μm to about 2000 μm, about 2000 μm to about 2500 μm, or about 2500 μm to about 3000 μm.

(h) Post (Obstacle) Diameter

In some cases, post (obstacle) diameter is about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 170, 175, 180, 185, 190, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or 3000 μm. In some cases, post (obstacle) diameter is at least 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 170, 175, 180, 185, 190, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or 3000 μm. In some cases, post (obstacle) diameter is less than 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 170, 175, 180, 185, 190, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or 3000 μm.

(i) Obstacle Cross-Sectional Shape

In some cases, the cross-sectional shape of a post or obstacle is a circle, triangle, square, rectangle, pentagon, hexagon, heptagon, octagon, nonagon, decagon, hendecagon, dodecagon, hexadecagon, icosagon, or star. In some cases, a triangle is an acute triangle, equilateral triangle, isosceles triangle, obtuse triangle, rational triangle, right triangle (30-60-90 triangle, isosceles right triangle, Kepler triangle), or scalene triangle. In some cases, the cross-sectional shape of a post or obstacle is a quadrilateral, e.g., a cyclic quadrilateral, square, kite, parallelogram, rhombus, Lozeng, rhomboid, rectangle, tangential quadrilateral, trapezoid, trapezium, or isosceles trapezoid. In some cases, the cross-sectional shape of a post or obstacle is a crescent, ellipse, lune, oval, Reuleaux polygon, Reuleaux triangle, lens, vesica piscis, salinon, semicircle, tomoe, magatama, triquetra, asteroid, deltoid super ellipse, or tomahawk. In some cases, a cross-sectional shape with a point has a sharpened point. In some cases, a cross-sectional shape with a point has a rounded point. In some cases, a cross-sectional shape with more than one point has at least one rounded point and at least one sharpened point. In some cases, a post (obstacle) has a cylindrical shape.

(j) Distance of Posts (Obstacles) from an Inlet

A first row of posts can be spaced less than about 1000, 950, 900, 850, 800, 750, 700, 650, 600, 550, or 500 450, 400, 350, 300, 250, 200, 150, 100, 50, 40, 30, 20, 10, or 5 µm from an input.

(k) Tilt Angle

In some cases an array of obstacles has a tilt angle $\epsilon$ (with respect to the direction of fluid flow) of 1/3, 1/4, 1/5, 1/6, 1/7, 1/8, 1/9, 1/10, 1/11, 1/12, 1/13, 1/14, 1/15, 1/16, 1/17, 1/18, 1/19, 1/20, 1/21, 1/22, 1/23, 1/24, 1/25, 1/26, 1/27, 1/28, 1/29, 1/30, 1/31, 1/32, 1/33, 1/34, 1/35, 1/36, 1/37, 1/38, 1/39, 1/40, 1/41, 1/42, 1/43, 1/44, 1/45, 1/46, 1/47, 1/48, 1/49, 1/50, 1/51, 1/52, 1/53, 1/54, 1/55, 1/56, 1/57, 1/58, 1/59, 1/60, 1/61, 1/62, 1/63, 1/64, 1/65, 1/66, 1/67, 1/68, 1/69, 1/70, 1/71, 1/72, 1/73, 1/74, 1/75, 1/76, 1/77, 1/78, 1/79, 1/80, 1/81, 1/82, 1/83, 1/84, 1/85, 1/86, 1/87, 1/88, 1/89, 1/90, 1/91, 1/92, 1/93, 1/94, 1/95, 1/96, 1/97, 1/98, 1/99, 1/100, 1/110, 1/120, 1/130, 1/140, 1/150, 1/160, 1/170, 1/180, 1/190, 1/200, 1/300, 1/400, 1/500, 1/600, 1/700, 1/800, 1/900, 1/1000, 1/2000, 1/3000, 1/4000, 1/5000, 1/6000, 1/7000, 1/8000, 1/9000, or 1/10,000 radian. In some cases, δ is less than 1/3, 1/4, 1/5, 1/6, 1/7, 1/8, 1/9, 1/10, 1/11, 1/12, 1/13, 1/14, 1/15, 1/16, 1/17, 1/18, 1/19, 1/20, 1/21, 1/22, 1/23, 1/24, 1/25, 1/26, 1/27, 1/28, 1/29, 1/30, 1/31, 1/32, 1/33, 1/34, 1/35, 1/36, 1/37, 1/38, 1/39, 1/40, 1/41, 1/42, 1/43, 1/44, 1/45, 1/46, 1/47, 1/48, 1/49, 1/50, 1/51, 1/52, 1/53, 1/54, 1/55, 1/56, 1/57, 1/58, 1/59, 1/60, 1/61, 1/62, 1/63, 1/64, 1/65, 1/66, 1/67, 1/68, 1/69, 1/70, 1/71, 1/72, 1/73, 1/74, 1/75, 1/76, 1/77, 1/78, 1/79, 1/80, 1/81, 1/82, 1/83, 1/84, 1/85, 1/86, 1/87, 1/88, 1/89, 1/90, 1/91, 1/92, 1/93, 1/94, 1/95, 1/96, 1/97, 1/98, 1/99, 1/100, 1/110, 1/120, 1/130, 1/140, 1/150, 1/160, 1/170, 1/180, 1/190, 1/200, 1/300, 1/400, 1/500, 1/600, 1/700, 1/800, 1/900, 1/1000, 1/2000, 1/3000, 1/4000, 1/5000, 1/6000, 1/7000, 1/8000, 1/9000, or 1/10,000 radian. In some cases, the tilt angle is between about 1/1000 to about 1/3, or about 1/100 to about 1/5, or about 1/1000 to about 1/100, or about 1/500 to about 1/100, or about 1/50 to about 1/3.

(l) Inlet Channel Width (e.g., Sample or Buffer)

A first (e.g., sample) inlet channel and/or second (e.g., buffer) inlet channel width can be about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 170, 175, 180, 185, 190, 200, 250, 300, 350, 400, 450, 500, 550, 600, 650, 700, 750, 800, 850, 900, 950, 1000, 1100, 1200, 1300, 1400, or 1500 µm. A first (e.g., sample) inlet channel and/or second (e.g., buffer) inlet channel width can be at least 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 170, 175, 180, 185, 190, 200, 250, 300, 350, 400, 450, 500, 550, 600, 650, 700, 750, 800, 850, 900, 950, 1000, 1100, 1200, 1300, 1400, or 1500 µm. A first (e.g., sample) inlet channel and/or second (e.g., buffer) inlet channel width can be less than 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 170, 175, 180, 185, 190, 200, 250, 300, 350, 400, 450, 500, 550, 600, 650, 700, 750, 800, 850, 900, 950, 1000, 1100, 1200, 1300, 1400, or 1500 nm.

A first (e.g., sample) inlet channel and/or second (e.g., buffer) inlet channel width can be about 1 to about 10 µm, about 10 to about 20 µm, about 20 to about 30 µm, about 30 to about 60 µm, about 60 to about 90 µm, about 90 to about 120 µm, about 120 to about 180 µm, about 180 to about 250 µm, about 250 to about 500 µm, about 500 to about 1000 µm, about 1000 to about 1500 µm.

(m) Product Outlet Channel Width

A product inlet channel width can be about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 170, 175, 180, 185, 190, 200, 250, 300, 350, 400, 450, 500, 550, 600, 650, 700, 750, 800, 850, 900, 950, 1000, 1100, 1200, 1300, 1400, or 1500 µm. A product channel width can be at least 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 170, 175, 180, 185, 190, 200, 250, 300, 350, 400, 450, 500, 550, 600, 650, 700, 750, 800, 850, 900, 950, 1000, 1100, 1200, 1300, 1400, or 1500 µm. A product inlet channel width can be less than 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 170, 175, 180, 185, 190, 200, 250, 300, 350, 400, 450, 500, 550, 600, 650, 700, 750, 800, 850, 900, 950, 1000, 1100, 1200, 1300, 1400, or 1500 µm. A product inlet channel width can be about 1 to about 10 µm, about 10 to about 20 µm, about 20 to about 30 µm, about 30 to about 60 µm, about 60 to about 90 µm, about 90 to about 120 µm, about 120 to about 180 µm, about 180 to about 250 µm, about 250 to about 500 µm, about 500 to about 1000 µm, about 1000 to about 1500 µm.

(n) Channel Configurations

In some cases, a device can have a configuration of a device as described in U.S. Pat. No. 8,021,614. In some cases, a channel in a device comprises mirrored arrays of obstacles, in which one array of obstacles is configured to deflect a particle of at least a predetermined size to a center bypass channel, and a second array of obstacles adjacent to the first array of obstacles also directs particles of at least a first predetermined size to the center bypass channel. In some cases, the bypass channel comprises a wall that separates the first array of obstacles and the second array of obstacles. In some cases, the bypass channel does not comprise a wall that separates the first array of obstacles and the second array of obstacles. In some cases, a channel with a mirrored array comprises at least two inlets. In some cases, a sample outlet is in fluid communication with the bypass channel. In some cases, channel with a mirrored array comprises at least one waste outlet.

In some cases, a channel does not comprise a mirrored array. A channel can comprise a first array of obstacles that direct particles of at least a predetermined size to a bypass channel adjacent to a wall of the channel. A channel can comprise a plurality of bypass channels. In some cases, a channel comprises a two mirrored arrays of obstacles, two inlets, and a central buffer stream for concentrating particles from each of the mirrored array of obstacles. In some cases, a channel comprises one inlet or two inlets. In some cases, opposing arrays in a channel direct particles of at least a critical or predetermined size to a central channel.

(o) Flow Properties

In some cases, flow through a device comprising an array of obstacles is laminar.

The methods, compositions, devices, systems, and/or kits described herein can facilitate rapid flow rate through a device. In some cases, a flow rate through a device is at least 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 170, 175, 180, 185, 190, 200, 250, 300, 350, 400, 450, or 500 mL/min. In some cases, a flow rate through a device is about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 170, 175, 180, 185, 190, 200, 250, 300, 350, 400, 450, or 500 mL/min. In some cases, a flow rate through a device is less than 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 170, 175, 180, 185, 190, 200, 250, 300, 350, 400, 450, or 500 mL/min. In some cases, a flow rate through a device is about 0.05 to about 0.1 mL/min, about 0.1 to about 0.5 mL/min, about 0.5 to about 1 mL/min, about 1 to about 5 mL/min, about 5 to about 10 mL/min, about 10 to about 20 mL/min, about 20 to about 50 mL/min, about 50 to about 100 mL/min, about 100 to about 200 mL/min, or about 200 to about 500 mL/min.

In some cases, a fluid velocity is at least 1, 5, 10, 20, 30, 40, 50, 60, 70, 80, 90, 100, 150, 200, 300, 400, 500, 600, 700, 800, 900, 1000, 2000, 3000, 4000, 5000, 6000, 7000, 8000, 9000, or 10,000 mm/sec. In some cases, a fluid velocity is about 1, 5, 10, 20, 30, 40, 50, 60, 70, 80, 90, 100, 150, 200, 300, 400, 500, 600, 700, 800, 900, 1000, 2000, 3000, 4000, 5000, 6000, 7000, 8000, 9000, or 10,000 mm/sec. In some cases, a fluid velocity is less than 1, 5, 10, 20, 30, 40, 50, 60, 70, 80, 90, 100, 150, 200, 300, 400, 500, 600, 700, 800, 900, 1000, 2000, 3000, 4000, 5000, 6000, 7000, 8000, 9000, or 10,000 mm/sec. In some cases, shear stress is about 10, 50, 100, 500, 1000, 5000, 10,000, 25,000, 50,000, 75,000, 100,000, 200,000, 300,000, 400,000, 500,000, 600,000, 700,000, 800,000, 900,000 or 1,000,000 s$^{-1}$. In some cases, shear stress is less than 10, 50, 100, 500, 1000, 5000, 10,000, 25,000, 50,000, 75,000, 100,000, 200,000, 300,000, 400,000, 500,000, 600,000, 700,000, 800,000, 900,000 or 1,000,000 s$^{-1}$. In some cases, shear stress is more than 10, 50, 100, 500, 1000, 5000, 10,000, 25,000, 50,000, 75,000, 100,000, 200,000, 300,000, 400,000, 500,000, 600,000, 700,000, 800,000, 900,000 or 1,000,000 s$^{-1}$.

(p) Pressure

In some cases, a sample is flowed through a device at a pressure of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 6, 7, 8, 9, 10, 11, 12, 13, 14, 15, 16, 17, 18, 19, 20, 21, 22, 23, 24, 25, 26, 27, 28, 29, or 30 atm. In some cases, a sample is flowed through a device at a pressure of at least 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 6, 7, 8, 9, 10, 11, 12, 13, 14, 15, 16, 17, 18, 19, 20, 21, 22, 23, 24, 25, 26, 27, 28, 29, or 30 atm. In some cases, a sample is flowed through a device at a pressure of less than 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 6, 7, 8, 9, 10, 11, 12, 13, 14, 15, 16, 17, 18, 19, 20, 21, 22, 23, 24, 25, 26, 27, 28, 29, or 30 atm.

(q) Predetermined Size (Critical Size)

In some cases, a device as described herein can be used to deflect particles of at least a predetermined size to a first outlet and particles less than a predetermined size to a second outlet. In some cases, a predetermined (critical) size is about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1000 μm. In some cases, a predetermined (critical) size is less than 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1000 μm. In some cases, a predetermined (critical) size is more than 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1000 µm.

A device can comprise an array of obstacles, wherein the obstacles comprise obstacles with a diameter of 18 µm, and the array of obstacles comprise rows or obstacles, wherein a subsequent row has a ¹⁄₄₂ row shift. In some case, the obstacles are semi-mirrored (see, e.g., FIG. 37A)

(r) Obstacle Coating

In some cases, obstacles comprise an affinity capture agent, e.g., an antibody, other protein-binding partner, or nucleic acid. Obstacles can comprise specific affinity-capture agent to capture specific particles in a sample. Affinity capture is described, e.g., in PCT Publication No. WO2012094642, which is herein incorporated by reference in its entirety.

(s) On-Chip Cleaning System

Figure 31:
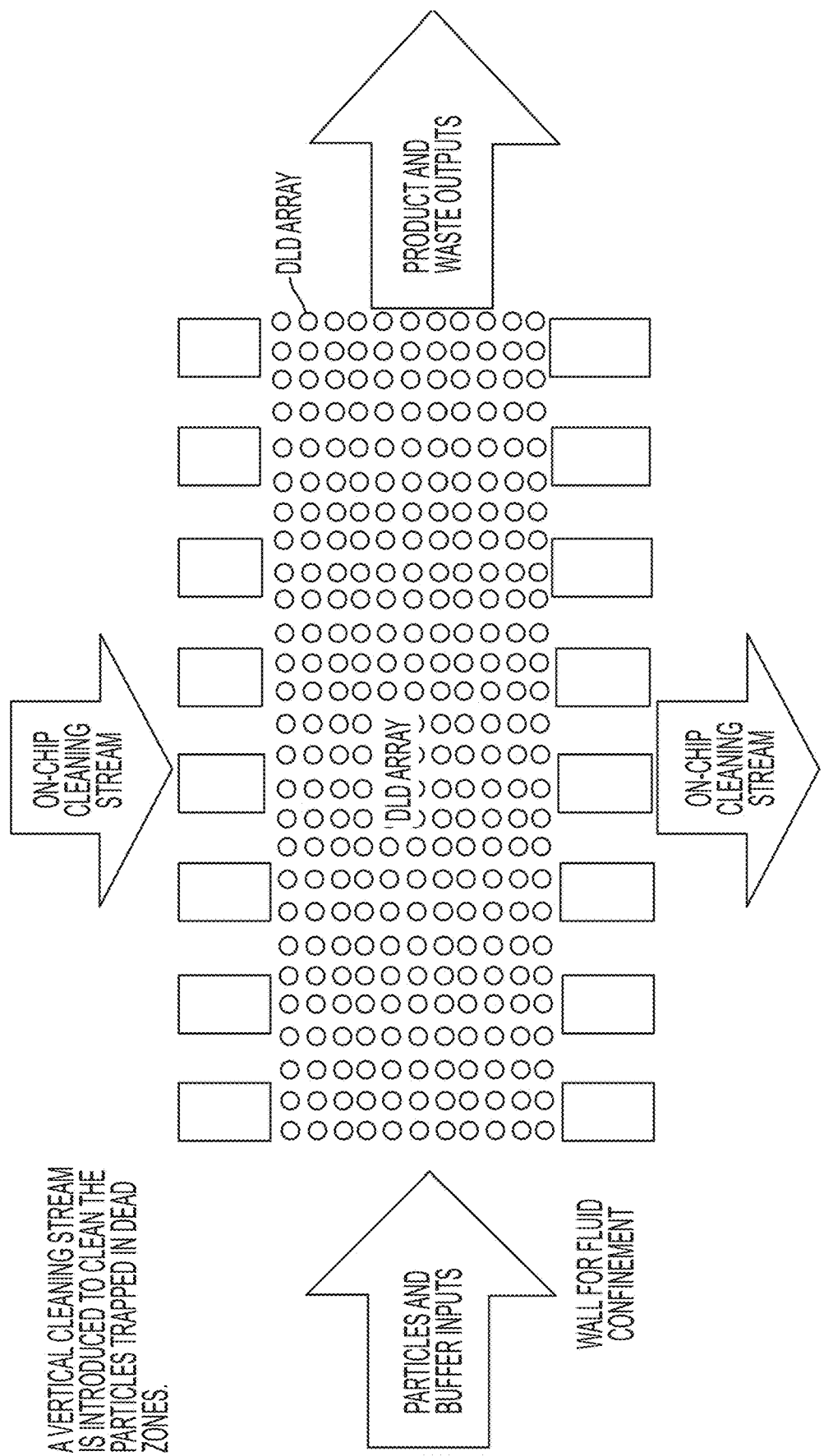
FIG. 31 illustrates a deterministic lateral displacement array with a self-cleaning system.
Figure 32:
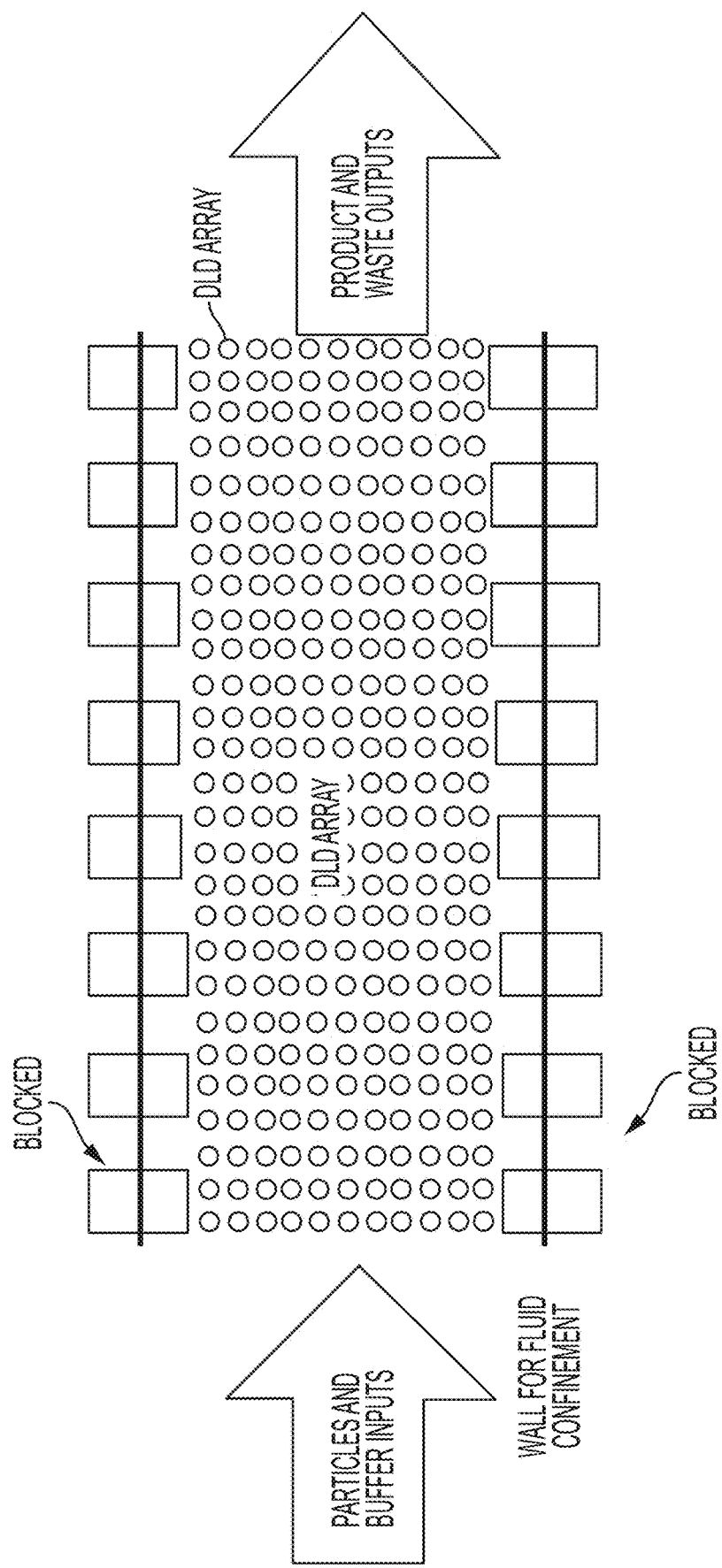
FIG. 32 illustrates a deterministic lateral displacement array with a self-cleaning system in "bumping mode."
Figure 33:
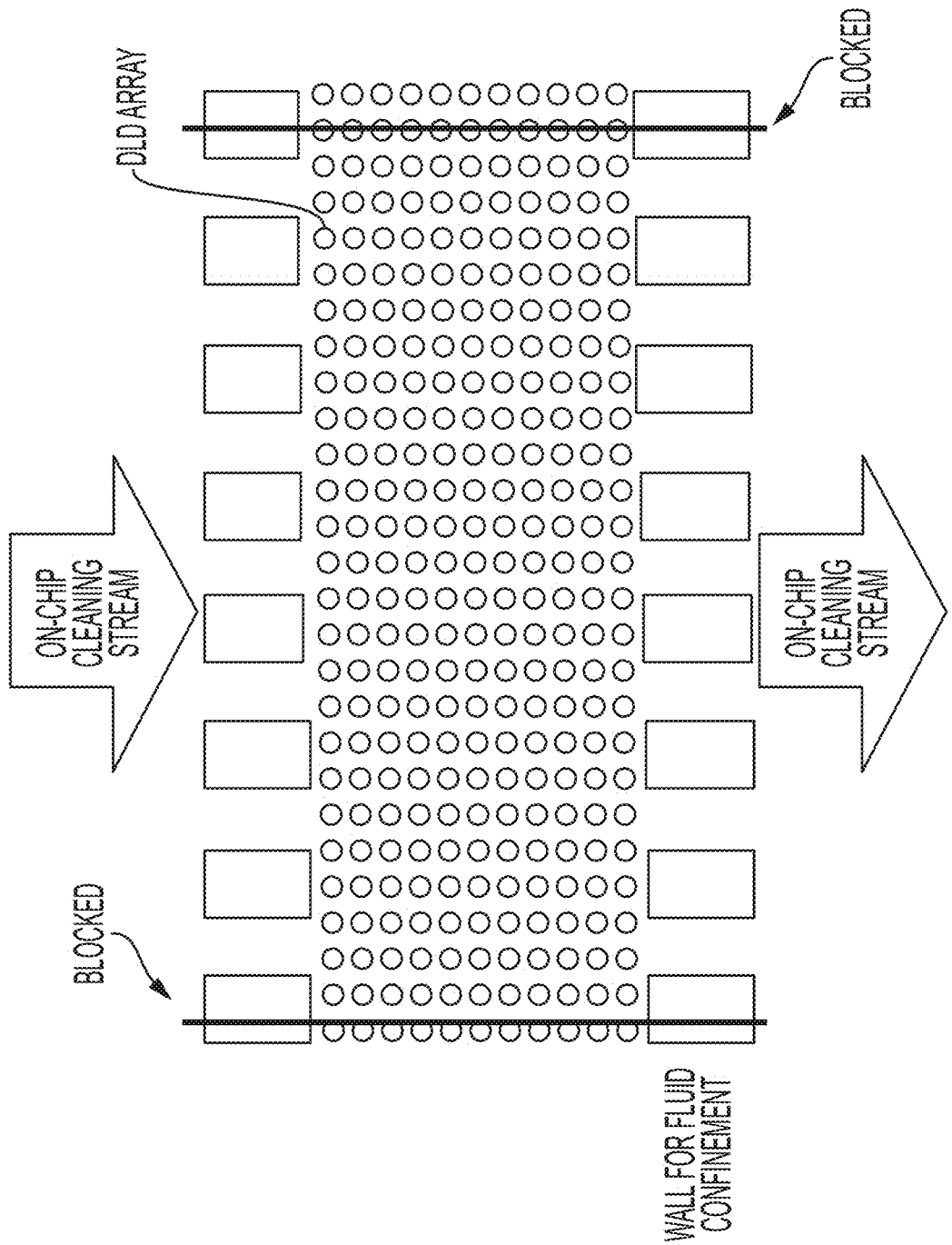
FIG. 33 illustrates a deterministic lateral displacement array with a self-cleaning system in "cleaning mode."
Figure 34:
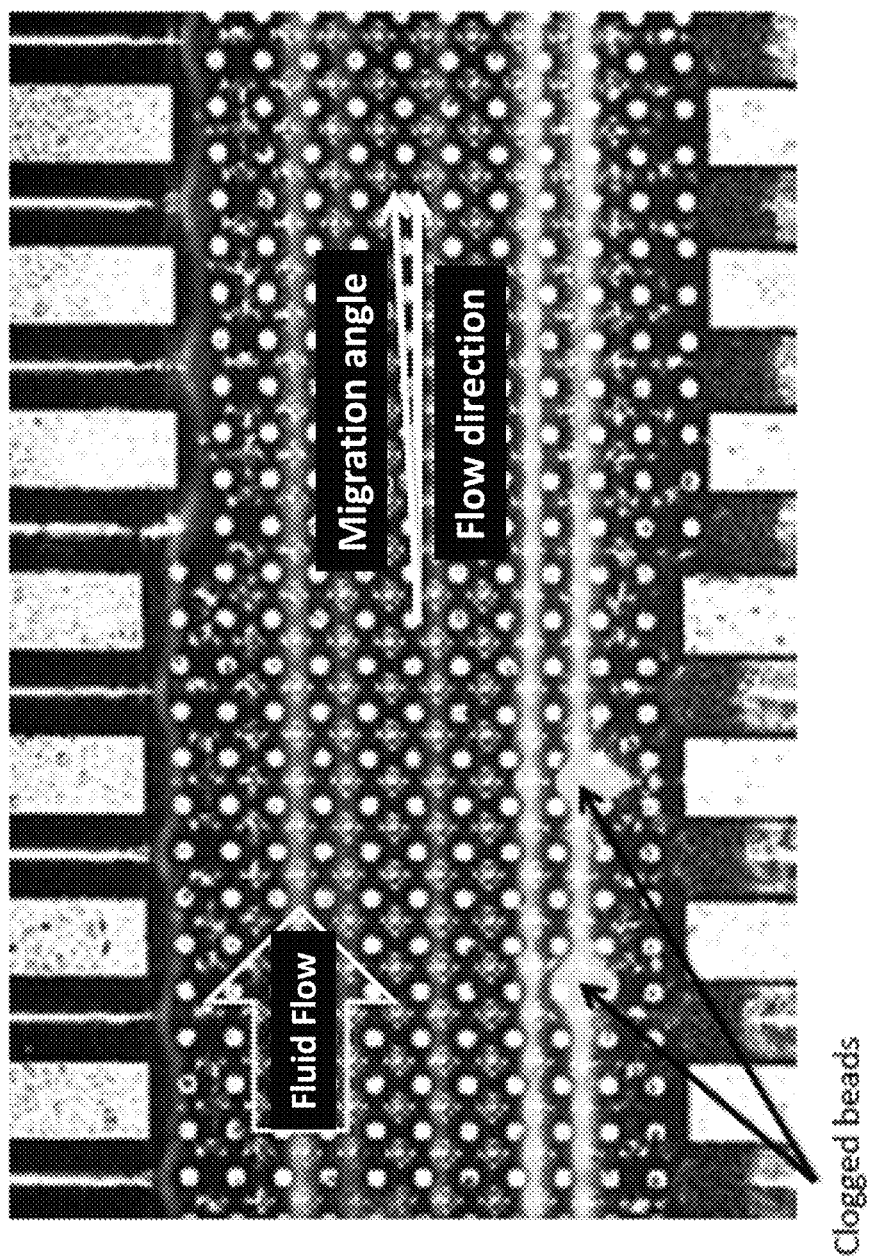
FIG. 34 illustrates a DLD array in "bumping mode" with clogged beads.

In some cases, devices described herein can comprise an integrated system for on-chip cleaning. Examples of the self cleaning system are illustrated in FIGS. 31-33. In some cases, the on-chip cleaning system comprises openings in walls of a channel such that fluid can be flowed through the openings, where the fluid flow is substantially perpendicular to the usual flow path of the channel. The cleaning system can be used to remove particles, e.g., cells trapped in an array of obstacles. In some cases, openings are present in only one wall that bounds a channel. In some cases, openings are present in both walls that bound a channel.

FIG. 31 illustrates a device comprising a deterministic lateral displacement (DLD) array also comprises an on-chip cleaning system. Sample and buffer inputs are illustrated at the left of the channel, and product and waste outputs are illustrated at the right. Walls for fluid containment are illustrated. The on-chip cleaning system is illustrated in an "open" configuration with openings in the walls that bound the DLD array. A fluid is illustrated flowing from the top of the schematic to the bottom of the schematic at a right angle to the particle and buffer flow direction.

FIG. 32 illustrates an on-chip cleaning system in a closed configuration. In this configuration, openings in the walls that bound the channel are blocked. FIG. 33 illustrates an on-chip cleaning system in an open configuration. In this configuration, openings in the walls that bound the channel are unblocked. In some cases, as illustrated in FIG. 33, the inlet and outlet ends of the channel can be blocked while the openings in the wall are in the open position. In some cases, inlet and/or outlet ends of the channel are not blocked when the openings in the wall are in an unblocked configuration.

In some case blocking and unblocking of the openings in the walls is controlled manually or automatically. In some cases, blocking and unblocking of the openings in the walls is controlled electronically. In some cases, an on-chip cleaning system is activated when a sensor is triggered. In some cases, the sensor is a pressure sensor (e.g., if backpressure in the device rises above a threshold (e.g., due to clogging), an alert can be sent that the on-chip cleaning system can be utilized, or the on-chip cleaning system can be activated automatically). In some case, the sensor is an optical sensor, e.g., an optical system, e.g., a microscope. In some cases, the optical system can monitor the device to detect clogging, e.g., by detection of trapped fluorescent particles. In some cases, the sensor is a spectrophotometer that detects obstruction of a light path through the bottom and top of the device (e.g., reduction in transmission of light through the device indicates clogging).

Any device comprising a channel comprising an array of obstacles can comprise an on-chip cleaning system. The array of obstacles can be a symmetric array of obstacles, asymmetric array of obstacles, mirrored array of obstacles, a mirrored array of obstacles with a central bypass channel with or without a wall, or a semi-mirrored array of obstacles.

The on-chip cleaning system can be organized in a variety of configurations. The number of openings in the walls that bound a channel can be dependent on the length of the channel. In some cases, each wall comprises a plurality of openings, e.g., at least 2, 5, 10, 20, 50, 75, 100, 200, 500, 750, 1000, 5000, or 10,000. In some cases, each wall comprises at most 2, 5, 10, 20, 50, 75, 100, 200, 500, 750, 1000, 5000, or 10,000 openings. In some cases, each of the openings in a wall is in an unblocked or blocked configuration. In some cases, not all of the openings in a wall are in an unblocked or blocked configuration. In some cases, at least 2, 5, 10, 20, 50, 70, 90, or 100% of openings in a side of a wall are configured to be a blocked or unblocked configuration. In some cases, less than 2, 5, 10, 20, 50, 70, 90, or 100% of openings in a side of a wall are configured to be in a blocked or unblocked configuration.

Each of the opening in the walls of a channel can have a diameter of at least 0.1, 0.2, 0.3, 0.4, 0.5, 0.6, 0.7, 0.8, 0.9, 1, 2, 3, 4, 5, 6, 7, 8, 9, 10, 20, 30, 40, or 50 um. In some cases, each of the openings in a wall of channel has a diameter of less than 0.1, 0.2, 0.3, 0.4, 0.5, 0.6, 0.7, 0.8, 0.9, 1, 2, 3, 4, 5, 6, 7, 8, 9, 10, 20, 30, 40, or 50 um. In some cases, each of the openings in a wall of channel has a diameter of about 0.1, 0.2, 0.3, 0.4, 0.5, 0.6, 0.7, 0.8, 0.9, 1, 2, 3, 4, 5, 6, 7, 8, 9, 10, 20, 30, 40, or 50 um. In some cases, openings in a wall of a channel are connected to flow paths. In some cases, each of the flow paths is under control of the same fluid flow system. In some cases, each of the flow paths is not under control of the same fluid flow system.

A flow rate of a cleaning solution using the on-chip cleaning system can be at least 0.1, 0.2, 0.3, 0.4, 0.5, 0.6, 0.7, 0.8, 0.9, 1, 2, 3, 4, 5, 6, 7, 8, 9, 10, 20, 30, 40, or 50 mL/min. A flow rate of a cleaning solution using the on-chip cleaning system can less than 0.1, 0.2, 0.3, 0.4, 0.5, 0.6, 0.7, 0.8, 0.9, 1, 2, 3, 4, 5, 6, 7, 8, 9, 10, 20, 30, 40, or 50 mL/min. A flow rate of a cleaning solution using the on-chip cleaning system can be about 0.1, 0.2, 0.3, 0.4, 0.5, 0.6, 0.7, 0.8, 0.9, 1, 2, 3, 4, 5, 6, 7, 8, 9, 10, 20, 30, 40, or 50 mL/min. Flow through the openings in a wall of a channel can be powered by a pump, e.g., syringe pump or high pressure pump. In some cases, operation of an on-chip cleaning system is automated. In some case, operation of an on-chip cleaning system is conducted through an electronic device, e.g., a computer.

A cleaning solution used in an on-chip cleaning system can comprise one or more agents, e.g., a detergent (e.g., 2-aminoethyl methan thiosulfonate hydrobromide, CHAPS, CHAPSO, digitonin, lithium dodecyl sulfate, n-dodecyl-beta-D-maltopyranoside, n-octyl-beta-d-glucopyranoside, NDSB-195, NDSB-201, NDSB-211, NDSB-221, NDSB-256, NONIDET-P40, Pluronic F68, Pluronic F-127, MTSES, Tween-20, Tween-80, Tween-40, sodium dodecyl sulfate (SDS), Triton X-100, Triton X-114, MTSET, sulfobetaine-10, sulfobetaine-12, or sulfobetaine-14), alcohol (e.g., ethanol, methanol), buffer (e.g., Tris-HCl, Trizma, HEPES, MES, phosphate buffer, potassium buffer), enzyme (DNase, RNase, protease, restriction enzyme), reducing agent (DTT, beta-mercaptoethanol), chelating agent (e.g., EDTA (e.g., 1 mM, 5 mM), EGTA (e.g., 1 mM, 5 mM)), anti-bacterial agent, antibiotic (e.g., chloramphenicol, ampicillin, kanamycin, erythromycin, gentamicin, neomycin, nelimicin, streptomycin, tobramycin, penicillin, bacitracin, polymyxin B, ciproflaxin, or tetracycline), anti-fungal agent, anti-viral agent, protease inhibitor, acid (e.g., hydrochloric acid, sulfuric acid, tartaric acid, nitric acid, phosphoric acid, boric acid, methanesulfonic acid, acetic acid, citric acid, formic acid, or fluoroacetic acid), base (e.g., NaOH). In some cases, the cleaning solution comprises about 1 to about 20% ethanol, or about 10 to about 20% ethanol, or less than 20% ethanol. A cleaning solution can comprise F108, which can be a difunctional block copolymer surfactant.

In some cases, multiple solutions are flowed through the cleaning system in succession.

In some cases, a cleaning solution is applied to a device and is allowed to remain in the device for at least 1, 5, 10, 30, or 60 min, or about least 4, 8, 12, 16, 20, or 24 hrs, or at least 3, 5, 7, 14, 21, or 28 days. In some cases, a cleaning solution is applied to a device and is allowed to remain in the device for less than about 1, 5, 10, 30, or 60 min, or less than 4, 8, 12, 16, 20, or 24 hrs, or less than 3, 5, 7, 14, 21, or 28 days. In some cases, a cleaning solution is washed out with water. Example 6 describes use of an on-chip cleaning system.

In some cases, the size-based separation methods described herein do not make use of a centrifuge and/or sedimentation. In some cases, the size-based separation methods described herein do make use of a centrifuge or sedimentation.

(t) Taper Angle

An obstacle, or pillar can be cylindrical. In some cases, obstacles on a device are not perfectly cylindrical. An obstacle, or at least 50% of obstacles in an array, can have a taper angle of less than 10, 9, 8, 7, 6, 5, 4.5, 4, 3.5, 3, 2.5, 2, 1.5, 1, 0.5, 0.4, 0.3, 0.2, or 0.1° An obstacle can have a taper angle of 0°. An obstacle, or at least 50% of obstacles in an array, can have a taper angle of about 0.1 to about 1°, about 1 to about 2°, about 2 to about 3°, about 3 to about 4°, or about 1 to about 4°.

F. Materials of Construction and Surface Chemistry

In some embodiments, a device is made by hot embossing PMMA and/or polycarbonate. Due to their low cost and compatibility with replication-based fabrication methods, thermoplastics can represent an attractive family of materials for the fabrication of lab-on-a-chip platforms. A diverse range of thermoplastic materials suitable for microfluidic fabrication is available, offering a wide selection of mechanical and chemical properties that can be leveraged and further tailored for specific applications. High-throughput embossing methods such as reel-to-reel processing of thermoplastics is an attractive method for industrial microfluidic chip production. The use of single chip hot embossing can be a cost-effective technique for realizing high-quality microfluidic devices during the prototyping stage. Methods for the replication of microscale features in two thermoplastics, polymethylmethacrylate (PMMA) and/or polycarbonate (PC), are described herein using hot embossing from a silicon template fabricated by deep reactive-ion etching. Further details can be found in "Microfluidic device fabrication by thermoplastic hot-embossing" by Yang and Devoe, Methods Mol. Biol. 2013; 949: 115-23, which is herby incorporated by reference herein in its entirety. In some cases, a device is made of polypropylene.

In some cases, a device comprises a polymer. In some cases, a device is made by injection molding. In some cases, a device is manufactured by a photolithographic technique. In some cases, a device is manufactured by soft embossing. In some cases, the embossing occurs on a polymer chip. In some cases, a device comprises plastic.

A device can be sealed and bonded in any suitable manner. The main challenge can be bonding planar microfluidic parts together hermetically without affecting the shape and size of micro-sized channels. A number of bonding techniques such as induction heating are suitable. The channels can be fabricated by using Excimer laser equipment. Further details can be found in "Sealing and bonding techniques for polymer-based microfluidic devices" by Abdirahman Yussuf, Igor Sbarski, Jason Hayes and Matthew Solomon, which is hereby incorporated by reference herein in its entirety.

Further bonding techniques include Adhesive Bonding, Pressure sensitive tape/Lamination, Thermal Fusion Bonding, Solvent Bonding, Localized welding, Surface treatment and combinations thereof. Further details can be found in "Bonding of thermoplastic polymer microfluidics" by Chia-Wen Tsao and Don L. DeVoe, Microfluid Nanofluid (2009) 6:1-16, which is herby incorporated by reference herein in its entirety.

In some embodiments, the device is made from a polymer and/or plastic. The polymer and/or plastic can be hydrophilic and/or wettable. FIG. 36 summarizes physical properties for common thermoplastics.

A device can be fabricated in any suitable manner. Some techniques include Replica molding, Softlithography with PDMS, Thermoset polyester, Embossing, Injection Molding, Laser Ablation and combinations thereof. Further details can be found in "Disposable microfluidic devices: fabrication, function and application" by Gina S. Fiorini and Daniel T. Chiu, BioTechniques 38:429-446 (March 2005), which is herby incorporated by reference herein in its entirety. The book "Lab on a Chip Technology" edited by Keith E. Herold and Avraham Rasooly, Caister Academic Press Norfolk UK (2009) is a resource for methods of fabrication, and such which is hereby incorporated by reference herein in its entirety. A device can be manufactured by cast molding or reactive injection molding.

Exemplary materials for fabricating the devices of the invention include glass, silicon, steel, nickel, polymers, e.g., poly(methylmethacrylate) (PMMA), polycarbonate, polystyrene, polyethylene, polyolefins, silicones (e.g., poly(dimethylsiloxane)), polypropylene, cis-polyisoprene (rubber), poly(vinyl chloride) (PVC), poly(vinyl acetate) (PVAc), polychloroprene (neoprene), polyetheretherketone (PEEK), polyethylene terephthalate (PET), polpolytetrafluoroethylene (Teflon), poly(vinylidene chloride) (SaranA), polysulfone, and cyclic olefin (co)polymer (COP) and cyclic olefin copolymer (COC), and combinations thereof. Other materials are known in the art. For example, deep Reactive Ion Etch (DRIE) can be used to fabricate silicon-based devices with small gaps, small obstacles and large aspect ratios (ratio of obstacle height to lateral dimension). Thermoforming (embossing, injection molding) of plastic devices may also be used. Additional methods include photolithography (e.g., stereolithography or x-ray photolithography), molding, embossing, silicon micromachining, wet or dry chemical etching, milling, diamond cutting, Lithographie Galvanoformung and Abformung (LIGA), and electroplating. For example, for glass, traditional silicon fabrication techniques of photolithography followed by wet (KOH) or dry etching (reactive ion etching with fluorine or other reactive gas) may be employed. Techniques such as laser micromachining can be adopted for plastic materials with high photon absorption efficiency. This technique is suitable for lower throughput fabrication because of the serial nature of the process. For mass-produced plastic devices, thermoplastic injection molding, and compression molding can be suitable. Conventional thermoplastic injection molding used for mass-fabrication of compact discs (which preserves fidelity of features in sub-microns) may also be employed to fabricate the devices. For example, the device features are replicated on a glass master by conventional photolithography. The glass master is electroformed to yield a tough, thermal shock resistant, thermally conductive, hard mold. This mold serves as the master template for injection molding or compression molding the features into a plastic device. Depending on the plastic material used to fabricate the devices and the requirements on optical quality and throughput of the finished product, compression molding or injection molding may be chosen as the method of manufacture. Compression molding (also called hot embossing or relief imprinting) can have the advantage of being compatible with high molecular weight polymers, which can be excellent for small structures and may replicate high aspect ratio structures but has longer cycle times. Injection molding can work well for low aspect ratio structures and can be suitable for low molecular weight polymers. A device can be made using any of the materials described herein. In some cases, the surface of the (plastic) device is treated to make it hydrophilic and/or wettable. Surfaces in devices, e.g., microfluidic devices, can play a critical role because they can define properties such as wetting, adsorption and repellency of biomolecules, biomolecular recognition using surface-immobilized receptors, sealing and bonding of different materials. In some cases, two types of treatments can be used to modify the surface properties of a device, e.g., a microfluidics device: wet chemical treatments and gas phase treatments. Wet treatments can be simple in terms of infrastructure requirements; they can be flexible and fast to develop from a research standpoint. Surface treatment of a device, e.g., microfluidics device, for production can be however best achieved using dry processes based on plasma and chemical vapor deposition. These treatments can eliminate the need for rinsing and drying steps have high throughput capability and are highly reproducible.

In some cases, the treatment is a wet chemical treatment. Among the wet chemical treatments available, the formation of self-assembled monolayers (SAMs) is one of the most versatile and easy to use surface treatments. SAMs have been developed on metals, silicon oxides and polymers. Molecules in SAMs can pack closely and can be composed of a headgroup that can bind covalently to the substrate, an alkyl chain and a terminal functional group. The thickness of the SAM can depend on the length of the alkyl chain and density of the molecules on the surface and is typically a few nanometers. SAMs can be easy to prepare and can be patterned with sub-micrometer lateral resolution. Different terminal groups can be used for defining the wetting properties of the surface as well as the affinity for or repellency of proteins. For glass surfaces, oxides and polymers that can be oxidized, grafting alkylsiloxanes to surfaces might be the simplest and most economical method. A wettability gradient from superhydrophobic to hydrophilic can be achieved by superposing a SAM-based wetting gradient onto microstructures in silicon that have varying lateral spacing.

Polymeric SAMs can comprise block copolymers and can have various three-dimensional structures, which can give the opportunity to vary their mode of grafting to a surface and the types of functionalities that they carry. Such layers can reach a significant thickness of several hundreds of nanometers and protect/functionalize surfaces more reliably than thinner monolayers. For example, a poly(oligo(ethyleneglycol)methacrylate) polymer brush can coat glass devices, e.g., chips, e.g., microfluidic chips, to make them hydrophilic and antifouling.

Coating polymers onto surfaces to modify their properties is possible. For example, poly(ethyleneglycol) can be used to "biologically" passivate device, e.g., microfluidic device materials and can be grafted onto PMMA surfaces of capillary electrophoresis microchips to make them hydrophilic. Poly(tetrafluoroethylene) can be used to make chemically resistant devices, e.g., microfluidic devices. Polymeric materials employed to fabricate devices, e.g., microfluidic devices, can be modified in many ways. In some cases, functional groups such as amines or carboxylic acids that are either in the native polymer or added by means of wet chemistry or plasma treatment are used to crosslink proteins and nucleic acids. DNA can be attached to COC and PMMA substrates using surface amine groups. Surfactants such as Pluronic® can be used to make surfaces hydrophilic and protein repellant by adding Pluronic® to PDMS formulations. In some cases, a layer of PMMA is spin coated on a device, e.g., microfluidic chip and PMMA is "doped" with hydroxypropyl cellulose to vary its contact angle.

Proteins can be used on surfaces to change surface wettability, to passivate a surface from non-specific protein binding and for functionalization. Proteins readily adsorb to hydrophobic substrates such as PDMS and polystyrene. By exploiting this property, PDMS substrates can be coated with neutravidin to immobilize biotinylated proteins or biotinylated dextran. Antibody coatings can be optimized depending on the hydrophobicity of the polymeric substrate. Bovine serum albumin can be used protein to passivate surfaces from non-specific adsorption and is easy to deposit spontaneously from solution to hydrophobic surfaces. On a hydrophilic substrate, a layer of hydrophobic poly(tetrafluoroethylene) can first be coated to enable the subsequent deposition of bovine serum albumin. Heparin, a biological molecule widely used as an anticoagulant, can be deposited from solution onto PDMS to make channels, e.g., microchannels hydrophilic while preventing adhesion of blood cells and proteins.

In some embodiments, a device undergoes a gas phase treatment. Plasma processing not only can modify the chemistry of a polymeric surface but it also can affect its roughness significantly thereby exacerbating wetting properties to make surfaces superhydrophilic and fluorocarbons can be plasma deposited to make surfaces superhydrophobic. Polymeric surfaces can be patterned using ultraviolet light to initiate radical polymerization followed by covalent grafting of polymers. Plasma-induced grafting can be used to attach poly(ethyleneglycol) onto polyamide and polyester surfaces to render them antifouling. Dextran can be a polysaccharide comprising many glucose molecules that can be coated to make hydrophilic antifouling surfaces. In some cases, a starting point to modifying polymers is to introduce surface hydroxyl groups using a plasma treatment followed by grafting a silane and dextran layer. Similarly, PDMS can be superficially oxidized using ultraviolet light for grafting a dextran hydrogel.

The large surface to volume ratio of devices, e.g., microfluidic structures can make any potential surface-analyte/reagent interaction a potential issue. Therefore, irrespective of the method used to treat the surfaces of a microfluidic device for POC testing, in some cases the surfaces of the device can not attract and deplete analytes or biochemicals that are needed for the test. In some cases, surface treatments do not interfere with signal generation and acquisition principles of the device. Further details can be found in "Capillary microfluidic chips for point of care testing: from research tools to decentralized medical diagnostics" a thesis by Luc Gervais, Ecole polytechnique federate de Lausanne, 23 Jun. 2011, which is herby incorporated by reference herein in its entirety.

To reduce non-specific adsorption of cells or compounds, e.g., released by lysed cells or found in biological samples, onto the channel walls, one or more channel walls may be chemically modified to be non-adherent or repulsive. The walls may be coated with a thin film coating (e.g., a monolayer) of commercial non-stick reagents, such as those used to form hydrogels. Additional examples chemical species that may be used to modify the channel walls include oligoethylene glycols, fluorinated polymers, organosilanes, thiols, poly-ethylene glycol, hyaluronic acid, bovine serum albumin, poly-vinyl alcohol, mucin, poly-HEMA, methacrylated PEG, and agarose. Charged polymers may also be employed to repel oppositely charged species. The type of chemical species used for repulsion and the method of attachment to the channel walls can depend on the nature of the species being repelled and the nature of the walls and the species being attached. Such surface modification techniques are well known in the art. The walls may be functionalized before or after the device is assembled. The channel walls may also be coated in order to capture materials in the sample, e.g., membrane fragments or proteins.

V. Properties of Particles Flowed Through Devices

The methods, compositions, devices, systems, and/or kits described herein can be used for high-throughput purification, isolation, and/or concentration of particles. The methods, compositions, devices, systems, and/or kits described herein can be used to isolate particles with relatively high purity, yield, and/or viability (if the particles are living, e.g., cells or organisms). One or more samples can be applied to one ore more inlets on a device. One or more buffers can be applied to one or more inlets on a device. Particles of at least a critical (predetermined) size can be passed through an array of obstacles and be deflected to one outlet, and particles less than the critical size can pass to another outlet. An array of obstacles can comprise any cross-sectional shape, obstacle diameter, gap size, tilt angle, and/or array pattern geometry described herein.

Temperature of a flowing liquid, or ambient temperature, or temperature of a device, can be about −20, −10, 0, 4, 10, 15, 20, 22, 23, 24, 25, 26, 30, 35, 37, 40, 45, 50, 55, 60, 65, 70, 75, 80, 85, 90, 95, or 100° C. Temperature of a flowing liquid, or ambient temperature, or temperature of a device, can be less than −20, −10, 0, 4, 10, 15, 20, 22, 23, 24, 25, 26, 30, 35, 37, 40, 45, 50, 55, 60, 65, 70, 75, 80, 85, 90, 95, or 100° C. Temperature of a flowing liquid, or ambient temperature, or temperature of a device, can be more than −20, −10, 0, 4, 10, 15, 20, 22, 23, 24, 25, 26, 30, 35, 37, 40, 45, 50, 55, 60, 65, 70, 75, 80, 85, 90, 95, or 100° C. Temperature of a flowing liquid, or ambient temperature, or temperature of a device can be about −20 to about −10° C., about −10 to about 0° C., about 0 to about 4° C., about 4 to about 25° C., about 25 to about 30° C., about 30 to about 37° C., about 37 to about 50° C., about 50 to about 65° C., or about 65 to about 100° C.

A. Purity

In some cases, methods, compositions, devices, systems, and/or kits described herein can be used to isolate first particles, e.g., cells, that are about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% pure. In some cases, methods, compositions, devices, systems, and/or kits described herein can be used to isolate first particles, e.g., cells, that are at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% pure. In some cases, methods, compositions, devices, systems, and/or kits described herein can be used to isolate first particles, e.g., cells, that are about 1 to about 10% pure, about 10% to about 20% pure, about 20% to about 30% pure, about 30% to about 40% pure, about 40% to about 50% pure, about 50% to about 60% pure, about 60% to about 70% pure, about 70% to about 80% pure, about 80% to about 90% pure, or about 90% to about 100% pure. In some cases, devices and methods described herein are used to isolate leukocytes from whole blood. In some cases, devices and methods described herein remove over 99% of erythrocytes, platelets, plasma proteins, and unbound staining from leukocytes. In some cases, leukocytes are removed from serum.

B. Yield

In some cases, methods, compositions, devices, systems, and/or kits described herein can be used to give a yield of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of first particles, e.g., cells from a sample. In some cases, methods, compositions, devices, systems, and/or kits described herein can be used to give a yield of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of first particles e.g., cells from a sample. In some cases, methods, compositions, devices, systems, and/or kits described herein can be used to give a yield of about 1% to about 10%, about 10% to about 20%, about 20% to about 30%, about 30% to about 40%, about 40% to about 50%, about 50% to about 60%, about 60% to about 70%, about 70% to about 80%, about 80% to about 90%, or about 90% to about 100% of first particles, e.g., cells from a sample. In some cases, devices and methods described herein are used to isolate leukocytes from whole blood. In some cases, at least 80%, 85%, or 90% of leukocytes are recovered from a whole blood sample without introducing bias among the leukocyte population.

C. Viability

In some cases, particles in a sample are alive (e.g., cell or organism). In some cases, methods, compositions, devices, systems, and/or kits described herein can be used to isolate particles (e.g., cells, organisms) that are about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% viable. In some cases, methods, compositions, devices, systems, and/or kits described herein can be used to isolate particles (e.g., cells, organisms) that are at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% viable. In some cases, methods, compositions, devices, systems, and/or kits described herein can be used to isolate particles (e.g., cells, organisms) that are at about 1% to about 10% viable, about 10% to about 20% viable, about 20% to about 30% viable, about 30% to about 40% viable, about 40% to about 50% viable, about 50% to about 60% viable, about 60% to about 70% viable, about 70% to about 80% viable, about 80% to about 90% viable, or about 90% to about 100% viable. In some cases, a sample comprises leukocytes and erythrocytes. In some cases, the method, compositions, devices, systems, and/or kits described herein can be used to isolate leukocytes from a sample such that the leukocytes are greater than 90% pure (i.e. less than 10% erythrocytes), greater than 90% of the leukocytes in the sample are isolated (greater than 90% yield), and greater than 90% of the leukocytes in the sample are viable.

VI. Applications of Particles Flowed Through Devices

Particles purified, isolated, and/or concentrated using methods, compositions, devices, systems, and/or kits described herein can be stored and/or used in downstream applications. Described herein are various applications for particles that have been purified, isolated, and/or concentrated using methods, compositions, devices, systems, and/or kits described herein A. Blood Banking (e.g., Cryopreservation)

In some cases, whole blood is separated into components using devices and methods described herein, and the components are stored. In some cases, erythrocytes are isolated or purified. In some cases, erythrocytes are stored at from about 1 to about 6° C. In some cases, erythrocytes are stored for about 20 to about 60 days, or about 30 to about 50 days, or up to 42 days. In some cases, erythrocytes are frozen (e.g., with a cryoprotectant, e.g., glycerol) and stored at, e.g., less than −60° C., for at least 10 years. In some cases, stored erythrocytes are used for transfusion. In some cases, isolated erythrocytes are administered to a subject after trauma, surgery, blood loss, or with a blood disorder, e.g., sickle cell anemia.

In some cases, plasma is isolated and frozen for later use. In some cases, plasma is stored for up to a year. Plasma can be administered to a subject, e.g., a burn patient, subject in shock, or subject with a bleeding disorder.

In some cases, platelets are isolated. In some cases, platelets are isolated, e.g., for transfusion. In some cases, isolated platelets are stored at room temperature, e.g., for about 5 to 7 days. In some cases, platelets are administered to a subject with cancer, an organ transplant, or a subject who is undergoing, or has undergone, surgery.

In some cases, an isolated blood component is cryoprecipitated anti-haemophilic factor (cryoprecipitated AHF). Cryoprecipitated AHF can be stored frozen for about a year. In some cases, Cryoprecipitated AHF is administered to a subject with hemophila or Von Willebrand disease.

Other blood components that can be isolated and stored are granulocytes. In some cases, granulocytes are used transfusion within 24 hrs after collection. In some cases, granulocytes are administered to subject to treat infections that are unresponsive to antibiotic therapy.

In some cases, lymphocytes are isolated and can be stored, with or without gene modification, prior to administration to a subject with cancer or infectious or other disease.

In some cases, purified particles, e.g., cells, e.g., stem cells, e.g., HSCs are preserved, e.g., cryopreserved. Methods of cryopreservation are described, e.g., in Berz et al (2007) Cryopreservation of Hematopoietic Stem Cells. Am J Hematol. 82: 463-472, which is herein incorporated by reference. In some cases, a heparinized plasmalyte solution and/or dimethylsulfoxide (DMSO) (e.g., 10% DMSO) are added to purified particles, e.g., cells, e.g., HSCs. In some cases, the purified particles, e.g., HSCs are in a solution with a final concentration of DMSO of less than 20, 19, 18, 17, 16, 15, 14, 13, 12, 11, 10, 9, 8, 7, 6, 5, 4, 3, 2, 1, or 0.5% DMSO. In some cases, particles, e.g., cells, e.g., HSCs, are in a solution with a final DMSO concentration of about 2 to about 10%, or about 5% to about 15%. In some cases, leukocytes are cryopreserved.

In some cases, purified particles, e.g., cells, e.g., stem cells, e.g., HSCs are combined with saline and or serum albumin. In some cases, a cryoprotectant is hydroxyethyl starch (HES), propylene glycol, alpha tocopherol, catalase, ascorbic acid, trehalose, or capase inhibitor (e.g., zVAD-fmk). In some cases, a cryoprotectant is a glycol (e.g., ethylene glycol, propylene glycol, or glycerol). In some cases, a cryoprotectant is 2-Methyl-2, 4-pentanediol (MPD). In some cases, a cryoprotectant is sucrose. In some cases, purified particles, e.g., cells, e.g., stem cells, e.g., HSCs are mixed with more than one cryoprotectant.

In some cases, purified particles, e.g., cells, e.g., stem cells, HSCs are frozen to a temperature of less 5° C., than −79° C., less than −155° C. or less than −195° C. In some cases, particles, e.g., cells, e.g., stem cells, e.g., HSCs are frozen to a temperature of about 4° C. of about −80° C., −156° C. or −196° C. In some cases, purified particles, e.g., cells, e.g., stem cells, e.g., HSCs are frozen to from about −196° C. to about −80° C. In some cases, purified particles, e.g., cells, e.g., stem cells, e.g., HSCs are stored in a liquid phase of a nitrogen tank. In some cases, purified particles, e.g., cells, e.g., stem cells, e.g., HSCs are store in a vapor nitrogen phase.

In some cases, purified particles, e.g., cells, e.g., stem cells, e.g., HSCs are frozen at a controlled rate freezing, e.g., at a rate of 1-2° C./min up to a temperature point of about −40° C. Then, the freezing process down to a target of −120° C. is performed can be performed a faster pace, about 3-5° C./min. In some cases, purified particles, e.g., cells, e.g., HSCs are cooled to a temperature of −4° C., then placed in a freezer at −80° C. In some cases, purified particles, e.g., cells, e.g., stem cells, e.g., HSCs are cryopreserved for at least 1, 10, 30, 180, or 365 days. In some cases, HSCs are cryopreserved for at least 1, 5, 10, 20, 30, 50, 75, or 100 years. In some cases, purified particles, e.g., cells, e.g., stem cells, e.g., HSCs are cryopreserved at a density of less than $10^{-11}$, $10^{-10}$, $10^{-9}$, $10^{-8}$, $10^{-7}$, $10^{-6}$, $10^{-5}$ cells/mL. In some cases, purified particles, e.g., cells, e.g., stem cells, e.g., HSCs are cryopreserved at a density of at least $10^{-11}$, $10^{-10}$, $10^{-9}$, $10^{-8}$, $10^{-7}$, $10^{-6}$, $10^{-5}$ cells/mL.

In some cases, cryopreserved purified particles, e.g., cells, e.g., stem cells, e.g., HSCs are thawed at 37° C. (e.g., in a water bath, gel pads). In some cases, cyropreserved purified particles, e.g., cells, e.g., HSCs are thawed at a temperature of about 0° C. to about 37° C.

In some cases, a cryopreservative (e.g., DMSO) is washed out of purified particles, e.g., cells, e.g., HSC sample after thawing. In some cases, a thawed purified particle, e.g., cell, e.g., stem cell, e.g., HSC sample is diluted in human serum albumin (HSA) (e.g., 2.5%) and dextran 40 (e.g., 5%). The sample can then be centrifuged or passed through a microfluidic device described herein, e.g., at a temperature of 10° C. In some cases, an HSA/dextran solution is added to the purified particles, e.g., cells, e.g., stem cells, e.g., HSCs again. In some cases, the DMSO concentration is less than 1.7%, e.g., washing and/or dilution. In some cases, stem cells, e.g., HSCs with a DMSO concentration of less than 1.7% is infused in a subject. In some case, cyropreserved purified particles, e.g., cells, e.g., stem cells, e.g., HSCs are stored in a container. In some cases, a container is an ethinyl vinyl acetate (EVA) container. In some cases, a container is gamma irradiated. In some cases, a container is a stainless steel container. In some cases, a container comprises, PVC, polyolefin, or polyethelene. In some cases, a container comprises Teflon, Kaplon, FEP, and/or polyimide. In some cases, purified cells, e.g., stem cells, e.g., HSCs are evaluated by cell counting for total nucleated cells and CD34+ cells (e.g., by flow cytometry); trypan blue exclusion for viability, 7-acinoactinomycin for viability, or propidium iodide for viability; engraftment in NOD/SCID (immunodeficient) mice, or a clonogenic assay (e.g., CFU-Sd12 assay in mice; CFU-GM; CFU-GEMM; BFU-E, or LTC-IC).

B. Cancer Treatment

In some cases, purified, isolated, and/or concentrated stems cells, e.g., HSCs can be used to treat cancer, e.g. cancer of the blood, e.g., leukemia or lymphoma. In some cases, purified, isolated, and/or concentrated stem cells, e.g., HSCs are obtained from a subject and subsequently administered to the same subject. The stem cells can travel to the bone marrow and begin to produce new blood cells.

In some cases, stem cells, e.g., HSCs are obtained from a first subject and administered to second subject (e.g., relative, e.g., sister or brother of the first subject). In some cases, the first subject and second subject are not relatives. In some cases, the second subject is a matched donor. In some cases, the first subject and the second subject have similar human leukocyte antigens. In some cases, the first subject and the second subject do not have similar human leukocyte antigens. In some cases, a subject diagnosed with or suspected of having, acute lymphoblastic leukemia, acute myeloblastic leukemia, chronic myelogoneous leukemia (CML), Hodgkin's disease, multiple myeloma, or non-Hodgkin' lymphoma is administered HSCs.

In some cases, administration of stem cells to a subject comprises use of an intravenous (IV) line. In some cases, the transplant takes about 1 to about 5 hours. After entering the blood stream, the cells can travel to the bone marrow. Engraftment (normal blood production) can occur within about 2 to about 4 weeks after transplantation. In some cases, the methods, compositions, devices, systems, and kits described herein are used to monitor engraftment.

In some cases, a subject receives a bone marrow transplant (BMT). In some cases, a subject receives a peripheral blood stem cell transplant (PBSCT). In some cases, a transplant is an autologous transplant (the subject receive his/her own stem cells).

In some cases, a transplant is a syngeneic transplant (a subject receives stem cells from his/her identical twin). In some cases, a transplant is an allogeneic transplant (a subject receives stem cells from his/her brother, sister, parent, or person unrelated to the subject).

In some cases, stem cells are purified from bone marrow in the pelvic bone or sternum. In some cases, PBSCs are purified by apheresis or leukapheresis. In some cases, stem cells are purified from umbilical cord or placenta cord blood.

In some cases, purified, isolated, or concentrated stem cells, e.g., HSCs are administered to a subject with CML, and the subject is also administered imatinib mesylate (Gleevec™). In some cases, the subject is administered stem cells, e.g., HSCs without receiving imatinib mesylate.

In some cases, a subject who receives stem cells e.g., HSCs is resistant to chemotherapy.

In some cases, a subject who receives stem cells, e.g., HSCs is a newborn, infant, child, teenager, young adult, middle aged person, or elderly person.

In some cases, a subject who receives stem cells, e.g., HSCs has neuroblastoma, Ewing's sarcoma, desmoplatic small-round cell tumor, or chronic granulomatous disease.

In some cases, a mini-transplant is used. In some cases, a tandem transplant is used, involving two sequential courses of high-dose chemotherapy and stem cell transplant.

In some cases, a subject, e.g., a cancer patient, is administered radiation or chemotherapy, and the radiation or chemotherapy targets hematopoietic cells, which can be destroyed by radiation or chemotherapy. In some cases, purified, isolated, and/or concentrated HSCs from the subject can be transplanted into the subject to replace cells destroyed by chemotherapy. Introducing the subject's own HSCs can reduce the chance of immune mismatch or graft-versus-host disease. In some cases, only CD34+, Thy-1+ cells are transplanted into the subject.

In some cases, stem cells are administered to a subject who is in remission (signs and symptoms of cancer have disappeared).

In some cases, the transplantation of stem cells purified using methods and devices described herein can result in a reduction of the risk of graft versus host disease by a least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% relative to transplantation of stem cells purified by conventional methods.

In some cases, a subject who is administered stem cells has one or more of the following cancers: acute myeloid leukemia; bladder cancer, including upper tract tumors and urothelial carcinoma of the prostate; bone cancer, including chondrosarcoma, Ewing's sarcoma, and osteosarcoma; breast cancer, including noninvasive, invasive, phyllodes tumor, Paget's disease, and breast cancer during pregnancy; central nervous system cancers, adult low-grade infiltrative supratentorial astrocytoma/oligodendroglioma, adult intracranial ependymoma, anaplastic astrocytoma/anaplastic oligodendroglioma/glioblastoma multiforme, limited (1-3) metastatic lesions, multiple (>3) metastatic lesions, carcinomatous lymphomatous meningitis, nonimmunosuppressed primary CNS lymphoma, and metastatic spine tumors; cervical cancer; chronic myelogenous leukemia (CML); colon cancer, rectal cancer, anal carcinoma; esophageal cancer; gastric (stomach) cancer; head and neck cancers, including ethmoid sinus tumors, maxillary sinus tumors, salivary gland tumors, cancer of the lip, cancer of the oral cavity, cancer of the oropharynx, cancer of the hypopharynx, occult primary, cancer of the glottic larynx, cancer of the supraglottic larynx, cancer of the nasopharynx, and advanced head and neck cancer; hepatobiliary cancers, including hepatocellular carcinoma, gallbladder cancer, intrahepatic cholangiocarcinoma, and extrahepatic cholangiocarcinoma; Hodgkin disease/lymphoma; kidney cancer; melanoma; multiple myeloma, systemic light chain amyloidosis, Waldenstrom's macroglobulinemia; myelodysplastic syndromes; neuroendocrine tumors, including multiple endocrine neoplasia, type 1, multiple endocrine neoplasia, type 2, carcinoid tumors, islet cell tumors, pheochromocytoma, poorly differentiated/small cell/atypical lung carcinoids; Non-Hodgkin's Lymphomas, including chronic lymphocytic leukemia/small lymphocytic lymphoma, follicular lymphoma, marginal zone lymphoma, mantle cell lymphoma, diffuse large B-Cell lymphoma, Burkitt's lymphoma, lymphoblastic lymphoma, AIDS-Related B-Cell lymphoma, peripheral T-Cell lymphoma, and mycosis fungoides/Sezary Syndrome; non-melanoma skin cancers, including basal and squamous cell skin cancers, dermatofibrosarcoma protuberans, Merkel cell carcinoma; non-small cell lung cancer (NSCLC), including thymic malignancies; occult primary; ovarian cancer, including epithelial ovarian cancer, borderline epithelial ovarian cancer (Low Malignant Potential), and less common ovarian histologies; pancreatic adenocarcinoma; prostate cancer; small cell lung cancer and lung neuroendocrine tumors; soft tissue sarcoma, including soft-tissue extremity, retroperitoneal, intra-abdominal sarcoma, and desmoid; testicular cancer; thymic malignancies, including thyroid carcinoma, nodule evaluation, papillary carcinoma, follicular carcinoma, Hiirthle cell neoplasm, medullary carcinoma, and anaplastic carcinoma; uterine neoplasms, including endometrial cancer or uterine sarcoma.

In some cases, stem cells, e.g., HSCs are purified, isolated, and/or concentrated, e.g., from an HLA-matched subject, and the HSCs are transplanted into another person, e.g., a sibling of the subject, wherein the sibling has cancer. In some cases, the transplanted stem cells, e.g., HSCs show antitumor activity (graft-verus-tumor treatment of cancer).

In some cases, Natural Killer (NK) cells are used in immunotherapy, e.g., for cancer, e.g., leukemia. Uses of NK cells are described, e.g., in Grywacz et al. (2008) Use of natural killer cells as immunotherapy for leukaemia. Best Pract Res Clin Haematol. 3: 467-483 and Miller (2013) Therapeutic applications: natural killer cells in the clinic. Hematology 2013:247-253, which are herein incorporated by reference in their entireties.

C. Cancer Diagnosis

In some cases, cells isolated using the methods, compositions, devices, systems, and kits described herein are used to diagnose a cancer described herein, e.g., a blood cancer, e.g., leukemia, lymphoma, or myeloma. In some cases, the leukemia is adult acute lymphoblastic leukemia, childhood acute lymphoblastic leukemia, adult acute myeloid leukemia, childhood acute myeloid leukemia, chronic lymphocytic leukemia, chronic myelogenous leukemia, or hairy cell leukemia. In some cases, the lymphoma is AIDS-related lymphoma, cutaneous T-cell lymphoma, adult Hodgkin Lymphoma, childhood Hodgkin Lymphoma, mycosis fungoides, adult Non-Hodgkin Lymphoma, childhood Non-Hodgkin Lymphoma, primary Central Nervous System Lymphoma, Sézary Syndrome, cutaneous T-Cell Lymphoma, or Waldenström Macroglobulinemia. In some cases, the blood cancer is a chronic myeloproliferative disorder, Langerhans cell histiocytosis, multiple myeloma, plasma cell neoplasm, a myelodysplastic syndrome, a myelodysplastic/myeloproflierative neoplasm.

In some cases, leukocytes are evaluated with a leukemia and lymphoma research panel. In some cases, a research panel is used to look for sets of proteins, e.g., cell surface and/or intracellular proteins that serve as markers for subtypes of normal leukocytes and hematologic malignancies. In some cases, the panel is evaluated with flow cytometry. The panel can be, e.g., a BD Euroflow multicolor antibody panel (see www.bdbiosciences.com/eu/documents/EuroFlow_datasheet_new.pdf). The marker in the BD Euroflow multicolor antibody panel can be, e.g., CD-11c CD22, CD24, CD45, CD49d, CD 123, Igk, CD10, CD27, CD38, CD43, CD81, TCRγδ, β-2 microglobulin, CD9, CD71, CD79b, Igλ, IREM-2 (CD300e), CD2, CD3, CD4,CD7, CD8, CD16, CD16, CD20, CD23, CD36, CD38, CD41a, CD42a, CD45, CD56, CD64, CD105, CD138, CD200, Igλ, Igκ and/or HLA-DR. A label (e.g., flurochrome) associated with the marker in the BD Euroflow multicolor antibody panel can be FITC, PE, V450, PE-Cy™7, PerCP-Cy5.5, APC-H7, V500-C, APC, PacB, or PacO.

In some cases, the panel is evaluated with flow cytometry. In some cases, leukocytes recovered using devices and/or methods described herein are evaluated in B-cell analysis (kappa and lambda ratio). Comparing the ratio of kappa-to-lambda can be used to determine whether a subject might have a plasma cell tumor, e.g., multiple myeloma, monoclonal gammopathy of undetermined significance (MGUS), Smoldering myeloma, solitary plasmacytoma of the bone, or AL amyloidosis. In some cases, free light chain production is assessed, which can be prognostic of a worse outcome in multiple myeloma or chronic lymphocytic leukemia.

D. Blood Disorders

In some cases, purified, isolated, or concentrated HSCs are administered to a subject with a hereditary blood disorder. The hereditary blood disorder can be, e.g., aplastic anemia, beta-thalassemia, Blackfan-Diamond syndrome, globoid cell leukodystrophy, sickle-cell anemia, severe combined immunodeficiency, X-linked lymphoproliferative syndrome, or Wiskott-Aldrich syndrome. Inborn errors of metabolism that can be treated with bone marrow transplants include: Hunter's syndrome, Hurler's syndrome, Lesch Nyhan syndrome, and osteopetrosis. In some cases, the hereditary blood disorder is Fanconi anemia. In some cases, purified, isolated, or concentrated HSCs are administered to a subject to treat a blood disorder, e.g., amyloidois, anemia, essential thrombocythemia, Fanconi anemia, Gaucher disease, hemochromatosis, hemolytic anemia, hemophilia, hypereosinophilia, idiopathic thrombocytopenic purpura, an inherited bone marrow failure syndrome, iron-deficiency anemia, Langerhan Cell histiocytosis, leucopenia, mastocytosis, myelofibrosis, a myeloprofilerative disorder, pernicious anemia, polycythermia vera, porphyria, sickle cell anemia, a thalassemia, thrombocytopenia, thrombocytosis, thrombotic thrombocytopenic purpura, or von Willebrand disease. In some cases, particles (e.g., cells) purified, isolated, and/or concentrated using methods described herein are used to diagnose a blood disorder, e.g., a blood disorder described herein.

E. Autoimmune Disease

Stem cells, e.g., HSCs purified, isolated, and/or concentrated using the methods, compositions, devices, systems, and/or kits described herein can be administered to a subject to treat an autoimmune disease. In some cases, stem cells, e.g., HSCs purified, isolated, and/or concentrated using the methods, compositions, devices, systems, and/or kits can be administered to a subject with an autoimmune disorder that affects heart, brain, nerves, muscle, skin, eye, joint, lung, kidney, gland, the digestive tract, or blood vessels. In some cases, an autoimmune disorder can be rheumatoid arthritis, Graves' disease, thryriodits, scleroderma, systemic sclerosis, vitiligo, systemic lupus erythematosus (SLE), alopecia areata, autoimmune hemolytic anemia, autoimmune hepatitis, dermatomyositis, diabetes (type 1), juvenile idiopathic arthritis, glomerulonephritis, Guillain-Barré syndrome, idiopathic thrombocytopenic purpura, myasthenia gravis, myocarditis, multiple sclerosis, pemphigus/pemphigoid, pernicious anemia, polyarteritis nodosa, polymyositis, primary biliary cirrhosis, psoriasis, scleroderma/systemic sclerosis, Sjögren's syndrome, uveitis, or granulomatosis with polyangiitis (Wegener's)

F. Other Uses of Stem Cells

In some cases, stems cells purified, isolated, and/or concentrated using the methods, compositions, devices, systems, and/or kits described herein can be used to treat Alzheimer's diseases, spinal cord injury, stroke, burns, heart disease, or osteoarthritis. In some cases, stem cells can be used to treat cardiovascular disease.

In some cases, stem cells are used to treat a subject with a neurological or neurocognitive condition. The neurological or neurocognitive condition can be a neurological disorder listed on the National Institute of Neurological Disorders and Stroke webpage (www.ninds.nih.gov/disorders/disorder_index.htm). In some embodiments, the subject can have a sign or symptom. The neurological or neurocognitive condition, or symptom, can be, e.g., abarognosis (e.g., loss of the ability to detect the weight of an object held in the hand or to discern the difference in weight between two objects), acid lipase disease, acid maltase deficiency, acquired epileptiform aphasia, absence of the septum pellucidum, acute disseminated encephalomyelitis, adie's pupil, Adie's syndrome, adrenoleukodystrophy, agenesis of the corpus callosum, agnosia, Aicardi syndrome, Aicardi-Goutieres syndrome disorder, AIDS—neurological complications, akathisia, alcohol related disorders, Alexander disease, Alien hand syndrome (anarchic hand), allochiria, Alpers' disease, altitude sickness, alternating hemiplegia, Alzheimer's disease, amyotrophic lateral sclerosis, anencephaly, aneurysm, Angelman syndrome, angiomatosis, anoxia, Antiphospholipid syndrome, aphasia, apraxia, arachnoid cysts, arachnoiditis, arnold-chiari malformation, Asperger syndrome, arteriovenous malformation, ataxia, ataxias and cerebellar or spinocerebellar degeneration, ataxia telangiectasia, atrial fibrillation, stroke, attention deficit hyperactivity disorder, auditory processing disorder, autism, autonomic dysfunction, back pain, Barth syndrome, Batten disease, becker's myotonia, Behcet's disease, bell's palsy, benign essential blepharospasm, benign focal amyotrophy, benign intracranial hypertension, Bernhardt-Roth syndrome, bilateral frontoparietal polymicrogyria, Binswanger's disease, blepharospasm, Bloch-Sulzberger syndrome, brachial plexus birth injuries, brachial plexus injury, Bradbury-Eggleston syndrome, brain or spinal tumor, brain abscess, brain aneurysm, brain damage, brain injury, brain tumor, Brown-Sequard syndrome, bulbospinal muscular atrophy, CADASIL (cerebral autosomal dominant arteriopathy subcortical infarcts and leukoencephalopathy), Canavan disease, Carpal tunnel syndrome, causalgia, cavernomas, cavernous angioma, cavernous malformation, Central cervical cord Syndrome, Central cord syndrome, Central pain syndrome, central pontine myelinolysis, centronuclear myopathy, cephalic disorder, ceramidase deficiency, cerebellar degeneration, cerebellar hypoplasia, cerebral aneurysm, cerebral arteriosclerosis, cerebral atrophy, cerebral beriberi, cerebral cavernous malformation, cerebral gigantism, cerebral hypoxia, cerebral palsy, cerebral vasculitis, Cerebro-Oculo-Facio-Skeletal syndrome (COFS), cervical spinal stenosis, Charcot-Marie-Tooth disease, chiari malformation, Cholesterol ester storage disease, chorea, choreoacanthocytosis, Chronic fatigue syndrome, chronic inflammatory demyelinating polyneuropathy (CIDP), chronic orthostatic intolerance, chronic pain, Cockayne syndrome type II, Coffin-Lowry syndrome, colpocephaly, coma, Complex regional pain syndrome, compression neuropathy, concussion, congenital facial diplegia, congenital myasthenia, congenital myopathy, congenital vascular cavernous malformations, corticobasal degeneration, cranial arteritis, craniosynostosis, cree encephalitis, Creutzfeldt-Jakob disease, cumulative trauma disorders, Cushing's syndrome, Cytomegalic inclusion body disease (CIBD), cytomegalovirus infection, Dancing eyes-dancing feet syndrome (opsoclonus myoclonus syndrome), Dandy-Walker syndrome (DWS), Dawson disease, decompression sickness, De morsier's syndrome, dejerine-klumpke palsy, Dejerine-Sottas disease, Delayed sleep phase syndrome, dementia, dementia—multi-infarct, dementia—semantic, dementia—subcortical, dementia with lewy bodies, dentate cerebellar ataxia, dentatorubral atrophy, depression, dermatomyositis, developmental dyspraxia, Devic's syndrome, diabetes, diabetic neuropathy, diffuse sclerosis, Dravet syndrome, dysautonomia, dyscalculia, dysgraphia, dyslexia, dysphagia, dyspraxia, dyssynergia cerebellaris myoclonica, dyssynergia cerebellaris progressiva, dystonia, dystonias, Early infantile epileptic, Empty sella syndrome, encephalitis, encephalitis lethargica, encephalocele, encephalopathy, encephalopathy (familial infantile), encephalotrigeminal angiomatosis, encopresis, epilepsy, epileptic hemiplegia, erb's palsy, erb-duchenne and dejerine-klumpke palsies, erythromelalgia, essential tremor, extrapontine myelinolysis, Fabry's disease, Fahr's syndrome, fainting, familial dysautonomia, familial hemangioma, familial idiopathic basal ganglia calcification, familial periodic paralyses, familial spastic paralysis, Farber's disease, febrile seizures, fibromuscular dysplasia, fibromyalgia, Fisher syndrome, floppy infant syndrome, foot drop, Foville's syndrome, friedreich's ataxia, frontotemporal dementia, Gaucher's disease, generalized gangliosidoses, Gerstmann's syndrome, Gerstmann-Straussler-Scheinker disease, giant axonal neuropathy, giant cell arteritis, Giant cell inclusion disease, globoid cell leukodystrophy, glossopharyngeal neuralgia, Glycogen storage disease, gray matter heterotopia, Guillain-Barre syndrome, Hallervorden-Spatz disease, head injury, headache, hemicrania continua, hemifacial spasm, hemiplegia alterans, hereditary neuropathies, hereditary spastic paraplegia, heredopathia atactica polyneuritiformis, herpes zoster, herpes zoster oticus, Hirayama syndrome, Holmes-Adie syndrome, holoprosencephaly, HTLV-1 associated myelopathy, HIV infection, Hughes syndrome, Huntington's disease, hydranencephaly, hydrocephalus, hydrocephalus—normal pressure, hydromyelia, hypercortisolism, hypersomnia, hypertension, hypertonia, hypotonia, hypoxia, immune-mediated encephalomyelitis, inclusion body myositis, incontinentia pigmenti, infantile hypotonia, infantile neuroaxonal dystrophy, Infantile phytanic acid storage disease, Infantile refsum disease, infantile spasms, inflammatory myopathy, inflammatory myopathies, iniencephaly, intestinal lipodystrophy, intracranial cyst, intracranial hypertension, Isaac's syndrome, Joubert syndrome, Karak syndrome, Kearns-Sayre syndrome, Kennedy disease, Kinsbourne syndrome, Kleine-Levin syndrome, Klippel feil syndrome, Klippel-Trenaunay syndrome (KTS), Kluver-Bucy syndrome, Korsakoff's amnesic syndrome, Krabbe disease, Kugelberg-Welander disease, kuru, Lafora disease, lambert-eaton myasthenic syndrome, Landau-Kleffner syndrome, lateral femoral cutaneous nerve entrapment, Lateral medullary (wallenberg) syndrome, learning disabilities, Leigh's disease, Lennox-Gastaut syndrome, Lesch-Nyhan syndrome, leukodystrophy, Levine-Critchley syndrome, lewy body dementia, Lipid storage diseases, lipoid proteinosis, lissencephaly, Locked-In syndrome, Lou Gehrig's, lumbar disc disease, lumbar spinal stenosis, lupus—neurological sequelae, lyme disease—neurological sequelae, Machado-Joseph disease (spinocerebellar ataxia type 3), macrencephaly, macropsia, megalencephaly, Melkersson-Rosenthal syndrome, Menieres disease, meningitis, meningitis and encephalitis, Menkes disease, meralgia paresthetica, metachromatic leukodystrophy, metabolic disorders, microcephaly, micropsia, migraine, Miller fisher syndrome, mini-stroke (transient ischemic attack), misophonia, mitochondrial myopathy, Mobius syndrome, Moebius syndrome, monomelic amyotrophy, mood disorder, Motor neurone disease, motor skills disorder, Moyamoya disease, mucolipidoses, mucopolysaccharidoses, multi-infarct dementia, multifocal motor neuropathy, multiple sclerosis, multiple system atrophy, multiple system atrophy with orthostatic hypotension, muscular dystrophy, myalgic encephalomyelitis, myasthenia—congenital, myasthenia gravis, myelinoclastic diffuse sclerosis, myoclonic encephalopathy of infants, myoclonus, myopathy, myopathy—congenital, myopathy—thyrotoxic, myotonia, myotonia congenita, myotubular myopathy, narcolepsy, neuroacanthocytosis, neurodegeneration with brain iron accumulation, neurofibromatosis, Neuroleptic malignant syndrome, neurological complications of AIDS, neurological complications of lyme disease, neurological consequences of cytomegalovirus infection, neurological manifestations of AIDS, neurological manifestations of pompe disease, neurological sequelae of lupus, neuromyelitis optica, neuromyotonia, neuronal ceroid lipofuscinosis, neuronal migration disorders, neuropathy—hereditary, neurosarcoidosis, neurosyphilis, neurotoxicity, neurotoxic insult, nevus cavernosus, Niemann-pick disease, Non 24-hour sleep-wake syndrome, nonverbal learning disorder, normal pressure hydrocephalus, O'Sullivan-McLeod syndrome, occipital neuralgia, occult spinal dysraphism sequence, Ohtahara syndrome, olivopontocerebellar atrophy, opsoclonus myoclonus, Opsoclonus myoclonus syndrome, optic neuritis, orthostatic hypotension, Overuse syndrome, chronic pain, palinopsia, panic disorder, pantothenate kinase-associated neurodegeneration, paramyotonia congenita, Paraneoplastic diseases, paresthesia, Parkinson's disease, paroxysmal attacks, paroxysmal choreoathetosis, paroxysmal hemicrania, Parry-Romberg syndrome, Pelizaeus-Merzbacher disease, Pena shokeir II syndrome, perineural cysts, periodic paralyses, peripheral neuropathy, periventricular leukomalacia, persistent vegetative state, pervasive developmental disorders, photic sneeze reflex, Phytanic acid storage disease, Pick's disease, pinched nerve, Piriformis syndrome, pituitary tumors, PMG, polio, polymicrogyria, polymyositis, Pompe disease, porencephaly, Post-polio syndrome, postherpetic neuralgia (PHN), postinfectious encephalomyelitis, postural hypotension, Postural orthostatic tachycardia syndrome, Postural tachycardia syndrome, Prader-Willi syndrome, primary dentatum atrophy, primary lateral sclerosis, primary progressive aphasia, Prion diseases, progressive hemifacial atrophy, progressive locomotor ataxia, progressive multifocal leukoencephalopathy, progressive sclerosing pohodystrophy, progressive supranuclear palsy, prosopagnosia, Pseudo-Torch syndrome, Pseudotoxoplasmosis syndrome, pseudotumor cerebri, Rabies, Ramsay hunt syndrome type I, Ramsay hunt syndrome type II, Ramsay hunt syndrome type III, Rasmussen's encephalitis, Reflex neurovascular dystrophy, Reflex sympathetic dystrophy syndrome, Refsum disease, Refsum disease—infantile, repetitive motion disorders, repetitive stress injury, Restless legs syndrome, retrovirus-associated myelopathy, Rett syndrome, Reye's syndrome, rheumatic encephalitis, rhythmic movement disorder, Riley-Day syndrome, Romberg syndrome, sacral nerve root cysts, saint vitus dance, Salivary gland disease, Sandhoff disease, Schilder's disease, schizencephaly, schizophrenia, Seitelberger disease, seizure disorder, semantic dementia, sensory integration dysfunction, septo-optic dysplasia, severe myoclonic epilepsy of infancy (SMEI), Shaken baby syndrome, shingles, Shy-Drager syndrome, Sjogren's syndrome, sleep apnea, sleeping sickness, snatiation, Sotos syndrome, spasticity, spina bifida, spinal cord infarction, spinal cord injury, spinal cord tumors, spinal muscular atrophy, spinocerebellar ataxia, spinocerebellar atrophy, spinocerebellar degeneration, Steele-Richardson-Olszewski syndrome, Stiff-Person syndrome, striatonigral degeneration, stroke, Sturge-Weber syndrome, subacute sclerosing panencephalitis, subcortical arteriosclerotic encephalopathy, SUNCT headache, superficial siderosis, swallowing disorders, Sydenham's chorea, syncope, synesthesia, syphilitic spinal sclerosis, syringohydromyelia, syringomyelia, systemic lupus erythematosus, tabes dorsalis, tardive dyskinesia, tardive dysphrenia, tarlov cyst, Tarsal tunnel syndrome, Tay-Sachs disease, temporal arteritis, tetanus, Tethered spinal cord syndrome, Thomsen disease, thomsen's myotonia, Thoracic outlet syndrome, thyrotoxic myopathy, tic douloureux, todd's paralysis, Tourette syndrome, toxic encephalopathy, transient ischemic attack, transmissible spongiform encephalopathies, transverse myelitis, traumatic brain injury, tremor, trigeminal neuralgia, tropical spastic paraparesis, Troyer syndrome, trypanosomiasis, tuberous sclerosis, ubisiosis, uremia, vascular erectile tumor, vasculitis syndromes of the central and peripheral nervous systems, viliuisk encephalomyelitis (VE), Von economo's disease, Von Hippel-Lindau disease (VHL), Von recklinghausen's disease, Wallenberg's syndrome, Werdnig-Hoffman disease, Wernicke-Korsakoff syndrome, West syndrome, Whiplash, Whipple's disease, Williams syndrome, Wilson's disease, Wolman's disease, X-linked spinal and bulbar muscular atrophy, or Zellweger syndrome.

G. Microscopy

In some cases, particles that are purified, isolated, and/or concentrated using the methods, compositions, devices, systems, and/or kits described herein (e.g., cells) can be analyzed by microscopy. In some cases, the microscopy can be optical, electron, or scanning probe microsopy. In some case, optical microscopy comprises use of bright field, oblique illumination, cross-polarized light, dispersion staining, dark field, phase contrast, differential interference contrast, interference reflection microscopy, fluorescence (e.g., when particles, e.g., cells, are immunostained), confocal, single plane illumination microscopy, light sheet fluorescence microscopy, deconvolution, or serial time-encoded amplified microscopy. In some cases, electron microscopy comprises transmission electron microscopy (TEM) or scanning electron microscopy (SEM). In some cases, a scanning probe microscope comprises an atomic force microscopy, a scanning tunneling microscopy, or a photonic force microscope. In some cases, a microscope is an ultrasonic force microscope (UFM). In some cases, microscopy comprises ultraviolet microscopy, infrared microscopy, digital holographic microscopy, digital pathology (virtual microscopy), or laser microscopy.

In some cases, a microscope is in fluid communication with a device for purification described herein. In some cases, a microscope is in fluid communication with a device for purification, wherein the microscope is downstream of a device for purification. In some cases, a microscope is in fluid communication with a device for purification upstream of the device for purification. In some cases, a microscope is in fluid communication with a device for purification upstream and downstream of the device for purification. In some cases, a microscope is configured to allow viewing a device for purification described herein.

H. Flow Cytometry

In some cases, particles (e.g., cells) that are purified, isolated, and/or concentrated using the methods, compositions, devices, systems, and/or kits described herein can be analyzed by flow cytometry. Manipulation of cells in devices in a flow cytometer can be accomplished using hydrodynamic forces. A suspension of particles (e.g., cells) can be injected into the center of a flowing sheath fluid. In some cases, forces of the surrounding sheath fluid confine the sample stream to a narrow core that can carry cells through a path of a laser that can excite associated fluorophores and create a scatter pattern.

Flow cytometry can comprise fluorescence-activated cell sorting (FACS). In some cases, a sample is subject to flow cytometry, e.g., FACS, before the sample is applied to device for purification described herein. In some cases, a flow cytometer is in fluid communication with a device for purification described herein; in some cases, a flow cytometer is fluidly connected upstream of a device for purification; in some cases, a flow cytometer is fluidly connected downstream of a device for purification described herein. In some cases, a flow cytometer is fluidly connected upstream and downstream of a device for purification described herein.

In some cases, particles (e.g., cells) that are analyzed by flow cytometry are labeled. In some cases, the particles are labeled with a fluorophore. In some case, a fluorophore is attached to an antibody, and the antibody attaches to a particle (e.g., cell). In some cases, an antibody can attach to a cell membrane. In some cases, a particle is labeled with a quantum dot.

FACS can be used to sort a heterogenous mixture of particles, e.g., cells, into two or more containers. FACS can be based on the light scattering and fluorescent characteristics of each type of cell. A suspension of particles (e.g., cells) can be entrained in a flowing stream of liquid. There can be separation between particles in the liquid. The stream of particles (e.g., cells) can be broken into droplets (e.g., by a vibrating mechanism). In some cases, only one particle (e.g., cell) is in each droplet. In some cases, the before the stream breaks into droplets, the liquid passes through a fluroscence measuring station. The fluorescence characteristics can be measured. A charge can be given to each droplet based on the fluorescence measurement, and the charged droplets can pass through an electrostatic deflection system that can divert droplets to containers based on charge.

In some cases, leukocytes recovered using methods and/or devices described herein are stained with anti-Kappa-FITC (fluorescein isothiocyanate), anti-Lamda-PE (phycoerythrin), 7AAD-PerCP, and/or CD-19-APC (allophycocyanin), CD-45-APC-Cy7.

I. Acoustic Focusing

In some cases, particles purified, isolated, and/or concentrated using methods, compositions, devices, systems, and/or kits described herein are subjected to an acoustic focusing flow cytometer (e.g., Attune® Acoustic Focusing Flow Cytometer; Life Technologies™). In some cases, a acoustic focusing is used on a sample before the sample is applied to a device comprising an array of ordered obstacles. Acoustic focusing cytometry can use ultrasonic waves (e.g., over 2 MHz) rather than hydrodynamic forces to position cells in a focused line along a central axis of a capillary. (see e.g., www.lifetechnologies.com/us/en/home/life-science/cell-analysis/flow-cytometry/flow-cytometers/attune-acoustic-focusing-flow-cytometer/acoustic-focusing-technology-overview.htm). Acoustic focusing can be independent of sample input rate. Acoustic focusing can enable cells to be tightly focused at a point of laser interrogation. Acoustic focusing can occur without high velocity or high volumetric sheath fluid. In some cases, volumetric syringe pumps can enable absolute cell counting without beads. In some cases, acoustic resonance is driven by a piezoelectric device. Acoustic focusing can make use of an optical cell for sample interrogation, one or more lasers, and electronics for collecting fluorescence and/or scatter information. In some cases, acoustic focusing makes use of a pump, e.g., a syringe pump. In some cases, a frequency used in acoustic focusing is about 0.1, 0.2, 0.3, 0.4, 0.5, 0.6, 0.7, 0.8, 0.09, 1, 1.5, 2, 2.5, 3, 3.5, 4, 4.5, 5, 5.5, or 6 MHz. In some cases, a flow rate in an acoustic focusing cytometer is operated at at least 10, 25, 50, 100, 200, 500, 1000, 2000, or 5000 µL/min.

J. Analysis of Nucleic Acids or Proteins

In some cases, a particle (e.g., nucleic acid and/or protein) purified, isolated, and/or concentrated using methods, compositions, devices, systems, and/or kits described herein can be analyzed using one or more of the following techniques: genetic testing using G-banded karotyping, fragile X testing, chromosomal microarray (CMA, also known as comparative genomic hybridization (CGH)) (e.g., to test for submicroscopic genomic deletions and/or duplications), array-based comparative genomic hybridization, detecting single nucleotide polymorphisms (SNPs) with arrays, subtelomeric fluorescence in situ hybridization (ST-FISH) (e.g., to detect submicroscopic copy-number variants (CNVs)), expression profiling, DNA microarray, high-density oligonucleotide microarray, whole-genome RNA expression array, peptide microarray, enzyme-linked immunosorbent assay (ELISA), genome sequencing, de novo sequencing, 454 sequencing (Roche), pyrosequencing, Helicos True Single Molecule Sequencing, SOLiD™ sequencing (Applied Biosystems, Life Technologies), SOLEXA sequencing (Illumina sequencing), nanosequencing, chemical-sensitive field effect transistor (chemFET) array sequencing (Ion Torrent), ion semiconductor sequencing (Ion Torrent), DNA nanoball sequencing, nanopore sequencing, Pacific Biosciences SMRT sequencing, Genia Technologies nanopore single-molecule DNA sequencing, Oxford Nanopore single-molecule DNA sequencing, polony sequencing, copy number variation (CNV) analysis sequencing, small nucleotide polymorphism (SNP) analysis, immunohistochemistry (IHC), immunoctyochemistry (ICC), mass spectrometry, tandem mass spectrometry, matrix-assisted laser desorption ionization time of flight mass spectrometry (MALDI-TOF MS), in-situ hybridization, fluorescent in-situ (SISH), polymerase chain reaction (PCR), digital PCR (dPCR), reverse transcription PCR, quantitative PCR (Q-PCR), single marker qPCR, real-time PCR, nCounter Analysis (Nanostring technology), Western blotting, Southern blotting, SDS-PAGE, gel electrophoresis, or Northern blotting. In some cases, analysis comprises exome sequencing.

In some cases, nucleic acid is analyzed using technology from Sage Sciences, Inc. In some cases, analysis comprises DNA sizing. In some cases, DNA sizing is performed with disposable gel cassettes with precast agarose (Pippin, Sage Sciences).

In some cases, nucleic acid is analyzed using reduced-representation genome sequencing. In some case, nucleic acid is analyzed using RADseq (restriction site associate DNA sequencing). DNA is separated along a gel column until a programmed fragment rage reaches a branch point. An active electrode is then switched to divert DNA to a membrane-bound buffer chamber. When a size range has been collected, an active electrode is switched back to a separation channel. A desired sample can be removed with a pipette. DNA sizing can be 90 bp to 1.5 KB (Pippen Prep) and 50 bp to 50 Kb (BluePippen). Pippen Pulse can be a pulsed-field electrophoresis power supply that can be used with analytical gels that can allow users to resolve DNA out to 100 kb and beyond.

In some cases, a SageELF (electrophoretic lateral fractionators) can be used for whole sample fractionation for DNA and/or protein. A whole protein or DNA sample can simultaneously be fractionated into at least 12 continguous size fractions. DNA and/or proteins are separated by size in an agarose separation column. Following separation, a second set of laterally positioned electrodes can be activated to electroelute samples into chambers.

K. Next Generation Sequencing

In some cases, a nucleic acid (polynucleotide) purified, isolated, and/or concentrated using methods, compositions, devices, systems, and/or kits described herein is analyzed using next generation sequencing. In some cases, the next generation sequencing comprises Helicos True Single Molecule Sequencing (tSMS) (see e.g., Harris T. D. et al. (2008) Science 320:106-109); 454 sequencing (Roche) (see e.g., Margulies, M. et al. 2005, Nature, 437, 376-380); SOLiD technology (Applied Biosystems); SOLEXA sequencing (Illumina); single molecule, real-time (SMRT™) technology of Pacific Biosciences; or nanopore sequencing (Soni G V and Meller A. (2007) Clin Chem 53: 1996-2001; Oxford Nanopore, Genia Technologies, and Nabsys); semiconductor sequencing (Ion Torrent (Life Technologies); Personal Genome Machine); DNA nanoball sequencing (e.g., Complete Genomics); sequencing using technology from Dover Systems (Polonator). Methods next generation sequencing are described, e.g., in PCT Publication No. WO2012149472, which is herein incorporated by reference in its entirety.

L. Nucleic Acid Library Construction

In some cases, nucleic acids purified, isolated, and/or concentrated using using methods, compositions, devices, systems, and/or kits described herein are used to construct a library, e.g., a next generation sequencing library. A liquid containing nucleic acid (e.g., cells, nuclei) can be flowed through a channel in a device comprising an array of obstacles. The array of obstacles can be configured to deflect particles of a predetermined size (critical size) into a flow path that is diagonal to the direction of bulk fluid flow. Smaller particles can be directed with the bulk fluid flow. Adapters can be added to nucleic acids before the nucleic acids are flowed through a device, while the nucleic acids are being flowed through a device, or after nucleic acids have flowed through a device. In some cases, adapters are compatible with sequencing using Iluminia sequencing or 454 sequencing. The adaptors can comprise sequences that are complementary to one or more sequencing primers. Nucleic acids larger and/or smaller than a critical size can be used for library formation, e.g., next generation sequencing library formation.

In some cases, nucleic acids are amplified before being flowed through a device comprising an array of obstacles. In some cases, nucleic acids are amplified after being flowed through a device comprising an array of obstacles. In some cases, particles of at least a critical size are amplified after being flowed through a device comprising an array of obstacles. In some cases, particles of less than a critical size are amplified after being flowed through a device comprising an array of obstacles.

In some cases, adaptors comprise barcodes. Barcodes can be used to identify a sample, organism, or cell from which a nucleic acid is derived.

Methods of next generation sequencing library formation are described in U.S. Patent Application Publication No. 20130079251, which is herein incorporated by reference in its entirety.

M. Cell Culture

In some cases, cells purified, isolated, and/or concentrated using methods, compositions, devices, systems, and/or kits described herein are used for cell culture. In some cases, isolated cells, e.g., stem cells, can be differentiated in culture. In some cases, purified, isolated, and/or concentrated stem cells are used for ex vivo expansion. In some cases, stem cell subjected to ex vivo expansion purified. Devices described herein can be used for exchange of cell culture media.

In some cases, an HSC is used to give rise to blood cells, e.g., red blood cells, B lymphocytes, T lymphocytes, natural killer cells, neutrophils, basophils, eosinophils, monocytes, and macrophages. A mesenchymal stem cell can give rise to, e.g., bone cells (osteocytes), cartilage cells (chondrocytes), fat cells (adipocytes), and other kinds of connective tissue cells such as those in tendons. A neural stem cell can give rise to, e.g., nerve cells (neurons) and two categories of non-neuronal cells, e.g., astrocytes and oligodendrocytes. In some cases, a stem cell is an epithelial stem cell. An epithelial stem cell can line the digestive tract and can occur in deep crypts. An epithelial stem cell can give rise to absorptive cells, goblet cells, paneth cells, and/or enteroendocrine cells. In some cases, a stem cell is skin stem cell. A skin stem cell can occur in the basal layer of epidermis and at the base of hair follicles. An epidermal stem cell can give rise to keratinocytes, which can migrate to the surface of the skin and form a protective layer. Follicular stem cells can give rise to both the hair follicle and to the epidermis.

In some cases, cells are grown in serum-free medium. In some cases, cell culture comprises one or more growth factors. In some cases, culture medium comprises Dulbecco's modified eagle medium (DMEM), sodium azide, ascorbic acid, alpha-MEM basal medium, Iscov'es modified Dulbecco's medium (IMDM), L-glutamine, MEM non-essential amino acid, 2-mercaptoethanol, sodium bicarbonate, poly (2-hydroxyehtyl methacrylate (p-HEMA), NaOH, Percoll, PBS, PBS (without calcium and magnesium), gelatin from porcine skin, Type A, EDTA, EDTA 0.5 M, pH 8.0, MTG, monothioglycerol, fetal bovine serum defined, tyrpsin 0.05%/EDTA 0.5 mM, collagenase Type IV, neupogen, leukine, human M-CSF, Human FGF-basi, human Flt3-ligand, human Il-1beta, Human IL-3, human IL-4, human IL-5, human sRANKL, human TGF-beta1, human TNF-alpha, 1alpha, 25-dihydorxyvitamin D3, trypan blue solution, 0.4%, immersion oil, 7-aad, 7-aminoactinomycin D, bovine serum albumin Fraction V, and/or ethanol.

In some cases, antibodies are used to analyze differentiation of hematopoietic progentiors and myeloid lineages form human pluripotent stem cells. Antibodies can include anti-human CD1a, anti-human CD2, anti-human CD3, anti-human CD3, anti-human CD7, anti-human CD10, anti-human CD11b, anti-human CD13, anti-human CD14, anti-human CD15, anti-human CD16, anti-human CD16, anti-human CD19, anti-human CD34, anti-human CD41a, anti-human CD45, anti-human CD64, anti-human CD66b, anti-human CD90 (Thy-1), anti-human CD115, anti-human CD117, anti-human CD123, anti-human CD163, or anti-human CD235a. Hematopoietic differentiation of stem cells is described, e.g., at crm.nih.gov/stemcell_types/HSC/UWisc_HSC.asp.

In some cases, total leukocytes and three main populations (lymphocyte, monocyte, and granulocyte) are compared to ABX hematology analyzer count.

VII. Systems

In some cases, devices comprising an array of obstacles as described herein are part of a system. In some cases, a system comprises at least 1, 2, 3, 4, 5, 6, 7, 8, 9, 10, 11, 12, 13, 14, 15, 16, 17, 18, 19, or 20 devices that are coupled, e.g., fluidly coupled. In some cases, a chamber is upstream of a device comprising an array of obstacles. A chamber can comprise a sample. A first chamber can be fluidly coupled to a second chamber. The second chamber can be used to manipulate particles, e.g., label particles.

In some cases, a system comprises a reaction chamber. In a reaction chamber, particles can be reacted, e.g., cells can be labeled, e.g., with a fluorescent antibody. In some cases, cells are lysed in a reaction chamber. In some cases, a cell lysis reagent comprises a detergent. In some cases, a detergent comprises Triton X-100, SDS, CHAPs, or Tween-20.

In some cases, a system comprises a pump. In some cases, a pump is fluidly connected to an inlet or outlet on a device comprising an array of obstacles. A pump can be connected to a device comprising an array of obstacles directly or indirectly. In some cases, a pump is connected to a chamber, e.g., a reaction chamber.

In some cases, a system comprises a means of propelling particles through a device or chamber. In some cases, electrical, electrophoretic, electro-osmotic, centrifugal gravitational, hydrodynamic, pressure gradient, or capillary forces are used to propel particles or fluids.

In some cases, a device comprising and array of obstacles is fluidly connected to a downstream apparatus. In some cases, the downstream apparatus permits analysis of particles from an outlet of the device. In some cases, the downstream apparatus is a microscope, flow cytometer, sequencing machine, next-generation sequencing machine, mass spectrometer, HPLC, gas chromatograph, atomic absorption spectrometer, fluorescence detector, radioactivity counter, scintillation counter, or spectrophotometer, cell counter, or coagulometer.

In some cases, a system comprises a computer. A computer can be in electrical communication with a device comprising an array of obstacles.

In some cases, a sample is filtered before being applied to a device comprising an array of obstacles. In some cases, a sample is passed through a filter after the sample has passed through a device comprising an array of obstacles. In some cases, a filtration system is in fluid communication with a device comprising an array of obstacles. In some cases, a filtration system is not in fluid communication with a device comprising an array of obstacles. In some cases, a filter is a syringe filter. In some cases, a filter comprises a pore size of 0.2 microns or 0.45 microns. In some cases, a filter comprises a 20 micron filter. In some cases, a filter comprises a pore size of at least 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or 200 microns. In some cases, a filter comprises a pore size of less than 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or 200 microns. In some cases, a filter comprises a pore size of about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or 200 microns.

Systems are described, e.g., in PCT Publication No. WO2012024194, which is herein incorporated by reference in its entirety.

Figure 30:
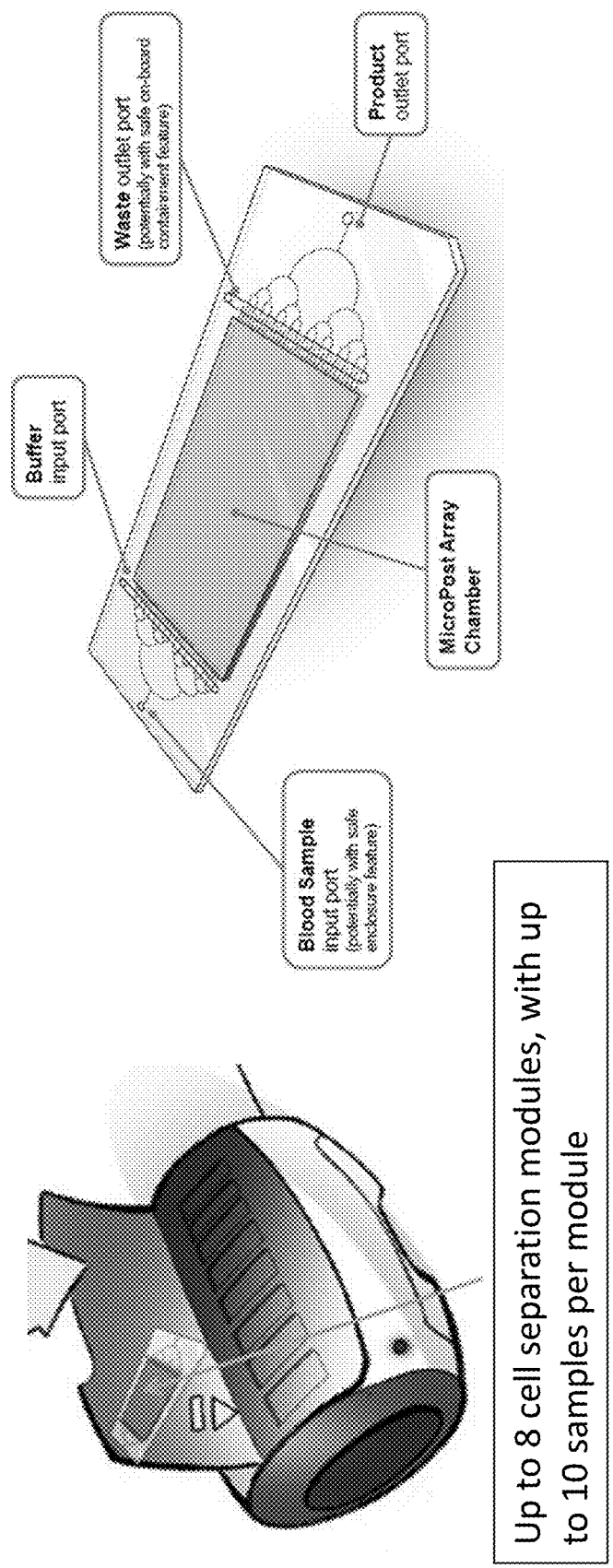
FIG. 30 illustrates a desktop instrument and a disposable cell separation module. Up to 8 cell separation modules can be used in the desktop instrument, with up to 10 samples per module. The instrument can be stand alone or can be integrated in-line with other equipment. A disposable cell separation module can comprise a blood sample input port (in some cases with a safe enclosure feature), a micropost array chamber, a product outlet port, a waste outlet port (in some cases with safe on-board containment feature, and a buffer input port.

In some cases, a plurality of devices, e.g., microfluidic chips, can be operated simultaneously with a module. In some cases, a plurality of devices (e.g., at least 2, 3, 4, 5, 6, 7, 8, 9, 10, 11, 12, 13, 14, 15, 20, 50, 100, or 200) can be operated simultaneously with a module. In some cases, a plurality of devices can be placed inside a module, wherein each device comprises at least one channel comprising an array of obstacles. In some case, sample application, buffer application, sample flow, buffer flow, and/or outlet collection in each of the devices can be controlled by the module. In some cases, a module is a desktop instrument as shown in FIG. 30. In some cases, a module is electronically coupled to a computer. In some cases, a module is coupled with one or more other components, e.g., microscope, flow cytometer, next-generation sequencing machine, etc.

VIII. Stem Cells for Transplantation

Hematopoietic stem-progenitor cell (HSPC) transplantation is an established therapy for many malignant and non-malignant diseases, with ~50,000 transplants performed per year using autologous or allogeneic HSPCs from mobilized peripheral blood stem cells (PBSCs), bone marrow (BM), or umbilical cord blood (UCB), in order of frequency. UCB is an especially attractive source of HSPCs due to its easy availability as a banked, HLA-typed and infectious disease-tested product with reduced risk of generating graft-versus-host disease in transplant recipients despite HLA mismatch. >20,000 UCB transplants have been performed in the last 20 years, and tens of thousands of UCB units are cryopreserved each year.

One of the major problems in UCB transplantation is the low total number of HSPCs in the available small volume of UCB units. This leads to high risk for delayed engraftment or engraftment failure (with attendant high mortality, morbidity and costs), especially when UCB is transplanted into adult or larger child recipients. Only ~100 (up to 300 ml rarely) of blood can be harvested from the placenta in the delivery room. Harvested units can be depleted of erythrocytes before storage but the techniques of centrifugation using apheresis technology (to obtain a leukocyte-enriched "buffy coat"), differential sedimentation in viscous media (e.g. hydroxyethyl starch [HES]), or density gradient centrifugation (even with newer automated apparatus) all result in both incomplete erythrocyte removal and average loss of ~25% of leukocytes and HSPCs. Since success and speed of engraftment have been shown to depend on the numbers of leukocytes and HSPCs administered per transplant recipient body weight, it is essential to develop new cell separation methods to provide high yields of highly pure, viable leukocytes and HSPCs from harvested UCB. Such efficient methods would also be valuable for processing of PBSC and BM harvests, to maximize the numbers of HSPCs for transplant and potentially reduce the amount of donor blood/BM collected.

A purification system using a microfluidic chip may be used to erythrocyte deplete UCB for clinical transplant; FIG. 16A is a schematic top view of device containing periodic array of microposts for Deterministic Lateral Displacement (DLD). The flow bifurcates around posts in successive rows, with 3 different "streamtubes" illustrated as purple, blue and green. The fluid streams change their relative positions, but do not mix as they flow in a laminar fashion from gap to gap through the matrix. Small cells will remain in the same streamtube, moving on average in the same direction as the fluid. Large cells will be bumped by the posts and displaced to the right into the next streamtube and be progressively separated from the original mixture; FIG. 16B shows a time lapse images of leukocytes being enriched from adult blood in DLD microchip. The circles are the tops of the microposts. On the left is the flow of erythrocytes, reflecting white light. The leukocyte path is the blue nuclear stain, leading to streaks moving away from the erythrocytes.

Described herein is a microfluidic technology for size-based cell separations that provides >90% yield of erythrocyte-depleted leukocytes from whole adult blood. This technology can be applied for small samples (100 µl) of adult blood prior to research or clinical diagnostic flow cytometry. The microfluidic technology can deplete erythrocytes from clinical UCB harvests for (cryopreservation and then) transplantation. In some cases, the method further characterizes this technology for sterile processing of UCB, PBSC and BM harvests. In some cases, the device is applied for additional purification of these and other types of stem cells, and potentially other cell therapy products.

There is a significant unmet medical need for a system to thoroughly deplete erythrocytes and recover leukocytes in high yield from UCB. This DLD microfluidic technique, can provide efficient, size-based depletion of erythrocytes from leukocytes in experiments using small, fresh samples of adult human peripheral blood. One aspect of DLD is that the path cells take through the microchip is based on size and is deterministic, i.e. determined and not subject to random processes. Unlike in bulk processes, such as HES and centrifugation, each cell is treated individually so that it interacts with the features in the microfluidic system and is directed into either the product or waste streams. The "continuous flow" nature of DLD offers the potential for high throughput without degrading resolution and for low-cost implementation. No previously existing UCB processing method can recover leukocytes that are >90% pure and >90% viable, and are obtained in >90% yield, i.e. the "90/90/90" performance criteria that will be able to achieve using the microfluidic device. Since 50% of donated UCB harvests cannot currently be used clinically due to low post-processing leukocyte and CD34+ cell numbers, the value proposition to blood banks and transplant centers is clear: the technology described here can deliver greater numbers of higher quality transplant grafts (i.e. more grafts that retain more HSPCs). This approach would replace the current standard processing procedures for UCB grafts because of its potential to significantly reduce morbidity, mortality and costs associated with failed or delayed hematopoietic recovery and engraftment. The commercial attractiveness of the UCB processing market continues to grow, with >100 UCB banks currently operating.

In some cases, the highly effective microfluidic separations of adult blood can be extended to UCB, and will results in an output product containing phenotypic HSPCs that is composed of >90% leukocytes (i.e. <10% erythrocytes) in >90% yield (based on starting leukocyte numbers), and with >90% leukocyte viability (90/90/90 criteria). In some cases, the method is scaled to a flow rate of >100 ml/hr, in order to process donated UCB units in <1-3 hrs.

The microfluidically-separated UCB leukocytes can be highly (>90%) viable and depleted of erythrocytes (>90% leukocytes). The types of leukocytes recovered may not differ significantly from their input distribution. Recovery of a higher number of phenotypic HSPCs (i.e. Procount: CD34+/CD45+) with this method is possible than generally observed using Ficoll-Paque or HES, and without skewing of any particular lineage. In some cases, Ficoll-Paque and/or hydroxyethyl starch (HES) are not used in a method described herein.

In some cases, >100 ml/hr may be difficult if the HSPCs are extremely sensitive to shear (from the flow rate, unlike leukocytes which can tolerate 30× faster rates as mentioned just above). In some instances, there are at least 5 combinable options for handling shear sensitive cells: (1) redesign the post shape to reduce the shear stress (i.e. asymmetric posts to enable wider gaps); (2) design taller posts to allow a greater flow cross section; (3) design asymmetric posts that enable a higher separation angle (design parameter c increasing from 0.03 to 0.06, and thus more arrays in a smaller area); (4) design a larger chip area; and (5) design tighter packing of parallel arrays onto an existing chip area. In some cases, these five options can combine for a 12-fold improvement. In some cases, these modifications, combined with a modest 2-fold faster flow rate, to allow one to process UCB at 144 ml/hr. In some cases, novel stacking of such sorting chips, so >10 chips can be run in parallel, with the same footprint and only 1 set of external connections (for low cost) is performed.

Designing the system as a closed, sterile system for UCB processing can prevent microbiological contamination and allow for functional assessment of HSPCs.

In some cases, the device is suitable for sterile separation of cells that will allow oen to functionally characterize HSPCs in the output product. This closed system can use parts that can be either sterilized and used just once (e.g. blood bags) or sterilized repeatedly (e.g. connecting devices, seals, and potentially microchips). In some cases, individual components are sterilized by gamma irradiation, steam, ethylene oxide or other standard methods. In some cases, a common sterilization process that is compatible with the various materials in contact with the cell stream is used. The common process can allow pre-assembly of microchips, manifolds, elastomeric seals and interconnecting tubing sets prior to sterilization, thereby minimizing the chance of microbial contamination during device assembly in controlled environments such as laminar flow hoods or clean rooms.

Deterministic lateral displacement (DLD)-based purification on the basis of cell size can be extended to purification of subsets of other types of blood cells and other types of stem cells. The technology can be quickly integrated into current clinical practice to process UCB and can also be adapted to purify HSPCs more highly as well as to isolate other stem cell types and sources (e.g. adipose tissue).

The use of DLD to deplete RBCs from >100 ml quantities of UCB for hematopoietic transplant is clinically beneficial. Furthermore, the issues associated with UCB, which can be "notoriously sticky and frequently clumps", may require that one develop innovative solutions for processing these samples in a microfluidic environment. These approaches are described herein.

Shear stress: Increasing pressure to disrupt cell aggregates can injure cells in some cases as the fluid stream squeezes through the gaps between posts, since shear force is proportional to flow rate. In some cases, one uses low fluid velocities (~5 mm/sec), >90% viability of leukocytes after they passed through the chip, where the calculated shear rates (shear stress normalized by viscosity) were ~500 $sec^{-1}$, similar to shear rates that circulating leukocytes experience in vivo.

Scale: In some cases scale up sorting of leukocytes, since flow rates of (only) ~100 mm/sec will achieve the desired ~5 ml/min throughput. The resistance to fluid flow of a chip is inversely proportional to the square of the gap size. In some cases, one may use a large gap size, but the critical sorting size, which is set by our need to isolate leukocytes, is typically 30-50% of the gap (depending on some detailed parameters). In some cases, engineering the shape of the posts (using asymmetric posts instead of the usual circular posts) allows one to make the gap (and thus the throughput rate) larger without raising the critical sorting size. Finally, in the unlikely event that, e.g. because of effects on cell viability, it is not possible to flow stem cells through our chips at high rates, even with optimized post geometries, one may etch deeper channels, increase the chip area, using a higher separation angle to add more parallel post arrays, and stacking chips.

Clogging: Higher flow rates can greatly reduce clogging, and larger gaps between posts can reduce clogging as well. UCB can be anticoagulated at the time of collection, which can effectively block the clotting protein cascade. Clotting can be also be addressed by careful visual macroscopic inspection followed by exclusion from our experiments of extensively clotted samples, which is consistent with clinical practice; no previous cell separation method can deal with donor cell harvests that are already extensively clotted. Furthermore, pre-filtration of samples through 20 uM mesh prior to processing is an explicit part of the protocol in some cases. In some embodiments, chemical chip surface treatments which resist cell or protein adhesion, such as an mPEG-silane polymer may be used.

The growing popularity of umbilical cord blood (UCB) as a source of hematopoietic stem-progenitor cells (HSPCs) for transplant results from its easy availability, reduced risk of graft-vs-host disease, and applicability for use across wide histocompatibility differences. However, the potential of UCB transplants is limited currently by the low total number of HSPCs that can be obtained from placental blood. Ideally, clinical grafts should be depleted of erythrocytes after harvest in order to (1) prevent transfusion reactions in patients, (2) reduce fluid volume loads and amounts of cryoprotectant administered to patients (e.g. toxic effects of dimethylsulfoxide [DMSO] cryoprotectant include hypertension and cardiac arrhythmias), and (3) minimize necessary expensive storage space in blood bank freezers[4-9]. Currently, blood banks rely on traditional depletion methods like hydroxyethylstarch (HES) sedimentation and density gradient centrifugation. HES sedimentation is a manual technique and can results in high residual erythrocyte contamination (with erythrocytes comprising >30% of the output volume) and significant loss of leukocytes and CD34+ HSPCs (>20% loss on average, considerably worse in some cases). Automated systems, such as Sepax and AXP, offer standardization of UCB processing, but these density gradient centrifugation processes do not typically improve erythrocyte depletion or leukocyte recovery. Prepacyte-CB, a sedimentation method, accomplishes more effective erythrocyte depletion but still loses >25% of leukocytes. Because any loss of HSPCs significantly reduces the clinical utility of UCB and leads to high risk for delayed engraftment or engraftment failure (with attendant high mortality, morbidity and costs), new processing methods are urgently needed to ensure high yields of highly pure, viable leukocytes for banking and transplant. In some cases, the methods described herein do not make use of sedimentation and/or density gradient centrifugation.

Described herein is a fully integrated, scalable, microfluidic cell separation system capable of thoroughly removing erythrocytes from clinical HSPC transplant grafts derived from UCB harvests. The optimized system will recover >90% of input leukocytes and HSPCs at >90% purity and >90% viability ("90/90/90" criteria). The system can be poised for preclinical evaluation and extension to other hematopoietic samples (e.g. PBSC, BM), as well as for further purification of HSPCs and other stem cell types. This disclosure leverages a unique combination of multidisciplinary skills in microfluidic design and optimization, integration and fabrication, and hematopoietic cell biology.

The devices and methods can process harvested UCB, with the goal of recovering viable leukocytes and phenotypic HSPCs at the 90/90/90 criteria. The separated cells can be evaluated phenotypically by methods including flow cytometry. UCB may be more prone than adult peripheral blood to cell clumping, resulting in blockages in the device. Thus, the devices and protocols remove, prevent, and disperse cell aggregates. Approaches to increase sample throughput to clinical volumes of 100-300 ml/hr, evaluating the effects of various DLD geometries and comparing leukocyte purification, yield and viability with increasing flow rates are also described.

In some embodiments, (a) the instrument platform and components can be sterilized and (b) cells can be introduced and recovered in convenient blood bags.

Hematopoietic stem-progenitor cell (HSPC) transplantation is an established therapy for many malignant and non-malignant diseases. HSPCs are harvested clinically from 3 sources: G-CSF mobilized adult peripheral blood (PBSC), bone marrow (BM), and umbilical cord blood (UCB). Because erythrocytes increase both the risk of harmful side effects in transplant patients and the cost of cryopreservation, they must be depleted from the harvested HSPC tissues. The major problem in UCB transplantation is the low total number of HSPCs in the small volume (100-300 ml) of UCB units. This leads to high risk for delayed engraftment or engraftment failure (with attendant high mortality, morbidity and costs), especially in larger children or adult patients. Previous techniques, including density gradient centrifugation and differential sedimentation, result in incomplete erythrocyte depletion and may lose 25% leukocytes (on average) during processing. Since success and speed of engraftment depend on the numbers of leukocytes and HSPCs per recipient body weight, it is essential to develop new cell separation methods to ensure high yields of pure, viable leukocytes and HSPCs from harvested UCB. In some aspects, the devices and methods improve stem cell banking and transplantation by providing an efficient and robust processing system that results in superior recoveries of viable leukocytes and HSPCs. Microfluidic deterministic lateral displacement (DLD), in which the paths cells take through the microfluidic system is based on size and is deterministic, i.e. absolutely determined, not subject to random processes. The use of DLD to deplete erythrocytes from UCB for hematopoietic transplant; this is a new clinical use. The technology will also be extended for use with PBSC and BM harvests. The value proposition is clear: the devices and methods deliver greater numbers of higher quality transplant grafts (i.e. more grafts with more HSPCs) that will lead to greater transplant success.

and etched into a silicon substrate based on CAD-generated designs. The chips to date have been made using methods borrowed from the electronics industry of photolithography and etching.

TABLE 3

|  | Starting | Product 1 | Product 2 | Product 3 | Product 4 | Product 5 |
|---|---|---|---|---|---|---|
| WBC count (K/ul) | 5.36 | 2.16 | 2.60 | 1.62 | 2.54 | 1.64 |
| RBC count (M/ul) | 2.41 | <0.01* | <0.01* | <0.01* | <0.01* | <0.01* |
| Volume (ml) | 3.00 | 0.45 | 0.42 | 0.47 | 3.5 | 1 |
| Yield |  | 87% (for the combined Products) | | | | |
| % Viability | >90 | >90 | >90 | >90 | >90 | >90 |
| % Purity |  | 0.54 | 81 | 88 | Not done | 86 | Not done |
| % Granulocytes | 63.9 | 61.6 | 56.8 | Not done | 51.9 | Not done |
| % Lymphocytes | 18.6 | 17.8 | 21.1 | Not done | 25.7 | Not done |
| % Monocytes | 7.21 | 6.61 | 7.19 | Not done | 9.83 | Not done |

EXAMPLES

Example 1

Leukocyte Enrichment from UCB

The methods can improve stem cell banking and transplantation by providing an efficient and robust processing system for clinical UCB, PBSC and BM harvests. The microfluidic separation method can efficiently and consistently deplete erythrocytes from UCB. In some cases, there may be problems with cell clumping in some clinical samples (principally due to dead/dying cells). In such cases, the device and/or protocol are optimized to address cell clumping. In some embodiments, the process is scaled up to purify >100 ml volumes of UCB per hour, preserving 90/90/90 performance.

In some cases, the blood sample is depleted of smaller-sized cells (i.e. erythrocytes, platelets) and the larger-sized cells of interest (i.e. leukocytes) are concentrated. Note that the unwanted smaller cells are present in blood at >1000-fold excess numbers over the desired leukocytes.

The microfluidic chips used can be approximately the size of a microscope slide. They contain arrays of microposts with geometries optimized to separate target cells by size via displacement of these cells from the blood sample into a product stream. The periodic array of micron-sized posts in the flow path creates an asymmetric bifurcation of laminar flow around the obstacles, leading to different flow directions for large versus small cells. As illustrated in FIGS. 16A and 16B, small cells (erythrocytes) move down the array in the direction of the fluid flow while the larger cells (leukocytes) move along the tilted axis of the posts, away from the erythrocytes. The leukocytes eventually collect and concentrate along the right wall of the array (out of the photo's range), where they are collected separately from the waste (erythrocytes). The critical threshold size for displacement is determined by the size of the gaps, the row-to-row spacing, and the tilt of the post axis with respect to the fluid flow. The cell separation microchips are defined by photolithography Table 3 shows results of leukocyte enrichment from UCB. The starting sample is 3 ml of one day old UCB, diluted 1:1 with running buffer (PBS, 2 mM EDTA, 1% BSA). The leukocyte-enriched output product contains erythrocyte levels below Hemavet detection, so product purity is determined by multicolor FACS analysis using labels against CD45, CD14, CD235a, and a viable nucleic acid dye. For the combined fractions erythrocyte depletion is 99%, leukocyte recovery is 87%, and leukocyte purity is 81-88%. Purities may be reduced by microscopic cell clumping. There is some dead volume in our current instrument configuration so that a small portion of sample remains in the system and is not processed. In some cases, the full sample will be sorted, and the leukocyte recovery will rise to 90% or better. Viability by trypan blue dye exclusion is >90% in all fractions. Granulocytes, lymphocytes, and monocytes are close to the initial "differential leukocyte" ratios. In some cases, leukocytes comprise lymphocytes and/or monocytes.

Figure 17:
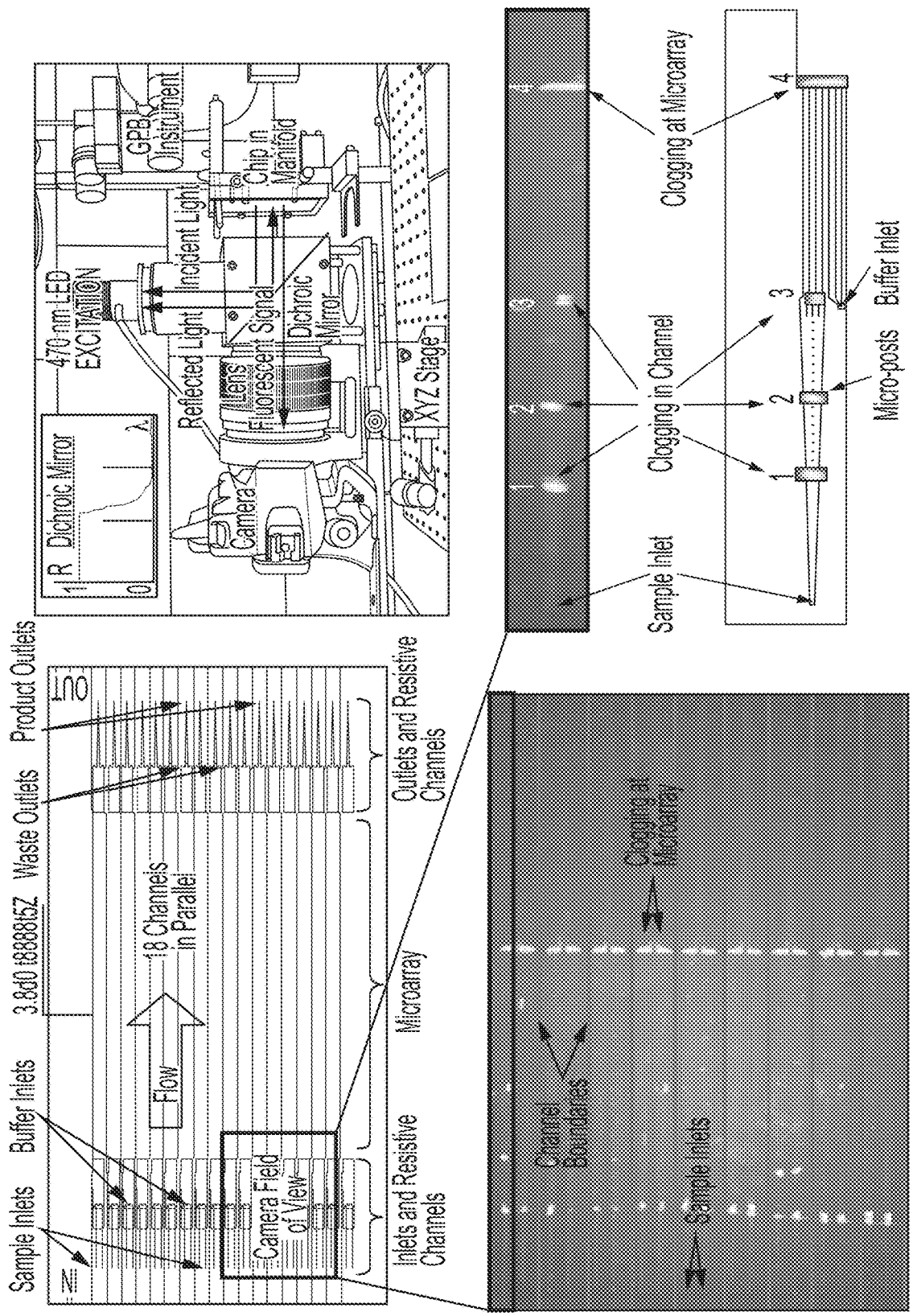
FIG. 17 shows an imaging setup with 470 nm source and dichroic mirror, flow direction is from left to right (top left panel), photo of nine parallel arrays exhibiting clogging as seen by fluorescent signal (bottom left panel), enlargement of one channel with clogging (bottom right panel).

The in-line imaging camera (FIG. 17) allows one to observe early events in a potential clogging process. FIG. 17 (bottom) shows aggregates of leukocytes (labeled green with Syto-13 dye Invitrogen) collecting in the sample inlet, with additional clogging at the DLD micropost array.

In some cases, there are not microposts near the inlet. In some cases, the device has deeper channels and made of less expensive materials (e.g. plastic) and new, cheaper materials.

Example 2

Characterize Performance of the Microfluidic Cell Separation Device with UCB Anticoagulated, deidentified UCB samples are obtained. Samples with visible macroscopic cell clumps are classified as inadequate and not processed further; the numbers of inadequate samples are tracked. For adequate samples, UCB samples are diluted in an equal volume of running buffer and filtered through a 20 micron strainer before microfluidic processing. Recovered output (vs filtered input) cells are rigorously analyzed. Erythrocytes, leukocytes, and leukocyte subsets are quantified by Coulter and Hemavet technologies. Viability of output leukocytes are confirmed by trypan blue dye exclusion with counting by manual and automated (Countess) methods. Apoptosis and cell death are measured using Annexin V/7AAD staining and flow cytometry. Leukocyte subtypes are quantified by immunostaining and flow cytometry. The number of CD34+ HSPCs are evaluated using Procount kits.

Optical imaging tools (FIG. 17) show any blockages and can be observed in real time. The removal of large cell clumps by filtration through a cell strainer reduces clogging in the device. To minimize cell clumping in the system, the input reservoirs are agitated (undulating rocking, per blood bank routines). To avoid cell aggregation at the beginning of the DLD microarray, the gap spacing is widened in the first post array. In some cases, the cell concentration is lowered by further dilution of the starting sample to avoid clumping. In some cases, the concentration of BSA is increased in the sample buffer from 0.1% to 5%, as albumin binding to all surfaces reduced clogging in magnetic separation technology.

To avoid clumping, short bursts of higher pressure can be applied across the device, which can disrupt cell clumps and cause large objects to deform and move through gaps. In some cases, pressure bursts in the reverse direction loosen clumped or stuck cells. In some embodiments, asymmetric microposts are used to increase the size of the gap for a given critical separation size, which would be less prone to clumping. In some cases, flow rates of >10 fold higher than used in previous DLD work. In some cases, such high flow rates can reduce the amount of cell aggregation and sticking in the microchip, presumably because the high viscous drag forces on any clumps is large enough to disperse them.

When the device and protocols are optimized to routinely produce output leukocytes meeting our 90/90/90 criteria, a series of 10 or more successive experiments (sample number subject to statistical significance and power) are conducted where leukocytes from a given donor are separated simultaneously in the microfluidic device versus by an experienced individual using Ficoll-Paque or HES, standard clinical techniques for erythrocyte depletion of UCB. Statistical comparisons of viability, yield, purity, and leukocyte subsets are performed.

Example 3

Increase Throughput to >100 ml/hr

In some cases, the throughput rate is scaled from 10 ml/hr in the system to >100 ml/hr. The most straightforward approach is to run the chips at a higher pressure differential. The system can operate at ~5 mm/sec fluid speed in the chips. Increasing the driving pressure, the DLD method works well at speeds of at least 150 mm/sec (a 30× increase) to separate leukocytes from adult blood, while still maintaining 99% viability of the leukocytes. This speed corresponds to a chip throughput of 300 ml/hour. (An human cancer cells (mdamb231 cell line) have been processed at speeds up to 1000 mm/sec, also still maintaining 99% viability).

Example 4

Reducing Clogging

FIG. 21 illustrates results of experiments identifying calcium-dependent integrins and thrombin-induced platelet activation as the dominant contributors to platelet-induced clogging of DID arrays. The bottom line in FIG. 21 shows how an approximately 3× increase in the flow rate can be used to achieve a further reduction in clogging on top of that achieved by 5 mM EDTA and 40 uM PPACK. [NOTE: these plots show on the x (horizontal) axis the volume of blood that has been processes through an array, and on the y (vertical) axis the fluorescence of leukocytes stuck in the array. Diluted blood was actually processed, but this x-axis represents the amount of undiluted blood that was used before dilution and which flowed through the chip. The leukocytes were tagged with a fluorescent dye before putting the blood in the array, so the fluorescence measures the number of stuck cells.] This array was an array with 40 micron triangular posts and the gap width is 27 micron.

The human blood was supplied by a vendor and treated with a level of 1 ml/ACD per 8 ml blood. (before the 3:1 dilution). Typical ACD is composed of 22.0 g/L C3434 (Citric Acid, trisodium salt, dihydrate); 7.3 g/L C0759 (Citric Acid, anhydrous); and 24.5 g/L G7528 (D-(+)-Glucose).

Standard test conditions involve diluting the sample blood 3:1 with a buffer before processing. The average flow rate is about 4 cm/s. The depth of the etched array in silicon was about 0.15 mm. The standard run time was 30 minutes. About 3 ml of the diluted blood mixture was processed in this time, corresponding to 0.75 ml of whole blood. Additives were added to the diluted mixture before processing.

Note in FIG. 21 that the following experimental observations for different additives to the input are noted: 1 mM EDTA (1 mM in the diluted blood input) gives a rapid increase in the fluorescence signal (from stuck leukocytes) indicating rapid clogging. 5 mM EDTA (in the diluted blood input) reduces clogging to about ⅛ of the level of 1 mM EDTA. ACD (1 ml per 9 ml of the diluted blood input) reduces clogging similar to 5 mM EDTA. Heparin (40 units per ml of the diluted blood input (with no EDTA) shows some reduction in clogging. Adding 40 uM PPACK to the 5 mM EDTA reduces the clogging to a nearly undetectable level. Increasing the flow rate by a factor of about 3× (with 5 mM EDTA and 40 uM PPACK) gives about 2.3 mL of whole blood throughput in the chip in one array in 30 minutes for one array, and still negligible clogging.

Figure 22A:
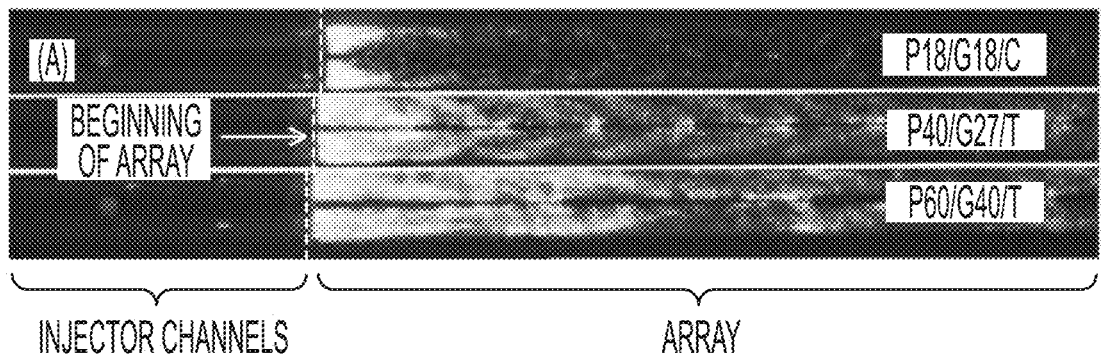
FIG. 22A and FIG. 22B show images of clogging in arrays with three different parameters for (a) 1 mM EDTA and (b) 5 mM EDTA and 40 uM PPACK. The volume of blood through each channel and the flow rate is the same in both FIG. 22A and FIG. 22B. Array parameters are given in the format Post size (μm)/Gap size (um)/Post Geometry (Triangle or Circle). The flow direction is left to right. Green indicates stuck leukocytes.
Figure 22B:
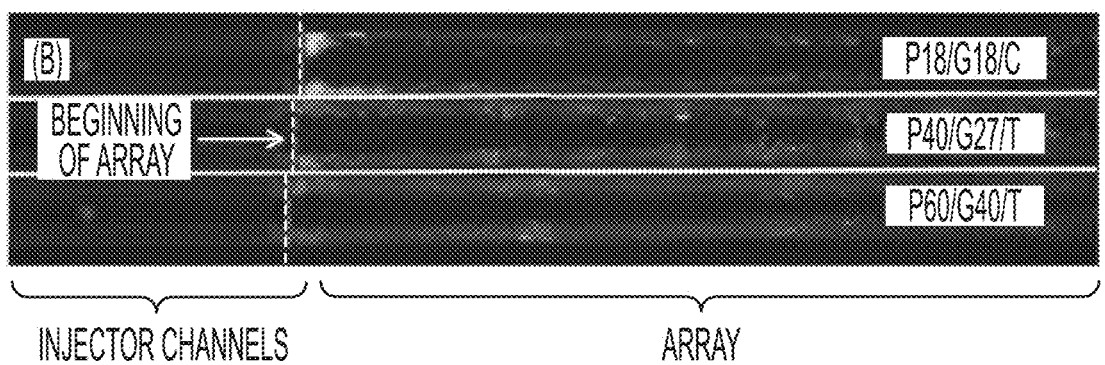

These results have been demonstrated for both circular and triangular posts with array parameters that are commonly used for isolation of leukocytes and circulating tumor cells from blood. FIG. 22A shows images of the clogging with 1 mM EDTA and with 5 mM EDTA+40 uM PPACK for each of three different array parameters. The top two arrays (P18/G18/C [[post diameter 18 um; gap 18 um; circular posts]] and P40/G27/T [[posts 40 um; gap 27 um; triangular posts]]) have parameters commonly used for isolation of leukocytes, while the bottom array (P60/G40/T [[posts 60 um; gaps 40 um; triangular post]]) can commonly used for isolation of circulating tumor cells. The conclusion is that the combination of an agent to reduce calcium dependent pathways (such as calcium chelating agent (5 mM EDTA)) and a thrombin inhibitor (40 uM PPACK) works best in all chip designs.

Figure 23:
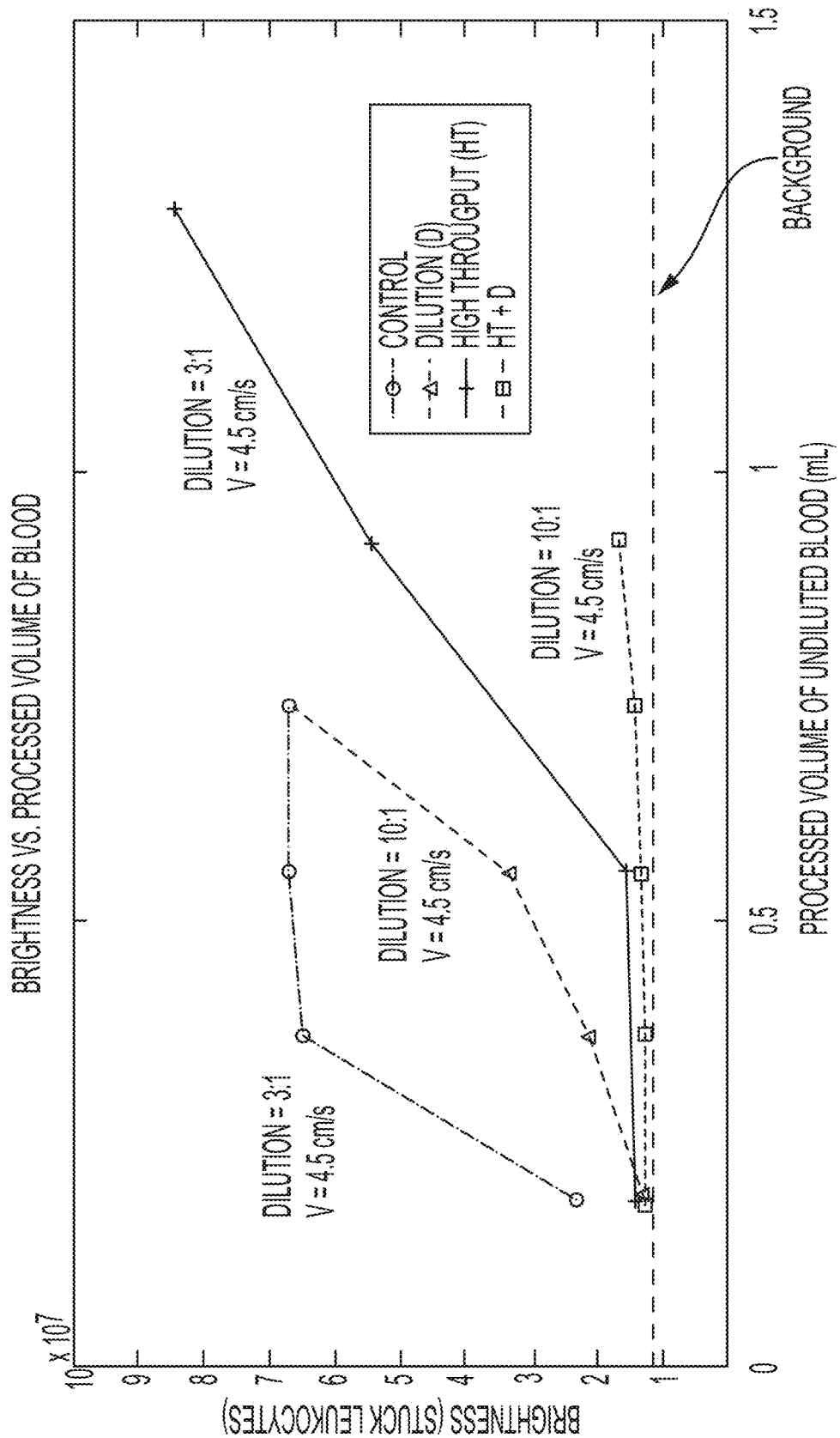
FIG. 23 illustrates an effect of flow rate and blood dilution on clogging of a micro-post array.
Figure 24C:
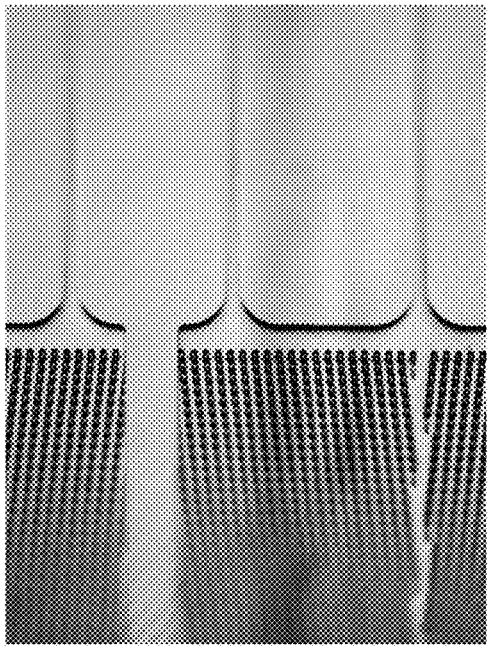
FIGS. 24A-24D illustrate the following.
Figure 24D:
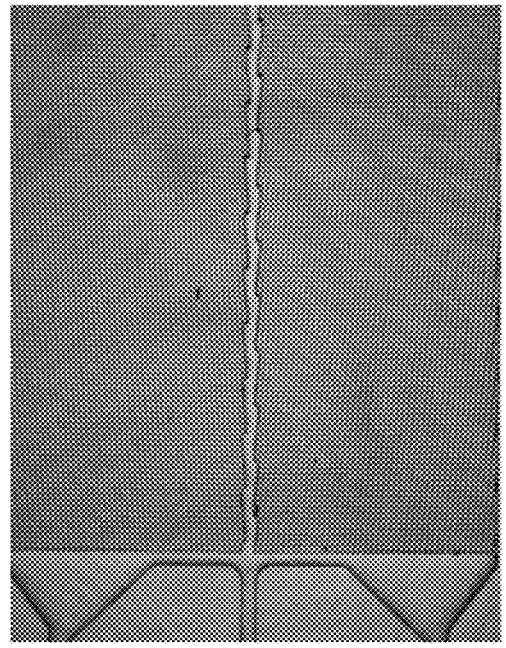
Figure 24A:
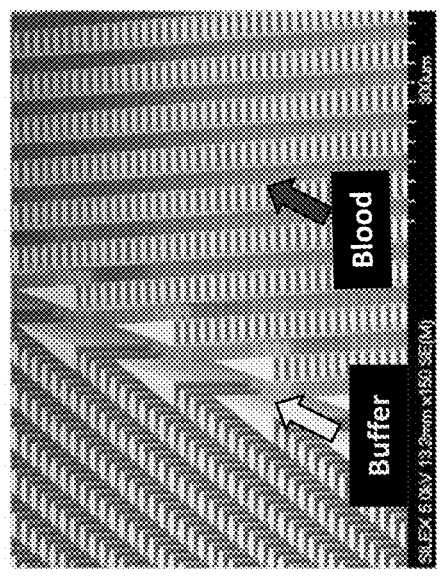
Figure 24B:
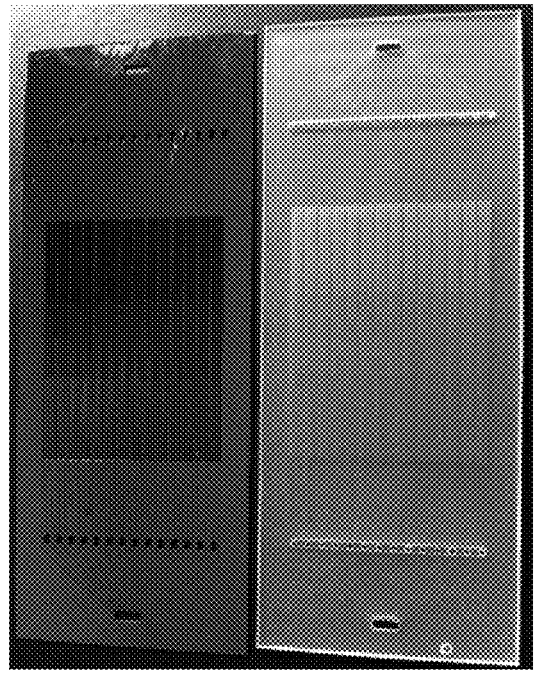
Figure 25:
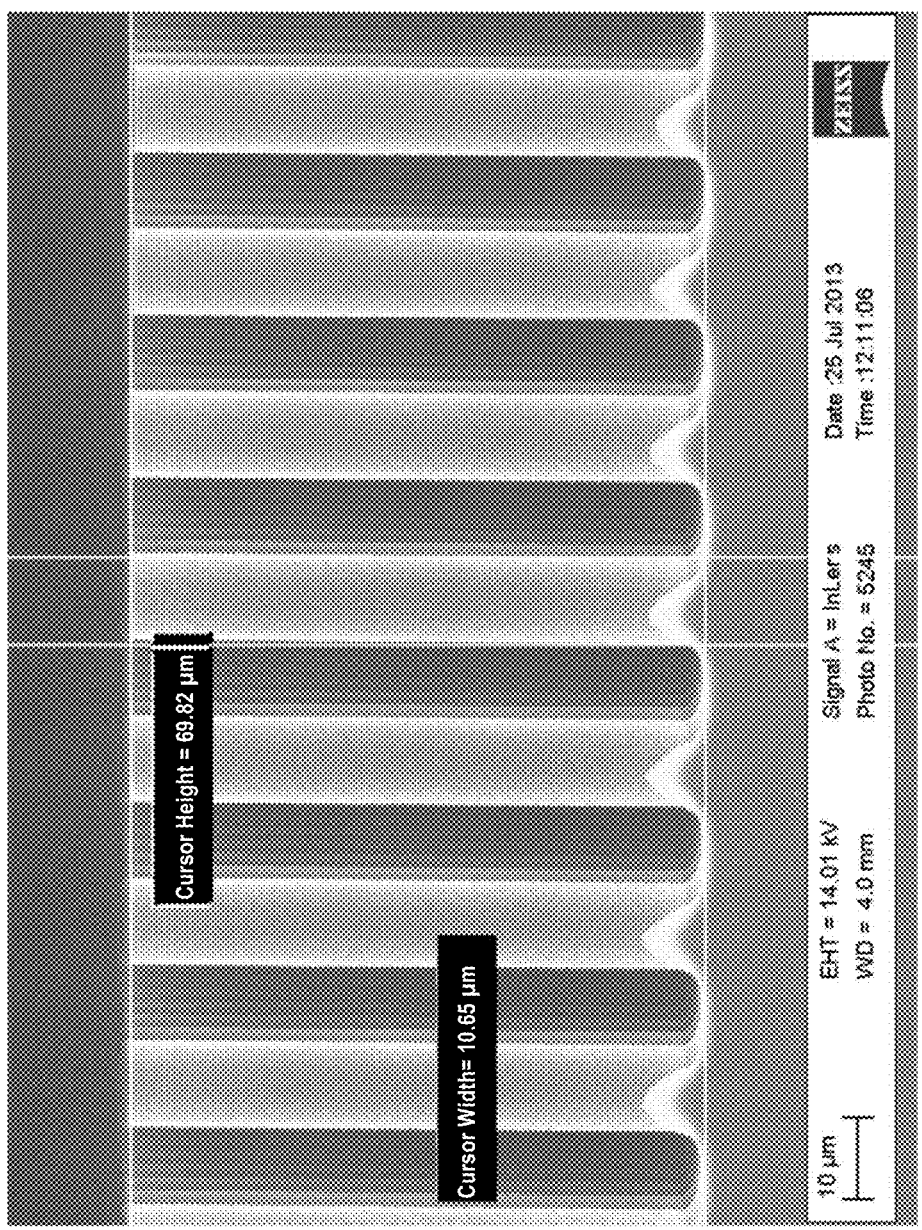
FIG. 25 illustrates an SEM of zone 3 of a silicon test wafer. Etch depth can be adjusted to 60 um on process wafer. Pillar (post, obstacle) geometry can be controlled to 0.5 um resolution.
Figure 26B:
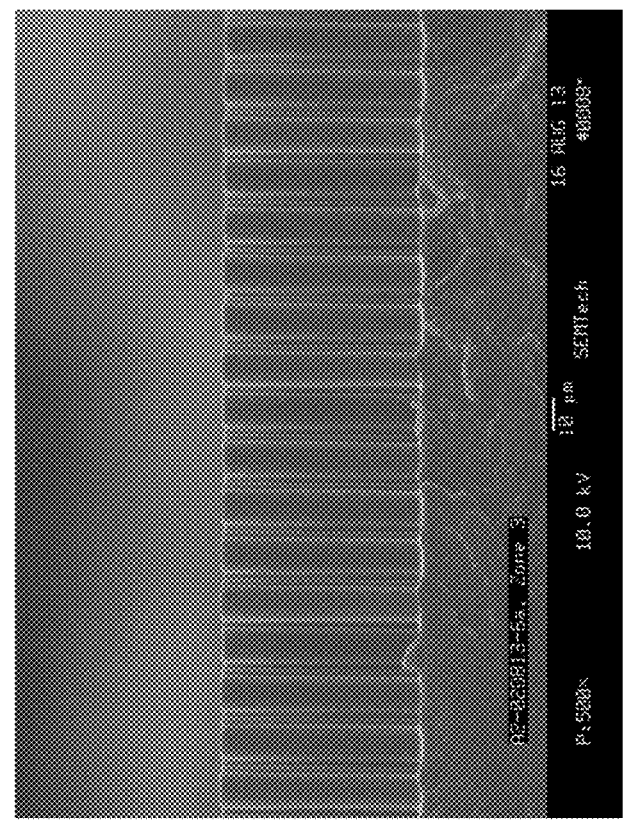
FIGS. 26A and 26B illustrate the following.
Figure 26A:
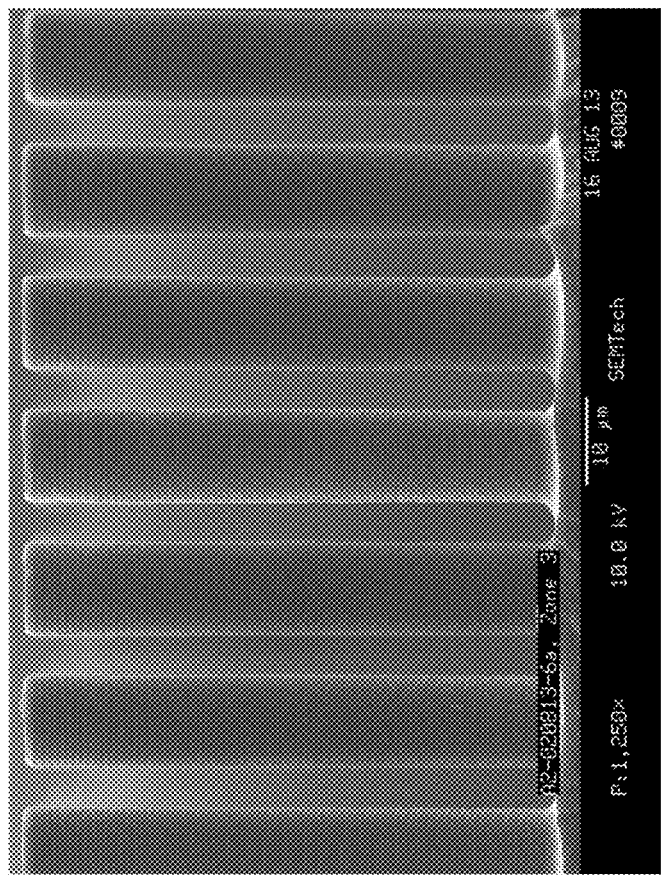
Figure 27:
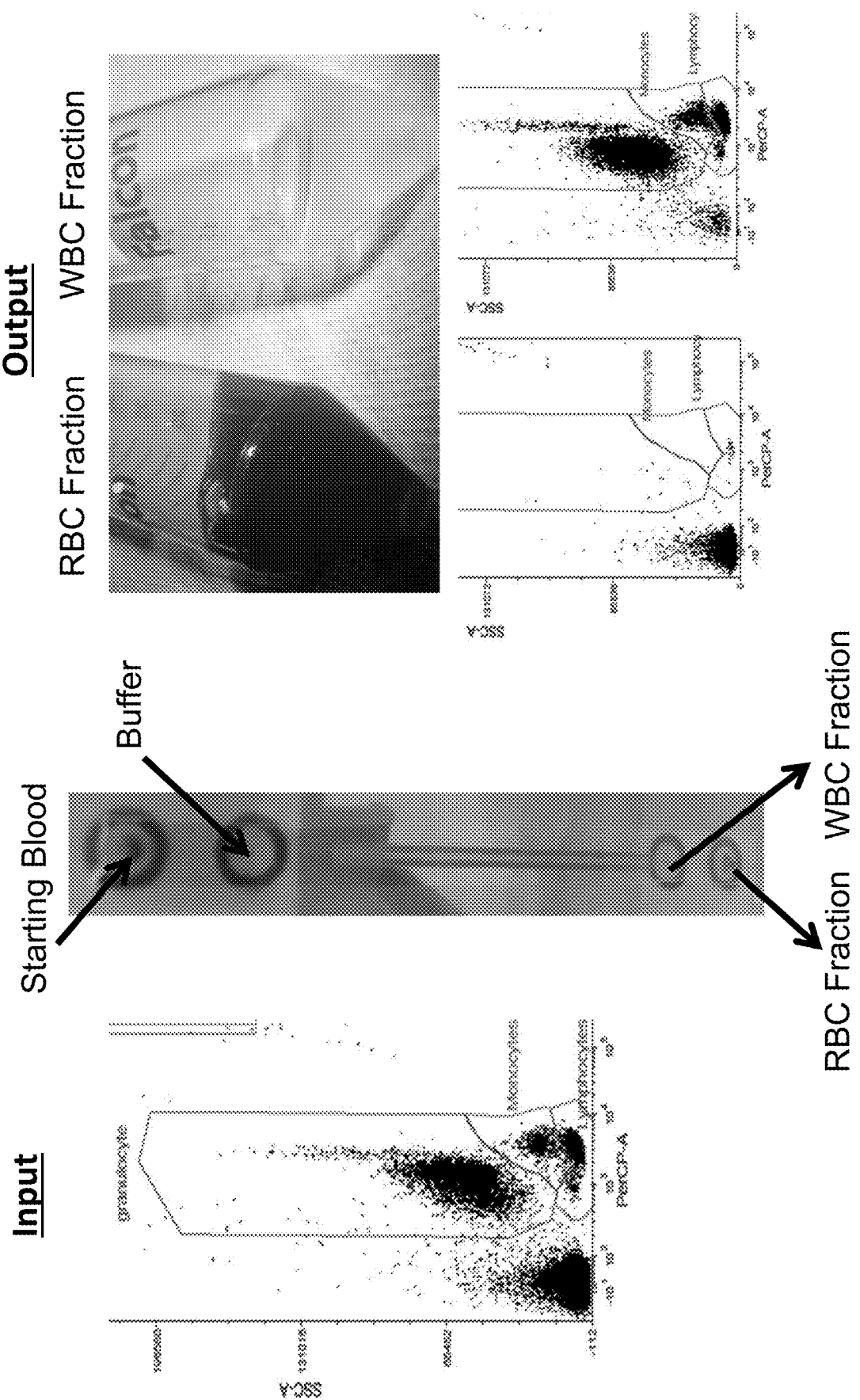
FIG. 27 illustrates flow cytometry data.

In a supporting experiment (FIG. 23) it is shown that higher flow rates and greater blood dilutions can be used to further reduce clogging of the micro-post array. The data is all for the same condition of a 1 mM EDTA in the diluted blood input to the chip. The times of each experiment are different, but the key is the amount of fluorescence (representing stuck leukocytes) for a given equivalent whole blood of input. This should be a small as possible for the same amount of blood input. The hypothesis that the higher flow rate allows less time for platelet aggregates to form in the array and provides a greater force to prevent platelet-post adhesion, and that the higher dilution prevents the formation of platelet aggregates by minimizing platelet-platelet interaction. FIG. 23 shows that a combination of a 3× increase in blood dilution and a 10× increase in flow rate each reduce clogging, with the combination reduce clogging by a factor of 10×. In summary, it has been demonstrated >2.25 mL of blood can be processed per DLD array at a level of clogging well below that at which chip performance begins to degrade. This corresponds to >30 mL of blood per standard chip with 15 DLD arrays. Furthermore, given the fact that clogging does not seem to increase vs time for the best case (high throughput, PPACK and EDTA in FIG. 21), from our results >250 mL of blood can be processed using a standard chip with 15 DLD arrays before clogging begins to significantly degrade device performance. This achievement can be attributed to four measures that reduced clogging: 1. Disabling the activity of calcium-dependent integrins on platelets and/or decreasing calcium dependent thrombin formation by increasing the concentration of EDTA from 1 mM to 5 mM. Other methods which reduce or block calcium can act similarly. 2. Preventing thrombin-induced platelet activation and fibrin production through the use of the direct thrombin inhibitor PPACK at a concentration of 40 uM. Other methods which inhibit or reduce thrombin can act similarly. The following 2 experimental conditions also reduce clogging: 3. Higher flow rate (which can be due to less time for reactions leading to clogging to occur). 4. Higher dilution (which can be due to minimized platelet-platelet interaction that leads to the formation of platelet aggregates.)

Methods of using devices are described in the following references, which are hereby incorporated by reference in their entirety: K. Loutherback, J. D'Silva, L. Liu, A. Wu, R. H. Austin, and J. C. Sturm, "Deterministic separation of cancer cells from blood at 10 mL/min," AIP Advances 2, 042107-1-7 (2012); J. A. Davis, D. W. Inglis, K. J. Morton, D. A. Lawrence, L. R. Huang, S. Y. Chou, J. C. Sturm, and R. H. Austin, "Deterministic hydrodynamics: Taking blood apart," Proc. Nat. Acad. Sci. 103, pp. 14779-14784, (2006); John Davis, PhD Thesis Princeton University, "Microfluidic Separation of Blood Components through Deterministic Lateral Displacement," (2008); Kevin Loutherback, Ph.D. Thesis Princeton University, "Microfluidic Devices for High Throughput Cell Sorting and Chemical Treatment," (2011).

Example 5

Separation of White Blood Cells and Red Blood Cells

Blood (diluted 1:1 and filtered) was stained with TriTest CD45, CD19, CD3 stain and run through chips (polypropylene device A2 chip). 200 ul loaded took ~12 minutes to run and air was used to push the last of the sample through the chip. On average, ~185 ul in the WBC fraction was recovered and ~430 in the RBC fraction was recovered. >94% WBC recovery by Ac-T diff2™ II in WBC fraction (RBCs below quantification). Cell population ratios in WBC fraction were maintained. Very few WBCs are lost to the RBC fraction. Loss of CD3 cells into RBC fraction ranged from 3.5% to 1.0% with an average loss of ~1.5%. See FIG. 27, FIGS. 28A and 28B, and FIG. 29. Flow cytometry was done as described at www.bdbiosciences.com/external_files/is/doc/tds/Package_Inserts_IVD/live/web_enabled/23-3025-04.pdf with the TriTEST (CD45, CD3, CD19) reagent from Becton, Dickinson and Company (BD Biosciences, San Jose Calif.). Briefly, samples were prepared as follows: Briefly, samples were prepared as follows: 1. Pipette 10 µL of TriTEST CD3/CD19/CD45 reagent into the bottom of the tube. 2. Pipette 50 µL of well-mixed, anticoagulated whole blood (whole blood diluted 1:1 with 1× phosphate buffer saline, 1% Bovine Serum Albumin, 5 mM EDTA {starting sample for chip runs}), or white blood cell fraction from chip, or red blood cell fraction from chip onto the TriTEST reagent. 3. Cap the tube and vortex gently to mix. Incubate for 15 minutes in the dark at room temperature (20-25° C.). 4. Add 450 µL 1× FACS Lysing Solution to the tube. 5. Cap the tube and vortex gently to mix. Incubate for 15 minutes in a dark at room temperature (20-25° C.). Sample is now ready to be analyzed on the flow cytometer. 6. Cell counting reference beads are added and mixed well just before analysis.

Figure 28A:
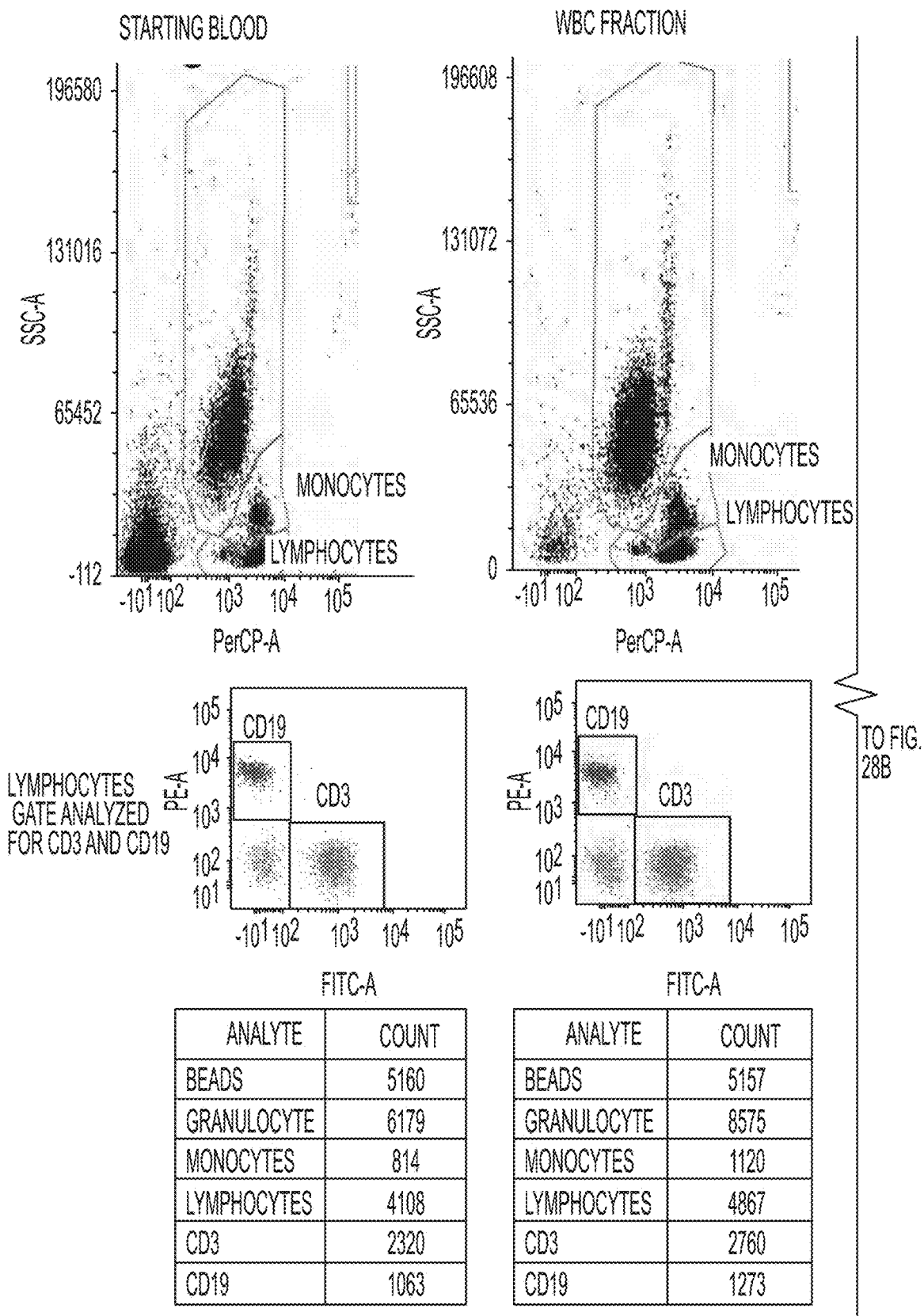
FIG. 28A and FIG. 28B illustrate an example run.
Figure 28B:
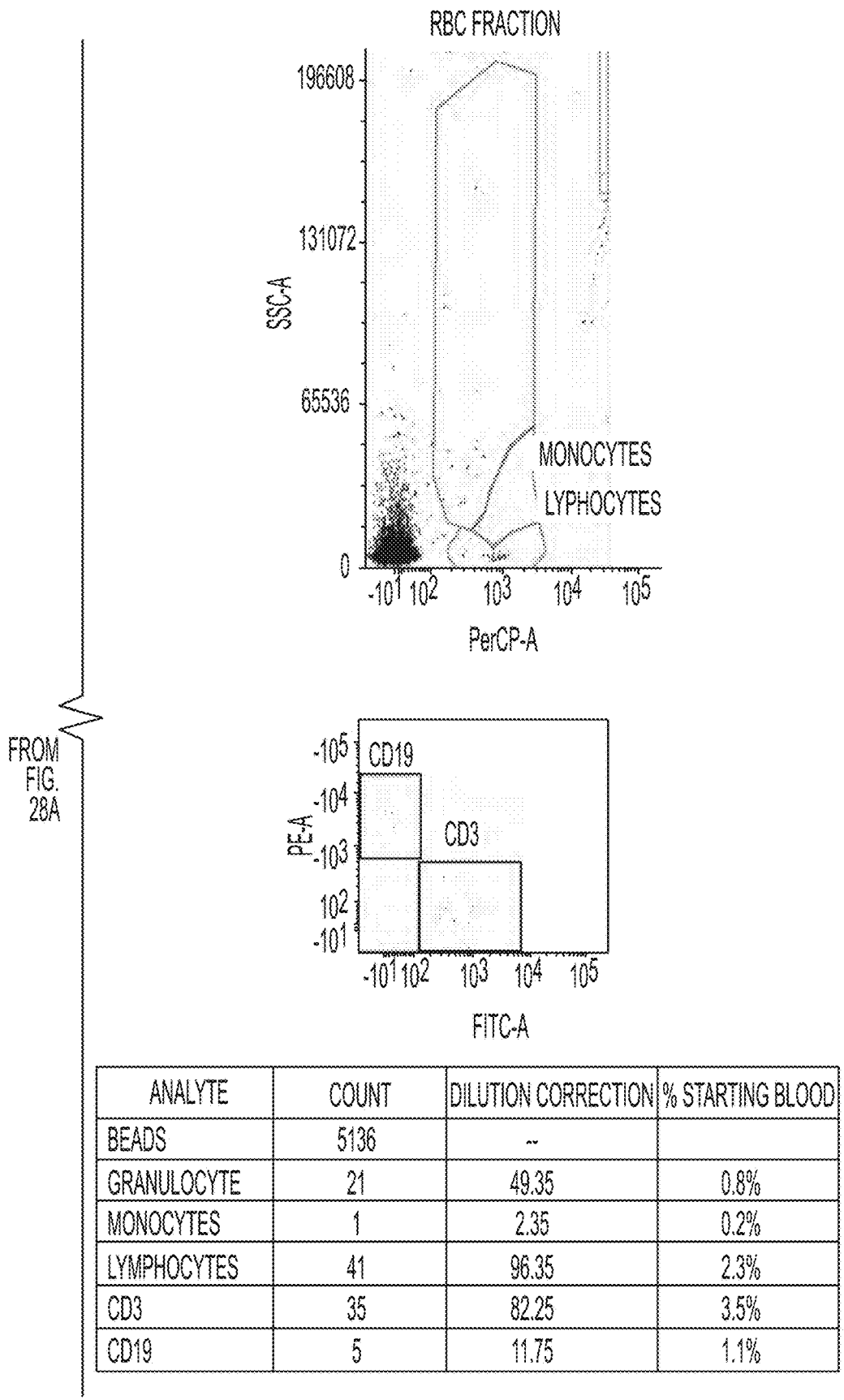

Samples were analyzed with a BD FACSCanto™ II flow cytometer. Monocytes, granulocytes, lymphocytes, CD3 positive and CD19 positive cells were gated as shown in FIGS. 28A and 28B and analyzed with DeNovo FCS Express Flow 4 software.

Example 6

On-Chip Cleaning System

A device comprises a post size: 18 um, gap size: 18 um, and row shift: 1/42 which gives critical size: 7 um. Six mL 10 um green beads ($1\times10^5$ beads/mL) flow through the device at 0.1 mL/min for 60 minutes. Then, 5 mL F108 buffer flow at 0.5 mL/min to remove the remaining unclogged beads. Finally, 5 mL cleaning stream at 0.5 mL/min (also F108 buffer) is applied to clean the device.

FIG. 35A illustrates a chip before running an on-chip cleaning system, and FIG. 35B illustrates a chip after running an on-chip cleaning system.

While preferred embodiments have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments described herein can be employed in practicing the disclosure. It is intended that the following claims define the scope of the invention and that methods and structures within the scope of these claims and their equivalents be covered thereby.

What is claimed is:

1. A method of purifying first particles of at least a predetermined size, the method comprising:
    (a) applying at least 100 mL of a sample comprising the first particles of at least the predetermined size to a deterministic lateral displacement microfluidic array, wherein the sample comprises blood, and further comprises a direct thrombin inhibitor at a concentration sufficient to inhibit clot formation when the sample is applied to the array; and
    (b) flowing the at least 100 mL of the sample through the array at a rate of at least 1 mL/min, wherein the array comprises an array of obstacles arranged in rows, wherein each subsequent row of obstacles of the array of obstacles is shifted laterally with respect to a previous row, wherein the obstacles of the array of obstacles differentially deflect the first particles of at least the first predetermined size to a first outlet and second particles in the sample of less than the predetermined size to a second outlet, thereby purifying the first particles of at least the predetermined size.

2. The method of claim 1, wherein the sample is a blood sample.

3. The method of claim 1, wherein the first particles of at least the predetermined size comprise stem cells.

4. The method of claim 3, wherein the stem cells are peripheral blood stem cells (PBSCs).

5. The method of claim 3, wherein the stem cells are hematopoietic stem cells (HSCs).

6. The method of claim 1, wherein the purified particles of at least the predetermined size are at least 90% pure.

7. The method of claim 1, wherein the purified particles of at least the predetermined size comprise at least 90% of the first particles in the sample.

8. The method of claim 1, wherein the purified particles of at least the predetermined size comprise purified cells and the purified cells are at least 90% viable.

9. The method of claim 1, wherein the obstacles comprise a cylindrical cross-section.

10. The method of claim 1, wherein the obstacles comprise a quadrilateral cross-section.

11. The method of claim 10, wherein the quadrilateral is a rhombus.

12. The method of claim 1, wherein a flow profile of the sample within a gap between two obstacles of the array of obstacles is symmetrical about a center line of the gap.

13. The method of claim 1, wherein the sample further comprises a calcium chelator at a concentration sufficient to inhibit clot formation when the sample is applied to the array.

14. The method of claim 13, wherein the calcium chelator is EDTA or acid citrate dextrose (ACD).

* * * * *